(12) United States Patent
Liu et al.

(10) Patent No.: US 6,762,042 B2
(45) Date of Patent: Jul. 13, 2004

(54) DNA MOLECULES ENCODING HUMAN NHL A DNA HELICASE

(75) Inventors: Xiaomei Liu, Lansdale, PA (US); Chang Bai, Norristown, PA (US); Michael L. Metzker, Houston, TX (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/148,806

(22) PCT Filed: Dec. 7, 2000

(86) PCT No.: PCT/US00/33065

§ 371 (c)(1),
(2), (4) Date: Jun. 5, 2002

(65) Prior Publication Data

US 2003/0138933 A1 Jul. 24, 2003

Related U.S. Application Data

(60) Provisional application No. 60/169,970, filed on Dec. 9, 1999.

(51) Int. Cl.$^7$ .......................... C12N 9/00; C12N 15/63; C12N 1/21; C12N 15/85; C07H 21/04
(52) U.S. Cl. .......................... 435/183; 435/193; 435/6; 435/320.1; 435/252.3; 435/325; 435/410; 536/23.1; 536/23.2; 536/23.5
(58) Field of Search ............................ 435/199, 183, 435/320.1, 193, 252.3; 536/23.1, 23.2; 530/350

(56) References Cited

U.S. PATENT DOCUMENTS

| 5,466,576 A | 11/1995 | Schulz et al. ................... 483/6 |
| 5,843,737 A | * 12/1998 | Chen et al. ................. 435/455 |
| 5,888,792 A | 3/1999 | Bandman et al. ........... 483/183 |

OTHER PUBLICATIONS

Ngo et al., Computational Complexity, Protein Structure Predition, and the Levinthal Paradox, in The Protein Folding Problem and Tertiary Structure Predition, 1994, Merz et al. (ed.), Birkhauser, Boston, MA, pp. 433 and 492–495.*
Genbank Accession No. AL080127, Wambutt, R. et al. Direct Submission, (1999).
Genback Accession No. AB029011, Kikuno, R. et al. "Prediction of the coding sequences of unidentified human genes. XIV. The complete sequences of 100 new cDNA clones from brain which code for large protens in vitro", (1999).

Bai, Chang et al. "Overexpression of M68/DcR3 in human gastrointestinal tract tumors independent of gene amplification and its location in a four–gene cluster". PNAS, vol. 97, No. 3, Feb. 1, 2000, pp. 1230–1235.

Zhou, J.–Q. et al. "Piflp Helicase, a Catalytic Inhibitor of Telomerase in Yeast". SCIENCE, vol. 289, Aug. 4, 2000, pp. 771–774.

Naumovski, Louie et al. "RAD3 Gene of *Saccharomyces cerevisiae:* Nucleotide Sequence of Wild–Type and Mutant Alleles, Transcript Mapping, and Aspects of Gene Regulation". Molecular and Cellular Biology, Jan., 1985, pp. 17–26.

Reynolds, Paul et al. "The nucleotide sequence of the RAD3 gene of *Saccharomyces cerevisia*: a potential adenine nucleotide binding amino acid sequence and a nonessential acidic carboxyl terminal region". Nucleic Acid Research, vol. 13, No. 7, 1985, pp. 2357–2372.

Weber, Christine A. et al. "ERCC2: cDNA cloning and molecular characterization of a human nucleotide excision repair gene with high homology to yeast RAD3". The EMBO Journal, vol. 9, No. 5, 1990, pp. 1437–1447.

Tuteja, Narendra et al "Inhibition of DN Unwinding and ATPase Activities of Human DNA Helicase II by Chemotherapeutic Agents". Biochemical and Biophysical Research Comm., vol. 236, 1997, pp. 636–640.

Lun, Lapman et al. "Antihelicase action of CI–958, a new drug for prostate cancer". Cancer Chemother Pharmacol, vol. 42, 1998, pp. 447–453.

* cited by examiner

*Primary Examiner*—Richard Hutson
(74) *Attorney, Agent, or Firm*—Jack L. Tribble; J. Mark Hand; Laura M. Ginkel

(57) ABSTRACT

The present invention disclosed isolated nucleic acid molecules (polynucleotides) which encode NHL, a putative DNA helicase. The present invention in turn relates to recombinant vectors and recombinant hosts which contain a DNA fragment encoding NHL, substantially purified forms of associated NHL, associated mutant proteins, and methods associated with identifying compounds which modulate NHL, which will be useful in the treatment of various neoplastic disorders. Both a genomic clone containing regulatory and intron sequences, as well as the exon structure and open reading frame of human NHL are disclosed.

17 Claims, 12 Drawing Sheets

```
AGTCAGCCCT GCTGCCAGCC AGTGCCGGGT GCTGGGGACT CAGGGAGGCC CGCCGGGACC ACTGCGGGAC
AGTGAGCCGA GCAGAAGCTG GAACGCAGGA GAGGAAGGAG AGGGGGCGGT CAGGGCTCTC AGGAGCCGGG
TCCTGGGCAA GGCGCAGCCG TTTTCAAATT TTCAGGAAAG CGGTCGGCTC ACACTCGAGC AGTAAAAAGA
TGCCTCTGGG GAGGAGGCCC GTGCAGCTCT CCGGGCAATG GTGGTGGCTC GGCCTAGAGA GGCGGTAGTG
GAACGCAGAC CCTGGTGGGG GAATGACATC AAGGGAGGAG ACGGGCGGGA CCCCAGATTT CTGCCTGTGG
GCGATGGAAG TGAGGTTCAC TGGCCAGCGG AGCCGGACAC AGAACGCGCA AAACGCCGTG TAGGCCTGGA
GGAGCCGAAG AGCAGGCGGA CCCCCTCCGC GGGGGAACAG TTTCCGCCGG GAGCACAAAG CAACGGACCG
GAAGTGGGGG GCGGAAGTGC AGTGGGCTCA GCGCCGACTG CGCGCCTCTG CCCGCGAAAA CTCTGAGCTG
GCTGACAGCT GGGGACGGGT GGCGGCCCTC GACTGGAGTC GGTTGAGTTC CTGAGGGACC CCGGTTCTGG
AAGGTTCGCC GCGGAGACAA GTGAGCAGTC TGTGCCATAG GGATTCTCGA AGAGAACAGC GTTGTGTCCC
AGTGCACATG CTCGCATCGC TTACCAGGAG TGCCCGAGAC CCTAAGATGT TCGGAGTGGT TTTTTCGCAC
AGACCCGAAT AGCCTGCCCC TCAGCCACGC TCTGTGCCCT TCTGAGAACA GGCTGAT<u>ATG</u> CCCAAGATAG
TCCTGAATGG TGTGACCGTA GACTTCCCTT TCCAGCCCTA CAAATGCCAA CAGGAGTACA TGACCAAGGT
CCTGGAATGT CTGCAGCAGA AGGTGAATGG CATCCTGGAG AGCCCTACGG GTACAGGGAA GACGCTGTGC
CTGCTGTGCA CCACGCTGGC CTGGCGAGAA CACCTCCGAG ACGGCATCTC TGCCCGCAAG ATTGCCGAGA
GGGCGCAAGG AGAGCTTTTC CCGGATCGGG CCTTGTCATC CTGGGCAAC GCTGCTGCTG CTGCTGGAGA
CCCCATAGCT TGCTACACGG ACATCCCAAA GATTATTTAC GCCTCCAGGA CCCACTCGCA ACTCACACAG
GTCATCAACG AGCTTCGGAA CACCTCCTAC CGGCCTAAGG TGTGTGTGCT GGGCTCCCGG GAGCAGCTGT
GCATCCATCC TGAGGTGAAG AAACAAGAGA GTAACCATCT ACAGATCCAC TTGTGCCGTA AGAAGGTGGC
AAGTCGCTCC TGTCATTTCT ACAACAACGT AGAAGAAAAA AGCCTGGAGC AGGAGCTGGC CAGCCCCATC
CTGGACATTG AGGACTTGGT CAAGAGCGGA AGCAAGCACA GGGTGTGCCC TTACTACCTG TCCCGGAACC
TGAAGCAGCA AGCCGACATC ATATTCATGC CGTACAATTA CTTGTTGGAT GCCAAGAGCC GCAGAGCACA
CAACATTGAC CTGAAGGGGA CAGTCGTGAT CTTTGACGAA GCTCACAACG TGGAGAAGAT GTGTGAAGAA
TCGGCATCCT TTGACCTGAC TCCCCATGAC CTGGCTTCAG GACTGGACGT CATAGACCAG GTGCTGGAGG
AGCAGACCAA GGCAGCGCAG CAGGGTGAGC CCCACCCGGA GTTCAGCGCG GACTCCCCCA GCCCAGGGCT
GAACATGGAG CTGGAAGACA TTGCAAAGCT GAAGATGATC CTGCTGCGCC TGGAGGGGGC CATCGATGCT
GTTGAGCTGC CTGGAGACGA CAGCGGTGTC ACCAAGCCAG GGAGCTACAT CTTTGAGCTG TTTGCTGAAG
CCCAGATCAC GTTTCAGACC AAGGGCTGCA TCCTGGACTC GCTGGACCAG ATCATCCAGC ACCTGGCAGG
ACGTGCTGGA GTGTTCACCA ACACGGCCGG ACTGCAGAAG CTGGCGGACA TTATCCAGAT TGTGTTCAGT
GTGGACCCCT CCGAGGGCAG CCCTGGTTCC CCAGCAGGGC TGGGGGCCTT ACAGTCCTAT AAGGTGCACA
TCCATCCTGA TGCTGGTCAC CGGAGGACGG CTCAGCGGTC TGATGCCTGG AGCACCACTG CAGCCAGAAA
GCGAGGGAAG GTGCTGAGCT ACTGGTGCTT CAGTCCCGGC CACAGCATGC ACGAGCTGGT CCGCCAGGGC
GTCCGCTCCC TCATCCTTAC CAGCGGCACG CTGGCCCCGG TGTCCTCCTT TGCTCTGGAG ATGCAGATCC
CTTTCCCAGT CTGCCTGGAG AACCCACACA TCATCGACAA GCACCAGATC TGGGTGGGGG TCGTCCCCAG
AGGCCCCGAT GGAGCCCAGT TGAGCTCCGC GTTTGACAGA CGGTTTTCCG AGGAGTGCTT ATCCTCCCTG
GGGAAGGCTC TGGGCAACAT CGCCCGCGTG GTGCCCTATG GGCTCCTGAT CTTCTTCCCT TCCTATCCTG
TCATGGAGAA GAGCCTGGAG TTCTGGCGGG CCCGCGACTT GGCCAGGAAG ATGGAGGCGC TGAAGCCGCT
GTTTGTGGAG CCCAGGAGCA AAGGCAGCTT CTCCGAGACC ATCAGTGCTT ACTATGCAAG GGTTGCCGCC
CCTGGGTCCA CCGGCGCCAC CTTCCTGGCG GTCTGCCGGG GCAAGGCCAG CGAGGGGCTG GACTTCTCAG
ACACGAATGG CCGTGGTGTG ATTGTCACGG GCCTCCCGTA CCCCCCACGC ATGGACCCCC GGGTTGTCCT
CAAGATGCAG TTCCTGGATG AGATGAAGGG CCAGGGTGGG CTGGGGGCC AGTTCCTCTC TGGGCAGGAG
TGGTACCGGC AGCAGGCGTC CAGGGCTGTG AACCAGGCCA TCGGGCGAGT GATCCGGCAC CGCCAGGACT
ACGGAGCTGT CTTCCTCTGT GACCACAGGT TCGCCTTTGC CGACGCAAGA GCCCAACTGC CCTCCTGGGT
GCGTCCCCAC GTCAGGGTGT ATGACAACTT TGGCCATGTC ATCCGAGACG TGGCCCAGTT CTTCCGTGTT
GCCGAGCGAA CTATGCCAGC GCCGGCCCCC CGGGCTACAG CACCCAGTGT GCGTGGAGAA GATGCTGTCA
GCGAGGCCAA GTCGCCTGGC CCCTTCTTCT CCACCAGGAA AGCTAAGAGT CTGGACCTGC ATGTCCCCAG
CCTGAAGCAG AGGTCCTCAG GGTCACCAGC TGCCGGGGAC CCCGAGAGTA GCCTGTGTGT GGAGTATGAG
CAGGAGCCAG TTCCTGCCCG GCAGAGGCCC AGGGGCTGC TGGCCGCCCT GGAGCACAGC GAACAGCGGG
```

FIG. 1A

```
CGGGGAGCCC TGGCGAGGAG CAGGCCCACA GCTGCTCCAC CCTGTCCCTC CTGTCTGAGA
AGAGGCCGGC AGAAGAACCG CGAGGAGGGA GGAAGAAGAT CCGGCTGGTC AGCCACCCGG
AGGAGCCCGT GGCTGGTGCA CAGACGGACA GGGCCAAGCT CTTCATGGTG GCCGTGAAGC
AGGAGTTGAG CCAAGCCAAC TTTGCCACCT TCACCCAGGC CCTGCAGGAC TACAAGGGTT
CCGATGACTT CGCCGCCCTG GCCGCCTGTC TCGGCCCCCT CTTTGCTGAG GACCCCAAGA
AGCACAACCT GCTCCAAGGC TTCTACCAGT TTGTGCGGCC CCACCATAAG CAGCAGTTTG
AGGAGGTCTG TATCCAGCTG ACAGGACGAG GCTGTGGCTA TCGGCCTGAG CACAGCATTC
CCCGAAGGCA GCGGGCACAG CCGGTCCTGG ACCCCACTGG AAGAACGGCG CCGGATCCCA
AGCTGACCGT GTCCACGGCT GCAGCCCAGC AGCTGGACCC CCAAGAGCAC CTGAACCAGG
GCAGGCCCCA CCTGTCGCCC AGGCCACCCC CAACAGGAGA CCCTGGCAGC CAACCACAGT
GGGGGTCTGG AGTGCCCAGA GCAGGGAAGC AGGGCCAGCA CGCCGTGAGC GCCTACCTGG
CTGATGCCCG CAGGGCCCTG GGGTCCGCGG GCTGTAGCCA ACTCTTGGCA GCGCTGACAG
CCTATAAGCA AGACGACGAC CTCGACAAGG TGCTGGCTGT GTTGGCCGCC CTGACCACTG
CAAAGCCAGA GGACTTCCCC CTGCTGCACA GGTTCAGCAT GTTTGTGCGT CCACACCACA
AGCAGCGCTT CTCACAGACG TGCACAGACC TGACCGGCCG GCCCTACCCG GGCATGGAGC
CACCGGGACC CCAGGAGGAG AGGCTTGCCG TGCCTCCTGT GCTTACCCAC AGGGCTCCCC
AACCAGGCCC CTCACGGTCC GAGAAGACCG GGAAGACCCA GAGCAAGATC TCGTCCTTCC
TTAGACAGAG GCCAGCAGGG ACTGTGGGGG CGGGCGGTGA GGATGCAGGT CCCAGCCAGT
CCTCAGGACC TCCCCACGGG CCTGCAGCAT CTGAGTGGGG CCTCTAGGAT GTGCCCAGCC
TGCCACACCG CCTCCAGGAA GCAGAGCGTC ATGCAGGTCT TCTGGCCAGA GCCCCAGTGA
GTGCCCACGG AGGCCCCCAG CACACCCAAC GTGGCTTGAT CACCTGCCTG TCCAGCTCTG
GTGGGCCAAG AACCCACCCA ACAGAATAGG CCAGCCCATG CCAGCCGGCT TGGCCCGCTG
CAGGCCTCAG GCAGGCGGGG CCCATGGTTG GTCCCTGCGG TGGGACCGGA TCTGGGCCTG
CCTCTGAGAA GCCCTGAGCT ACCTTGGGGT CTGGGGTGGG TTTCTGGGAA AGTGCTTCCC
CAGAACTTCC CTGGCTCCTG GCCTGTGAGT GGTGCCACAG GGCACCCCA GCTGAGCCCC
TCACCGGGAA GGAGGAGACC CCCGTGGGCA CGTGTCCACT TTTAATCAGG GGACAGGGCT
CTCTAATAAA GCTGCTGGCA GTGCCC (SEQ ID NO:1).
```

FIG. 1B

```
MPKIVLNGVT VDFPFQPYKC QQEYMTKVLE CLQQKVNGIL ESPTGTGKTL CLLCTTLAWR
EHLRDGISAR KIAERAQGEL FPDRALSSWG NAAAAAGDPI ACYTDIPKII YASRTHSQLT
QVINELRNTS YRPKVCVLGS REQLCIHPEV KKQESNHLQI HLCRKKVASR SCHFYNNVEE
KSLEQELASP ILDIEDLVKS GSKHRVCPYY LSRNLKQQAD IIFMPYNYLL DAKSRRAHNI
DLKGTVVIFD EAHNVEKMCE ESASFDLTPH DLASGLDVID QVLEEQTKAA QQGEPHPEFS
ADSPSPGLNM ELEDIAKLKM ILLRLEGAID AVELPGDDSG VTKPGSYIFE LFAEAQITFQ
TKGCILDSLD QIIQHLAGRA GVFTNTAGLQ KLADIIQIVF SVDPSEGSPG SPAGLGALQS
YKVHIHPDAG HRRTAQRSDA WSTTAARKRG KVLSYWCFSP GHSMHELVRQ GVRSLILTSG
TLAPVSSFAL EMQIPFPVCL ENPHIIDKHQ IWVGVVPRGP DGAQLSSAFD RRFSEECLSS
LGKALGNIAR VVPYGLLIFF PSYPVMEKSL EFWRARDLAR KMEALKPLFV EPRSKGSFSE
TISAYYARVA APGSTGATFL AVCRGKASEG LDFSDTNGRG VIVTGLPYPP RMDPRVVLKM
QFLDEMKGQG GAGGQFLSGQ EWYRQQASRA VNQAIGRVIR HRQDYGAVFL CDHRFAFADA
RAQLPSWVRP HVRVYDNFGH VIRDVAQFFR VAERTMPAPA PRATAPSVRG EDAVSEAKSP
GPFFSTRKAK SLDLHVPSLK QRSSGSPAAG DPESSLCVEY EQEPVPARQR PRGLLAALEH
SEQRAGSPGE EQAHSCSTLS LLSEKRPAEE PRGGRKKIRL VSHPEEPVAG AQTDRAKLFM
VAVKQELSQA NFATFTQALQ DYKGSDDFAA LAACLGPLFA EDPKKHNLLQ GFYQFVRPHH
KQQFEEVCIQ LTGRGCGYRP EHSIPRRQRA QPVLDPTGRT APDPKLTVST AAAQQLDPQE
HLNQGRPHLS PRPPPTGDPG SQPQWGSGVP RAGKQGQHAV SAYLADARRA LGSAGCSQLL
AALTAYKQDD DLDKVLAVLA ALTTAKPEDF PLLHRFSMFV RPHHKQRFSQ TCTDLTGRPY
PGMEPPGPQE ERLAVPPVLT HRAPQPGPSR SEKTGKTQSK ISSFLRQRPA GTVGAGGEDA
GPSQSSGPPH GPAASEWGL* (SEQ ID NO:2).
```

FIG.2

```
RepD     ESNGKEIL-EGVYSLEDKEYQLHQMCPYFLSRHMLNFANMIFSMQMLQPKIASLI
RAD3     YNIEVEDYLPKGVFSFEKLYCEEKTLCPYFIVRMISLCNIIYSMHYLQPKIAERV
RAD15    EDLEPHSLISNGWTLDDITEYGEFTVRMLPFCNVIYSMHYLQPKIAERV
XP_GroupD DAHGREVPLPAGIYNLDDKALGRRQGWCPYFARYSILHANVVYSHYLQPKIADLV
NHL      EEKSLEQEASPILDIEDLVKSGSKHRVCPYYLSRNLKQQADVFMPMYNLLDAKSRRAH RepD     SSSFPSNSIWEDEAHNIDNVCINALSINIDNKLDTSSKNIAKINKQIEDIKKVDEKRL
RAD3     SNEVSKDSIVFEDEAHNIDNVCIESLSLDLTDALRRATRGANALDERISEVRKVDSQKL
RAD15    SRELVSKDCIWEDEAHNIDNVCIESLSIDLTESSSRKASKSILSLEQKVNEVKQSDSKKL
XP_GroupD SKELARKAVVFEDEAHNIDNVQIDSMSVNLRRTLDRCQGNLETLQKTVLRIKETDQRL
NHL      NIDLKG-TVVIFDEAHMVEKMQESASFDLIPHDLASGLDVIDQVLEEQTKAAQQGEP--
              |-----II-----|

RepD     KDEYQRLVNGLARSGSTRA--DETTSDPVEPNDVIQEAVPGNIRKPSIFISLRRVVDYL
RAD3     QDEYEKLVQGLHSADILTQEEPFVETPVLPQDLLTEAIPGNIRRAEHFVSFLKRLIEYL
RAD15    QDEYQKLVRGLQDANAAND-EDQFMANPVLPEDVLKEAVPGNIRRAEHFIAFLKRFVEYL
XP_GroupD RDEYRRLVEGLREASAARELEDAVELPDDSGVTKPGSYIFELFAEA
NHL      HPFFSADSPSPGLNMELEDIAKLKMILLRLEGAIDAVELPDDSGVTKPGSYIFELFAEA
```

| | |
|---|---|
| REPD | NRLDKBNKLPQMILQFC-QPQHLNLSTDMAISLSKTFLREMGQFSREEQLGKSLWSLEH |
| RAD3 | SR---KRSQLPKMIAQGL-SDADLNLSTDMAISNTKQFLRTMAQTDPKDQEGVSVWSYED |
| RAD15 | GRSDKRTIKLPKMIQQYI-TEGATNLSTDMSLAAKKFLRTMAQFTASDQEGISWWSLDD |
| XP_GroupD | ARGDKRGKLPRMIQEHL--TDAKLNLTVDEGVQVAKYFLRQMAQFHEDQLGLSLLSLEQ |
| NHL | AFADABAQLPSWRPHVRVYDKFGHVIRDVAQFRVAERTMPABAPRATAPSVRGEDAVS |

| | |
|---|---|
| REPD | VEKQSTSKPPQQQNSAINSTITTSTTTTTSTISETHLT (SEQ ID NO:35) |
| RAD3 | LIKHQNS--RKDQGGFIENENKEGEQDEDEDEDIEMQ (SEQ ID NO:36) |
| RAD15 | LLIHQK--KALSAAIEQSKHEDEMDIDVVET (SEQ ID NO:37) |
| XP_GroupD | LESEETL--KRIEQIAQQL (SEQ ID NO:38) |
| NHL | EASPGPFFSTRKAKSLDLHVPSLKQRSSGSPAAGDPESSLCVEYEQEPVPARQRPRGLL |

FIG. 3E

NHL  AALEHSEQRAGSPGEEQAHSCSTLSLLSEKRPAEEPRGGRKKIRLVSHPEEPVAGAQTDR
NHL  AKLFMVAVKQELSQANFATFTQALQDYKGSDDFAALAACLGPLFAEDPKKHNLLQGFYQF
NHL  VRPHHKQQFEEVCIQLTGRGCGYRPEHSIPRRQRAQPVLDPTGRTAPDPKLTVSTAAAQQ
NHL  LDPQEHLNQGRPHLSPRPPTGDPGSQPQWGSGVPRAGKQGQHAVSAYLADARRALGSAG
NHL  CSQLLAALTAYKQDDDLDKVLAVLAALTTAKPEDFPLLHRFSMFVRPHHKQRFSQTCTDL
NHL  TGRPYPGMEPPGPQEERLAVPPVLTHRAPQPGPSRSEKTGKTQSKISSFLRQRPAGTVGA
NHL  GGEDAGPSQSSGPPHGPAASEWGL  (SEQ ID NO:2)

FIG. 3F

SEQUENCE LISTING

<160> NUMBER OF SEQ ID NOS: 38
<210> SEQ ID NO 1
<211> LENGTH: 4946
<212> TYPE: DNA
<213> ORGANISM: Homo sapien
<220> FEATURE:
<221> NAME/KEY: CDS
<222> LOCATION: (828)...(4487)

<400> SEQUENCE: 1

```
agtcagccct gctgccagcc agtgccgggt gctggggact cagggaggcc cgccgggacc      60
actgcgggac agtgagccga gcagaagctg aacgcagga gaggaaggag aggggcggt       120 cagggctctc aggagccggg tcctgggcaa ggcgcagccg ttttcaaatt ttcaggaaag      180
cggtcggctc acactcgagc agtaaaaaga tgcctctggg gaggaggccc gtgcagctct      240
ccgggcaatg gtggtggctc ggcctagaga ggcggtagtg aacgcagac cctggtgggg       300 gaatgacatc aagggaggag acgggcggga ccccagattt ctgcctgtgg gcgatggaag      360
tgaggttcac tggccagcgg agccggacac agaacgcgca aaacgccgtg taggcctgga      420
ggagccgaag agcaggcgga ccccctccgc gggggaacag tttccgccgg gagcacaaag      480
caacggaccg gaagtggggg gcggaagtgc agtgggctca gcgccgactg cgcgcctctg      540
cccgcgaaaa ctctgagctg gctgacagct ggggacgggt ggcggccctc gactggagtc      600
ggttgagttc ctgagggacc ccggttctgg aaggttcgcc gcggagacaa gtgagcagtc      660
tgtgccatag ggattctcga agagaacagc gttgtgtccc agtgcacatg ctcgcatcgc      720
ttaccaggag tgcccgagac cctaagatgt tcggagtggt ttttttcgcac agacccgaat      780 agcctgcccc tcagccacgc tctgtgccct tctgagaaca ggctgat atg ccc aag        836
                                                   Met Pro Lys
                                                     1 ata gtc ctg aat ggt gtg acc gta gac ttc cct ttc cag ccc tac aaa       884
Ile Val Leu Asn Gly Val Thr Val Asp Phe Pro Phe Gln Pro Tyr Lys
    5                  10                  15 tgc caa cag gag tac atg acc aag gtc ctg gaa tgt ctg cag cag aag       932
Cys Gln Gln Glu Tyr Met Thr Lys Val Leu Glu Cys Leu Gln Gln Lys
 20                  25                  30                  35 gtg aat ggc atc ctg gag agc cct acg ggt aca ggg aag acg ctg tgc       980
Val Asn Gly Ile Leu Glu Ser Pro Thr Gly Thr Gly Lys Thr Leu Cys
                40                  45                  50 ctg ctg tgc acc acg ctg gcc tgg cga gaa cac ctc cga gac ggc atc      1028
Leu Leu Cys Thr Thr Leu Ala Trp Arg Glu His Leu Arg Asp Gly Ile
            55                  60                  65 tct gcc cgc aag att gcc gag agg gcg caa gga gag ctt ttc ccg gat      1076
Ser Ala Arg Lys Ile Ala Glu Arg Ala Gln Gly Glu Leu Phe Pro Asp
        70                  75                  80 cgg gcc ttg tca tcc tgg ggc aac gct gct gct gct gga gac ccc          1124
Arg Ala Leu Ser Ser Trp Gly Asn Ala Ala Ala Ala Gly Asp Pro
    85                  90                  95 ata gct tgc tac acg gac atc cca aag att att tac gcc tcc agg acc      1172
Ile Ala Cys Tyr Thr Asp Ile Pro Lys Ile Ile Tyr Ala Ser Arg Thr
100                 105                 110                 115 cac tcg caa ctc aca cag gtc atc aac gag ctt cgg aac acc tcc tac      1220
His Ser Gln Leu Thr Gln Val Ile Asn Glu Leu Arg Asn Thr Ser Tyr
                120                 125                 130 cgg cct aag gtg tgt gtg ctg ggc tcc cgg gag cag ctg tgc atc cat      1268
Arg Pro Lys Val Cys Val Leu Gly Ser Arg Glu Gln Leu Cys Ile His
            135                 140                 145
```

```
cct gag gtg aag aaa caa gag agt aac cat cta cag atc cac ttg tgc    1316
Pro Glu Val Lys Lys Gln Glu Ser Asn His Leu Gln Ile His Leu Cys
        150                 155                 160 cgt aag aag gtg gca agt cgc tcc tgt cat ttc tac aac aac gta gaa    1364
Arg Lys Lys Val Ala Ser Arg Ser Cys His Phe Tyr Asn Asn Val Glu
165                 170                 175 gaa aaa agc ctg gag cag gag ctg gcc agc ccc atc ctg gac att gag    1412
Glu Lys Ser Leu Glu Gln Glu Leu Ala Ser Pro Ile Leu Asp Ile Glu
180                 185                 190                 195 gac ttg gtc aag agc gga agc aag cac agg gtg tgc cct tac tac ctg    1460
Asp Leu Val Lys Ser Gly Ser Lys His Arg Val Cys Pro Tyr Tyr Leu
                200                 205                 210 tcc cgg aac ctg aag cag caa gcc gac atc ata ttc atg ccg tac aat    1508
Ser Arg Asn Leu Lys Gln Gln Ala Asp Ile Ile Phe Met Pro Tyr Asn
            215                 220                 225 tac ttg ttg gat gcc aag agc cgc aga gca cac aac att gac ctg aag    1556
Tyr Leu Leu Asp Ala Lys Ser Arg Arg Ala His Asn Ile Asp Leu Lys
        230                 235                 240 ggg aca gtc gtg atc ttt gac gaa gct cac aac gtg gag aag atg tgt    1604
Gly Thr Val Val Ile Phe Asp Glu Ala His Asn Val Glu Lys Met Cys
245                 250                 255 gaa gaa tcg gca tcc ttt gac ctg act ccc cat gac ctg gct tca gga    1652
Glu Glu Ser Ala Ser Phe Asp Leu Thr Pro His Asp Leu Ala Ser Gly
260                 265                 270                 275 ctg gac gtc ata gac cag gtg ctg gag gag cag acc aag gca gcg cag    1700
Leu Asp Val Ile Asp Gln Val Leu Glu Glu Gln Thr Lys Ala Ala Gln
                280                 285                 290 cag ggt gag ccc cac ccg gag ttc agc gcg gac tcc ccc agc cca ggg    1748
Gln Gly Glu Pro His Pro Glu Phe Ser Ala Asp Ser Pro Ser Pro Gly
            295                 300                 305 ctg aac atg gag ctg gaa gac att gca aag ctg aag atg atc ctg ctg    1796
Leu Asn Met Glu Leu Glu Asp Ile Ala Lys Leu Lys Met Ile Leu Leu
        310                 315                 320 cgc ctg gag ggg gcc atc gat gct gtt gag ctg cct gga gac gac agc    1844
Arg Leu Glu Gly Ala Ile Asp Ala Val Glu Leu Pro Gly Asp Asp Ser
325                 330                 335 ggt gtc acc aag cca ggg agc tac atc ttt gag ctg ttt gct gaa gcc    1892
Gly Val Thr Lys Pro Gly Ser Tyr Ile Phe Glu Leu Phe Ala Glu Ala
340                 345                 350                 355 cag atc acg ttt cag acc aag ggc tgc atc ctg gac tcg ctg gac cag    1940
Gln Ile Thr Phe Gln Thr Lys Gly Cys Ile Leu Asp Ser Leu Asp Gln
                360                 365                 370 atc atc cag cac ctg gca gga cgt gct gga gtg ttc acc aac acg gcc    1988
Ile Ile Gln His Leu Ala Gly Arg Ala Gly Val Phe Thr Asn Thr Ala
            375                 380                 385 gga ctg cag aag ctg gcg gac att atc cag att gtg ttc agt gtg gac    2036
Gly Leu Gln Lys Leu Ala Asp Ile Ile Gln Ile Val Phe Ser Val Asp
        390                 395                 400 ccc tcc gag ggc agc cct ggt tcc cca gca ggg ctg ggg gcc tta cag    2084
Pro Ser Glu Gly Ser Pro Gly Ser Pro Ala Gly Leu Gly Ala Leu Gln
405                 410                 415 tcc tat aag gtg cac atc cat cct gat gct ggt cac cgg agg acg gct    2132
Ser Tyr Lys Val His Ile His Pro Asp Ala Gly His Arg Arg Thr Ala
420                 425                 430                 435 cag cgg tct gat gcc tgg agc acc act gca gcc aga aag cga ggg aag    2180
Gln Arg Ser Asp Ala Trp Ser Thr Thr Ala Ala Arg Lys Arg Gly Lys
                440                 445                 450 gtg ctg agc tac tgg tgc ttc agt ccc ggc cac agc atg cac gag ctg    2228
Val Leu Ser Tyr Trp Cys Phe Ser Pro Gly His Ser Met His Glu Leu
```

-continued

| | | |
|---|---|---|
| gtc cgc cag ggc gtc cgc tcc ctc atc ctt acc agc ggc acg ctg gcc<br>Val Arg Gln Gly Val Arg Ser Leu Ile Leu Thr Ser Gly Thr Leu Ala<br>470                 475                 480 | 2276 |

Column headers above first row: 455, 460, 465

```
gtc cgc cag ggc gtc cgc tcc ctc atc ctt acc agc ggc acg ctg gcc    2276
Val Arg Gln Gly Val Arg Ser Leu Ile Leu Thr Ser Gly Thr Leu Ala
        470                 475                 480 ccg gtg tcc tcc ttt gct ctg gag atg cag atc cct ttc cca gtc tgc    2324
Pro Val Ser Ser Phe Ala Leu Glu Met Gln Ile Pro Phe Pro Val Cys
        485                 490                 495 ctg gag aac cca cac atc atc gac aag cac cag atc tgg gtg ggg gtc    2372
Leu Glu Asn Pro His Ile Ile Asp Lys His Gln Ile Trp Val Gly Val
500                 505                 510                 515 gtc ccc aga ggc ccc gat gga gcc cag ttg agc tcc gcg ttt gac aga    2420
Val Pro Arg Gly Pro Asp Gly Ala Gln Leu Ser Ser Ala Phe Asp Arg
                520                 525                 530 cgg ttt tcc gag gag tgc tta tcc tcc ctg ggg aag gct ctg ggc aac    2468
Arg Phe Ser Glu Glu Cys Leu Ser Ser Leu Gly Lys Ala Leu Gly Asn
            535                 540                 545 atc gcc cgc gtg gtg ccc tat ggg ctc ctg atc ttc ttc cct tcc tat    2516
Ile Ala Arg Val Val Pro Tyr Gly Leu Leu Ile Phe Phe Pro Ser Tyr
        550                 555                 560 cct gtc atg gag aag agc ctg gag ttc tgg cgg gcc cgc gac ttg gcc    2564
Pro Val Met Glu Lys Ser Leu Glu Phe Trp Arg Ala Arg Asp Leu Ala
    565                 570                 575 agg aag atg gag gcg ctg aag ccg ctg ttt gtg gag ccc agg agc aaa    2612
Arg Lys Met Glu Ala Leu Lys Pro Leu Phe Val Glu Pro Arg Ser Lys
580                 585                 590                 595 ggc agc ttc tcc gag acc atc agt gct tac tat gca agg gtt gcc gcc    2660
Gly Ser Phe Ser Glu Thr Ile Ser Ala Tyr Tyr Ala Arg Val Ala Ala
                600                 605                 610 cct ggg tcc acc ggc gcc acc ttc ctg gcg gtc tgc cgg ggc aag gcc    2708
Pro Gly Ser Thr Gly Ala Thr Phe Leu Ala Val Cys Arg Gly Lys Ala
            615                 620                 625 agc gag ggg ctg gac ttc tca gac acg aat ggc cgt ggt gtg att gtc    2756
Ser Glu Gly Leu Asp Phe Ser Asp Thr Asn Gly Arg Gly Val Ile Val
        630                 635                 640 acg ggc ctc ccg tac ccc cca cgc atg gac ccc cgg gtt gtc ctc aag    2804
Thr Gly Leu Pro Tyr Pro Pro Arg Met Asp Pro Arg Val Val Leu Lys
    645                 650                 655 atg cag ttc ctg gat gag atg aag ggc cag ggt ggg gct ggg ggc cag    2852
Met Gln Phe Leu Asp Glu Met Lys Gly Gln Gly Gly Ala Gly Gly Gln
660                 665                 670                 675 ttc ctc tct ggg cag gag tgg tac cgg cag cag gcg tcc agg gct gtg    2900
Phe Leu Ser Gly Gln Glu Trp Tyr Arg Gln Gln Ala Ser Arg Ala Val
                680                 685                 690 aac cag gcc atc ggg cga gtg atc cgg cac cgc cag gac tac gga gct    2948
Asn Gln Ala Ile Gly Arg Val Ile Arg His Arg Gln Asp Tyr Gly Ala
            695                 700                 705 gtc ttc ctc tgt gac cac agg ttc gcc ttt gcc gac gca aga gcc caa    2996
Val Phe Leu Cys Asp His Arg Phe Ala Phe Ala Asp Ala Arg Ala Gln
        710                 715                 720 ctg ccc tcc tgg gtg cgt ccc cac gtc agg gtg tat gac aac ttt ggc    3044
Leu Pro Ser Trp Val Arg Pro His Val Arg Val Tyr Asp Asn Phe Gly
    725                 730                 735 cat gtc atc cga gac gtg gcc cag ttc ttc cgt gtt gcc gag cga act    3092
His Val Ile Arg Asp Val Ala Gln Phe Phe Arg Val Ala Glu Arg Thr
740                 745                 750                 755 atg cca gcg ccg gcc ccc cgg gct aca gca ccc agt gtg cgt gga gaa    3140
Met Pro Ala Pro Ala Pro Arg Ala Thr Ala Pro Ser Val Arg Gly Glu
                760                 765                 770 gat gct gtc agc gag gcc aag tcg cct ggc ccc ttc ttc tcc acc agg    3188
Asp Ala Val Ser Glu Ala Lys Ser Pro Gly Pro Phe Phe Ser Thr Arg
```

-continued

```
                Asp Ala Val Ser Glu Ala Lys Ser Pro Gly Pro Phe Ser Thr Arg
                            775                 780                 785 aaa gct aag agt ctg gac ctg cat gtc ccc agc ctg aag cag agg tcc      3236
Lys Ala Lys Ser Leu Asp Leu His Val Pro Ser Leu Lys Gln Arg Ser
            790                 795                 800 tca ggg tca cca gct gcc ggg gac ccc gag agt agc ctg tgt gtg gag      3284
Ser Gly Ser Pro Ala Ala Gly Asp Pro Glu Ser Ser Leu Cys Val Glu
805                 810                 815 tat gag cag gag cca gtt cct gcc cgg cag agg ccc agg ggg ctg ctg      3332
Tyr Glu Gln Glu Pro Val Pro Ala Arg Gln Arg Pro Arg Gly Leu Leu
820                 825                 830                 835 gcc gcc ctg gag cac agc gaa cag cgg gcg ggg agc cct ggc gag gag      3380
Ala Ala Leu Glu His Ser Glu Gln Arg Ala Gly Ser Pro Gly Glu Glu
            840                 845                 850 cag gcc cac agc tgc tcc acc ctg tcc ctc ctg tct gag aag agg ccg      3428
Gln Ala His Ser Cys Ser Thr Leu Ser Leu Leu Ser Glu Lys Arg Pro
            855                 860                 865 gca gaa gaa ccg cga gga ggg agg aag aag atc cgg ctg gtc agc cac      3476
Ala Glu Glu Pro Arg Gly Gly Arg Lys Lys Ile Arg Leu Val Ser His
            870                 875                 880 ccg gag gag ccc gtg gct ggt gca cag acg gac agg gcc aag ctc ttc      3524
Pro Glu Glu Pro Val Ala Gly Ala Gln Thr Asp Arg Ala Lys Leu Phe
885                 890                 895 atg gtg gcc gtg aag cag gag ttg agc caa gcc aac ttt gcc acc ttc      3572
Met Val Ala Val Lys Gln Glu Leu Ser Gln Ala Asn Phe Ala Thr Phe
900                 905                 910                 915 acc cag gcc ctg cag gac tac aag ggt tcc gat gac ttc gcc gcc ctg      3620
Thr Gln Ala Leu Gln Asp Tyr Lys Gly Ser Asp Asp Phe Ala Ala Leu
            920                 925                 930 gcc gcc tgt ctc ggc ccc ctc ttt gct gag gac ccc aag aag cac aac      3668
Ala Ala Cys Leu Gly Pro Leu Phe Ala Glu Asp Pro Lys Lys His Asn
            935                 940                 945 ctc ctc caa ggc ttc tac cag ttt gtg cgg ccc cac cat aag cag cag      3716
Leu Leu Gln Gly Phe Tyr Gln Phe Val Arg Pro His His Lys Gln Gln
            950                 955                 960 ttt gag gag gtc tgt atc cag ctg aca gga cga ggc tgt ggc tat cgg      3764
Phe Glu Glu Val Cys Ile Gln Leu Thr Gly Arg Gly Cys Gly Tyr Arg
965                 970                 975 cct gag cac agc att ccc cga agg cag cgg gca cag ccg gtc ctg gac      3812
Pro Glu His Ser Ile Pro Arg Arg Gln Arg Ala Gln Pro Val Leu Asp
 980                985                 990                 995 ccc act gga aga acg gcg ccg gat ccc aag ctg acc gtg tcc acg gct      3860
Pro Thr Gly Arg Thr Ala Pro Asp Pro Lys Leu Thr Val Ser Thr Ala
            1000                1005                1010 gca gcc cag cag ctg gac ccc caa gag cac ctg aac cag ggc agg ccc      3908
Ala Ala Gln Gln Leu Asp Pro Gln Glu His Leu Asn Gln Gly Arg Pro
            1015                1020                1025 cac ctg tcg ccc agg cca ccc cca aca gga gac cct ggc agc caa cca      3956
His Leu Ser Pro Arg Pro Pro Pro Thr Gly Asp Pro Gly Ser Gln Pro
            1030                1035                1040 cag tgg ggg tct gga gtg ccc aga gca ggg aag cag ggc cag cac gcc      4004
Gln Trp Gly Ser Gly Val Pro Arg Ala Gly Lys Gln Gly Gln His Ala
            1045                1050                1055 gtg agc gcc tac ctg gct gat gcc cgc agg gcc ctg ggg tcc gcg ggc      4052
Val Ser Ala Tyr Leu Ala Asp Ala Arg Arg Ala Leu Gly Ser Ala Gly
1060                1065                1070                1075 tgt agc caa ctc ttg gca gcg ctg aca gcc tat aag caa gac gac gac      4100
Cys Ser Gln Leu Leu Ala Ala Leu Thr Ala Tyr Lys Gln Asp Asp Asp
            1080                1085                1090
```

| | | | | | | | | | | | | | | | |
|---|---|---|---|---|---|---|---|---|---|---|---|---|---|---|---|
| ctc | gac | aag | gtg | ctg | gct | gtg | ttg | gcc | gcc | ctg | acc | act | gca | aag | cca | 4148 |
| Leu | Asp | Lys | Val | Leu | Ala | Val | Leu | Ala | Ala | Leu | Thr | Thr | Ala | Lys | Pro | |
| | | 1095 | | | | 1100 | | | | 1105 | | | | | | |
| gag | gac | ttc | ccc | ctg | ctg | cac | agg | ttc | agc | atg | ttt | gtg | cgt | cca | cac | 4196 |
| Glu | Asp | Phe | Pro | Leu | Leu | His | Arg | Phe | Ser | Met | Phe | Val | Arg | Pro | His | |
| | 1110 | | | | | 1115 | | | | | 1120 | | | | | |
| cac | aag | cag | cgc | ttc | tca | cag | acg | tgc | aca | gac | ctg | acc | ggc | cgg | ccc | 4244 |
| His | Lys | Gln | Arg | Phe | Ser | Gln | Thr | Cys | Thr | Asp | Leu | Thr | Gly | Arg | Pro | |
| | 1125 | | | | | 1130 | | | | | 1135 | | | | | |
| tac | ccg | ggc | atg | gag | cca | ccg | gga | ccc | cag | gag | gag | agg | ctt | gcc | gtg | 4292 |
| Tyr | Pro | Gly | Met | Glu | Pro | Pro | Gly | Pro | Gln | Glu | Glu | Arg | Leu | Ala | Val | |
| 1140 | | | | 1145 | | | | | 1150 | | | | | 1155 | | |
| cct | cct | gtg | ctt | acc | cac | agg | gct | ccc | caa | cca | ggc | ccc | tca | cgg | tcc | 4340 |
| Pro | Pro | Val | Leu | Thr | His | Arg | Ala | Pro | Gln | Pro | Gly | Pro | Ser | Arg | Ser | |
| | | | | 1160 | | | | | 1165 | | | | | 1170 | | |
| gag | aag | acc | ggg | aag | acc | cag | agc | aag | atc | tcg | tcc | ttc | ctt | aga | cag | 4388 |
| Glu | Lys | Thr | Gly | Lys | Thr | Gln | Ser | Lys | Ile | Ser | Ser | Phe | Leu | Arg | Gln | |
| | | | 1175 | | | | | 1180 | | | | | 1185 | | | |
| agg | cca | gca | ggg | act | gtg | ggg | gcg | ggc | ggt | gag | gat | gca | ggt | ccc | agc | 4436 |
| Arg | Pro | Ala | Gly | Thr | Val | Gly | Ala | Gly | Gly | Glu | Asp | Ala | Gly | Pro | Ser | |
| | | 1190 | | | | | 1195 | | | | | 1200 | | | | |
| cag | tcc | tca | gga | cct | ccc | cac | ggg | cct | gca | gca | tct | gag | tgg | ggc | ctc | 4484 |
| Gln | Ser | Ser | Gly | Pro | Pro | His | Gly | Pro | Ala | Ala | Ser | Glu | Trp | Gly | Leu | |
| | 1205 | | | | | 1210 | | | | | 1215 | | | | | |
| tag | gatgtgccca | gcctgccaca | ccgcctccag | gaagcagagc | gtcatgcagg | | | | | | | | | | | 4537 |
| * | | | | | | | | | | | | | | | | |

| | | |
|---|---|---|
| tcttctggcc agagcccag tgagtgccca cggaggcccc cagcacaccc aacgtggctt | | 4597 |
| gatcacctgc ctgtccagct ctggtgggcc aagaacccac ccaacagaat aggccagccc | | 4657 |
| atgccagccg gcttggcccg ctgcaggcct caggcaggcg gggcccatgg ttggtccctg | | 4717 |
| cggtgggacc ggatctgggc ctgcctctga aagccctga gctaccttgg ggtctgggt | | 4777 |
| gggtttctgg gaaagtgctt ccccagaact tccctggctc ctggcctgtg agtggtgcca | | 4837 |
| caggggcacc ccagctgagc ccctcaccgg gaaggaggag accccgtgg gcacgtgtcc | | 4897 |
| acttttaatc aggggacagg gctctctaat aaagctgctg gcagtgccc | | 4946 |

<210> SEQ ID NO 2
<211> LENGTH: 1219
<212> TYPE: PRT
<213> ORGANISM: Homo sapien

<400> SEQUENCE: 2

Met Pro Lys Ile Val Leu Asn Gly Val Thr Val Asp Phe Pro Phe Gln
1               5                   10                  15

Pro Tyr Lys Cys Gln Gln Glu Tyr Met Thr Lys Val Leu Glu Cys Leu
            20                  25                  30

Gln Gln Lys Val Asn Gly Ile Leu Glu Ser Pro Thr Gly Thr Gly Lys
        35                  40                  45

Thr Leu Cys Leu Leu Cys Thr Thr Leu Ala Trp Arg Glu His Leu Arg
    50                  55                  60

Asp Gly Ile Ser Ala Arg Lys Ile Ala Glu Arg Ala Gln Gly Glu Leu
65                  70                  75                  80

Phe Pro Asp Arg Ala Leu Ser Ser Trp Gly Asn Ala Ala Ala Ala
                85                  90                  95

Gly Asp Pro Ile Ala Cys Tyr Thr Asp Ile Pro Lys Ile Ile Tyr Ala
            100                 105                 110

Ser Arg Thr His Ser Gln Leu Thr Gln Val Ile Asn Glu Leu Arg Asn

-continued

```
            115                 120                 125
Thr Ser Tyr Arg Pro Lys Val Cys Val Leu Gly Ser Arg Glu Gln Leu
        130                 135                 140

Cys Ile His Pro Glu Val Lys Lys Gln Glu Ser Asn His Leu Gln Ile
145                 150                 155                 160

His Leu Cys Arg Lys Lys Val Ala Ser Arg Ser Cys His Phe Tyr Asn
                165                 170                 175

Asn Val Glu Glu Lys Ser Leu Glu Gln Glu Leu Ala Ser Pro Ile Leu
            180                 185                 190

Asp Ile Glu Asp Leu Val Lys Ser Gly Ser Lys His Arg Val Cys Pro
        195                 200                 205

Tyr Tyr Leu Ser Arg Asn Leu Lys Gln Gln Ala Asp Ile Ile Phe Met
    210                 215                 220

Pro Tyr Asn Tyr Leu Leu Asp Ala Lys Ser Arg Arg Ala His Asn Ile
225                 230                 235                 240

Asp Leu Lys Gly Thr Val Val Ile Phe Asp Glu Ala His Asn Val Glu
                245                 250                 255

Lys Met Cys Glu Glu Ser Ala Ser Phe Asp Leu Thr Pro His Asp Leu
            260                 265                 270

Ala Ser Gly Leu Asp Val Ile Asp Gln Val Leu Glu Glu Gln Thr Lys
        275                 280                 285

Ala Ala Gln Gln Gly Glu Pro His Pro Glu Phe Ser Ala Asp Ser Pro
    290                 295                 300

Ser Pro Gly Leu Asn Met Glu Leu Glu Asp Ile Ala Lys Leu Lys Met
305                 310                 315                 320

Ile Leu Leu Arg Leu Glu Gly Ala Ile Asp Ala Val Glu Leu Pro Gly
                325                 330                 335

Asp Asp Ser Gly Val Thr Lys Pro Gly Ser Tyr Ile Phe Glu Leu Phe
            340                 345                 350

Ala Glu Ala Gln Ile Thr Phe Gln Thr Lys Gly Cys Ile Leu Asp Ser
        355                 360                 365

Leu Asp Gln Ile Ile Gln His Leu Ala Gly Arg Ala Gly Val Phe Thr
    370                 375                 380

Asn Thr Ala Gly Leu Gln Lys Leu Ala Asp Ile Ile Gln Ile Val Phe
385                 390                 395                 400

Ser Val Asp Pro Ser Glu Gly Ser Pro Gly Ser Pro Ala Gly Leu Gly
                405                 410                 415

Ala Leu Gln Ser Tyr Lys Val His Ile His Pro Asp Ala Gly His Arg
            420                 425                 430

Arg Thr Ala Gln Arg Ser Asp Ala Trp Ser Thr Thr Ala Ala Arg Lys
        435                 440                 445

Arg Gly Lys Val Leu Ser Tyr Trp Cys Phe Ser Pro Gly His Ser Met
    450                 455                 460

His Glu Leu Val Arg Gln Gly Val Arg Ser Leu Ile Leu Thr Ser Gly
465                 470                 475                 480

Thr Leu Ala Pro Val Ser Ser Phe Ala Leu Glu Met Gln Ile Pro Phe
                485                 490                 495

Pro Val Cys Leu Glu Asn Pro His Ile Ile Asp Lys His Gln Ile Trp
            500                 505                 510

Val Gly Val Val Pro Arg Gly Pro Asp Gly Ala Gln Leu Ser Ser Ala
        515                 520                 525

Phe Asp Arg Arg Phe Ser Glu Glu Cys Leu Ser Ser Leu Gly Lys Ala
    530                 535                 540
```

-continued

```
Leu Gly Asn Ile Ala Arg Val Val Pro Tyr Gly Leu Ile Phe Phe
545                 550                 555                 560

Pro Ser Tyr Pro Val Met Glu Lys Ser Leu Glu Phe Trp Arg Ala Arg
                565                 570                 575

Asp Leu Ala Arg Lys Met Glu Ala Leu Lys Pro Leu Phe Val Glu Pro
            580                 585                 590

Arg Ser Lys Gly Ser Phe Ser Glu Thr Ile Ser Ala Tyr Tyr Ala Arg
        595                 600                 605

Val Ala Ala Pro Gly Ser Thr Gly Ala Thr Phe Leu Ala Val Cys Arg
    610                 615                 620

Gly Lys Ala Ser Glu Gly Leu Asp Phe Ser Asp Thr Asn Gly Arg Gly
625                 630                 635                 640

Val Ile Val Thr Gly Leu Pro Tyr Pro Arg Met Asp Pro Arg Val
                645                 650                 655

Val Leu Lys Met Gln Phe Leu Asp Glu Met Lys Gly Gln Gly Gly Ala
                660                 665                 670

Gly Gly Gln Phe Leu Ser Gly Gln Glu Trp Tyr Arg Gln Ala Ser
            675                 680                 685

Arg Ala Val Asn Gln Ala Ile Gly Arg Val Ile Arg His Arg Gln Asp
        690                 695                 700

Tyr Gly Ala Val Phe Leu Cys Asp His Arg Phe Ala Phe Ala Asp Ala
705                 710                 715                 720

Arg Ala Gln Leu Pro Ser Trp Val Arg Pro His Val Arg Val Tyr Asp
                725                 730                 735

Asn Phe Gly His Val Ile Arg Asp Val Ala Gln Phe Phe Arg Val Ala
            740                 745                 750

Glu Arg Thr Met Pro Ala Pro Ala Pro Arg Ala Thr Ala Pro Ser Val
        755                 760                 765

Arg Gly Glu Asp Ala Val Ser Glu Ala Lys Ser Pro Gly Pro Phe Phe
770                 775                 780

Ser Thr Arg Lys Ala Lys Ser Leu Asp Leu His Val Pro Ser Leu Lys
785                 790                 795                 800

Gln Arg Ser Ser Gly Ser Pro Ala Ala Gly Asp Pro Glu Ser Ser Leu
                805                 810                 815

Cys Val Glu Tyr Glu Gln Glu Pro Val Pro Ala Arg Gln Arg Pro Arg
            820                 825                 830

Gly Leu Leu Ala Ala Leu Glu His Ser Glu Gln Arg Ala Gly Ser Pro
        835                 840                 845

Gly Glu Glu Gln Ala His Ser Cys Ser Thr Leu Ser Leu Ser Glu
850                 855                 860

Lys Arg Pro Ala Glu Glu Pro Arg Gly Gly Arg Lys Lys Ile Arg Leu
865                 870                 875                 880

Val Ser His Pro Glu Glu Pro Val Ala Gly Ala Gln Thr Asp Arg Ala
                885                 890                 895

Lys Leu Phe Met Val Ala Val Lys Gln Glu Leu Ser Gln Ala Asn Phe
            900                 905                 910

Ala Thr Phe Thr Gln Ala Leu Gln Asp Tyr Lys Gly Ser Asp Asp Phe
        915                 920                 925

Ala Ala Leu Ala Ala Cys Leu Gly Pro Leu Phe Ala Glu Asp Pro Lys
930                 935                 940

Lys His Asn Leu Leu Gln Gly Phe Tyr Gln Phe Val Arg Pro His His
945                 950                 955                 960
```

-continued

```
Lys Gln Gln Phe Glu Glu Val Cys Ile Gln Leu Thr Gly Arg Gly Cys
                965                 970                 975
Gly Tyr Arg Pro Glu His Ser Ile Pro Arg Arg Gln Arg Ala Gln Pro
            980                 985                 990
Val Leu Asp Pro Thr Gly Arg Thr Ala Pro Asp Pro Lys Leu Thr Val
        995                1000                1005
Ser Thr Ala Ala Ala Gln Gln Leu Asp Pro Gln Glu His Leu Asn Gln
    1010                1015                1020
Gly Arg Pro His Leu Ser Pro Arg Pro Pro Thr Gly Asp Pro Gly
1025                1030                1035                1040
Ser Gln Pro Gln Trp Gly Ser Gly Val Pro Arg Ala Gly Lys Gln Gly
                1045                1050                1055
Gln His Ala Val Ser Ala Tyr Leu Ala Asp Ala Arg Arg Ala Leu Gly
            1060                1065                1070
Ser Ala Gly Cys Ser Gln Leu Leu Ala Ala Leu Thr Ala Tyr Lys Gln
        1075                1080                1085
Asp Asp Asp Leu Asp Lys Val Leu Ala Val Leu Ala Ala Leu Thr Thr
    1090                1095                1100
Ala Lys Pro Glu Asp Phe Pro Leu Leu His Arg Phe Ser Met Phe Val
1105                1110                1115                1120
Arg Pro His His Lys Gln Arg Phe Ser Gln Thr Cys Thr Asp Leu Thr
                1125                1130                1135
Gly Arg Pro Tyr Pro Gly Met Glu Pro Pro Gly Pro Gln Glu Glu Arg
            1140                1145                1150
Leu Ala Val Pro Pro Val Leu Thr His Arg Ala Pro Gln Pro Gly Pro
        1155                1160                1165
Ser Arg Ser Glu Lys Thr Gly Lys Thr Gln Ser Lys Ile Ser Ser Phe
    1170                1175                1180
Leu Arg Gln Arg Pro Ala Gly Thr Val Gly Ala Gly Gly Glu Asp Ala
1185                1190                1195                1200
Gly Pro Ser Gln Ser Ser Gly Pro Pro His Gly Pro Ala Ala Ser Glu
                1205                1210                1215
Trp Gly Leu

<210> SEQ ID NO 3
<211> LENGTH: 114793
<212> TYPE: DNA
<213> ORGANISM: Homo sapien

<400> SEQUENCE: 3
tgaagagctt tgaccaagag gctgtgacga ggccctacga ggactctggc tctcctcctg      60
ctaagcacac ccaggcaggt gtcctggcag atgaggacca catgcagagc ctcggccagc     120
ccaccaatgc ccggatatgc aagtgagccc agcctggacc cccggcgag gcccagcagc      180 accagcccag gccgaaaac cttaagaaat gaccagtgtc tgctgcttta agccaccaag      240
ctctgcggtg gtttgttagg ctgcaagcat ggctaattca gaaactgcca gaaacaagca     300
ctgctgtccc cagcctggga cacacagcac cgcctctgcg tggggagagg gcacaggcta     360
agggcacaaa tgccatccca gacccggctc ttgtgtgtgg aaggggccac tgtgccatga     420
ggcagaggaa accttggcag gaccttatgc cacagcaatt taaaagagaa gaaacaggct     480
gggcgtggtg gctcatgcct ataatcccag cactttggga ggccaaggtg gtggatcact     540
tgaggtcagg agttcaagac cagcctggcc aatatggtga aaccctgtct ctacgaaaaa     600
tacaaaattt aggcaggcgt ggtggcgggt gcctgtaatc cctgctattc aggaggctga     660
```

-continued

```
ggcaagagat ttacttgaac ccaggaggtg gaggctgctg cagtgagctg agatcatgcc    720
actgcactcc agcctgtgtg acggagtgag acttggtctc aaaaaaaaaa aaggaaacac    780
atctgactag tgtgatctcg caaggaacat tccagacaca gtggagctag aaggttcttc    840
tccaaacaag gaatccccag gggatcaaat tgttttgcat cggccagaca tggtggctca    900
agcctgtaac cccagtgctt cgggaggctg aggtgggagg actgcttgag tccaggagtt    960
caagactagc ttgggcaaca cagtgagagc ccattagcca ggcgtggtgg cacatgcctg   1020
cagtcccagc actgtactaa aaatctacac ggggccgggc atggtggcac atgcctgtag   1080
agtcccagct actcaggagg ctgaggcagg acgattcctt gaacccagga ggtcacggct   1140
gccatgagcc gtgactgtgc cactgcactc cagtctgtgc aacagaacga gactctgttt   1200
cgaaaaacaa aaaatcattt catgtctcca gtttctccac tggcaaaaga ctctgtcaag   1260
gtaaaaaatg gttctgaccc acagaaatct aagaaggaa aaaatataaa aaatagaaaa   1320
tttaaaaaag agatggtctc agaataaaga ccaacctggg ctatggttgt cactcttccc   1380
tcacacctta gaaagctttc tggccgcatc tggccaaagg gccaccctgc ccatcttgg   1440
atcagtgagg tgccttcgaa caagccacct gccctggagc ccgtcctgtc ttgtctgcca   1500
ccgcacgctc agtaggggag gggaagtcgc taggttttag ttccaccagtc tctggatcaa   1560
gacgtgccat aaccaagaag ccccagccac acccagaccc gatgtggcca caaggggtga   1620
gctgggaagg cccaggaaaa ggcgggaggc ggacgaatgg aaatgtcatt ctgtggccac   1680
agaaatgatc tcaacgtttt gtaacttcct accaagaggc agtcttagct ctgcccttga   1740
accagcactt ggtgatgtcg cttgcgtcaa tcaaggcaac agaagtgagc aggaggccca   1800
cttttcctctg caactgtggg cttacggggc aaagaagtcc aggcctccag gtggaggatc   1860
acagaccggg caaagcagag gagagccacc cagccgagcc tacctgtgcc tcagactgcc   1920
tccctccaga gacccctgtg gccaaggcca cccagaccag caggtccttg ccaagctgtc   1980
agctgacgac agggttggt gaggccggcc cagaccagca gaaccacgaa ccaaccaaca   2040
gaattaaaaa taataacaac tatgtcttgt cttaagccac taagttttgg atggtttctt   2100
tctttcttt tcttttttt tttcggagac gcagtctcac tctgttgccc aggctggagt   2160
gcagtggcgc aatcttggct cactgcaagc tctgccccc ggattcacgc cattcccctg   2220
cctcagcctc ctgagtaact gggactacag gtgcctgcca ttgggtgttt tcttaaacag   2280
caaaagaaaa ctgacacaat cataaacaga gcaagcaaga gaacttggca attatttcct   2340
ctctacttct cactgttctt caaagagtta actcaagcat aagatgtgag caaattcttt   2400
taacatccta gaaaaaaagc tcctactcag tgttcataaa gcaaagctaa cctacaggag   2460
ccaccttcca cagtgaccac aggaaaccaa gacagcaagt gggacaccag cctccagggc   2520
actgcgccag ccgtgcgcct gtgtctgcca ctgccctggt ccgtcactgc caccagccgg   2580
caagacaccc acagaggaga gctctaagcc acaactgtgt acgaagacaa ctgtgcagga   2640
ttttattact acaacatttt tgttttcttt tttttttttt tttgagactg agtctcgctc   2700
tgtcacccag gctggagtgc agtggcacaa tctcggctca ctgtaacctc catctccctg   2760
gttcaagcaa ttctcctgct gcagcctccc aactggatta caggcgcccg ccaccacgcc   2820
tggctaattt ttgtactttt agtagagatg gggtttcacc atgttggcca gactggtctc   2880
aaattcctga caagtgatcc acccaccctg gcctcccaaa gtgctgggat tacaggtgtg   2940
agccactgcg cctggcccat ttttgtttat caataaaaat gtacttaatg ttgaactctc   3000
```

```
cacatttcaa atgggtaact ccagtgtcct tgatgctcct gcgacatgtt cgtgagactt    3060
ctcttgggtg tgagagtcta gcatgtgggt ggtctggaca ggaggggag ggaagagtgc    3120 agagccgggc agggtaaaga acccctag gatgtgaagg ccgccctgca tttgtcagac    3180
tgggcaacac ccactccatc agatggaccc tggtatgggc ggcaagccac ctaggtgccg    3240
aggcaagaga ccgagggcac gagctgttcc ggtgtaataa aatgcataaa ataagaatag    3300
ttatactaga tatagatcat aaatatgatt atatatgaat atcattcatc attagtttgt    3360
agcaattact ctttattcca atattataat aatccttgcc taagcataac ctaggaaaaa    3420
ctaggaaatc ataacctagg aaaaactagg ccatacagag ataggagctg agggacata    3480 gtgagaactg accagaagac aagagtgcga gccttctgtt atgcctggac agggccacca    3540
gagggctcct tggtctagcg gtaacgccag catctgggaa gacgcccgtt gccaagtgga    3600
ccgtggtcta gcggtagcct cagtgtcaag gaaaaacacc cgctacttag caaaccagga    3660
aagagagtct cccttttcccc gggggagttt agagaagact ctactcctcc acctcttgcg    3720
gagggcctga catcagtcag gcccgcccgc agttatccgg aggcctaacc gtctccctgt    3780
gatgctgtgc ttcagtggtc acgctcctag tccgccttca tgttccatcc tgtgcacctg    3840
gctctgcctt ctagatagca gcagcaaatt agtgaaagta ctgaaagtct ctgataagca    3900
gaaataatgg cgtaagcggt ctctctctct ctctcctctc tctctgcctc agctgccagg    3960
aagggaaggg cccctggcc agtgggcacg tgacccacat gaccttacct atcactggac    4020
atggttcaca ctccttaccc tgccgctttg tcttgtatcc aataaatagc gcaacctggc    4080
attcggggcc gctaccagtc tccgcgtctt ggtggtagtg gtccccagg cccagctgtc    4140 tttttctttt atctttgtct tgtgtcttta tttctacact ctctcatctc cgcatacgag    4200
gagaaaaccc accaaccctg tggggctggt ccctacaccc tggctttgta gactggagcc    4260
taggcacgac tcagctgctg tagtgaattg cgatcctcca acccagcaa ggcacctgca    4320 ggacatctgg cccagtctcc tcgttgagcc agttcacgaa aaagagactt tctgagtga    4380 catgctaatg ggcaatatga ggactaaatg ggatggtctc caacttggac aaaccaacag    4440
taaaagccac tttgcgggga aagaaacttt tccttttttc tttttttga gacaggatct    4500 caccctgtca cccaggctgc agtgcagtgg catgaccttg gctcactgca gcctcaacct    4560
ctctcaggct caagcaatcc tcccgcctca acctcccatg cagctgggac ataggtgca    4620 tgccaccaca cccaaataat ttttatattt tttgtagaga cgagtttca ctatgttgct    4680 cgggctggtc tcaactcctg ggctcaagca accctcccac ctcagcctcc caaagtgctc    4740
agattacagg caggagccac caggcctggc caacatagga agaaatttaa atttgaattg    4800
aatattagaa gagatgaaaa ttcatcaaca tggaaagaca aagatcatta actaaagcca    4860
aaccagaatg gaagctgtgt gtacagtggg gtctcatgct gggaacgcga ggggcacgtg    4920
cagggctcca cggtgtggcg acgccccatg ctccctttgt gggggttcat ccagcggaac    4980
atgaggacct ggggtgcttt tcaacatgta cgtgagttta ataataaaa ggtttaagga    5040 aagaaaaatt catatgtttc tatataaaca gaacatctgg aaagatctat tctaaggtgt    5100
tgacagtagg aatctctagg tagtagtaat atggcctttt tgaattttg cttatcagta    5160 ttttctaatt ttctttttct ttctaaataa ttctagctat gaaataattt tctaccatat    5220
atattttgta ataaaaatgg ttatatttaa ttttttaaag gctgtacaaa cttcctgata    5280
aaatggcaaa ttgacacac acatgtgggc cgggtacagt ggctcgcgcc tgtaattcca    5340
gcactttggg aggctgaggc aggcagatca cctaaggtca ggagtttgag accagcctgg    5400
```

-continued

```
ccaacatggt gaaacccccgt ctctactaaa tatacaaaaa tgagctggat gtggtggcac    5460
acacctatag tgccagctac ttgggaagct gaggcaggaa aattgcttca acccgggagg    5520
cagaggttgt agtgagccga gatcatgcca ctgcactcca gcctaggcaa caagagcgag    5580
actccaactc aaaaaaaaat aaaaataaca cacacgtgaa taggctcctc atggaagtca    5640
tcacaacaat gcagagggaa gagcttccaa agtgtaaacc cagaagcgag gagcaggagg    5700
gtgcgcgcag acgcagagag cagcaaggtg cagactgaga ggcggaggct ggccgtgggg    5760
agatgactga tgctcagttt ataccccaaa tccgtaaatc tagaggcctg gcacatcaac    5820
tacctctgcc agcaggaatg agggaaagga gggcaaccaa aagatgtccc accctcaccc    5880
atccagctac ctgccatcct cagccccact ggcagaagac cctgagaggt ggaggcaggc    5940
ccctgcctac aggaccctga gagctagggg aaggcgttat cctgaactgt gtccccgta    6000 aaattcatat gttgaaggcc tcatcccag tgtgactgta tttaaagatg gggtcttcag    6060
gagataattt aaatgaggtc atataagttg gccctcatcc agtaagactt tgaccttctg    6120
gtggtttttt ttttttttgga gactgggtct cactctatca ctcaggttgg agtacagtgg    6180
cacgatcacg gctcactgct gtctccaact cctgggctca ggtgatcctc ctgcttcagc    6240
ctcctgagta gctgggacta caggtgctta ccaccgcacc cagctggtgg tgcattgtgt    6300
tttttgtaga gatggggttt tgccatgtcg cccaggctgg tcctgaactg ggctcaagtg    6360
atctgtctcc ctcggcctcc tgcagtgctg gaattacagg tatgagccac cgcgcctggc    6420
cgaccgtgac cttctaagaa gtgaaagaga agatctttc tctctccctc cctctccatc    6480
atgaggacac agcaagaagt cggccatctg caaggtagaa agcgagtcct cccaacagct    6540
gaacctggca gaccctgatc ttggacttca gccttcagag ctgtaagaaa ataactctct    6600
gctgttcagg ccacgcggtc tacggcagcc cgagcagact aagacacacg ccatctgggg    6660
agtcagacca gatcaggaag aaaggcctag agctcaggat actgaaggtc caacccggt    6720 gctggaccag accaccccgg cagccgcggc cacggagtca cggctcgggt gaggtgacct    6780
ggacaccatc ccggcagccg cggccacgga gtcacggctc gggtgaggtg acctggacac    6840
catcccggca gccgcggcca cggtgtcacg gctcggatga gatgactcgg acaccacccc    6900
ggcagccgcg gccacggtgt cagggctcag gtgaggagag ttggatatgg gactgggcct    6960
accccgaggc tgcttccacc cagacgcctg ggtgggtgac acgaaagctg ggctcagttg    7020
ggatcagagc agcctctccc caggtcagaa atgaccctgg gctcctcaca gtagccctag    7080
ggcaccatga gaaagctacg tggacttctc tgaccaaggg tcactgctgc cacactactc    7140
attgcaggcc atgtcagggc tcagctgagg agacgtggac accacccag cagccgcggc    7200 cacggcgtcc caagggaggg acttgggcac tgcctctctg gcaagagtg gggaggtgtg    7260 gggtgggaga tgtctggaaa catcatggac acatgccggg aaaacacgga agctgtgcac    7320
caaggtgctg acaaaggaaa aaggagaatg gaggtgtgaa catccagcta gcaggtccca    7380
ctcagaaact cctgcatttc cagacatggc caccagctct gtggatgaga caggggagga    7440
cagggtacct cacaccagga acccacacag gtccatgtct tgctctgtga tcacacaaca    7500
gcctccacca ccctgacatg caggagggag gtcaaagcct cgggtccaac aacaggctcc    7560
acagcaaggg aagaaaggca ggaaggaact cagggccagg tcctcccagg cagcagctgc    7620
ctgcacgctg tccaccaagg gaggtctgac ctacaccgca caggggttgg cagtctagag    7680
tcgtcctctg tcaaacggtg agaaagtcaa aagctcatgc tcagtgatat gctaggtcag    7740
```

-continued

```
catgaagatg ccacacatga gacacagcaa ggatgagacc aacgggaaga ctgccccaga    7800
ccagagcccc agagccctct ggggaggaag aataaggatg gcagcctggg actgcccgga    7860
gctgactctg cctttatttc accccagcag aggcaggagt gacaccggct cacagcagga    7920
gcagctctgc cacctcctag cagttccacc tacgggcagc aaaacaaagc tggcagtttg    7980
ggcaaatgtt agcgtttttg ccaactaaca tttgaatcgg acatctggta cagagatgag    8040
gaagaaaaca ctcacagttt catgaagact gtcaagaaaa tcactgactc ttcacttcat    8100
ttatgaaagg ccagctctct gacatcccta ccactccctc tcacatgaga aatcacggcc    8160
tttcaggacg tggagccacg tggccatgca ggtacgggag gcctcccgc agctgcagct    8220 gggtcttctg gtccccgtgc catttctgct tttcttcgct ctctacttac acacacattt    8280
gagtccagtc tcagaagaac tggaactaga aaaatcctga cacttgtccc ttactacgtt    8340
aatgccagct gtgccaagga cagcccaacc caagccccca tcagcccaa tggcaccgag    8400 gcccgagctt acccgtgagg ggccaagttg gtcgtcacca acacggtctt cacccccctcc   8460 acaccactgc cgtccactgc agtgtccgga gttgtcacaa ccaccacctc ctccatgtgc    8520
acactcacgt cgggagtcgc catggctcag cggaagggga cgcccaggcc agcagcgtca    8580
gtcctccagg gtcccaagtc ctggaggaag caaggcaggg cacagggatg gagtcatctc    8640
cacatccaca caacatagca ctcacaaagg catctctaat cagctccaaa gacccaccct    8700
tgagtcccag actgctacct cctgacaaaa acgagcggca acagaagggc tactccaggc    8760
tctggttccg agggcggtgt aagcgcactc cacccgtttt tcccactgga taagccgaaa    8820
cccttgggta gaaagcacag agccactccc tccacgtggg gctcagagca ggaggacagg    8880
aggggcctgg aattccaagc aacttccctg gacgcaggct cccggcttgc cagttcttcc    8940
gtctctcctg gcctgaactc aaagccagcc ccaatccctg aactgagttt caggtgcaga    9000
aagcactcca agaagtcctc gctggtctgt ggaacgggaa gggaaaccca ttcaagacag    9060
aaagagagga gggaaacgcc ctgggttttt ttgggttttt gggttttttt tgagacggag    9120
tctcgctctg tcgcccaggc tggaatgcag tggcacgacc tcggctcact gcaagctcca    9180
cctcctgggt tcaagtgatt ctcctgcctc agcctctcca attgctggga ttacaggttt    9240
caccatgttg cccaggctgg tctcaaactc ctgacctcag gtgatccact cacctcggcc    9300
tcccaaagtg ctgggattgc aggtgtgagg caccatgcct ggcctgcccc gggtttaaaa    9360
attattatta ttttgtcttt cctggctttg ccttcagcaa gtccaacccc tgctaaaacc    9420
cggtgataat ggctgtcctg gcccaaaaag cttggagaca ggggaatctt cctcctgact    9480
aaaggaatgg tggcccaaga gtgtggggg tccctgttgc cctctcactc tccatcccct    9540
acctagcaca gggaacacaa aagccctgg ttccagcca gagggcaacg agcctggagt     9600
cagagtgtgg gggaggcgac aagaggagag gggagaagag aggatggcac acagctgtgt    9660
gtgagcgcct gggtcgtccc aagacagtct ctacgtggtc ctgaccctaa agggcaaagg    9720
gaagaaaact gacctacagg ataggccact gcccaggtct cagatgggcc ccagtggcgc    9780
atatgggaca gatccacagt gcactggaaa gtctctaaaa taaactggcc taagaacaca    9840
gacacaggaa cggggtgcaa aatttgcagc ctgaacctaa ccaggtcgat ttcttgctat    9900
gaaaaaaaaa agtctacatt ctctgtgaaa cttaaaacaa gacctagagt ccatagcaca    9960
gtagtcaaag catccagaac acgatcaaac ttcctggcaa agggtagtct ggttgattct   10020
caaaggaaca aatacacaag agaagctggc tcttgaacgc agaatccaga gactttcagg   10080
tgctatcgga ccagctccaa gaggaaagca aacattgtca accaagtgga aagaaaatct   10140
```

-continued

```
tggtatagaa acaggagtta taaccaaaca gaaatgtgaa aattaaaaac gacaaccaaa    10200
agaaaataca caaagctggg atagtctcag ctactcggaa ggcggggctg gaggatcgtt    10260
tgagcctagg agattgaggc tgcaatgagc tgtgatcaca ccaccgcact ccagtctggg    10320
caacagagtg agaactctct caaaaaacga aaagaaaga aagtagaaca gaagtgacca    10380
ggggctgggg gagggagtac agggagttgt tctttaatga gtacagaatt tctgtttggg    10440
atgatgaaaa gctctggaaa tggacggcgg tgatggctgc acaatcactg tggctgttct    10500
gaatggtgct gaaccacaca tttaaaaaca gttaaaatgg gctgggcgtg gtggctcacg    10560
cctgtaatcc cagcactttg ggaggcggat cgcctgaggt caggagttcg agaccatcct    10620
ggccaacaca gtgaaatcct gtcttgacta aaaatactaa aaattagcca ggcatggtgg    10680
caggcacctg tagtcccagc tacttgggag gctggggcag gagacctgct tgaacccagg    10740
aggcagaggt tgcagtgagc cgagatcgtg ccactgcact ccagcctggg caacaagagc    10800
gaaactccat ctcaaaaaaa aaaaaaaaa aaaaaaaaa aagtttaaaa tggttaaatt    10860
ttatgttatg tatattttac cgtaataaaa acactgtaat gctactataa tagaatgact    10920
cattaggatt agatatagac tagaaagtac agaatataaa aacttttaa acaaagaaaa    10980 attttcatgg ccaggcatgg tgtcacacct gtaatcccag gactttggga ggccaaggca    11040
agaggaatgc ttgagctcag gggtttgaga ccagcctggg caacacagca acccccatc    11100 tctgctaaat aaataataaa aaatagccag gcatggtggt gtgcacgcct gtagttgcag    11160
ctactctgga ggctgaggca ggaggatcac ttaagcccag gaggtcaagg ctgcagtgag    11220
ccatggttgt gccactgcgc tccagcctgg gcaacagatc aagaccttgt cacaaaaaaa    11280
agaaagaaag aaaagaaaaa agaaagaaaa taaaatcttc cagaactttt aaaatcatca    11340
ttgttaatat aaaaataaca tcacctgccc ctaggactgt aacaaacaag tgtgtctaag    11400
gacaggagtg ggtccacccc aacctggcac gcagtggtcc cctgcggaga gtctggccct    11460
gcactcacta agaggaggca ctcatagccc agccaggcct ctgcaattat gccttcaatg    11520
ccagaactaa ctcacccaaa ctgaacaatc gatcacaaaa tgtgccttca ggtctcaagg    11580
ttcttgctaa atcttactca accgacattt ccagcatgg gaacattttt ctgaatgtct    11640
tagggagagg aagtccgcaa gagaacaaaa ggtcctcagg ccaccctagc ttcttttcct    11700
ccattccaca ggctgtcttt tgtctgggta tgcactggac caggggctc tacttcttcc    11760 tacctgggca tgggtctcca cacaactcca aggtaaaggg ccacaggcaa gataaagggg    11820
agaaaagaaa gctacgattt cctgggccac caatcgcaaa tggcagccag tctctgaagt    11880
aacccttgac cagagatcca aggaaccaag aaatgtaggt gatctgaaca gaggggatgg    11940
tggttaaaca ccatgaagga aagacccatt ctcaaagaaa aggaagcaaa aagaaaccgt    12000
ggggagctgg gtaccacccg cagcaaagac cccgcacgcg ttactgacgc cagcctggcc    12060
tgggagagca gtgagtgtgg cggacggtga gtggcgggga gggctgtggt aggtttaggg    12120
taagaagggg cagcgcccag agcccagaga acaccagtga gggctccaca ggaacactac    12180
tcaaagtatt cacggaacac atctaaacac aagcactaag gactaagtgc gagggacaag    12240
aaaatattcc ccgtttcctg tttcaggagg gtatcgaaaa tgagtgatgg aaggaaaatg    12300
tattgtttaa atgaggaaaa aaaatttta caaattaaga acatcctgga acatgatgag    12360
ccgtttactg tcactcaatt taaatggtgg ccatctagga cagagcgcct aaggggaaag    12420
ggggctcaca ggtgaacccc tccagctgct ggtgggcaat ttcccattag ggcatcaggg    12480
```

```
tctctgaaga ctgtcttcag atgctttta gccaggaaag ttacaatgat gaattcgttt    12540
acactggcgg aattacttcg tatttctcaa atataatgtt ttcactagca taactttgtt    12600
gttgtagact taggcttcaa aataaagaac tttaaacaaa catgaataaa agccacttt    12660 aggccgggcg cggtggctca cacttgtaat cccagcactt tgggaggccg cggcgggtgg    12720
atcataaggt cagaagttca agaccagcc tgatcaatac ggtgaaaccc cgtctctact    12780
aaaaatacaa aaattagccg ggcgcggtgg caggtgcctg taatctcagc tacttgggag    12840
gctgaggcag gagaatcgct tgaacctggg cagcagaggt tgcagtgagc caagatcatg    12900
ccactgcact caagcctggg tgacagagtg agactctctc ttaaaaaaaa aaagccactt    12960
taaaatttta ctcaggccag gtgtggtggc tcacgcccat aatcctagca ctttgggagg    13020
ccgaggcgag cagatcacct gaggtcagga gttagaccag cctggccaac atggtaaaac    13080
cttgtctcta ctgaaaacac aaaaattagc tgggcgtggt ggtgtgccca tgtaatccca    13140
gctactcagg aggctgaagt gagagaactg cttgaacccg ggaggcagag gctgcagtgt    13200
gccaagactg caccactaca cttcagcctg ggcgacagag caagaccctg tctcagaaaa    13260
aaaaaaaatt caaaaatttg gccaggcgtg gtggctcacg cctgtaatcc catcactttg    13320
gaaggccgag gcgggtggat cacctgaggt caggaattca agaccagcct ggccaccatg    13380
atgaaaccct gtctctacta aaaatacaaa aaaaaaaaa caaattggcc gggcatggtg    13440
gcgggtgcct gtaatcccac ctacttggga ggctgaggca ggagaatctc tcgaactccg    13500
gaggcagagg ttgcagcgag ccaagattgt gccactgcac tccagcctag acaacagagc    13560
gagactctgt ctcaaaaaaa aaaaaattaa aattaaaaaa taaaaatttc atttaaaata    13620
ctactgatct cccgtgctga cttctcgggg tttaactctc actgaggaga cgctgctttc    13680
ataagggtaa gctcagcagg ggcaactaaa gtcatttaag cagagagctg caaagaggca    13740
acagcctcac tgcaggcagg ggtcctcgtc acagcttcag ggctttgcag aggattacgc    13800
aatgtacacg cacaaaactg aattccagcc tctccattgg caactgcata catacatata    13860
ttcttttttt gagacggagt ctcgctctgt agcccaggtt ggactgcagt ggccgatct    13920 cggctcaatg caagctctgc ctcccgggtt caagcgattc tcttgcctca gcctcctgag    13980
tagctgggat tacaggcgcc caccaccacg cccggctaat ttttgtattt ttagtagaga    14040
cggggttcca ccatgttggc caggacagtc tcgatctcct gacctcgtga tccgccgcc    14100 tctgcctcc aaagtgctgg gattacaggc gtgagccact gagcctggcc tccaatggca    14160
actatattaa aggttcaaag caatatgcac aaaagttacc tcacagaaaa tagtgcaagt    14220
ccttgataca atgctcttta gacacagaag aagcactata gaatagagca cctcgcccta    14280
ttgccttccc aagggcgagc accccctcct ctctccacag ctccttcttt gtttttttga    14340
gatggagtct cgctctgtca cccaggctgg agtgcaatgg caaaatcttg gctcactgca    14400
acctccgcct cccgggttga agtgattctc ctgcctcagc ctcccgagta gctgggacta    14460
caggcaccca acacgcctag ctaattttg catttttggt agagacgggg tttcatcatg    14520
ttggccaggc tggtctcgaa ctcctgacct ccagtgatcc tcccaccttg acctcccata    14580
gtgctgggat tataggtgtg agccactaca cctggcctct ccacagcccc ttctgtgttg    14640
aagccaagac ccacccagct tgatcccaa ggcttgggtt cccactagt gtgaagtgag    14700 tttccaaatt attaggtaaa tcagatatga gaaatatttt tattttactt tttttttttt    14760
gagacgcaat cttgctccgt cacccaggct ggagtgcaat ggcaccatct ccactcactg    14820
caacctctgc cttctgggtt caagcaattc tcctgcctca gcctcccaac tagctgggat    14880
```

-continued

```
tacaagtgca caccaccacg cccggctaac ttttgtattt ttagtagaga cagggtttca   14940
ccgtgttagc caggctgctc tcaaactcct gacctcatga tccgcccacg tcgggctccc   15000
aaagtggtgg gattacaggt gtgagccatc acacctggcc caagaaaata tttttaaact   15060
agtattcttg accggcacgg tcaacactga tgtaattgaa actgttgtat ttgaagtgtt   15120
agcaaagaaa gagaattctg gttcaacaga aaagtcagtc acgactttc agtcacgcat    15180 gaattacaca gtaaccaaat agataacatg ccatgactga cgacgggccc acaacaaatc   15240
agctccgacc aacagggtcc acaccaccat gggtctacac agatccaggt cccgcctgtg   15300
agcctacagt gacgcgggcc cctgtggggt ggtccctgca ggtcaggtcc ctgagagtgg   15360
gtcccagtgg ggtgatccct gcgggtcgcg tccctgcgag ttgggtgcct gccgggtggc   15420
ccctgcgggt cgggtgcctg cggggtggtc cctatgggtc gcgtccctgc gggtcgggtg   15480 cctgcgggt ggcccctggg aatcgcgtcc ctgcgggtcg ggtgcctgcg gggtggcccc    15540
tggggatcgc gtccctgcgg gtcgggtgcc tgcggggtgg cccctgggga tcgcgtccct   15600
gcgggtcggg tgcctgcggg gtggtccttg tgggtcgcgt ccctgtgggg tggtccctgt   15660
gggtcgcgtc cctgtggggt ggcccctgcg ggtcgcgtgg tggcccctgc gggtcgggtg   15720 cctgcgggt ggtccctgtg gtcgcgtcc ctgcgggtcg ggtgcctgcg gggtggtccc     15780
tgcgggtcgc accctgcgg cgtggtcccc ccgggatggg tccaccgagg aggccgctgg    15840
aggccgagcc cgcgcccgcc cgcggcgcca agatggaggc aggaagcgcc gccgcccgcg   15900
cccgccaccg cccgcgccgc ccgcctgacg ccgccgttgc gcctgacgcc gccgcccgcg   15960
cggccgcccc tcccccggcc ctcccctccc cccgccgtaa cgtcctgacg ctccgcaggg   16020
acccctgact ggacggcggc gcgtgagcgg agcgagaggc ctcgccgcgg gggggccgcg   16080
ggctcgccgg cgccgcttac ctggggccgc gccgggcctg cttaggcacc cggcgggggc   16140
ggcggcgtcg ggagctgcgg cggcggcggg cggcggcggc ggccgcgggc ttcgctcctt   16200 gttgggatt cggcggcggc ggcggcgcgg gcgcgcgctt cctagtgacg caggcggcgg    16260
ggccgcgcac gcacgggct gggagggccg gacacttatt tggcgctcgc ggaggaggaa    16320
ggcggggccg tgaaataagg cccgacgggc cccggggcgc gtgcgcggac cgacactgtc   16380
agctcctaac gccgcaggtt cctcctggtc cccgaggccc ccggtcgggc gttgcctgcc   16440
ccgcgcgggc ggccgggccg agggacgatg gtcagtggac ggacggcgcc agggagcagt   16500
gcccacgcgc ggcagggcgg taccttcagg cctccaggta cgggcgctcc tcgcccggac   16560
gctgctgtgt gtgaatgggc gcgaggggac tcccctgcgg ggcggacgcc tgaacacgag   16620
gctgtggagg aggacgctgt agggtgcgcg gactcacgcg gaacatgcca gaggctcagc   16680
cagccacggc gctcccagcg tggagggcga ggggcatccg ggagcggccg ggagggctcg   16740
gtcacccctc aagctgtcac cccagtccca caaccagcac cccgatccta tcgcagtccc   16800
acagccgaca ccccgatccc acccctgccc aacagccggc acccacccca atcccatagc   16860
taacaccccg gtcccaccgc tgtcccacgc ccggcacccc gatcccaccc cagtcccgca   16920
gctggcaccc cgatcccacc ccagcccaac agctggcacc caccccgatc ccaccgctgt   16980
cccacagccg gcaccccgat cccaccccag tccgcagcc ggcaccccga tcccacagcc    17040
ggcactcacc ccgatcgcat agcatagctg atacccgat cccaccccag tcccatagcc    17100
agcaccccga tcccacccca gtcccatagc cagcacctcg atcccataga tgacaccccg   17160
atcacgcccc agtcctatag cccgcacccc gatcccaccc gagtcccgca gccggcaccc   17220
```

-continued

```
catcccaccc atgtcccaca gtcggcaccc cgatcccact cggatccggc agccagcttg    17280
gatcctgtgg ccctcctcca gccccaggg ctcatttata tgttttattg gcagaggctg    17340
gggctggctc tgttggcctc tgtgctgggt ttcttcctct gcaccgcagg actggctctc    17400
ctgacctctc caggtgtcat cgaacaccct tgtgcttgct gtcacccgct gcctgtctgc    17460
aggatcccgg attccgtatc agggaccga aattagtcgg aaaataggaa gcaggtgctc    17520
gcttggatgg aaccctgacc ctgtgctcac acttgtagga ggagggctct gcaggccgcc    17580
tcccggaacg ggaggttccc aagccactgc acttcggagg ggctgtaatt agagttgcac    17640
attcattcag ttcccagtaa agtagaacgt gctccagcca gtgaggaaaa ggtgttttta    17700
aaaattagat tggccgagtg cggtggctca tgcctttac ctcaacactt tgggagacaa    17760
aggtgggagg atcacctgtg gccaggagtt caagaccagc ctgggcaaca gagcctgtct    17820
ctggggaaga ataaaaaaaa aaattgagcc tttgtcagtg ctactatttt attatctggt    17880
aaatatgaga gggttcacgc ggtctatgtg tgtcatttat ctgagtttgc ctatcgtcac    17940
gttttggaaa taaatgtcaa taaagtcgaa gaggagtgct gagggggcc tggggatggg    18000 agggtggcta catcatgcct gtgtgttgcg caagcccacc gaggtcggcc tggggtgagc    18060 cctgggcct gttctgcctc cttcactctg gggctccaag agacaaactg gcaacaaga    18120 gagaaactcc atctaaaaaa aaagaaaaat cacctccaag ataacttagc tttcttctgc    18180
tggcataaca aattatctca aacttagtcg cttaaaaatg caaatttagg ctgagtgcgg    18240
aggctcacgc ccataatcct agcactttgg gaggccaagg caggattgct tgaggccagg    18300
agttcgagac caacatggcc agaactgtct cttttaaaa aatgcaaatg tgtccggcac    18360
ggtggctcac gcctataatc ccagcacttt gtgaggccaa ggcgggcaga tcacgaggtc    18420
aggagataga gaccatcctg gctaacactg tgaaaccccc tctctactaa aaatacaaaa    18480
aattagcctg gcgtggtggc aggcgcctgt agtcccagct actcgggagg ctgaggcagg    18540
agaatggcgt gaacccagga agcggagctt gcagtgagcc gagatggcgc cactgcactc    18600
cagcctaggc aacagagcaa gactccgtct caaaaaataa ataaataaaa ctgcaaatgt    18660
attctctaac tgttctgtag gtcggaagtc cagcccagcc tcactccgcc aaaatcaggg    18720
tgtctgcagg gccgattgct tttggagctc caggggagaa gctgttctgg cctttccagt    18780
ttctggaagc acttgagccc cttgtctcgt ggcctatccc acacctgaaa gccagccaaa    18840
gccagttgag tcctcaccct gttggcccg acactgatct cctgcctccc tcatctgctg    18900
tcaaggcccc ttgtgatgac atggggccac cagctggccc agggcacctc ctgtcagagt    18960
ccgccgacca gtgaccttca ttccatctgt cgctgtaatt ccccttgct tggaaccaac    19020 gttcacagat cccagggtt aggatgtgaa tatcttgggc agggctgtgg ggggctatt    19080 cttccttcta aaatatttat catttttgtt ttggggattt ttttggttgg gtttttttg    19140 agacagagtc tcgctctgtc gcccaggttg gagtgcaatg gtgcaatctc agctcactgc    19200
aacctctgcc tccgggcaga cgtgagccac tgcaccaggc ctgttttgt tttgtttgt    19260 tttgtttgt tttgagatg gagtctcggc cgggcgcggt ggctcacgcc tgtaatccca    19320
gcactttggg aggccgaggc gggcggatca cgaggtcagg agatcgagac catcctggct    19380
aacacggtga aaccccgtct ctactaaaaa tacaaaaaat tagccgggcg tggtagcggg    19440
cgcctgtagt cccagctact cgggaggctg aggcaggaga atggcgtgaa cccgggaggc    19500
ggagcttgca gtgagccgag atcgcgccac tgcactccag cctgggcgac agagcgagac    19560
tccgtctcaa aaaaaaaaa aaaaaaaaa aaaaaagag atggagtctc actttgtcac    19620
```

-continued

```
ccaggctgga gtgtagtggc gggattatag gtacgcgcca tcatgcccag ttacttttg    19680 tatttttagt agagacaggg ttttaccatg ttggtcagac tggtctcaaa ctcctgatct    19740
caggtaatcc acccgcctca gcctcccaaa gtgctgggat tacagacgtg agccaccgtg    19800
tctggccata tttattaact acaaagggaa agatgataat tttttttttt gagatggagt    19860
ctcactctgt cacccaggct ggagtacaat agcgtgatct tggctcactg aaacctctgc    19920
ctcccaggtt caagcgattc tcctgcctca gcctcccaac tagctgggat tacaggcgca    19980
cgctaccaag cccagctaat ttttgtattt ttagtagaaa cggagtttca ccatgttggt    20040
gaggctggtc tcgaactcct gaccttgtga tctgcccacc tcggcctccc aaagtgctgg    20100
gattataggc atgagccact gcaaccggct gaaagatggt aattttaaag tagagaaact    20160
gggttggctg gcatggtgg  cttatgcctg taagctcagc actttggaag tccaaggcaa    20220
gaggatcgct tgagtccagg agtttgagac cagcctggac aatatagcaa gaccccatct    20280
ccgcaaaagc taaaaagtta gccaggtgtg gcggcacatg cctgtagtcc cagctactca    20340
ggaggctgac gtgggaggat cacttgagac caggaggtca aggctgaagt gagctgttat    20400
tgtgccactg cactcagcct gggcaacaga gcgagagtct gtctccaaag gtaaaaaaag    20460
gtccaggcac agtggctcac acctgtaatc tcagcacttt gggaggccga ggcgggcaga    20520
ttcgttgagg tcaggagttc aaaacgagcc tggctaaatg gtgaaacccc gtctctacta    20580
aaaatacaaa aaaattagcc aggcatggtg acgggcgcct gtaatctcag ctacttggga    20640
gactgaggca ggagaatcat gtaaacccag gaggctgagg ttgcagcgag ccaagatcat    20700
gccactgcac ttcagcctgg gcgacagagc aagactgtct caaaacaaaa caaaagaatc    20760
ttgagtcctg agttcctcta agggaaattc caggcacctc gccacccttg acaggcaaag    20820
gaacaatctg atgaggaaga agatagaaac agcttaaaca atagtctccc ggccgggggc    20880
agtggctcac gcctgtaatc tgagcacttt gggaggccga ggcgggtgga tcacaaggtc    20940
aagagatcaa gaccatcctg gctaacatgg tgaaaccccg tctctactaa aaatacaaaa    21000
aattagccgg gcgtggtggt gggtgcctgt agtcccagct actcgggagg ctgaggcagg    21060
agaatggcgt gaacccagga ggcggagctt tcagtgagct gagatcgcgc tctgcactc    21120 cagcctgggc gacagagcct cgagactcca tctcaaaaaa aaaaaaaaat tagctgggtg    21180
tggtggctca cacctgtaat cccagctacg tggcaggctg aggcaggaga atcgcttgaa    21240
cctgggaggc ggaggttgta gggagctgag atcgcaccac tgcactccag cctgggcaac    21300
agagcgagac tctgtctcaa aaaaaaaaa aaaaacaaaa aaacaatag tctcccaagt    21360 aagtcagagt cacaaggtgt tttgattccc tgtggaaact aaaatataac agcttaacat    21420
atgttcttga gttattttc agaaacttgg acatccacca ggtggaaaat gctgagctag    21480
gaacagtggc tataatttca gccttttgag aggccaaggt ggaaggatca cttgaggcca    21540
ggagttagag accagcctgg ccaacatggt gaaacccgt ctctagtaaa aatacaaata    21600
ttagctgggc atggtggtgc aacctgaaat cccagctact tgggagacct agctgggagg    21660
atcgcttgaa cctggtagga ggagtttgca gtgagctgaa attgtgccac tgcactctag    21720
cctgggcaac agagtgagac tctgtctcaa aaataaata aataaaaga gaaaaagtg     21780 ttgcctgcag gccgggcaca gtggctcacg cctgtaatcc caacactttg ggaggccgag    21840
atgggcagat caccctgaggt caggagtgca agaacagcct ggccaacatg gtgaaacccc    21900
atctctacta aaaatacaaa agttagctgg gtgtgtacat gtagtctcag ctacttggga    21960
```

-continued

```
agctgaggca ggagaatctc ttcaaccggg gaggtggagg ttgcgatgag ctgagatcac    22020
gccaccacac tccatccagc ctgggtgaca gagtgagact ccatctcaaa gcaaaaaaag    22080
aaacataggt gggacccttg gtgtgtcctt agggcatgat ggttgaggta tactgctggt    22140
cctgtcatgt aaagaaaac gagccgactc tgtgtctact ggagaaagca ctgcatatat    22200
cagccacagt caatacctcg cttctgcagg gacggtggct gccagagtgg gaggctttgg    22260
tagcacccat gtcgtggaat cacaatgttg tcgatagctc tggggtcttg tacaaaatgc    22320
cagatcctcc catttggttt ccttatggga aggatcgcag tactataata catgggcttg    22380
tgcaagggat cattataccc ttttctcttt ttttgctttt ctttgagaca gagtttcact    22440
ctcgtcaccc aggctggagt gcaatggcgc gatcttggct cactgcaacc tccacctcct    22500
gggttcaagt gattttcctg gctcagcctt ctgagtagct gggattacac atgcccgcca    22560
ccaggcctga cttatttttg tatttttagt agagacaggg tttcaccaag ttggtcaggc    22620
tggtcttgaa ctcctgacct caggtgatcc acccacctcg gcctcccaaa gtgttgggat    22680
ttcaggcata agccaccagg cccagccttt ctttcttttt aaaattaatc tttgtttaaa    22740
aatactctca ttttttattt aattgtagca ctcctagatc ccgaaagcag atacactctt    22800
gttatgggtc tgattctttt cattgcttca cgccttagag gatattgtcc aatactggat    22860
aaaagtttac tcaggtctac ttccactta acggggatgg ctgaatatct cttccacttg    22920
gctgtttgtt tataatgaac tgacaaacat acaaatttc ttgagttctg tgagacattc    22980
tagtaaatca tctaacctga agagcaggtt gtgagaaccc ctgatttaga aagcccagtg    23040
gtcataaata taagtggctc tggactggct cccggggtct gaagtgtggg cagtcggtta    23100
ggattgagcc cttgtaattt gtaggatctg acacacactc caggaaggca gtgtcagaat    23160
ttacctgtat tatattggac acccagttag cgtttggaga attggttgct ggtatagaaa    23220
aataccaaat atttttatgtc agggggagtga aagaaaaaac aaaaacccgg ccgggcgcgg    23280
tggctcacgc ctgtcatccc agcactttgg gaggccgaga cgggcggatc acgaggtcag    23340
gagatcgaga ccatcctggc taacacggtg aaaccccatc tctactaaaa atacaaaaat    23400
tagccgggcg tggtggcgcg cgcctgtagt cccagctact cgggaggctg aggcaggaga    23460
atggcgtgaa cccgggaggc ggagcttgca gtgagcccag atcgcgccac cgcactccag    23520
cctgggcgac agagcgagac tccgtctcaa aaaaaaaa caaaaaaaa aaacaaaaa    23580 aaaaaaccca tacactttaa ggaaagcaac tgacagcatt tgttaccagt gataaaattt    23640
gagctttgaa gtaagaataa caattttgcc attgtgcccg ggccaagaaa aaaaaagaa    23700 ttttgccatt gtgaaaggct tcccagtact ttctgatgag cttgacggtg atattaacaa    23760
ataacttttt ttttttttt ttgagatggg gtcttgctct gtcacccagg ctggagtgca    23820
gtggttcaat ctcagctcac tgcaacctcc gcctcccagg ttcaagcgat tctcctgcct    23880
caacgtccca agtcgctgga ctacaggtgt gcgccaccac gtccagataa ttttgtatt    23940 tttagtagag atgggttttc accatgttgc ccagactggt ctcaaactcg tgacctcagg    24000
cgacccgccc acctcggcct cccaaggtg ggaggccttg ctgggattag aggtatgagc    24060
cgctgcacct ggcctcttgt ccttgtgttt tgcagtgatg caatgaccat gtcttacatt    24120
tgcaaccaga aaaaaggtt agtgtaacaa tgtttatcct gttttccca gagtagacat    24180 tatgaagatt aaaaaaattt gaaagtgttt tgaatataat aaactatgct atacacacaa    24240
cattttggtg actagaaata caagtttatt gtttgttgtt tgttgagaca gggccctgct    24300
ctgtctccca ggctgggtgg cacaatcatg gctcactaca gtcttgaact cctgggctta    24360
```

-continued

```
agcgatcctc ccacctcagc ctccagagta gctgggactg caaacagcaa ccaccacgcc    24420
tggctaatat ttgtattttt tgtagagatg gggtttcacc atgttgccca gactggtctc    24480
aaactcctgg gctcaagcaa tgctcctgcc tcggcctccc aaagtgctgg gatcacaagt    24540
atgagccact gcacccggct gagtttctgt tgttttaagc cgcttcattt gtggtacttc    24600
ttacagcagt cccaggaaac tgagcaactg cagaacatca aaattgtttt tcttcagcaa    24660
aaggagaagc acttgtggtt ggaccagct tttcctgtgc tcacttctgc atggccgcac    24720
ctttgcccga cacgagtgca cagcaggctg tgggggagca actggttgag tcaggcctcc    24780
acttgtgccg tatccccacc tgctttgctg gacacccctg tttgggggc acccactgct    24840 gccccagaca ccaagcaagc accagctgtg tccaaaactt acagtcactg tcttggcccg    24900
ttttgtgctg ctgtaacaga atgccacaga ctgggtaatt taatacagaa cagaaattta    24960
tttcctcaaa gttttggagg ctgggaagtc caagagcaag gggccatcag gtcagggcct    25020
ggtctctgct tccacgatgg caccttgacc accgtgtcct cacgtggtca gagagagccc    25080
actcccagga gcccttttaa tagagcagaa cactgctgcg ctgcggttaa gtttccaaca    25140
cgtgaacttc ggaggtgaca cattcagatc atagcagtca ctctaggcag agtgtctgat    25200
gtggttttaa aatacgttca cagactggcc gggcactgta gctcacgtct gtaatcccaa    25260
cagtttggga ggccaaggtg ggtggatcac ctgaggtcag gagttcaaga ccagcctcac    25320
caacatggtg aaaccccatc tctactaaaa atacaaaatt agccaggtgg tgcatgcctg    25380
taatcccagc tactcgggag gccgaggctg gagaatcgct tgaatccagg aggtggaggt    25440
tacagtgagt cgagatcatg ccattgcact ccagcctggg caacaagagc gaaactctgt    25500
ctcaaaaaat aaaataaaat aaaatacatt cacaaggccg ggcactgtgg ctcacgcctg    25560
taatcccagc tacttgggag actgaggcag gagaatcgct tataacctgg gaggtggagg    25620
ttgcagtgag ctgagatcac accgctacac tctagcttgg gcaacaagag tgaaactccg    25680
tctcaaaaaa gtaaaataag gccctgcagg catggtggcc cacacctgta atcccagcac    25740
tttaggaggc caaggcggtc ggatcacgag gtcaggagtt cgagaccagc ctggccaaca    25800
tgatgaaacc ccgtctctac tagcctagcc aacatgggga accctgtctc tactaaaaa    25860 tacaaaaatt agccgggcat ggtggtgcgt gcctgtaatc ccagctactc aggaggctga    25920
ggcaggagaa tcgcttgaac ccaggaagca gagggtgcag tgagccaaga ttgcgccgct    25980
gctctctagc ctgggcgaca gagcgagact ccatctctaa ataaataaat aaaataagaa    26040
aataaaatat gttcacaaat cctttgacat tcctcacctc aaaagctgga acccaactcc    26100
ctcctaagca tgagtcttct cagtgactca cttctaacag cagaacttac atggttcccc    26160
acacccagag gacattgggt tcctcccaat atcccccac ccagcgaccc ccacccaggt    26220
cgctggcttt gggtccccca gagccatgtt tcaaggacac tcaggcagcc cctgatgtc    26280 catgtggtaa ggaatgaagg cctcctgcct gcagcctcgg gagggagcat tctcagaaga    26340
ggatgcccca cctcctgccc agccttcaga tggccaggac ctcgtccaac gtcctgactg    26400
caacatcatg agagactccg agccagaaac ccccaggttt tgtactcctg acttatggga    26460
actgacagat aatgttcgtt gttaattaag gggtgacttg tcacacacaa taggtcacta    26520
aacagctctg tctggcctcc caggaggagc ctgccttttc ttttcttcat gggaaaagtg    26580
cgatcagttt gtgaaggaat gtccgccccc acttgatgcc agaggctcca catggtgact    26640
gtcataaact ccatctgccc tcagtgcctt gccagcaccc ggcctgcgat cagcttggtc    26700
```

```
ttgcgggagg ccaaggccca cgtgtgtttg tgtgtggtgt ctgtgtctgc gtgcccatgc    26760
atgcccaggg tacagggatg ccatatacaa attctttcaa tgttgtatgt ggcatgtgtg    26820
tgtctgtatg cccaggatac agggatgcta tatacaaact ctgttttttc gttttttttt    26880
ttttgagaca gagtcttgct gtttcgccca ggccggactg cagtggcgct atctcggctc    26940
actgcaagct ccacctcccg ggttcacgcc atcctcctgc ctcagcctcc tgagtagctg    27000
gaactacagg cgcccgccac cacacccggc taattttttg tattttttagt agagacgggg    27060
tttcaccatg ttagccagga tggtcttgat ctcctgacct cgtgatccac ccgcctcagc    27120
ctcccaaagt gctgggatta caggcatgag ccaccacgcc tggcctacaa actctttctt    27180
tttttttttt ttttttttga gatggagtct cactgtcttc caggctggag tgcagtgatg    27240
cgatctcagc tcactgcaag ctccacctcc cgggttcatg ccattctcct gcctcagcct    27300
cccaagtagc tgggactaca ggcacacacc accacgccca gctaattttt tgtgttttta    27360
gcagagatgg ggtttcacca tgttagccag gatggtctcg atctcctgac ctcgtgatcc    27420
gcccgcctcg gcctcccaaa gtgctgggat tacaggcgtg agccactgcg cccagcctgc    27480
aaactctttc aatgtctttc ttttctctct cctgccatct tctcccttgc agatttcttt    27540
tgtctctacg tcttccccag ctgagtccga ggtcctgact tgcccacgct ccctggactg    27600
gaggagaggt gatagcaaga gctccttcaa gcccaggaat gccaccaggg ctgccccggg    27660
agaggaggaa gctgggtctc tcggggttgt ggggaccaga cacccttcta agacatggac    27720
tcagcacaga aagtctagac atccactaca aacacatctc cctcctaaca gggggcccct    27780
gggcaccca  agtggctgtt tggtgggaca ggcatgtcca tcagtcagaa tatctttatt    27840
tttattttt  tattttttat ttttgagaga gtttcactgg agtgcaatgg cacgatctca    27900
gctccctaca acctccgcct cccaggttca agcgattctc ctgcctcagc ctgccacgta    27960
gctgggatta caggtgtgag ccaccacacc cagctaattt ttttttttttt tttttgagat    28020
ggagtctcga ggctctgtcg cccaggctgg agtgcagagg cgcgatctca gctcactgaa    28080
agctccgcct cctgggttca cgccattctc ctgcctcagc ctcccgagta gctgggatta    28140
caggcatgag ccaccgcgcc cggccaattt tgtatttttta gtagagacag ggtttcacca    28200
tgttggtcag gctggtcttg aactcctgac ctcaggtgat ccacctccct cggcctccca    28260
aagtgctggg attacaggcc tgagccacca cgcccagccc agaatgtctt cttactttt    28320
attactctgt cccccatcct gggtccgac  ctgtgaccgt gaacaaccgg ctgcccaggg    28380
gtgaatgggg tgagtggggt gagtccacag aacagtgggg tgcagcccca gggtctcgt    28440
agcacctgcc cccaggtcag gaagtccac  agcctagagg ctccagcctc agatgcatac    28500
atatgtaggc cctgccccttt cctcctgagc ggcgggccac agagtcctga acaacaggaa    28560
gccctgagg  agggctccgc cctgagggag ggcaggggag ccccgccag  ccccacccac    28620
agcagcgggc cctgccaccc cccacccctga cacctcaccc cttggattcc agagaggaaa    28680
gtgggcttgt gtgtagttta catgctcata tcttaaaatc accgttgtca atagaacaat    28740
tcataataat gatgataaaa taagatttat aaccagcttc agtctggaga tacacacaga    28800
gcagatcttc actcccagac agggagcccg cagctgcccc cgaccccaca ggtgcaggac    28860
acacacagac agttcaacca tgtcttaaac acacaggtgt ttatttaatt gttcatttga    28920
ttgaattttt aagttcactt tactacgtgg atgagatggg tgcatattac agtaggcttt    28980
cgctatgagc gctgccacca tgaggaatat cccagccctc agttctgctt ccctttctga    29040
gtcccacaaa agccagatgt ggacagcctt gggttcccat cccagctggc tgctccttct    29100
```

-continued

```
ggggctgtct tggtggggag agggagatgg ggcagtgggt ccctgctgac ccctgagccc    29160 tgcagggtc aggatcctcc cgtggtccct gggtgtggct ctggaagaca ctggcagtgc     29220
ccggccaagg cctcccgcag gatggaagtt gagggccctg gctctgggtc ctaagagaac    29280
tcagccgccc ccttcacact ttacagcaag gggccaggca gcagctttgg gatgggcttt    29340
ccgtggagaa gtgggggatg ctgcagtggt acaaagacag cctcccccac cgccatcctc    29400
cagctgaccg tcctccaagg ccagcactgg gcgtccaagg gaaagaagga actcagccca    29460
gagggtgtgg gcaggagagg cctggagtca ggcctccacc cacagccccc tctgggtgcc    29520
aagtgggaag ggtgttgggg ctggcttggg aaccttaccc gctgcccttc caacacctgg    29580
atctgtgggc agcggtccca caaaatcccc cttggggctc cctgaggagg acttgtggct    29640
gccgcttcca ccagggcaga gggcacagga gggccagca ctccaaaggg ctctagggtg      29700 ggtcttttcaa ggacatctgc aaagccctgg tggggagggg cctgggccag aggctctttg   29760
gaactcttgc acttctgagt gggggactgt ccatgctgcc cacaacctct agaccatgca    29820
gcctgctcat gggtccctgg cagagaatgc ccactcccca gcagactcag ggcaggcccc    29880
caactgcagg cttccaggaa ggcccagggt gtccacctca cgccaggtgg tctcagagga    29940
cccctgtgca accacattaa ggaaagctgc agccccacc cacccgcctg ccagttcaac       30000
aagcaccggc tgcacacgca ggctcccagg caccatcacc cccctccccc gtcgcccctc    30060
cctcacgggg agccccttcc ccctggaaag acagcaggta ctgtagcctc gcctgctggc    30120 cagggcgcc ggctcagagg acctgccctg acctgcacgt gctgaccaga cagcccagcg      30180
taaggacccg cgatcccacg ccaccgccct gggtttacca cggtcaccac cacctctctc    30240
acagggcccc cggggggaccc agccgcgccc ggcctggtgt ctgcaccgag ggaccgcgtc   30300
tcacgcccgg cggctcctgc aggggaagcc gtggtcagcg actcaccacg aggacagggc    30360
agggcggctg agtgcggaag agaagcatga agctgggggc ggggtgggg gaggaggaac      30420 aaaagttgca tctagacaga ggtgaacgaa acaaaaccaa aacccgaacg tgttccgtcg    30480
caggatgggc gccgcccgtc ccgggccctt agcccgacat ctcttctcgc tgctccttgt    30540
tcctgcgcac ctcggccgcg tgcagctcct gcaggacagg gggcgggagg gcctgagggc    30600 ggggggtggct tggggcgact ccgggaaccc ccaggcgcgc aggccgtggc gccctggcac   30660
ccgcccggcc tcatccgggc tggccttcgg caggaccctg actgagttga gggggcggga    30720
gcaccgggga ggcgcagagc aaggccaggg accaaggacg ggtttcctgg gagctggctg    30780
ggccccgctt ctagctcgta ccggagccga gcttccttca gggcactttc aatataatga    30840
atttagccat ctattactgc ggctagttac tgtcccgcca ggaccagact ctggacctgc    30900
ctcgtgcgct gctggggacg cccagtaaac acgggaggag ccccgaccc ccaccccagc     30960 tcagcgcctc ggagtccccg gccccgctct gcgcccctcc gagctccgcc ctagcccgc     31020 ccccgcccag tgccccgccc cctgcctgct gctagccctg ccccgcccc ggcccctgcc     31080 cgctccgagc tccgccctgg ccccgcccg gccctgccc gctccgagct ccgcctggc       31140 cccgcccccc gcccagtgcc ccgcccctg cctgctgcta gcctgcccc cgcccgcc        31200 cctgcccgct ccgagctccg ccccggcccc gccccggccc ctgccgctc cgagctccgc     31260 cctggccccg ccccgcccca gtgcccgcc cctgactgc tgctagccct gccccgccc       31320 cggcccctgc ccgctccgag ctccgccccg gccccgcccc ggcccctgcc cgctccgagc    31380
tccgccccgg ccccgccccg gccccgccccg gccccgcccc gccccgcccc ggccccgccc   31440
```

```
ccctgcccg ctccgagctc cgccccggcc ccgcccccgc accttctcgc gcagccgctc   31500
gcgcagtgcg gccaggtgtg cctcgcggat ctccttgctg agctccatct tgtagttgag   31560
cttctcctcc gcctggcggc tgaagttgtt attctcctcc agcgccttgt gcagcacctc   31620
gcgctcgtgc tcgcgccgct ccgccagctg cttcagcacc tgcgcctcct gcgtctgtgc   31680
ggggccggcg ggcgcgcgtg agcggcaacc ccgggccctg cccggccgga ctcctccctg   31740
ctctccgcct cccgcccagc gcccgctcgc ctcacctggc gcctccacct gcccaggcct   31800
cggtgggcgc cgggaccccc gggcgctgcc ctgggaaccc tcgcctgcca tccggcctgt   31860
ggtcggggca gggccagggg gtcgcgatcc gccgccccg ccccgtccc tgcctcgcgc   31920 gcgggtcccg cggtcctggc tgcgcccagg gccccgcca taccctgccg ccactgcaca   31980
ccctgccctg cgcgtctgcc cctccaagga ccagcagcaa gaaaccctaa acttgtgggc   32040
ggtctctgag ctttgtctct tcctcggaca tccgcccact gagcagagta gctgcttgtt   32100
acacaccggg ttcccagctc ccaattaggt gcccaggagc ggagggtccc cagggatgct   32160
gggggagggg ccggctggtg acccctggga ggagagcggg gcagcaggac ccgcacccac   32220
atgccagtcc ctactagtca gccctgtgaa ccctggtctc tggcctcacc gggaagggaa   32280
cggagccgct tcccctgccc aatgcgttgg cctccagggt ggcaccccca aaaggacatt   32340
tttatctctg tttcagtctc agaggggctg gtgggagggg aggctgcagg gaggggacct   32400
ggagcccaca cccacctctc ccagggcccc tccgccctcc agcaagcctc agggtcttca   32460
cacatgaggc ccttcctcca gcttccctgt ctgggagagg gatgccccac ccgacgtccc   32520
cagggcccat ctggggacca cccctagca tcctgctggc cctgacaagg gtgcctccca   32580
ccctcaccag aggctcctgc tccttccagg tggccgcctc ggaacccttc ctcctctcca   32640
tcccttcttt tttttgttct tgtttgtttt ttgaaatgga gtctcaccct gtcgcccggg   32700
ctgaggagtg cagtggcgca gtctcggctc actgcatcct ccacttcttg ggttcaagca   32760
attcccctgc ctcagactcc ctagtaggtg ggattacagg tgtgcaccac cacacctggc   32820
taattttgta ttttttagtac agatggggtt tcaccatgtt ggccaggctg atcttgaact   32880
tccaacctca agtgatctgc ctgcctcagc ttcccaaagt tctgggatta caggcgtgag   32940
ccaccacacc cggcctctcc ccatcccatt cttatctctc agaaagaggc ccagggagcc   33000
acagcccctc ctgctccagg ccaaggcact gaccaagcct gtccgggagc accctgcttc   33060
ttgcaggccc tgtccccgtg ggccgcctcc gttgaaactc ctgggggtg ggggatggag   33120 gactccttgc cttcctccgc tcctcggctg cctccagccg cttttgcagc tcctccaggg   33180
aggtgtcctt cttcttgggt ggggaggaga gcatagggct ctctggggac aggtcagaag   33240
gggacttgag gatgacctcg aagctctggc ctgaggcccg cttgtccagc tgcttcacct   33300
ccatgtctgc agggcaagac cagagtagag cttcagaggc ccggccaggg catggcgtgg   33360
gctgagcggg atgctcccag cacacatcca accccagggg tgggcgagag ggggtggctg   33420
ctcccgcagg aatcccaggc ttcagccccc aggatgggcc ccttcccct agaacctccc   33480 tctccagagg cagccaggac gggagttcag agagactgcc ggaggccggg ggaaaaggtg   33540
aggtgggcag gcaccgcagg gaagggcagg cggcagccag gcactcaccc ccgtactggt   33600
agacggtatt ggggtgcggc tgtgtgtaga agcaggagca gatgagcgac agcaccgaca   33660
gctccttcat cttctccttg taggctgtgg gcacaaggct gggctgagca agcaccactg   33720
gggcctgccc acctgggccc ccgttttccc tccccatggc tgcctctatc atgtctctgt   33780
gagacacgga gctgcccagc acgctctctt gtgtgtctcc acaccgccgg cccttcgtc    33840
```

```
tctccagctc tctcgcttcc agacgtcggc actgtctccg tggtgtgtcc cctgccttct    33900
gtctctctcg ccctctgcct ctcccgctt ttcctctctc tcggcattaa tgtctgtctc    33960
atcttccaca ctgacttgtt tctccatcct tctcctgcct gctgtggtct gaatgtttcc    34020
attacccaaa actcatgtgt tgaaatcgta accccaaggt gccggtgtgc ggaggtgagg    34080
cattcggagg gaattaggcc atgaggatag agccctccta agtggcccca gagtgggggct   34140
tcagagaact ccctcacctt ccatcatgtg aggacacagc cagaagacgc cacccgtcta    34200
tgtaccagga ggcgagacct ctccaggcac cgactctgcc ggcaccttga tcctggactt    34260
tctggcctcc agagcgatgg gaaataagtt cctgtcgtct ataaaccact cagtctcagg    34320
tacctgccca gactgacaaa gtggctaccc ctgcctgtct gggtctctgt ttaccttctg    34380
tgtgtctgac tctgtcactg tcattgtatc tttctgtgtc tctggggta gcccctgact     34440
ctgtctttct ccctgagtgc atctttctgt gattccttgt cactgtgtgt ctttctgact    34500
cttacctccc tctgtcccgc tacttctctc tcccctcctc ctccttccca ctcctcgcca    34560
gctcaagcag gcaagattta ctcatgacgg gaccagcaca gatgcaaacc ctctgtgggc    34620
aggactttct tgggctgtaa acctggatga agccctcaga ccctccttttt tccttcccaa   34680
tgattgtgtg gtcaccttga gatgaaacca ggccctctcc aggcacatgc tctctgtcta    34740
tctagggctg ggcttgggcc actgatgcca ccaaggagca agggagggaa gctgtccgtt    34800
cagcaccaca gccagccctc ttgcccattc aggtcaatca agtgcccacc agccagtgtc    34860
cctgctgccc aacccaaacc agaagcaagc cgggctcctg tggccctgtg ccctgtcagg    34920
ggaagaggaa ggcgcctgct gtcacagtga aaataattta gctcttttgg tctattcagg    34980
gcgaacctca ttcctaagca gacacgctgg cccggtttct cactagtgct cgataatcct    35040
tttggctggg tgcagtggct catttaactg taatcccagc actttgggag gccaaggcag    35100
gtggaacacc tgaggtcagg agtttgagac cagcctgacc aacatggtga acccgatct     35160
ctactaaaaa tataaaaatt agccaggcgt ggtggcaggc acctgtaatc ctagctactt    35220
gggaggctga ggcaggagaa tcgcttgaac ctggggaggcg gaggttgcag tgagccgagg   35280
tcgcgccatc gcactccagc ctgggtgaca gtgtgagact ccgtctcaaa acagaaagaa    35340
aaagagagag aggaagaaag gaaggaggga ggagggagg aaaagaagaa aggaaaggaa     35400
aggaagacag acaaggcaga agtaatcaag cctttcatgg tgagctgggt cttctggtga   35460
cagtgcagag aatggtctgt cctgacttaa atttcctggt gacctacact tttctggaca   35520
gagcagcaca gagcccaaga gggtgtaagg aggagcagaa aggaatccca gggtgggcag    35580
gcccgtgcga gagcctttgg gggaaggaat gagactttga gccgggaagc gaggcaaagc    35640
tacctgtctt ggtcattgtc ttcagggagg gagatggagg gggaccaggt gggggagcct    35700
cacagggac tttggtctga cttgtcaagt tttctttttt tcttttttgag atggagtctt    35760
gcactgttgc ccaggctgca gtgcagtggt gcgatctcgg ctcaccgcaa gctccgcctc    35820
ctgggttcac accattctcc tgcctcagcc tcccgagtag ctgggaccac aggcaccgcc    35880
accacaccca gctaattttt tgtatttta gtagagacgg ggtttcacta tattagccag    35940
gatagtctcg atctcctgac ctcgtgatcc gcccgcctcg acctcccaaa gtgctgggat    36000
tacaggtgtg agccactgtg cctggcctac tttattttt agaaacagga ctgtgctctg    36060
ttgcccatgc tggagtgtag ggtgcagctg tgcggttcac tgcagccttg aacttctggg    36120
cttgacggat cctgccatct tagcagctgg gactacaggt gcatgccagc acaccagttt    36180
```

-continued

```
tcttttttttt tttatctctg ctcactgcaa ttccgcctcc tgggttctag cgattctcct   36240
gcctcagcct cccaagtagc agggattaca cgcacatgcc accacacccg gctaattttt   36300
gtattttttag tagagacagg gtttcactat gttggtcagg ctggtcttga gccaccgcgc   36360
ccgcccggcc tacacaccag cttaaaaaaa agaaaaaaat agctgggcgt ggtggctcat   36420
gcctgtaatc ccagcacttt gggaggctga ggcaggcaga tcacctgagg tcaggagttc   36480
aagaccaacc tggccaacat ggcgaaaccc tgtctctact acaaatataa aaatcagcca   36540
ggcgtggtgg cgggctcctc taattccagc tacttgggag gctgaggcag gagaatcact   36600
tgaacccggg aggtggaggt tgaagtgagc caagatcgag ctactgcact ccagcctggg   36660
agcaagactc ccgtctcaaa aaaaaaaaa aatttgtag tggtatggag gccgggcatg      36720
gtggctcacg cctgtaatcc cagaactttg aggggccaag gcgggcagat catgaggtca   36780
ggagttcgag accagcctga ccaacatgat gaaaccctgt ctctactaaa ataacaaaa     36840
attagccagg catggtggcg ggcacgtgta gtcccagcta ctcgggagac tgagacggga   36900
gaatcgcttg aacccaggag gcagaggttg cagtgagctg agatcacgcc actgcactcc   36960
agcctgggtg acagagtgag actctgtctc aaaaacaaac acaaacaaac atatatatat   37020
atacatgtat atatataata tatatatacg tatatataca cgtgtatata taatatat     37080
atacgtatat atacacgtgt atatataata tatacgta tatatgtata tattaatata     37140
tatacgtata tatacacgtg tatatattaa tatatatacg tatatataca cgtgtgtata   37200
tattaatata tatacgtata tatgtgtgtg tgtgtatata tatatgtata tatatatata   37260
tatatacata tatatataca gagagagaga gagtagtgat aggtcttgct gtcttgtcca   37320
ggctgatctt gaactcccgg cctcaagaga ccctcccacc tcagcctccc aaagcactag   37380
gattataggt gtaagccaca gtacctagcc tattaaaaat taatgttaaa caagaggatg   37440
tgatgaggga gttagagggt gtgccagcca tgtgttccac agcagcaggt caggagacat   37500
tggggacatt tagaggagct gaagaggtgg ccaaccctgt gctcaggagg acggggagg    37560
gagagagcaa gagggagttt gggctggggc agaacgtacc tgggtcctga gggataaga    37620
aggtagggac ttggcccctc caggcctgac tctgccagca accagctccc tatcagcaga   37680
ctccaggccc ctaccttca gctcatcctt cctatcaca catccaaaac tctgaatgtg      37740
gccgggcgca gtggctcacg cctgtaatcc cagaactttg ggaggctgag gcaggaggat   37800
cgcttgagaa caagagtttg agaccagcct aggcaacatg gtgaaacccc atctctacta   37860
aaaatataaa aattagctgg gtgtggtggc acatgcctgt gccccagct actcaggagg    37920
ctgaggcagg agaatcactt gagcctggaa ggcggaagtt gtagtgagca gagattgtgc   37980
cactgcgttc cagcctgggc aacacagcga gactctgtct caaaaacaa aaactggaat   38040
gtgtttacca taaaggccag aaaatgtgat taacagctgc tcaaagcccc tgtctgccct   38100
aagcctgaaa ttttcaccga aaaaagatc tgtaggctca tacagaggaa ggacaaacac    38160
cagggaggct ctcttccagt ttgcttcacc tcagcaagca gacggctggc agcaatttgg   38220
gggcaggtgt gagcacctgc atcatcagga aagaaggggc acgtggggga cgcaggtcag   38280
acctctcaca ggtcttggct ctgcccagga gacacgtgtc caactgagag gtgaggaact   38340
gggttctgca gctgcagaca caggtgcggc tcagcatctg atggccacgg agacccctg    38400
gcttggcttc tcccagctgg tggcccatga ggagcttcta tcccaagaga ctgtccctca   38460
aggagcaagt gggaccaggt acccacagga cggagcctgg gagtgaggcc tgccctgtgg   38520
tctggctaca gggaggaagg gcagattgga gggggcagga cagcaggtca ggaattggcc   38580
```

-continued

```
aactctggag agagcaagca aggggaagtc tgcgcacagg gcagggctgg tcaggggcga    38640
ggcagggcat tggaccagta ttttcagagc tggtgaggct taaagagcat gtctactgcc    38700
tcttattaca gagagaggat gccgaggccc agacccatcc aggccacctc tccacagaca    38760
cagctggtgc cagggaagcc cctcccagag cctcaaggca ttgctccctc tctctctctc    38820
ttttgtttt tttggagacg gagtctcact ctgtctccca ggctggagtg cagtggtaca    38880
atctcggctc acggcaagct ccgcctcccg gattcacgcc attctcctgc ctcagcctcc    38940
cgaatagctg ggactacagg cgcccgccac cacgcccagc taatttttg tatttttagt    39000
agagacgggg tttcactgtg ttagccagga tggtctcgat ctcctgacct tgtgatccgc    39060
ccgtctcagc ctcccaaagt gctgggatta caggtgtgag ccaccgcgcc tggactttt    39120
tttttttta agacggggtc tcactctgtc acccaggctg gagtgcagtg gcgcgatgtc    39180
ggctcactgc aacctctgcc tcccagttc aagtgattct cctgcctcag cctcccaagt    39240
agctagaatt acaggcacat gccaccatgc ccagctaatt ttctgtattt ttagtagaga    39300
tgaggtttca ccatgttggc caggctggtc ttgaactcct gacctccggt gatctgccca    39360
cctcagcctc ccaaagtgct gggatgacag gcgtgagccc ccgcgcctgg cccccgcag    39420
tgctgggatt acaggcgtga gccccgcgc ccggccctc cctctctttg actcccttct    39480
ttctcaccgc cccctcccca ccatccttcc ccttcactga cttcagggag ttaaaaacaa    39540
ttctcgcagt gagctgggct tgttttgtct ccctgcttct cttgtacta aacattagat    39600
accgaggaaa tgcggattgg cctttggatg attcatgagc aggagtcaga aaaaggcacc    39660
aggttggcct caagcagcag ggtatagtag tgcccgctcc cagggtcaca cctcacgccc    39720
accctcccg ccgtccaggt ggatggtgcc cactcccagg gtcacacctc acgcccaccc    39780
ctcccgccgt ccaggtggat ggtgcccact cccagggtca cacctcacgc ccacccctcc    39840
cgtcgcccag gtgatggtg cccactccca gggtcacacc tcacgccgcg ccctcccacc    39900
cacccgggtg gatggtgccc gctcccaggg tcacacctga cgcccaccg gtggatggt    39960
gcccgctccc agggtcacac ctcacgccca ccctcccgc cgccgggt ggatggtgcc    40020
cgctcccagg gtcacacctc acgcccaccc ctcccgccgt ccaggtggat ggtgcccact    40080
cccagggtca cacctcacgc ccaccctcc cgccgcccag gtggatggtg cccactccca    40140
gggtcacacc tcacacccac cctcccgcc cacccgggtg gatgcccta tcagctctcc    40200
ttctcctct ctttcgtctt cttcgtcttc tcctcttct ttcttctttt tttttttt    40260
tagaaagagt ttctactctt gctgcccagg ctggagtgca atggcacaat ctcagctcac    40320
tgcaacctcc ctctccccgg gtcaagcaat tatcctgcct cagtctccca gattgctggg    40380
atcacaggag tgtgtcacca cacctggcta attttgtact tttagcagag agggggatt    40440
tcaccatgtt ggccaggcta gtctcgaact cttgacctca gtttatccac cggcctcagc    40500
ctctcaaagt gctgggatta caggcatgag ccaccctatc tgcctcactt ctacagagga    40560
ggaatgaagg ctcagagagg gcaagcattc cacccagcat cacacagagt gccgggtgag    40620
agcccagtca tgagcctggg cctgactgca ggctcctgtt gggagctcgc ggaggtgggg    40680
gatctgtcca gaactgagag gccagggac cacagtggcc tctgaccct ggagggccct    40740
ggaggctgct gccggctccc cccggggca gatggaggtc actgtcaccc aggctgcttc    40800
tcatggtgcc aggagcacag catggcagga gccaccagcc gatttgcctt tccctgggca    40860
ggaaactcag aaatgtggct accacagtca ggctgcttga cgtgcggtga gcactcatct    40920
```

-continued

```
cttagcaggc aagcggccaa gcacctttcc tgaaatattg aggcctcaga acaagcccca    40980
ggagaggtgc cagcaccgtc atctctaccc agataaggag acccaggtcc tgagaggtta    41040
ggcagctcgg acaacaccac acagctggag gaggtcagac tctgggttgc agaaggagaa    41100
tgtgagcaga ggccacaaaa gagcgaggag ccagtgccca gatgccgaga tgccctcgcc    41160
ctcccagctc agccccagga accgagccca tggggaggga ccgtcaggga aaggctgtca    41220
ggaagggcag gaggcggccc tggagaggac ggcgctgccc tcaggggcag gagggagtc    41280
ccctccgctg agaccccccc cacccccagt atccccgggg gtgtccagga ggaggcggag    41340
ggaggaagcg cagatggaca ggactcccag ataggctggg gaggtgtggc cggtgacaca    41400
cacggtcccc tcctggcagg tgctgaagtc acctggagcc tccaagcccg tggggcctga    41460
ggggcggggt caggtcgggc acgcgtgggt ggcggagtt ctgcgccccg gccaaggcg    41520
cccgagttga accagtcagc tcgggagagg gaccgcggcg acctgtcccg ggggcgtaag    41580
aaaaggtggg agggagtgcg gctcgtgaac ggggcggcg atgggaagga ggtgcggccc    41640
ttcgtcctgt cctcccaaac gtcgagtgaa aacgaagcg ggttctgcgg cctcgcggcg    41700
gagcagagcg tttcgggaag ggcgggccca gcgtcctcgc gcccgaggtc gcccggcagc    41760
tcccctgcgt ccagaatccg ccccccgccc gggcctgcgc ccgcccctcc gcctgagctc    41820
cgcgcgggac gggccgggag gccggggtgg gcgctacctt cgaaggcggt gggtccgccc    41880
cgcgggaggt ggaggggcgg gaggggcgga gccctctggt ctccggaggg tttggggatc    41940
gcagtcgccc ctcccccatc cagacccgc ggcgcaaagg gcagtggctt ttctggccag    42000
agcaggtggc gcgggcgtcg caaagggtgg tccccgaggc cgcagcggtg tgggggagg    42060
gcgcggtccc cctcactccg ggctccgccg tgtctggccc gccccctcc ttcagcgccc    42120
cctccagccc ctgtgctgca ctggcgcggg gagcgccggg ttccggctg gggcttggc    42180
agagggtccc accctctccc cgcctcccca cgaaggctct gcggacccca gatctcgggt    42240
cgccggacgc cccagggacc ccgcccgcac atcgcgagcg cgcccacccg gtcgcgagcc    42300
cacgcccggg tctgggagcc accctgcggc agtcgcgccc tgcgtggcac gctgctcccc    42360
caggggcgag gcgcccccgc ccgacgtccc ggtcccgagc gctccccggc gcggcgcctc    42420
gcagcccagc gccccaccag ccccgccggc gccgcagacc ccagcctcgg gcgggtcggg    42480
cccaggcttg caacgcgcag ggtaggagaa gggaaattgg cgtccgctgc cggccgctgc    42540
cccaggcgag gccagacgag gcctctgctc agatcccgcc gccccacaaa gcccgtggcc    42600
ccggagccta ccggaaatgg tgctggccat ggtgctggcg gcggttgggc ctgcggaggc    42660
tggagaggcg caagtggcgg ccggagctgc agacggctgg tgctgcagtg ccggggaggg    42720
gagggggagag gagtggaggg agcgagggcg ggcgggaggc gggcgcggcg ggagagagag    42780
agggagggag acagagggag agagagagag ggttggggga aggagcgggg ggaggaggga    42840
gggagggttg ggggaaggag agagagagag agagagactg cggggcggg ggaaggaggg    42900
agggaggaag ggagggagga agagagagag gagcaagcgc ctggctgcgg aaggggccgc    42960
ggctctcagg gggagagggc ggaggagggg ggctacccga actgcaacaa gacccccac    43020
cctccaaccg ctcacagcgg gacagctgct tctccaactt ggctttgtga ggcctgagag    43080
tggggtgggg gtggagatga gccccattc cccaggcag gcggggcagg gcaatgccg    43140
gaggagcagg tcccacccat gggtgtgggc gcagagctc ttcgccgcca aggccgctgt    43200
aggctgggct ggcgccaaca gggtccaggt ctgtgcctgc catcggagag gatgccacag    43260
ccacagggt gggcgctggc ctggaggcct ccaagggca tctcctgtga gcccagggga    43320
```

-continued

```
tgggcaggat ctgagcggag aagagtgaaa gtggaggagt gaggccagaa caaaggcttt    43380
gccgtgaaag aggtggtttc ccgcctgggc tcagaccttc actcactgtg tggcccaggc    43440
caagggcaag cgtctgacct cgctgggcct ttgtttctca ggggtaagat gaaacaatga    43500
tgcccccaga cgatggagag gagggtgcc  agggttgtgc gcacttagtg agtgggggc     43560 aacctatcct gcctccccct ctcctcataa ctcccaaagg gaaagcctgg taggcaaacg    43620
gagcgtcttt gccattgcag ggatgaagcc accgaggcag ggagaaaagt gctttgccct    43680
acaagcaact aagtcatagg gccaggagca aaaccctgaa aacctcagga gacttgcaga    43740
gccatgaggc tggctcagca acacaaaagc caggggcaag cctcagctct agcagtgcgg    43800
tgggagcacc caaggccagt cacatcctag ggtggcctgg agagtcctga cccctgacgt    43860
gcaagccggc atcatccccg ggactgtgag tctggtgggg gtgatgccca ggaatgtgac    43920
attgtgtggc ccagaggtac ccttaagact ggaggatcac caggcgggcc ctgacctcat    43980
cacaggagcc ctttaaaagc agtttccttt gcctggttga agaaatcgga gggatcaaac    44040
caaagaaggt tttctgttgt tgagatgagg gggccacgtg gcaaggatct gagaactgct    44100
cccagccaac agccagcaag acaacaagac cttaactgca aggaagtgag ttctgccaac    44160
aagaagagaa tgggcttgga ggcaggtttg accccagggc ctccacacaa gaactgagcc    44220
caactgccca cttggtttca gccttgggtt actaagaatt aggaggtaat gaatgagagt    44280
tgttttaagc tgttggtttt gtggtgattt gctatgaagc catatcaaac taatatacac    44340
acagaggtgt tggcccctgg gccattccta ggaagccagc tctgcgaagg aggaagaagg    44400
gcagagaggc acacagagct gcccaccaca gcagctgtgt cctccctgtt ggccaccaca    44460
gtagcagttg gggatggtca gcatccttca ggcagactcc agccccgggt gctggagctc    44520
aggtgctagg gatcaagaga agtagccctc tctgggacct ccagagtctt ctcatgtggg    44580
tggggtagga cccacccagt caggctcaga gcaccgcaat gcctcacact cattgtgact    44640
ctggccaggc cctctctgag cctctgtgtc ctcatctgga gcacagggac caggtgtgtg    44700
gaagcccgtg gcatagtgcc aggaacacag tagatgtgca cagtgtgcac tagcaggaac    44760
acacaacagg ggtactgact gtcagcacct aggcaggcac acgcaatggg gtactgactg    44820
tcagccatac tgactgtcag cgtgctagca ggcatacaca acagctgtac tgacagcaca    44880
ctagcaggca catgccatag gtgtactgac tctcagtgca ctggcaggca cacgcaatag    44940
gagtaatgac agcatgctgg caggcacaca atagctgtac tgactgtttg ccccaatata    45000
gtgccaggtc ttggagcaga ttttgacttc tcaccaagat caaatgcaga aagtgcacga    45060
gcatttcaaa gatgttttc  acatgcacat tagtgctagt taaaaaaatg tttttgactgg   45120 gtgcagtggc tcacaactgt aatcccaaca ctttgggggg ccgaggtggg cagatcacct    45180
gaggtcagga gtttgagacc agcctggcca acatggtgaa accccatcta ccctaaaaat    45240
acaaaaatta gccaggtgtg gtggcaggtg cctgtaatct cagctacttt ggaggctgaa    45300
gcaggagaat cacttgaatc caggaggcag aggttgcagt gagccgagat cccaccactg    45360
cactccagcc tgggcaacaa tatcaagact ccacctcaaa aaaaaaatg tttttcataa     45420 agtgtgactt ttatcagacc tctgcattct tgaaattaac tctggcttgg ctgggcgtgg    45480
tggcccacac ctgtaatctt aacactttgg gaggctgagg tgggcagatc acgaggtcag    45540
gagttcaaga ccagcctgac caacatgatg aaaccccatc tctactaaaa atacaaaaat    45600
tagccgggcg tggtggcatg cacctgtaat cccagctact caggaggctg aggcaggaga    45660
```

```
atcgcttgaa cccaggaggt ggaggttgca gggagccgag atcgcaccac tctattccag    45720
cctgggcgac agagcaagac tctgtctcaa aaaaaaaaaa gaaagaaaga aattaactct    45780
ggctcctaga aggagcccta tatctcagca ggacactcag tcattcaaca gacatctgtc    45840
aagcacctgc tgtatgctgg agctgtgggt acgtcagcaa ttagaggaag agggcagggg    45900
tacaggagtt cctgaccacc ccaggccagc acgctcctat agcagctggc aaggagcaga    45960
tgactcagac ttcagctcag tccacaggac agccttttct ggccactgct ctcaggagat    46020
gagatgtgtg gctgcaaaag gtaaactcct ggctcctgag caggctctgg caatctgct     46080 caacgctctg tgcctcactt tctcacccag aaagtgtgga caatgagagg acttatctgg    46140
ctgggcgcgg tggctcacgc ctgtaatccc agcactttgg gaggccgagg cgggtggatc    46200
acctgaggtc aggagttcaa gaccctgcctg gccaacacgg tcaaactcca tctctactaa    46260
aaatataaaa aattagccgg gcttagtggt gcacacctgt aatcccagct acttgagagg    46320
ctgaggcagg agaatcactt gaacccagga ggtggaggtt gcagtgagcc aagattgtgc    46380
cactgcactc cagcctgggc aaaaagccaa aactctgtct caaagaaaaa agaatcatgg    46440
cagaaggtga agtctatgtt agtcccagtt cccaggtcgt acatggcggc aggagaaaga    46500
gagagagaag gggaaactgc cacttttaaa ccatcgggtc tcctgagcac tcactgtcag    46560
aacagcctgg aggaaactga ccgcatgatc caaccacctc cctccaggtc cctccctcca    46620
cacgtgggga ttacaattcg aggtgagact tgggtggaga cacagagccg aaccatatca    46680
gcatgtatgg ggggcactga aacttgtgct tggtgcccat tcattcaacg agtgtgtgtg    46740
gctggtctcc tcatcttcaa ctccctgccg agtctcagat aggcagcctg cagttccttc    46800
accacaacag gcacatgggg ctgggtgcca gtgagtgctg gggcttctcc gagcactatc    46860
tcacacccag gagcgtgggc acgcatggca ttcgcatgtg ccgtcagtgg acattaaaca    46920
cagccatgaa gaagccacga agaagtgctg cctgccggcc gtgcgcggtc acgcagcgcc    46980
aactccctcc tggggccttc tggggccttc tggggcatgg gagctggggc cgcctgagac    47040
aaacatccgt gacgctgggc tgaccccaca gaacggtgcg ggcctcgctc ttggagtcag    47100
ccctgctgcc agccagtgcc gggtgctggg gactcaggga ggcccgccgg gaccactgcg    47160
ggacagtgag ccgagcagaa gctggaacgc aggagaggaa ggagaggggg cggtcagggc    47220
tctcaggagc cgggtcctgg gcaaggcgca gccgtttca aattttcagg aaagcggtcg     47280
gctcacactc gagcagtaaa aagatgcctc tggggaggag gcccgtgcag ctctccgggc    47340
aatggtggtg gctcggccta gagaggcggt agtggaacgc agaccctggt gggggaatga    47400
catcaaggga ggagacgggc gggacccccag atttctgcct gtgggcgatg gaagtgaggt    47460
tcactggcca gcggagccgg acacagaacg cgcaaaacgc cgtgtaggcc tggaggagcc    47520
gaagagcagg cggaccccct ccgcggggga acagtttccg ccgggagcac aaagcaacgg    47580
accggaagtg ggggcggaa gtgcagtggg ctcagcgccg actgcgcgcc tctgcccgcg    47640
aaaactctga gctggctgac agctggggac gggtggcggc cctcgactgg agtcggttga    47700
gttcctgagg gaccccggtt ctggaaggtt cgccgcggga acaagtgagc agtgagtcgc    47760
agtgacccta caagtggttc ttttacccga gcggctcgta ggcgcgttgc ggttttttcga    47820 aactacagct cccggcaggc cccaagccgc cctcggggcc gcgggtcggc ggattggccg    47880
cgctgcattt tgggacctgt agtttcctgc gctcgtggcg ctggcgccgc ggcgttggct    47940
gagcccttga ccggggctgg agggaagggc cgacattcag tgtgtccgcg tctgttctgt    48000
tagtcccagt tcccgggcgg gattgaggct tagagaagtt gagtgatttg ctgagggctg    48060
```

```
cacgggttgg catcccggca tgctctttcg ctactttggc tgcatctggt tgcccacccg    48120
ggcggatggg gaatggactc cagccagcca ggagggcaga gggctggaga ggcagggccg    48180
gaggttcaga ccctccgctc tgacgttgcg cctggtgagg ccgggagggg tgccgcttgc    48240
ctcttcagcc ctcacgctct tgtggaagtc gcggaattac tgcaggcgga acttgcagca    48300
ctgtgggcgt cttttccaga gaaggacgga gttgtgggc gggaggataa ggcaaggccc     48360
agccacttcg catcttcgcc ccgccagctc ctcgagatgg gatataccag ggttgctctc    48420
caaccctctc cgcaggaggg actgatgaa acgcctggga aagtagcccg gtacccacaa     48480
aggctgtcta caaacagagt cttactgtct ttcccaggtc tgtgccatag ggattctcga    48540
agagaacagc gttgtgtccc agtgcacatg ctcgcatcgc ttaccaggag tgcccgagac    48600
cctaagatgt tcggagtggt tttttcgcac agacccgaat agcctgcccc tcagccacgc    48660
tctgtgccct tctgagaaca ggctgatatg cccaagatag tcctgaatgg tgtgaccgta    48720 gacttcccctt tccagcccta caaatgccaa caggagtaca tgaccaaggt cctggaatgt    48780
ctgcagcagg tagagcacag gccccgagga aaggactgcg ggtgggtgga gcttcagcca    48840
ggacggggtg tgcttccctc tcccggccca ttccagccag gcccctccgg gccagaggca    48900
gcgtctgtca taaaagggc tggtgttcca ggtggggtca gagagaggat tgacaagtaa     48960
aaacgatcgt cctttgaagg gggccggccc ctccacacct gtgggtattt ctcatcaggc    49020
gggacgagag actgagaaaa tgaataagac acagagacaa agtatagaga gaaagtggg     49080 cccaggggac cggcgctcag catacagagg acctgcaccg gcaccagtct ctgagtttcc    49140
tcagtattca ttaattacta ttttcactat ctcagcaaga ggaatgcggc aggacagcaa    49200
ggtgatagtg gggagaaggt cagcaagaaa acgtgagcaa aggaatctgg gtcacaaata    49260
agttcaaggg aagtactat gcctggatgt gcacgtaggc tagttttatg cttttctcca     49320
cccaaacatc tcggtggagt aaagagtaac agagcagcat tgctgccaat atgtctcgcc    49380
tcctgccaca gggcggcttt tctcctatct cagaattgaa caaatgtaca atcgggtttt    49440
ataccgaaac attcagttcc caggggcagg caggagacag tggccttcct ctatctcgac    49500 tgcaagagc tttcctcttt tactaatcct cagcacagac ccttcacggg tgttgggctg     49560
ggggactgtc aggtctttcc catcccacga ggccatattt cagactatca catggagaga    49620
aaccttgggc aatacccggc tttccagggc agaggtccct gcggctttcc gcagtgcatc    49680
gtgcccctgg tttatcgaga ctggagaatg gcgatgactt ttaccaagca tactgcctgt    49740
aaacatattg ttaacaaggc atgttctgca cagctctaga tcccttaaac cttgattcca    49800
tacaacacat gtttctgtga gctcaaggct ggggcaaagt tacagattaa cagcatctta    49860
gggcaaagca attgttcagg gtacaggtca aaatggagtg tgttatgtct tccctttcta    49920
catagacaca gtaacagtct gatctctctt ttccctacag tccttgaggg tgacagactt    49980
aggagtgcct tggggggcctc tctgaggagc agctgatatt cacgggtcag gaggaagcat   50040
ttccattaga ggggcagccg gtggccagcc tcacttggaa ggtctttgaa cctcgggggt    50100
gcagggaggt ggcagtggtg caggttgcct tctcctgggt tccttgaggt gccctcttgt    50160
acccggctca cacccttccc ctccccgagt ttcctgctca ggttcccgtc tgagagcttg    50220
tatgtaggac gtcagatagg acagcataaa tgtttggatc cagaaacgca gaacagtttc    50280 ctatttgag acttgacacc taattagtca tcttactatt taagctgaaa aatagtgtcg     50340
tgttttgggt aacgttctgc aaatcgtttg ctaatggcgg ctgagttgct tcacgccctt    50400
```

```
tagggcaaga gtgggacttg cctgtggact tctccgcggt cccacagggc tctcgccacc    50460
tggcagtggc ctctgcatct gcaaagagct gcccgctggc tgccgaagct tgtctcaggg    50520
cagcttgtgt ggcctcgcct cttcctggct tccccgtaac ccttgctccg aactccgttc    50580
agaaggtgaa tggcatcctg gagagcccta cgggtacagg gaagacgctg tgcctgctgt    50640
gcaccacgct ggcctggcga gaacacctcc gagacggcat ctctgcccgc aagattgccg    50700
agagggcgca aggagagctt ttcccggatc gggccttgtc atcctggggc aacgctgctg    50760
ctgctgctgg agaccccata ggtgacccta gttcccaggc ctcctggcc ctcctgtggg    50820
gatggttggc aagggatggc gctgagggtg gggtgggccc atgggactc ctgccgtctc    50880
tcaagcagaa ctcaaggaga attttttagc tgctgtataa tttctcgcca tcgtgggtgt    50940
aaacctaggg ttgggctttt ttgctgaatt agggcacggc agatgcccac ttcacccatt    51000
tttgataaac cagtatctgg ggtgtcagat tcttggctgt ctgcagggcc gagttagccg    51060
aatgccacct gcctttgata cgtgagaacg ttgtctgaga accgtgactt ctgtgcttgc    51120
ttgtgtctgg tcagcttgct acacggacat cccaaagatt atttacgcct ccaggaccca    51180
ctcgcaactc acacaggtca tcaacgagct tcggaacacc tcctaccggt gggtcagacg    51240
agtttacacc tgtctcgggg tcctcaagag aaccagcttg gcatggtgct gagtccacag    51300
ccccatgctg tgctgtggtg gagggtggtg gtctttctag acgctccccc gaagtgtgca    51360
gagcgctggt gcccagggt ggggtgcggc ctgggctgcc tccaatgccc attacttgtg     51420
aggaagcagc tttgcatctg tgtgctgacc ttgggcgggc gtcctgagct cctcgcaggt    51480
gctgttgtag cagctgtgca gtaggtcagg gctggcccc agtgcagctt tgcacatgaa     51540
gtaggaggag gccctgctgc ttgtcagagc ccagcagagt cttggtgttc tgtcgggttc    51600
ctgtggccgg accagtggca gggtgctgtg gaagctgtcg aatctcctcc ctctgtccag    51660
tacccccgct cgtcttctag ctccctccta cgcccgggcc acgtttcagt tatgctcact    51720
tcctctgacc gccgaggctc ctgcgtgtct ccatacagct cacgctgcag ggccacgctg    51780
tgggtgttgg agacagctcc tcctcgaccc acggtgctct ctcccaccag gcctaaggtg    51840
tgtgtgctgg gctcccggga gcagctgtgc atccatcctg aggtgaagaa acaagagagt    51900
aaccatctac aggtaggctc ctgggctccc gctccggctc agtgtccgac aggcgagtgc    51960
tgctgggtgt ccagagcccc aggctgcgct cccgctgggc tagggtttga agttcactgg    52020
gggactgcag gggaggacct ggtgggggtg gggactggct tcggtcctttt cttggccgtg    52080
cttcagctgc gcactctgcc cttcctccca cagatccact tgtgccgtaa gaaggtggca    52140
agtcgctcct gtcatttcta caacaacgta gaaggtacaa gcagctgggt gggaccaggg    52200
tcgggttgga gtgtgtgcag cctctcaggg tggagctcag tggtgtcaca gcctggttgt    52260
gcttgcccgg tggggcggcc agtgcggcca tgtacctggg ccctgtcttc tgactcgggg    52320
ccacccatgt tagacttctg tgtggaagag ctcacacagt ggtctgagac agccagccgg    52380
caagactgcc tctggctggt gcctggggcc ttggattttg ggaaggctcc ctccatttcc    52440
tgatgagagg gtctccctgc acctaacctg ctggtgcaaa cagtagggt tttgctgaac     52500
accggctttc tcttcgggga ctttgttgct tgcccagcag caggtgctcc agtgaccggc    52560
cctcatacca tcttgggagg gtgtcctgga agccgtgtct ggcctccgc gaccctgccc     52620
cgtgtgtctt tttcctgtgc tgaccttgct gcggaaaatt atgggcctga gtgtgactcc    52680
aggctgagtc ctgggtcc aacacgggat gccttgggc ctcttctgga dacgggatgt       52740
gagtgacagg agccggccgg ggcagcttgc cctgtgactg cacgtggcca cagcctgtga    52800
```

```
gggccggggg tgcttctcca cccacgtggc tgcccctcgg gtatgtcaag ggcttctggg    52860
gctcatcacg gggtcctaga gacagtggca gggtgcaccc ccgttggctg cccttacagt    52920
ttctgtgacc tgagggtggc atctgtgcag tcggcgcggt ctgtgcttct gtgggatcag    52980
ggttccctct gtttcctgcc tcagttgggg ctcaagcctc aggtgaggtg gccccggagc    53040
actcagaagg catcggcggt cctgtgggct gctttctgca ctcacgtttg ctgagtgctc    53100
agtgtgccag gactgaggac cctgaagctg ctcttgtatt tagggcggcg ctcccctggc    53160
agagactgag ccaggtggtc ccgcatgacc cactaccagg cgtttctggg ccctggccct    53220
tggagggaca gggtgggcgg aacatgggcc tgcagggagg ctcccgctta ctggaggcat    53280
gtgctgtgtt gctggagaca tcctctgtgt tgcttcttgt tcgctgtggt ttttggtctg    53340
gtggcaccaa ggaccctcag tcatcttgat gtgtggttgt ccaggccttt ttgttggtcc    53400
taagaagggg ctctgccttt gtgccccag gttccctgac aggagctgcc ggctcgtccc    53460
ggtgatgcct gcaggacgtg actctgggac gggggttgg gcagatgtgc tgatggaaat    53520
tctcaagcag gcgtcatttc cgaggtcctc acctggattt ccaggacagg agtgcctgct    53580
gggtgtcccc agtcccatgc agcggggtc cttgggatag catggaacgc tgagcatggg    53640
cctggccggc cgtggtcctg acaagggca gtgccccggt ggctgctggg cctgggacct    53700
ggtggggacg ctgggcctgg tacctggtgg ggatgctggg cctgggacct ggtggggagg    53760
cctctgactg cctcctggtg ctgcttccgt ctgtgttagg cctctgggta ttggggcccc    53820
catctgtctc ctcctccagg cctgtggact cagaccagga agacacaggc cagcccctgc    53880
ctgtccccct tggcttgggc tctcactgcc cgacctggcg ggaggttgcc tagccgtgaa    53940
ccttcgcacc ctgtctgcca ccggacaggc tgtgaggggg tgtctgcagc acctgcaccg    54000
gcctgagcat cttcagagtg ggctgcagct cctggagggg tctgagagga agggaggcag    54060
gtatttgggg cgaatgagga gacagctgga gagctggcac ccttcctggc ctgcgtcctg    54120
tgaggactct ggttggggac agcaagcttg gggtcagcct ggggcagagc ctctgggacg    54180
gccccgcccc tcgtgcccct tccctcgca gctcctgtcc tcgccccgcc ctcagctctc    54240
cgccaggcaa ggtttggcaa gtgccgctgt gcggcagtgc ctgctgattg gctggtctgt    54300
tgctatggtg ctgcccaggg gtgtgctttt cctcccctgc cttccctgct atccctggga    54360
gtatctgggg ttgggtcatc gctggtgtgt gtgagtgtgt gtgtgtgtgt atgtgcacgt    54420
gtgcatatgt gtgcgcttct ggcctctgca gctgagtcct ggcctcgggg gggcctggca    54480
cctcctgggg acaggcacaa agcagccatg atggagtcgg gagctggggg aggcccatt    54540 gccccacgtg gctgccctgt gactctgggg tgcttgttag aagaggtatc tggttctgtc    54600
tgtgtttaag caactcccta aggaattctt gtggttccag tttgggggc ctgtactgta    54660 gaggcaaggg aggggcagga catcccccag actctgactt ctgaagcctt ttctgcccgg    54720
ggcctctccg ccagtacagg cagtgtcctt tgccagggct gccatgctgc agaggggagt    54780
gggccactgt ttagcccagg aaaacctggc tctcccttag ctggaagttc tgggcctgtt    54840
gtggttggca gggaagctga gtgacggtgc taatcacagg ggcacctgca ggggtttgtg    54900
ggagatgcct ctgtgggttg gggcgatagg ctgaggggct gttcttccct gccctgagga    54960
gggctgagtg tagccgccac tcctgtcctg tcttgggctg tctcggagag gatgcgtaga    55020
accctcggga tcctgctggc ctccgtctgg tccaccctga acctcaggcc ttctgggggc    55080
agaggaggat tccctcagga tcactcgggt gggggcctct cttgggcacc tgagaccctc    55140
```

```
agtgggtgct tgtggcgcg ttcacggttg gtgggggacg cccagccctg cccgccgtgt    55200
aggagccgtt ctgtcctggg catcccctg tggtctggga cttagtggac cctgagggtg    55260
tgtgtttacc cctgcctcac acctgcagaa aaaagcctgg agcaggagct ggccagcccc    55320
atcctggaca ttgaggactt ggtcaagagc ggaagcaagc acaggtgaga cccctcagtg    55380
aggccacgac cactgtcctt ccatggccca gctctcctgt gacctgtgga ggcccggata    55440
tatttcttca cttttctttg ttccttttta aattatgaaa ctaaccacca ttcagtacga    55500
aaaagtttaa gcagctctga ggaagataga gtaaaaaatt gtctccctct tccctggccc    55560
tcagccatcc ccggtggcca ccgtggagtg tggacggagc cctgcaggcc tgtgtctgtg    55620
cggaagcacg cgcagttttg tctgcacaga ctgtcctgca gttggctgtt ttcactcagc    55680
gttgtgggta tagcttccca tgctggtgct ggcagctcgg ccttgttctt ttgaggacag    55740
cagatgtctc ctatgtctac ctcttacagc ttcagagatt caagttataa taaagctctt    55800
cttatattga gggggaaacc tccctccccc ttttttttga aacagggtct cgctctgcta    55860
cccaggctgc agtgcagtgt cacagtcttg gctcactgca gcctcagcct cccaggctca    55920
agcgattttc ccacctcagc ctcccaagta gccgggactg caggcacgca ccaccatgcc    55980
tggttaattt ttgtattttt tgtacagaca gggtctcact ctgttgctca ggccagtctc    56040
ctgagctcga gagttccacc tgccttggcc tcccaaagtg ctgggattac aggcgtgaga    56100
ccccatgcct ggccagctct tttttttttt tttttttttt ttgagacgga gtctcgctct    56160
gtcgcccagg ctggagtgca gtggtgcgat ctcggctcac tgcaagctcc gcctcccgag    56220
ttcacgccat tctcctgcct cagcctcccg agtagctggg actacaggtg cccgccacca    56280
cgtctggcta ttttctgta tttttagtag agacggggtt tcaccgtgtt agccaggatg    56340
gtctcgatct tctgaccttg tgatccgccc acctcggcct cccaaagtgc tgggattaca    56400
ggagtgagcc accgcgcccg gcccagctct gcttttctt agtggttctg cgttgtgttt    56460
gtttctatcc aggaataggg ttggttttac ttttccatcg agttttttaaa gagacgacga    56520 tttacatggt cggaaactca cgaggactcc ccatcccttg gtcggaaact cacatggact    56580 ccccatcccct tggtcagaaa ctcacgtgga ctcccatcca tcccaggcag cagcttccca    56640 cctgggcccct acgtgcagga tgagggctcc ttccgggtca gaagacatgg cggcctcggg    56700
gcaccgtccc ctgcatgggg tgctcacagg atcttctcct ctctccttcc cagggtgtgc    56760
ccttactacc tgtcccggaa cctgaagcag caagccgaca tcatattcat gccgtacaat    56820
tacttgttgg atgccaaggt gggggctcag tcctgtagct gacgactcct gatgtccagg    56880
ggtgtccctg ggcttgggaa cagctgtccg agcctttgct gcttcagggc cttagatcag    56940
caggcctggg tgggaggact cacctctgtc actgggcagg ggctcaacct ggccagacac    57000
acttgtgagc agccccaggc cacaggtcag ttttctgagc agtctgggag cgggcaggct    57060
ggtgggagtg aggagagacc tccaggctgt ggtccatagg ccagtgcccg ctcttgatcc    57120
tgacagctca ggttctctcc ttcacgtcag gccatgggag gcaccgagaa cacaggaagc    57180
ccactgactc ccctcttccc agcgcgtgcc cggcccaca ctcactcccc ctcccagcat    57240
gtgcccggct tcacactcac tccctcttc ccagtgcatg cccggcccca cactcactcc    57300
ccccacagca tgtgcccggc ctgacactca ctccctcct cccagtgtgt gcccagcccc    57360
actcccttcc gccccgtgtg cccagcccca cgctcactcc cccgccagc atgtgcccgg    57420 ccccacactc aactcccctc ctcccagtgt gtgcccggcc ctgctgccct cctccccatg    57480
tgccctgctt ttgtgcccca cacttttttac ttagtgcagg tgggatcaca cgccacgggt    57540
```

-continued

```
caatggtttg tgtgttcacg tgacgatggc gtggtgacgt ttccagatcc cgtcgttggt    57600
tcgctcattc tcgggtgta tatttattga gagctcatca tgctgggtgc tattccaggc    57660
atagcaagac tggcttcact cacatggagc tttgattcta gtggtgggga caggtggaca    57720
gcaaaagagt aagcacgtga gctgacgata ctgaagggaa atagagcaga gggaggaggc    57780
ggagaccgag ccaagcgggc ccaagtgcga tgtcggcggg aggtggggaa tgctggtggg    57840
tctgagggga gcctcagcag gtgcagcaga gcaagggaag aggtgagtgg gggcggctgg    57900
ggggccgact cctgggaagc tgtagcagaa ccccacagag agctggtgag gtttgccgtg    57960
gttgtgggtg actcggtgct tgagccctg gctgcccctg ggaaccatct ggagagcttc    58020
taacccaacc aggcccctcc ctgggacagt tatatcacag ctggtaagcc gagtctaaca    58080 cttttcacgga aacgcagaag atctaaaaca gcaagatgac cgtgaagaag aacagagctg    58140
gaggactcac ctcgctggtt tcaagactcc tctaaagctg caggagtgga ggtggagatg    58200
gcccagctca ggcacaggcc tgcaggccat ggagaaggca gcaagctcaa gctgacccac    58260
acgcatgtgg tcattgtttt ttttttcagt tggaatctca ctctgtcacc caggttggag    58320
tgcagtggca ccatctcggc tcactgcagc ccccgcccct aggttctagc gattctccca    58380
catcagcctc ccgagtagct gggattacag gcgtgcgcca ccatgcctgg cccttggtga    58440
ttgttttttg acaaacatgc caatttaatt gagagaggaa atgaaggttg atttctggtt    58500
ttctgaaaaa atggtgctaa gaacagctgg atatctgttc ggaaaacagt gaatcttaac    58560
tcttgtttta ccctgtataa acctaaatgt aaaagctaaa ctaaaagtta tagaaaggaa    58620
catgggggag gtcttttgcaa cttttgggta ggcagagatt tcttagtatg gatacacaag    58680
gcactagcca tgaagaaaaa cattaaaatt tagacttcac caaaatttaa agcttcaact    58740
ctgtggaaga gttgagaaaa tgaaaaagca gttaaagaaa gggagaaaat acttctttca    58800
aaggacttaa aaaatttttt cagccctcct ctgatttgaa aggacctttg accagagtat    58860
gtaaaattct cccataacta agcaaacaac ccacttaacc actgggaagg gatctggaca    58920
gacgtttcac caagatgggt ggaatggcca gttaaccact gggagagcat ccggacagac    58980
gtttcgccaa gatgggtgga atggccagtt aaccactggg agagcatccg gacagacgtt    59040
tcgccaagat gggtggaatg gccagttaac cactgggaga gcatccggac agacgtttcg    59100
ccaagatggg tggaatggcc agttaaccac tgggagagca tccggacaga cgtttcgcca    59160
agatgggtgg aatggccagt taaccactgg gagagcatcc ggacagacgt ttcgccaaga    59220
tgggtggaat ggccagttaa ccactgggag agcatccgga cagacgtttc gccaagatgg    59280
gtggaatggc cagttaacca ctgggagagc atccggacag acgtttcgcc aagatgggtg    59340
gaatggccag ttaaccactg ggagagcatc cggacagacg tttcgccaag atgggtggaa    59400
tggccagtta accactggga gagcatccgg acagacgttt cgccaagatg gtggaatgg    59460 ccagttaacc actgggagag catccggaca gacgtttcgc caagatgggt ggaatggcca    59520
gttaaccact gggagagcat ccggacagac gtttcaccaa ggtggatgga atgaccagtt    59580
gagcacatgg aaagtcgccc agcatctcca gtcataggag aaggcagatt aaagccacgg    59640
ggagccgaca ctgtggtccc actggcatgg ctgaaattca gaagccctga gtgtggcatg    59700
aggatgtgga acagctggat ctcatccatc gctgtgaagt tgtgtagcca ctccacaaac    59760
gtgtggcaaa cagccgagcc gggagaaggg aagacgtgtt caaagattca tatgtggcca    59820
ggctcagtgg ctcacgcctg taatcccaga actttagggg ccaaggctgg gggatcgctt    59880
```

-continued

```
aagcccagga gtttgagacc agcctaggca acatagggag accccatctc aaaaaaaaaa   59940
aaaaagaaaa aagaaaagac ttcagtgtgc aggtttacca gagttttgtt tgcagttgcc   60000
aaaactggga agcagcccgc gtgagcccat ccacaggtga atggacagac cgtggtaccc   60060
gaacactaac agcagccacg ggcgtggact gtggtcacac agcagcaggg agccgatgag   60120
tctcggacat gctaacccag agaggcccat tgaggaggac ctactgtttt ttgtgttttt   60180
gtttttgtt ttgaaatgga gtctcgctct gtggtgcagg ctggagtgca gtggtgtggt   60240
cttggctcac tgcagcttcc gcctcttggg ttcaaacagt tctcctgcct cagccttccg   60300
agtagctggg actacaggca cccgccacca cacccggcta atttttgtat tttcagtaga   60360
gacggcagtt cgccatgttg gccaggctgg tcccaaactc ctgaccttgt catccactca   60420
cttttggcctc ccaaagtgct gaggttgcag gcatgaacca ccgcacccgg ctggacctac   60480
tgttttattc catttatgtg acactctatt aatagaaaag gcaggggtgg ggctggtggt   60540
tatatggtgc acataactgc cagaactcag tacacttaaa atgaacatct taatgtgtga   60600
aattttttt tttgagacgg ggtcttgctc tgtcacccag gctagagtgc agtggtgcga   60660
tctccactca ctgcaagctc tgcctcctgg gttcacgcca ttctcctgcc tcagcctccc   60720
gagtagctgg gactacaggc gcccgccacc acgcctggct aattttttt ttttttttgt   60780
atttttagta gagacggggt ttcacagtgt tcgccaggct ggtctcgatc tcctgacctc   60840
gtgatccgcc tgcctcggcc tccgaaagtg ctgggcttgc aggcgtgagc caccatgccc   60900
ggccaatgtg tgaaaattta aaagtaccaa agctggaccc cacccagat tgctcccatg   60960
acactctgtg ggtgggacct gggagttggg ttttgttttg ttttgttttg tttttgagat   61020
gaagtctcac tctgtcgcct aggctggagt gcagtgacac aatctcggct cacattaacc   61080
tctgcctccc agatgaaagc gattctcctg cctcagcctt ctgagtagct gggattacag   61140
gcacacacca ccacccctg ctaatttttg tattttagt agagacgggg ttttaccatg   61200
ttggccaggc tggtcttgaa ctcctgacct cgtgatccgc ccgcctcggc ctcccaaagt   61260
gctgggatta caggcgtgag ccaccgcgcc tggctgggag ttgggtttgt aaatctccct   61320
gagtggggct ggggcaggga actgctgggt ctgggtcttc ctggctcctc tggtctgtgg   61380
cttcctgact gcggtggccg ggggctccca gggcatcgtg gccgtctgtc ttgctgagcg   61440
tggcacgtgc cttttccatgc tgtggaggag cgtctcccgg tatggcgaac tgctggttag   61500
ggtgggcgg tgttgccagg tcatccaggt ctggcctctg ctctcgacat cgccggcgct   61560
gttgctcatc tgcgcttgtg atgttcgatg cctgctgcac atgtcttggc ttccctcttt   61620
cccggcctct gtgagctcca gcgctgcgtc ccttctcttc ctcctgtaga gccgcagagc   61680
acacaacatt gacctgaagg ggacagtcgt gatctttgac gaagctcaca acgtggtgag   61740
tctccgctgg cctcctaaac acctcctatt gcttctggcc ttttgtcaa gagccacgca   61800
aaccttcctg gaggggctct ggccaaactc ctgaagccct aggtgcccag gactggggac   61860
tgagcacacc aggagcttct gccacccct cccgccctga tccgatgcct ctgctggggc   61920
tggagactgg ccagctgggc caggacctg cccgtcaggc gcagggcccc cacaggccgc   61980
tcaccagacc cttccctcc agccagctcg gggtcagcct gggccagggc tgtctcctct   62040
gccctcggca gcagcaggct tgtggtcttg cctgcagtgt ctctgccctt ccggccacat   62100
ggcttgagac tgaggcagga gaatcgcttg aaccttggag gcagaggctg cagtgagcca   62160
ggatcacacc actgcattcc agcctgggtg acaaagcggg attctgtgtc aaaaaaaaa   62220
atgttgactg ggcgcgctag ctcatgccta taatcccagc actttgggag gctgaggtgg   62280
```

```
gcggatcacg aggtcaagag atcaagacca tcctggccaa catagtgaaa caccgtctct   62340
actaaaaata caaaaaaatt agctgggcgt ggtggcgtgt gcctatagtc ccagctactc   62400
aggaggctga ggcaggagaa tcactcgaac ccaggaggta gaggttgcaa tgagccaaga   62460
tcacaccact gtactccagc ctggtgacag agcaagactc cgtctcaaaa aaataaaat    62520 caaaagaat aattggcaat tccagtgaaa taattgtttg tttgtttgtt gagacagggt    62580
ctccttctgt cgtccaggct ggagttcagt ggtatgatct tggcccactg caacctccac   62640
ctcctgggct caagccatcc tcccacctca gcctcccgag tagccgggac tacaggtgca   62700
caccaccacg cccggctaat ttttgtattt tttgtagagg cggggtttcc cagcgttgcc   62760
caggctggtc ttgaacccct gagctcaagt gatctgccca ccttggcctc ccaaagtgct   62820
gggattacag gtgtgagcca ccgcgcccgg cctgaaacaa tcgtttctaa atattggtgt   62880
gggccacaca gtcatgtttg gacctacttg tggccttta cagacccag gccaaggctt    62940 tgggaacttg gctgtcagcc tcctgtgcct tctgcacccc caccccattt ctgctttctg   63000 gaaccccga tcctgtcctg ttctgtggtg attcgggtgt gcttgggctc taggagaaga   63060
tgtgtgaaga atcggcatcc tttgacctga ctccccatga cctggcttca ggactggacg   63120
tcatagacca ggtgctggag gagcagacca aggcagcgca gcaggtgag ccccacccgg    63180 agttcagcgc ggactccccc agcccaggtg cgttcatagc cagactgctt ggtcctgagg   63240
cctgcgctgc tgcagggtga gccccacccg gagttcagca cggactcccc cagcccaggt   63300
gcgttcatag ccaggctgct tggtcctgag gcccgtgcta ctgcagtggg cagcctgccc   63360
tgtggctgtg tgtggtcggc ctgggcacca tctattcagg ctggcactgc agggcatccg   63420
cttctctcag aggcttcttg ggtgtgaatt cttcagggtc ctgtagcctg tggaagggct   63480
ggtattgttc agtagttctg gtattttcca aagacctatg tcttctccca gccagtatca   63540
acttggcctc tactgtgtaa aactggaaaa ctctactttg tgaagctgag ttgggagcat   63600
cgcttgaggc caggagtttg agaccagcct gggcaacatg gcggaacctc gcccctgcca   63660
aaaaattagc caggtgtggt ggtgtgctcc tgtggtccaa gcttttctgg aggccgaagt   63720
gggaggcgtg cttgagcctg ggaggcagag cttccggtgc cccagatgac tccactgcac   63780
tccagcctgg gcggcagagt gaggccatct caaaaaaaa aaaaggaaa actaaatata    63840 ttcactgtaa gggcatttg catctttaaa tgacccacaa atctggcatg catcagctgc   63900
tctgcctgta ggttccttcc cagtgtttgt ccagaggtgt atttccacac agcgctagtc   63960
acggcatatg tggaaaacgt ggaaacccct catggatgtt gtcagttggt ctatattttc   64020
tttctttttt ttttttttga gatggagttt cacttttgtt gcccaggctg gagtgcaatg   64080
gcgcgatctt ggctcactgc aacctccgcc tcctgggttc aagcaattct cctgcctcag   64140
cctcccaagt agctgggatc acaggcgtgc accaccacgc ccagctaatt ttgtattttt   64200
agtagagatg gtttctccgt gttggccagg ctggtctcga actcctgacc tcacgtgatc   64260
cacccgcttc ggcctcccaa agtgctggga ttacaggcgt gagccgccac gcccggcctt   64320
tgtccatatt ttctacatgg cttctgtaaa cagctgacta ggagtctgtg tgaatatctt   64380
cataggttct gctgtgacac tacttgctcg tgagcatctc caggtgtaaa cagcatcagc   64440 ttccccatt ttcctttaaa atcgcacatg tggacggaca ccacgggac cctggaccct    64500 ggggagcccc gtcctcaccc ttctcaccag gatggctgct tggtagagag tgagtttgca   64560
aagttggcat ttgtttagta cagaagttat caggtgttct ggctttagaa tccctttata   64620
```

-continued

```
tatatatata tatacatata tttaagtgac agggtctcac tctgttgccc aggctggaat    64680
gtggtggtac aatcaaagtt ccctgtagcc tcggcctcct gggctcatgg gatcttcccg    64740
tctcagcgtc ttaaagcgcc gggaccacag gtgtgcacca ctgccaccgg ctctcaagat    64800
tgccacgcag ggagttgcag tgggggaagg ggttcctggg actttgaacg ctccacctcc    64860
ctcctctcca cagtccccca accccacctc tctaacgggg tggacggccg cctctttcca    64920
tccttcgctt ggcgcagggt ggggagagtg acaggtctcc ttccctcatc tcggcagctg    64980
ccatttcatc gcttacataa cgtgggagaa acatccaccc accccaggc ctgtgtgaac     65040 atcaccacgg ggccttctcc actcttcagt tttgttagtt acttgatgtg cagggctttt    65100
tgttgtaact agtgggggac gtgtggtggg gtgggcttct gccatctcat tcaggaccag    65160
aacttcagtt ttcatcccta tctgttcccc cacccctttg gagatggggt ctcactctgt    65220
cacccaggct ggagagcggt ggtgccatca cggctcactg cagcctccac ctcctgcagc    65280
ctccacctct tgggctcaag tgatcctcct gcctcggcct cccaagctcc tgggactaca    65340
ggcgtgtgcc actgtgcttg gcagggtcca ttcttttcct cacactttat ttattgaaga    65400 gcccaggcc tttaccctgc agagtcggaa tctgtacagg aggggcagcc acacgagttc     65460
cccggtttac tctgaactta ggtggcttga gggccccagt tagactgcgg ccaccgtttg    65520
ccgggctcca gatgggacgt cctttctatc agaaggctca cagtatctcc tttcccgttt    65580
cttcccatgt gaacattgtt gctgctgaac acctgaatat gttaatcact ggggcttgc     65640 aagatggcag tgtgctaatt ccatcatcta gtcagttagc aggaataact taggaccacg    65700
ccctgcacca tatcagctat gtggtgatcc cattcacaca ggaaaggtgg gacaaatgct    65760
gggggtgggc cgggtgtgct gtctcacacc tgtcatccca gcactttggg aggcccaggc    65820
aggcggatca cgaggtcaga gattgagacc atcctggcca acacggtgaa accccgtctc    65880
tactaaaaat acaaaaaaat tagccaggtg tggtggtgca tgcttgtaat cccagctact    65940
tgggaggctg aggcaggaga atcacttgaa cccaggaggc ggaggttgca gtgagccgag    66000
atcgcaccat tgcactccag cctgggcaaca gagcgagact ccgtctcaaa aatcaatcag   66060
tcaatcaagt gtcatcactg aatgtttgtg tgtgaacgtg gggattggtc ctgccccatg    66120
ctccctcctg aatctcactc ctgacctcag ttgctgcacc ttgaggtgtt ttctgtgggc    66180
tcttgtgtcc tgaccccggc ggttgtggcc tctgctgtct gggagtcagg attttttcaca   66240 ctcatgtcct gctccagacc tggaatcagc caagtctcca agaagccctg ctttctttc     66300 ctgcaagacg gtatttcaag acccgccgtg cggcagcggg ttggtcatgg ttactgggtt    66360
ggtcgttgtg actgggtgtt ttcgtggaga tacagccata cgcacaggtg tgttcacaaa    66420
tgttaattct aaaggtcaaa cacccggcca ggcataaggg ctcagcggta atcccagcac    66480
tttgggagac caagactggt ggatcacctg aggtcaggag tttaagacca gcctgagcaa    66540
cagggtgaaa ccccatctct actaaaaatg cgaaaattag ccgggcatgg tggcgcacac    66600
ctatagtccc agctagtcgg gagacagaca cgagaattgc ttgaacctgg gacatggagg    66660
ttgcagtgag cagagatggc gctgctgcac ccctgcctgg gtgacagagt gacaccctgt    66720
ctcaaaaatg aatagataaa taaagataaa acacctgctc ctcttggtgt ctccagtttg    66780
gatttggcct gtgtagcctc ttccttcgcc tgttggtgga tttggcctgc acggattctg    66840
tgtggcctct tccttcccct gttggtggat ttggcctgca cggattctgt gtggcctctt    66900
ccttcccctg ttggtggatt tggcctgcac ggattctgtg tggcctcttc cttccctgt    66960 tggtggattt ggcctgcacg gattctgtgt ggcctcttcc ttcccctgtt ggtggatttg    67020
```

```
gcctgcacgg attctgtgtg gcctcttcct tccctgttg gtggatttgg cctgcacgga    67080
ttctgtgtgg cctcttcctt cccatgttgg tggatttggc ctgcatggat tctgtgtggc    67140
ctcttccttt ccatgttggt gtccttttt ccatgccagg aatcctggtt ctcaagggcg    67200
gggttgttgg cacgagcgtg atgcagactg cctttgctgc ctttctcttg cccagggctg    67260
aacatggagc tggaagacat tgcaaagctg aagagtaagt gttgccctcc ccgcctcctt    67320
gcagctgggt ggggcctcct ccttgcgagg aggtgggtga cacctcctcg acccacagtg    67380
atcctgctgc gcctggaggg ggccatcgat gctgttgagc tgcctggaga cgacagcggt    67440
gtcaccaagc cagggaggtg agaggcgggg agccagcccc ttcactgcag gcccagccta    67500
gagctagaaa cgggccatgg tgcagtcctg ggctgtcaca tcacgagtga ggcctgtttt    67560
caggcctgtt ttccctttt gagacctggg aggagcacct gctttgcatg atctggttgc    67620
tgagatgttg agaggagcag cacacactcc cacgggacag cacacagccc cccacggaac    67680
ggcacacaca cccatggaac agcacacaca ctcccacgaa cagcacacac actcccacga    67740
acagcacaca cactcccacg gaacagcaca cacccacg gaacggcaca cacccacg       67800 gaacagcaca cacactccca cggaacagca cacacaccca cggaacggca cactccca     67860 cggaacagca cactcccca cggaacagca cactcccca cggaacagca cacacactcc     67920
cacggaacag cacacacacc cacggaacgg cacacactcc cacggaacag cagactctcc    67980
cacggaacag cacacacact cccacagaca gcacacacac acccacggaa cagcacactc    68040
tcccacgcgg ggccgctggg tttcctgcag tttctcctcc tccaggcctt tccctggacc    68100
ctggtccagt ccgtcatttg agcacaggtg cctgttagaa cgagaccttc ttgttaggac    68160
gatgagtgtc ccagccacca cctcttttgg actccgggag gcctggaacg ttctgaacgc    68220
tccgtggggc tccagtcttc tccgcagcca gggcagcagg gtttgctgtc tgtcctgcag    68280
gcagatgagg agtcagggct ggggcctgtg tggggctct cctgagcgcg cagccgccga    68340
ggtggagcgt gttctgcctg agcgccgacc tggtcggggg aatcccagtt gcttccaggt    68400
ggagccactg tcctcagcgt aatgctcaag gctctggcct ggctcctcgg ccaccctgca    68460
ccctcagggt cccctcctgt agcttctgct gccccatcac tgtcactctc caaagctttg    68520
gggactctgc ccagagccac cgcctcccag aagccctga caacctcttg acgaccccct    68580
agtgacccca tcctccct ctgacggcgg ccctgctct gaggcggctt cttttcctcg    68640
gtgctgttct cgtgctggcc aggcctcctc tccccacctg gaggcctg agggcggagg    68700 cctctcacct ccaatgctgg cgtcccctgg agggctgaat ttgttccga gggaaggaaa    68760 cttccacagt tgttgccttc agttccaaag ctgcagcctg atttcccct ccaggctcga    68820 gcctgttttc ttctcggcag ctacatcttt gaccagtgtc gtcccccctc aggcccgagc    68880
ctgccttctt ctcctcagtt cccaaagctg cagtctggtc cccccgccag gctcgagcct    68940
gccttcttct cctcggcagc tacatctttg agctgtttgc tgaagcccag atcacgtttc    69000
agaccaaggg ctgcatcctg gactcgctgg accagatcat ccagcacctg caggacgtg    69060 agtgctggca cggggtcttt ggtgcgggca aatgtggcgt aggggtgca gcaggcctcc    69120 atcttggcag tcagggctcc cctggccgtc acctggccgt cagcaggaac aggcccacag    69180
aacctcatct tctgatcggg gcgtggaggc gttagtgcca cttgccagct gccgtagagc    69240
ctgtcccagt tctgcagctg gcggcttcgt cctacagcct catcccatta ttctgctttt    69300
gagaaagagc agcccaaggc cctagctggc ttgtggggcc tctggcttct ccacaccacc    69360
```

-continued

```
ccgagttctg cttctcagag ttgtggggtc cagaggcttt gcccagaggc ggtgtcccca    69420
tgggctgctc tggtttgaga cgccgggccc agcggggtct ctcctctgct gcgctcccgg    69480
gtgctgggga gggtggcttt tgctgcttca acccttaggc gaccatagag cctcttttca    69540
agtcccactg accccttgg agactctgtc cctgcctggc ttctctcctg gctgctggga     69600
agagcaggcg aactgcccgc cctgaatgga tgctgcgctc caccctgggc cccccattgg    69660
gcaggagatg gagcttggca gtcgggctga gcgggctcat gctggaaggg ccggggctgg    69720
ggtcggggcc tcccctgcct gcagtgtggg tgtcagcgcc ctgctgccct ccaggtgctg    69780
gagtgttcac caacacggcc ggactgcaga agctggcgga cattatccag gtggggcctg    69840
ctcctctgtg gcatctcctt ccctgatgga agccgggcgg gtgccttctc ctgctgtatt    69900
agttaactga ttctagactt ggggatggga gaaaggcccc tacaccacct gtttctgatt    69960
ggcaaactct cggctccttt ccagtgccct aaacccacac tgggcctcct gcagggatgg    70020
gggaggacga ggtctggtgg cacatgccca gggtgatgct ggtgagggag gacgcaaagg    70080
acagtggggg ccggggagcc gctcctgccc tgtccgggcc ctcaggccag gggggaccca    70140
ctgctggcag cccagcagc cccagctgca cgcagatgaa gagctctgga cacacgcggc     70200
ttcctgaaca gcttctccag ggacagacaa atggggaccc tgcaggttcc cggcaggggt    70260
gtccctggga gcccatgatt gggggtgcga ccctggcccc cttctcattg gccccgtcct    70320
gtcctgcaat gcccgtccca tgtgaggtct gcttctggct ccatgcctat ggcagcacct    70380
gctttccctg gcgtagaggt gcttgtccgg tttgtggagg gcacgcccca ttttgggtgc    70440
tctgggcacg ttgcctctcc ggggcctcgg tggcttttt agaagcagac tcagaagtcc     70500
ctgactgggg aagccaaggc acaggtggct gtgtggagcc ctgtgaggcc tcctctgtgc    70560
tgcccacgct gtacctgctg gccacacgag atcatggcag ggttaggcag ggctgcccag    70620
cgctatgaca gcttcatgag tgtccatctg gcctgtgggg tgcttgagct gggggaggcc    70680
gcagaagaac cctgggatgc atggctggcc tgtgcatgct gctgggcatg gagctgcaga    70740
tcccggaaca gcaggcact gccttctcct tcacagacgc agctctgagc gggggcgaga     70800
cctgggcagg gaccaggtgg ggtgggcaca gggtggtggg gcccaggctc agccctccct    70860
ccactgtggc cgtctctgtg gccagtgacg ccacagcctg tgtcttctct gtgcggtagc    70920
tggggctgga aggacagcac tgccttgtcc tcccaactcc tccccaaagg cacggtgggc    70980
atcccaggcc cagacccctc tgtctgtggc tcctgcctgc caagggctgc tgtgctgtcc    71040
cgcatggagt gtggttggct cttcaagcag gaggccgtgc acctatcagg cggacctgct    71100
tccatgtccc tgatgggtca ctgcaaagca cctccagcac atggccaggc gaggtagccc    71160
tgcagcccag ggcctggagg gcaggtgtga gctggcccgg gcctgtccct ccctggaata    71220
cagcttccca ggctcccact tatgagaag tctcctccac actatggaac tgaatcctag     71280
aatgtggctt ctgaggttcc tacactcgaa ctgaatcctg gaatgcggct tccaaggctt    71340
ccagctatgg agaagactcc acactctgga accgaatcct ggaacgcggc ctcccaggcc    71400
cccagctatg agaagactc cacactctgg aaccgaatcc tggaacgcgg cctcccaggc     71460
ccccagctat ggagaagact ccacactctg gaaccggatc ctggaacgcg gcctcccagc    71520
ctcccactta aggagaagtc tccacactct ggaaccggat cctggaacgt ggcctcccag    71580
gcccccactt aaggagaaga ctccacactc tggaaccgaa tcctgcacac tccatcggtt    71640
tggaatttcc tttggctgct gctctaagta gccgctggtg gatgactcag cttctgccag    71700
ccctcggggtg cctggaggat gagggactgc acacagtgct cacccgcgtt ggctcctgag   71760
```

-continued

```
cccctgcagg tgtgggcggt gcccataggg ctggtgctgg gttgggcctg cagccctgag    71820
tcacaggtga ccctgggggc agagtggggc cagtggcccc aggaagagga tgtgggatgc    71880
acagctcagc tggaggcgaa ctccaggcag ggtcaggccg tgtgctcgga agtcagggct    71940
tagctggagg caaactctgg gcagtgctgg cccgtgttgg ggaaccagtt gcccctgggc    72000
ccccgtgaga ctgctgggtc ctcatccctc tctgcctgag gccggagctg ccctgggctg    72060
aggcacaggg ggatttgtgg tggtgttttt ttgagaaagg gtctcgcttt gtcacccggg    72120
ctggagtgca ggggcttgat cacagctcac tgcagcctca acctcctggg cccaagtgat    72180
cctcttgcct cagccacccg aggagctgtg aacacaggtg tgcaccaccg cactcagcta    72240 attttttaaaa ttttttttgta gagatgaggt cttgccatgt tcccaggct ggtctcaaac    72300 tcctgggctc aggcagtctg cccgccttgg cctcccaaag tgctgggatt acaggcaaga    72360
gcttccatgc ctgcccagca gaaggctttt cgaaggaagc tgtttcctga ggcagactca    72420
gccctgctca tggcagccac cagcgtgggg gtgaacttgt tctgttactt ccatccccgt    72480
gggccaaatg ctttggtaaa acacaaggcc ctgtgtttag ctgtcttgac agtgaaaatg    72540
gctgggaagg aaggaaggaa cggaaggaaa tttctctctc cttctgtgcg tacccaggca    72600
cgtgcacatg catgcagagt acgcacacac gcacgcacgc ctgcacaaat ccacgcatgt    72660
tgccaagtct ctgtgttcca gccgtggtgt ctgcccccg tgttctcta gttcggcttc    72720 tccgcatttc tgtgaatgat tccggcttct tggtgttccc agcagaactc cctcaagtct    72780
gcggcggggc tctgacggcg gtggcttggc tgacatggcc acattgctga gcctgttggg    72840
ggctttgcgt tcctgttctg gccgttttg gctcgttttc caggaacggt cgtcacgcgc    72900
tcctctccta gtgcaggcat cattcctttc ccattgattt gcagggttct ctgtaagttc    72960
tgaggatccc atatacatat actctctgta agttctgagg atcccatata catattctct    73020
ctctaagttc tgaggatccc atatacatat tctctctcta agttctgagg atcccatgcc    73080
gacatacata ttcttttcctt gtctcatgct ggtcattttt tccattttca tgacaggttt    73140
ggtgaacaca tgtttccttg tcagatttt gttctgagct tgtgcctccc gaccaagatg    73200
ctaaaccggg tcttgtgtat tctccaaact gcactgtaga gtgacggagc tttgtgtctg    73260
ggcctccatg ccttctgacg tcacctgtgg gggtgtgaaa gcagactct accttgattt    73320 ttcccagcac gccacaccgg tggttctgtg cgctgaccga gcggctcggc ttcccccaac    73380
tccactgggc acctgccaca cttttcctca tgttttgtt cactgtggtt ttgtcgtaag    73440
tcctggtgtt ggcctgaacc aatttctttt tgtttgtttt tgagacagag ttttgctctt    73500
gttgcccagg ctggagtgca gtggcgcgat ctcggctcac tgcaagctcc gcctcccggg    73560
ttcacgccat tctcctgcct cagcctccca aatacctggg attataggca cctgccacca    73620
cgcctggcta ttttttgta tttttagtag agacgaggtt tcaccgtgtt agccaggatg    73680
gtctcgatct cctgacctcg tgatccgcct cccaaagtgc tgggattaca ggcatgagcc    73740
accgtgccca gcctgatatt tttagtagaa atgggttttt gccatgttgg ccaggctggt    73800
ctcgaactcc tgacctcagg tgatcctctc accttggcct cccagagtgc tgggattacg    73860
ggtgtgagcc accacgcccg gcctcttgtt cttttgaaac ctgccctgac gttttttcca    73920
tagtgcatct tggagtcagc gtgtctactt cctgtaaaaa tcttactgtg attttgacta    73980
gaatgtgttg aattcctgtt tttttttga gtcagggtct ctctgttgcc caggctggag    74040
tgcagtggga ccatcacagc tcactgcagc ctcaacctcc tgggctcagg ggatcctctc    74100
```

-continued

```
agctcaacct cccaagtagc tgggaccaca ggcacatgcc accatgcccg gctaggtttt   74160
tttttttttt tttttggtga cacccctggg gttgcaccat gttgcccagg ctggtctcga   74220
actcctgggt tcgggcagtt tgctcctctc agcctcccgg agtgctggga ttacaggcct   74280
gagccactgc actaggccat gttgaatttc tagattaatt tggggccctc aggggcacag   74340
agaggagggc tgggccagtt ggcgggagga gaggcccctc gggctgccgc attttcagtg   74400
catggagatg gcctatgttg ggggaacaca gagctcaccg ggggtccctg cagggaggag   74460
aaagggtcag gcaggtgcca gctcctgtcc attggcctgg ggctgcatga tggcaggggc   74520
cggtgaaccg atgaccctg ggtgtcctgt gaccttctgt gtatgcggct gatgctgcag   74580
aaagtcgggt ggcctcaggc tcctgacggg gctgcacttc ctctgccttt cagattgtgt   74640
tcagtgtgga cccctccgag ggcagccctg gttcccagc agggctgggg gccttacagt   74700
cctataaggt aggggccacc tccaggaggc aggtggaggg cagcccttgt tccccggcag   74760
ggctgggggc cttacagtcc tataaggtgg gggccacctc caggaggcag gtggggctgg   74820
gggtcttctg gtcctaaaag gtaaggggct gcccccagga catgggcggg gcctccacac   74880
tcctggtcct gtcccctcca ggtgcacatc catcctgatg ctggtcaccg gaggacggct   74940
cagcggtctg atgcctggag caccactgca gccagaaagc gaggtacaga cctgggccca   75000
cacgctcccc gcccgcccgg gtgcagtgcc cggcaccacc atgccacagg ctaggcacat   75060
gcccagccgt ggatctcctg ccccatgggg cctggccacc ttctccatat ccaggccaat   75120
ccagagcatt ctcctcactg tccctctgaa gattggagtt actgagagac gtaggagatg   75180
gcctgatggc accgtgacct gcccagagtc acctggttgg tggtggcaga gccacagccc   75240
agccaggcct ccctgctggg acacgctcgt ttatgccgag gccgtcagca cagagcctcc   75300
acagtgaggc acggctctgc ctgctgcctc cacgcagcgc ctggccgggc caagcctcag   75360
ggtcacatct gaaggggggcc cggctggccc tgttgtccga agcccctggt gcgctcagcc   75420
ccgaggcccc acgtgccttc ttggcttcct gtgctccgtg gcgtcttcga gtcggtgctg   75480
ccggggacgc tgtgtggatg gggtctgtga gtgtgccctc ggctccgtgt ccggagccct   75540
gtggttcttg gggtgtatct ggccccaccc ccactgcgtg gtgtccaggg tggggcttca   75600
cggctgcagc tgcgggagct gctgcccctg ccttgtgctc cagtggggcc ttgcctctgg   75660
gcttggttcg tccctctctg gaacattctt tctcagctgc tgtccgaccc atggtggcat   75720
gacgtggccc tggctgaagc agcccttgtg cggttgctgt ggttgggtct gcctggccga   75780
gccggaaggg aagggctggg agggcgtcag ggtggcgtgg cttgaccccc gctcggtgat   75840
ggtcctgcag caaggcctct cccagcagga agcgtccatc ccgggggggag gccggcgccc   75900 ctcacgcagt tggggttgcg ggaggcagtg cgtgcctgag gcagccggtg cacagattcc   75960
aagggcctgg aatctgtttg ttccattgac ctctgatgtc acttgacttc tcagaagcag   76020
ccactccctg cactgggcgt tgtaggaaa tgagctcctg gaggagggg tggggaagtt   76080 cccccattgc agggcacact cagccccagg aaggaaacgt gcctcgtccc tgctgactcc   76140
gaatcgcagt cagagtcgtt ctgcttgtgc cgtgttgaat tcccggcatc cggcatccag   76200
actcagcctc ctccccaggc cacggccgcc gtggccagtc ggtcaagccc ttctaggaac   76260
ttcctttgag ctggcgccct tgttcactgc tgacgccact cagaggcttg tgcacgtgtc   76320
ctgcttccag gcagagctgg gaactcgcac cccgtcttct gcacgcggcc gtggaatgtc   76380
gggatgccgc cgcttccttc ccgtgtgctc ttggcgtggt gggcttcttg ccctgagccg   76440
catgtcacag tttctgcaga agtttagggt tggagtgggc tgacctctct gcaggtgtcc   76500
```

-continued

| | |
|---|---|
| ccagcctctg cctgggtct gcctcctact cccaggaccc cctgtccccc agaggggccc | 76560 |
| caagctggca ggctcacact cagggcagcc tcctttgttc tgacttctgc acagtgggcc | 76620 |
| tgggtggctg cccgcggctc gcttgcttga tgccagtggg tggagagggt gatgggcaga | 76680 |
| gaggcaggtg gtcaggcccc cagtcccgtc ctcacactct gtgccctctg ccgcccccg | 76740 |
| ccccacaggg aaggtgctga gctactggtg cttcagtccc ggccacagca tgcacgagct | 76800 |
| ggtccgccag ggcgtccgct ccctcatcct taccagcggc acgctggccc cggtgtcctc | 76860 |
| ctttgctctg gagatgcaga gtacggggcc acccctgcca gggcctgagc accggtgaca | 76920 |
| cctctgacat cagcggggtg gaagtggtgg gggtccccat gagccgggtg ctgggggtct | 76980 |
| cgggcctcga gggctaaagg ggtgctggtg cacttcccca ctgtctgctc cctctggcca | 77040 |
| cgctcagccc tttcccagtc tgcctggaga acccacacat catcgacaag caccagatct | 77100 |
| gggtgggggt cgtccccaga ggccccgatg agcccagtt gagctccgcg tttgacagac | 77160 |
| ggtgagggcc tgtccctggg ccctgctggg gtgggaggtg ggggagcact gaggcctgag | 77220 |
| gccctgagca gtggcctctc cggctctagg ttttccgagg agtgcttatc ctccctgggg | 77280 |
| aaggctctgg gtgagtgccc tgaatgcccc agctgtgcgc atcctggatc ctggacccct | 77340 |
| gctcccaaga gctggtaggg acccctgcag acatcctgcc cctgccttga ccccggcccc | 77400 |
| tgcacttcca ggcaacatcg cccgcgtggt gccctatggg ctcctgatct tcttccttc | 77460 |
| ctatcctgtc atggagaaga gcctggagtt ctggcgggtg cgtctcccct gtgttctggg | 77520 |
| cggggtgggt gagggcaggg ctggagcatg aagcaggcag tggtcacagc tcctgcttgc | 77580 |
| cctcatcgga tcggcggcgt gaccagggct gccgtgtccc tgcctcttcc tcccacaggc | 77640 |
| ccgcgacttg gccaggaaga tggaggcgct gaagccgctg tttgtggagc ccaggagcaa | 77700 |
| aggcagcttc tccgaggtcg gcacttggcc ggggctctgg gcctgctgcc ccctcgtgcc | 77760 |
| tcccctgcct ctcacagctt ccccaaggct gaccactggc cctgaccatg gctccggcg | 77820 |
| gctcccgctg cctcttcagg gctcctgcgt ttccttcctg gccctgagtg ttgcctctta | 77880 |
| tcttacaaag ccccccagcac cgggtgggtg tggtaacagt ggccctcctg tctgagtagc | 77940 |
| cctagtcggc caccctggcc ctggggttcc ccgtgttttc tgggaagcac tgagcaggcg | 78000 |
| tggggtcagc ctgggatccg tgccaggaag aagcttccag aacccgattg gccttcctgg | 78060 |
| ctaggacgat ccttcatctt ggagcatgag acctgggtct ccctcatggg ggaggaaggg | 78120 |
| gctgggggg ggctccaggc tcagcctcac caactttcct tccagaccat cagtgcttac | 78180 |
| tatgcaaggg ttgccgcccc tgggtccacc ggcgccacct tcctggcggt ctgccgggc | 78240 |
| aaggtgagct ctccagggcc ctctgccctg acctggttgc ctgttccctg gtgggtgctt | 78300 |
| atggctcccc agcagactct gggccctggg ggctgcccgg tccctccttt gggtcccacg | 78360 |
| agagcgactg ctgccctgc tgggagcgtg tcctgctctg gcctgggca ggcaggatgg | 78420 |
| gagtttcctg gccacaagag ttggaggtgg cgtctgggag ctgtggaccc caagtgggt | 78480 |
| cctgacccac agatggagct tcctcccacc cctggttggg gacggagcct cggggaaggt | 78540 |
| ggctgggctg ggtgtgggca ccagggagag gagcccccac ggcccaggc agctccctgg | 78600 |
| tgtgtccct aggccagcga ggggctggac ttctcagaca cgaatggccg tggtgtgatt | 78660 |
| gtcacgggcc tcccgtaccc cccacgcatg gacccccggg ttgtcctcaa gatgcagttc | 78720 |
| ctggatgaga tgaagggcca gggtggggct ggggccagg tgagttacag cagggtgggg | 78780 |
| ctggggtaag gcggtctggt gactgagccc ccgccccgtg gccaagggag ccccgtgac | 78840 |

```
cgagccgcct cgccccacag ttcctctctg ggcaggagtg gtaccggcag caggcgtcca    78900
gggctgtgaa ccaggccatc gggcgagtga tccggcaccg ccaggactac ggagctgtct    78960
tcctctgtga ccacaggtgc gtgcagtccg gtggcaggcg cggcgccagg ggacacgccc    79020
acccccact gggccctgg actctccttc cccacatgag gccccgtctc ctccagagcc      79080
tctccggcta ctcggggtca gcgtggggcc cctgcagcag atgagggtct tcacttcggt    79140
gaactgaacc cttgaagcgg ctgtgggcag ggcagcaggg ctatggccac ccccaggtt     79200
cgcctttgcc gacgcaagag cccaactgcc ctcctgggtg cgtccccacg tcagggtgta    79260
tgacaacttt ggccatgtca tccgagacgt ggcccagttc ttccgtgttg ccgagcgaac    79320
tgtgagttcc tgcccaggga ggggatgagg gtgttgtccc cagaggagcc agaaatgggt    79380
ccacccaccc ccatggttct gcagatgcca gcgccggccc cccgggctac agcacccagt    79440
gtgcgtggag aagatgctgt cagcgaggcc aagtcgcctg gccccttctt ctccaccagg    79500
aaagctaaga gtctggacct gcatgtccc agcctgaagc agaggtcctc aggtgcggac      79560
gggcagcgct gggtgggcgg tgtgggggtg gcggagcggg cggcgtgggg cgggcagcac    79620
caggcgccca gggcggaggc gactcacctg gctttgtgcg cttcccctcc cacctccaaa    79680
ggctgcctct ccctcctagg gcagggcccc cacgggctgc aaccctcccc tacaggcaga    79740
gaacgcccca ggcaaggatg ccccccgagg ctgagactcc cccaatagc agggaggaca     79800
cccacaggca ggaccccaag tgctgggact ctccccaag aggggctttg ccacaggcag      79860
ggaccccagc tggggccccc cgtgggcttc actgcgcact cgggtgcccc tgcagggtca    79920
ccagctgccg ggaccccga gagtagcctg tgtgtggagt atgagcagga gccagttcct      79980
gcccggcaga ggcccagggg gctgctggcc gccctggagc acagcgaaca gcgggcgggg    80040
agccctggcg aggagcaggt acagttccag ggccttggga tggacacaga ccctctgtct    80100
cctgaggcca acccgacccc gcccatctgg cctcaggcac ctccccacac acccctgtaa    80160
atccctgcc tggcaggcag gcgggcaagc gggcgggga tcccagctgc ctggctgtct      80220
gtgggtcctc caccccacct cacccacagg ctgctggctc ccaggtggtg catgcccctgg   80280
ccctccgcgg gtgccccca catcactttg gttctctggc gggtcagctt ggctcagtgc     80340
actcaaggtc gggtgcccct gccactggct gcgcttgagg ctggcctttc tccaggaatg    80400
tgctgcgggt ggaacccagg ttccttcttc cttggggcct tttgccccag aagcccataa    80460
ttcctcaggc caacccgaaa ttttctccct gcttcctgct gggagccatt ccctcttcc     80520
tgcccatccc tgcccttcag gccctggag tgagctccag gtgcaggcac caggcacctg      80580
tgtccccttc ctgccagccc ctcgctgtgg tcggactgtc ttccctggac ctgctcttac    80640
aagtcaccac ctgcgagcct catgagccgc tggtgtgact tggacaggac caagttgtgg    80700
cactgtcacc ggggtgtgct gtgccccct cccccgacct ccatcttggc tcagggctcc     80760
ttgggaccat cttccctgtg cgtccaggtg ctttgggacc ccagagtgtg tggttggggt    80820
ctgtgtgtgg ttgtgagctg tgtcctcctc aggcccacag ctgctccacc ctgtccctcc    80880
tgtctgagaa gaggccggca gaagaaccgc gaggagggag gaagaagatc cggctggtca    80940
gccaccgt gcgtgagctg tccctgcacc tgtgccgacc accatagaca cgcatgggaa      81000
cgcagccgtg ggtgccccca gccacggctg gtccgatgg gaccagggaa tccaccccca     81060
ggagctgatg tccagggcag ctgtgatgct gacggccagg ggctcaagtg tgtggtttct    81120
tctgcagggg gctcatgagt cccagctgga atcaggcccc acccttgggc aggtttggca    81180
tggggcctgc agcactgggc ttggccctgg catttccctc aagtgtggat gcacacctgc    81240
```

-continued

```
ctcatgtgag ggacacagcc cattcctagc cttggatcaa agaacggagt tatagccgga    81300
gccaggaagc cccctgcctg ctggaaaacc ccaagtgtgg cggcctttgt ccatgtccct    81360
tggcttctgg gaagaactgg gtggtgccca ggcagggctg gtgccatcag gaagtgggtg    81420
gctgctgagg ggcctgggct ggcgagggcc tgggtgggga gtgcctgggc cgcccctgcc    81480
ttggtttcca cgtttccgtg ttggtctggg gtgtgtagag agatgggcac tgctcatccg    81540
gaagcccctc cttgtgcgct gccatcctgg gagcctcagc cgcatccgct gtggggcagg    81600
gggcttgagg gaggaggaga gagacgggcc atgcaggacc cctggcttga ggcagagcca    81660
atctacccTt tgcccattca ctgctctcag ttccctgcca gcctctcact gtgtgacctc    81720
agacgggccc agcccacag ctttcttccc gcagcccctc cctatgtcca tccagccagc    81780
cagtttctca ggcagcagcc ccacctcggc agtcactgtc ccagggaacg ctcaatgttc    81840
caaggaaggc tctgcagccc cagggaccag atgatgaggc tggccctgat ggagcctcgg    81900
gcctgtgtcc tgcaggagga gcccgtggct ggtgcacaga cggacagggc caagctcttc    81960
atggtggccg tgaagcagga gttgagccaa gccaactttg ccaccttcac ccaggccctg    82020
caggactaca agggttccga tgacttcgcc gccctggccg cctgtctcgg ccccctcttt    82080
gctgaggacc ccaagaagca caacctgctc caaggtgccc tggcttgcag aggccaccca    82140
ccctgagggc agtgctgccg ccgcgtgtgg ggtggggcc atctgggtcc aaggtggtct    82200
ctgttctcta gagaaaaagg ggcagatggg gacagacgcc ccttcctcta caggcttcta    82260
ccagtttgtg cggcccacc ataagcagca gtttgaggag gtctgtatcc agctgacagg    82320
acgaggctgt ggctatcggc ctgagcacag cattccccga aggcagcggg cacagccggt    82380
cctgaccccc actggtaaat gggggcccag gtgggaccct cagactcctg cgtggaaggc    82440
agtgtgggcc agagtcctgg gctgcttggg gtgggcatcc tcgggccctg cttggccccg    82500
cctctctgtt cccctatggg agtgatgggg gcctccacct ccaccaccag caccagcagc    82560
accacctcca ccttcaccac caccacctcc accaccacca cctccaccac ctccacctcc    82620
accacctcca cccacctccac cacctccacc accaccacca cctccaccac caccaccacc    82680
accacctcca ccaccaccac caccaccacc cctccacct ccaccacctc caccaccacc    82740
tccacctcca ccaccaccac cacctccacc tccaccacct ccacctccac ctccaccacc    82800
accacctcca ccaccaccac caccacctcc acctccacca gcagcagcat cacttgttgg    82860
ggagaccctg tgcaactcca tgcacagccc tgtccctgcc atagcccga ccctaagca    82920
cagccctgtc caactgccac acgtcccctg cctcccatgc atggtcctgg ggggtcaact    82980
gcacacgcca gggtcctagg gtcctagacc cctgtcctcc ctgtttctgc ctctgtttgg    83040
ggtggagtcc aagtctccag aggcggaagc atctgtgttc gtgtgttaat gaacagcccc    83100
tacagagttc ccctagttca cccagggggg aacctagcct gttgggacga ccccagatcc    83160
cttctgggct tggtactcac tgggatatcc tcatgcctgc acccagccta cggctctgag    83220
ctcctgagtg gggctttggc ctgcccgcca ctgttccagc cccatccag caggctggtg    83280
tctcctctga tgcccccagc acccaggcgt gtacctgcct gggttttccc gccctggtct    83340
gaggtgggtg aggcctggcc tcctagcca gccctgcccc ccacccag ggaactttcc    83400
agatgctccc gaccagcttt gtggctctac atctcttcat caggaagaac ggcgccggat    83460
cccaagctga ccgtgtccac ggctgcagcc cagcagctgg accccaaga gcacctgaac    83520
cagggcaggc cccacctgtc gcccaggcca ccccaacag gtagctgact cctgaaccgt    83580
```

```
gtgcagccta cgacttggtg ggtccctcag tggcttcacg aggctaactc ttgagtgtgg   83640
ccggggctgc ccctgtgggg agccatctca tggtggggac tgctcccggt tctgcacccc   83700
gcagttgtcc tgagcagctc tccaggagtt cctggaggaa gggcgggcag ggcggtggga   83760
ctctcagtcc tccacccag cgccactctg agccatgcta ctcccacacc aggagaccct   83820
ggcagccaac cacagtgggg gtctggagtg cccagagcag ggaagcaggg ccagcacgcc   83880
gtgagcgcct acctggctga tgcccgcagg gccctgggt ccgcgggctg tagccaactc   83940
ttggcagcgc tgacagccta taagcaagac gacgacctcg acaaggtgct ggctgtgttg   84000
gccgccctga ccactgcaaa gccagaggac ttccccctgc tgcacagcaa gtggccctgg   84060
cgtggggaac agccggtggg gtgggggca ggggacaaaa tggggggtgt ccgggtctg   84120 attgaagctc cccgcagggt tcagcatgtt tgtgcgtcca caccacaagc agcgcttctc   84180
acagacgtgc acagacctga ccggccggcc ctacccgggc atggagccac cgggacccca   84240
ggaggagagg cttgccgtgc ctcctgtgct tacccacagg gctccccaac caggtagggc   84300
acctgcctgg ctgctcctgg cagcgcccca accgcacgca gccctgggag tgagcagcaa   84360
agccccaggc cccctcaga ctcaagtctc tgtctccagg cccctcacgg tccgagaaga   84420
ccgggaagac ccagagcaag atctcgtcct tccttagaca gaggccagca gggactgtgg   84480 gggcgggcg tgaggatgca ggtcccagcc agtcctcagg acctccccac gggcctgcag   84540
catctgagtg gggtgagcct catgggagag acatcgctgg gcagcaggcc acgggagctc   84600
cgggcgggcc cctctcagca ggctgtgtgt gccaggctg tggggcagag gacgtggtgc   84660
ccttccagtg ccctgcctgt gacttccagc gctgccaagc ctgctggcaa cggcaccttc   84720
aggttggtgc ctggccacta cagttcctgc tgggtgtagc cccaggtgat gggctgaggg   84780
ggaaagggca ggcccttgtc ctggtggcaa cgcctggcag acgtgtgcag tgggccggtt   84840
gtctcacagg cctctaggat gtgcccagcc tgccacaccg cctccaggaa gcagagcgtc   84900
atgcaggtct tctggccaga gccccagtga gtgcccacgg aggccccag cacacccaac   84960 gtggcttgat cacctgcctg tccagctctg gtgggccaag aacccacccca acagaatagg   85020 ccagcccatg ccagccggct tggcccgctg caggcctcag gcaggcgggg cccatggttg   85080
gtccctgcgg tgggaccgga tctgggcctg cctctgagaa gccctgagct accttgggt   85140 ctggggtggg tttctgggaa agtgcttccc cagaacttcc ctggctcctg gcctgtgagt   85200
ggtgccacag gggcacccca gctgagcccc tcaccgggaa ggaggagacc cccgtgggca   85260
cgtgtccact tttaatcagg ggacagggct ctctaataaa gctgctggca gtgcccagga   85320
cggtgtcttc gtggcctggg cttgtggtg ggagttgagg gacagggagt tggcagaggc   85380
ccctcccagc ctgccatgtg acactgtact tcctccacgg tgggctcagc cctgccctca   85440
tcctcacagc cgcagccaag ctgcagttgg tagggatcc accgacacac caggctgcct   85500
gggctggtct ctgggtttggg agctgccca ggtgctgagg agggcagctc cctggctggt   85560
gaggcccctc ccagaaccac ccttggactg agctctgggg agggatggta ccaggtgggt   85620 gagggggct gcctggggag ggaggggttc ctatggggcg tggcgaggct ggcccagccc   85680
tctccccgcc catatatgta gggcagcagc aggatgggct tctggacttg gcggcccct   85740 ccgcaggcgg accggggggca aggaggtgg catgtcggtc aggcacagca gggtcctgtg   85800
tccgcgctga gccgcgctct ccctgctcca gcaaggacca tgagggcgct ggaggggcca   85860
ggcctgtcgc tgctgtgcct ggtgttggcg ctgcctgccc tgctgccggt gccggctgta   85920
cgcggagtgg cagaaacacc cacctacccc tggcgggacg cagagacagg ggagcggctg   85980
```

-continued

```
gtgtgtgccc agtgccccccc aggcacctttt gtgcagcggc cgtgccgccg agacagcccc  86040
acgacgtgtg gcccgtgtcc accgcgccac tacacgcagt tctggaacta cctggagcgc  86100
tgccgctact gcaacgtcct ctgcggggag cgtgaggagg aggcacgggc ttgccacgcc  86160
acccacaacc gcgcctgccg ctgccgcacc ggcttcttcg cgcacgctgg tttctgcttg  86220
gagcacgcat cgtgtccacc tggtgccggc gtgattgccc cgggtgagag ctgggcgagg  86280
ggaggggccc ccaggagtgg tggccggagg tgtggcaggg gtcaggttgc tggtcccagc  86340
cttgcaccct gagctaggac accagttccc ctgaccctgt tcttccctcc tggctgcagg  86400
cacccccagc cagaacacgc agtgccagcc gtgcccccca ggcaccttct cagccagcag  86460
ttccagctca gagcagtgcc agccccaccg caactgcacg gccctgggcc tggccctcaa  86520
tgtgccaggc tcttcctccc atgacacgct gtgcaccagc tgcactggct tcccctcag   86580
caccagggta ccaggtgagc cagaggcctg aggggcagc acactgcagg ccaggccac    86640
ttgtgccctc actcctgccc ctgcacgtgc atctagcctg aggcatgcca gctggctctg  86700
ggaaggggcc acagtggatt tgaggggtca gggtccctc cactagatcc ccaccaagtc   86760
tgccctctca ggggtggctg agaatttgga tctgagccag ggcacagcct ccctgggga   86820
gctctgggaa agtgggcagc aatctcctaa ctgcccgagg ggaaggtggc tggctcctct  86880
gacacggaga aaccgaggcc tgatggtaac tctcctaact gcctgagagg aaggtggctg  86940
cctcctctga catggggaaa ccgaggccca atgttaacca ctgttgagaa gtcacagggg  87000
gaagtgaccc ccttaacatc aagtcaggtc cggtccatct gcaggtccca actcgcccct  87060
tccgatggcc caggagcccc aagcccttgc ctgggccccc ttgcctcttg cagccaaggt  87120
ccgagtggcc actcctgccc cctaggcctt tgctccagct ctctgaccga aggctcctgc  87180
cccttctcca gtccccatcg ttgcactgcc ctctccagca cggctcactg cacagggatt  87240
tctctctcct gcaaacccc cgagtgggcc cagaaagca gggtacctgg cagccccgc    87300
cagtgtgtgt gggtgaaatg atcggaccgc tgcctcccca ccccactgca ggagctgagg  87360
agtgtgagcg tgccgtcatc gactttgtgg cttttccagga catctccatc aagaggctgc  87420
agcggctgct gcaggccctc gaggccccgg agggctgggg tccgacacca agggcgggcc  87480
gcgcggcctt gcagctgaag ctgcgtcggc ggctcacgga gctcctgggg gcgcaggacg  87540
gggcgctgct ggtgcggctg ctgcaggcgc tgcgcgtggc caggatgccc gggctggagc  87600
ggagcgtccg tgagcgcttc ctccctgtgc actgatcctg gcccctctt atttattcta   87660
catccttggc accccacttg cactgaaaga ggctttttt taaatagaag aaatgaggtt   87720
tcttaaagct tattttata aagcttttc ataaaactgg ttgtagttgc acagctactg    87780
ggagggcagc cggggacacc tgagccgccc gctgtgccca gatccctcag gctgcctgcc  87840
atcagaactg ctgcccgggg cttcccctac ctcagacaga ccctccctgg gaggatcagt  87900
ggggagtgcc acctctgccc ccagtggctg tggcacgtgg cagggccccc tgaagctcag  87960
cgagggtcag ggcctgggag ggtatcattg ctggaagaac aggatggggc tcaggccagc  88020
cctagtcgcc ggggcccaca ctaaccccccc acttatgaat tcctcccact cccaactcac  88080
agggggatttc ccgagagggg acctgccaaa gacctcctcc aggcctccca tgcttcccgg  88140
gaagtgaagc ttctccccct ctggggcagg ctctgaagcc tcccgatgca cccagagcaa  88200
ccaggggggct gcaccagcca ctcgcctccc cagcacggcc aggttccggg gctggaggt   88260
cccccccagg tcctgggaac caacctgcag aacacacaca gggtcccctg gagaggacgc  88320
```

```
ggggacttcc agggcccgac tcctgtgagt cacagcccg cagctgctgc gccacccca    88380
ccctgactca tgccccttcc cagcagctcc tcccaggacc ccatgtcctt cccacatccg  88440
caggaaggga gtgcctggac tctccaggcc cacctgggga gcccctcacc tgcccaccag  88500
cccctgagca gcccagtaac accatcaccg tgtccaacag ccaggagcct ccaccctcca  88560
ggagggaagg gatggacaga gccacactcg ccgtctttat tttgcactca ccctgggtga  88620
cactgggcag gccgctcctg cccacagcca gactgaggaa gaacacagca ctcggcaggc  88680
ccagtggggt ccgtgcaggg aggacccag gaccagcctt actcccgagc aggggacaca  88740
gggccccaca gagaacccct ccgggaggtt ctctcctggc tgggggaggg ctctggaccc  88800
ccacaaacac tccccaactt gcggggctgg ggcataaaaa cagccactcc cagcaggccc  88860
cctcagcttt ttgcatcagt cagctccctc ccggggatt agggtgaggt gaagccaggc  88920
ccaggcgtgg ggtataggtc ttcccccgca ggcctcagcc ctgtcccgag gctgcatcac  88980
aatccagggc ccccgctggc ctttgggaac atggcctggg tcttcctcaa ggcaagatca  89040
gccccagacc acttccgggg tcacggggtc acagggcaga agccagatgg cagccatggc  89100
tgacgggcct cctcctcgat ggggcggaga cagccacggg gtctcccgag ggtcccacag  89160
ggctgtcctc atgcagccca agccagcctg agcactggag ccccaattcc caaccaggtc  89220
tccctcagac ccccccagaaa gggcctcgaa aggccgccgc tgcgccctgt ggaaaggctg  89280
ccgctgcagg gcctgggcca gccgggctgc cagactcccc tccaaagcct ccggatgcct  89340
acgctttttcc agacatagag gaaagtttgt cttcgagaaa acaaagtaaa tagaagaacc  89400
ccaaagcaaa gcaaacccac cccccagatc agcagcatgg gagccaacag gaggccactc  89460
ctccagcacc aggggaccag ccgtcccgac ggcagcgcgg ctgcgcctac gtgatgtccc  89520
tctgccgcgg cggccggtgc acattccgca cgacacactt caccatccac tcgatgccct  89580
cgcgcacccc tttgctgtga agacagcggg tgtgaggcgg ggggtctcgg tccccaaagc  89640
ccccgcaggt gcagccccca ctcaccctgt gagggccgag caggcctggg tcaggcaatc  89700
gcgcctgccg atcttgctgg tgcagtcgct gaaggccgtc ttgatgtcag ggattgagag  89760
gcacgtctgg gggaggtaag gccgtgagga gcagccccca cgtctggccc tgtcctgcct  89820
gtgggcccgg gactctcaga agggcgtatg cccttcaccc cagggaaaca gccagagctc  89880
caccagggtc ccagtgtctc ccacagagac cacagcagtg aggaccctgt gctcagcccg  89940
aggctgaaca tggctggtag tgcctgagac aaactagacg tccacacggc tccaaggagt  90000
ccacccccca tcccctccct gggggacacc ctgagcccg aggtggggcg ctgaggactg  90060
aggcctcctg ggcagtggcg gaggcaggtc ccagggccc acacagccgg ggatgatgga  90120
gaggtgggag ccctgcatca gtgatggggg cagtctgcag tcatggtggc ttctgctcac  90180
aaccacctgc ccagtcttca aaaagcagcc ctcccctccc cttttcctcc gaggggagac  90240
ccctgccccg taccagatgt ccctcttgtc ggctgagatt gtaggggagg ccagccttac  90300
aggctggggg caacagagcc accccagaga aggcaggaag tgaagattca cccggccctc  90360
tggacgccgg gctgcttctg tgcaaagcca ctccaagaga acagctagaa ctcagcgtgg  90420
ccagtgctcc cggggcagt ggcacctcag agggtcttg aggggctgcc ctggggtgg   90480
ggctggcaca gatgccacct ccaagggtag caggaacagg taagggtcag agctgactcc  90540
caccagggcc ccagcatcac ttctttgagc tctgagtttc acctgggtgt cccacagct   90600
tggccacaca ctcctgagac acggccgccc tcctggggag aggtgccctg catagcagga  90660
agaggcctct gggcgcctgc cctgaggtgg gagaacctcc agggctggca gcagcaggtc  90720
```

-continued

```
tggagaggaa ccaagcttgg gaagctgctg ggggcagggc aggccttgag aatggctctg     90780
taccccctgg gcagtcactg ggcctgggt gtctgggtgc acacctactc cccttgctgt      90840
gggggaggct ggggactcgg gaagctgctg cgggaggcag gggtggggct cacctccaca     90900
tcctgcttgt tggccagcac aagacgggga acaccgcaca gcgcctcgct ggtcaccacc    90960
ttctctgggg agggcaggag aggcagcgcc tcacacccag catcctgcct ctgactgccc     91020
aggggcccac aggcgtggac actgtgacag ccactccctc tgccccccccc ccgtcaccca    91080 ctaggcagga gcacttctga ccagacactg agcctgcccc aggcacagag ctgcccaagc    91140
tggacctgcc cccactcacc atccatccct cccagagcag ccaggccgca ctcaccaaac    91200
gcctgcttgg actcagccag cctctcctcg tcggtggagt caatgacgta gatgacgccg    91260
tgacactccg cataatactg ggaggaagca ccaggagttg gggctcagtc cccaccctgc    91320
caagggccag cagagccagg cctgtgtcat ggccacagtg aggggctcac atgaggaagg    91380
ggcaagaggg cagcccccaa ctgcaagacc cttctgggat gcattctggg gttgcgggga    91440
gatctggtgg aggtgtcccc agacgctgct cctgagaacc tgccggcaac ctttggcctg    91500
atggtggcca aaggtgaaag acagggattg gccaggcgt ggtggctcac acttattatc      91560
ccaacacttt gggaggcaga agcaggagga tcacctgagc ccacttcacg gccaacctgg    91620
gcaacacagt gagactccgt ctgtacaaaa gcttatggta atgtgcgcct gcagtcctag    91680
ctactcggga ggctgaggtg ggaggatggc ttgagcctgg gaggttgagg ctgtagtgag    91740
ctctgatcac accactgcac tccagcctgg gtgagaatga gagaccctgt ctcaaaaaaa    91800
agatagggtt tgggggctgg aggaacctag accacagcct ggcccgttga gggagtgcac    91860
ctgtggggct ctgtgccagc acctcgcaca gggagggagt gtggccatgc ggataagact    91920
gaccagcacc atctacgaag cgagccttcc ctgccaggac agggccagag tcactgagct    91980
cagacctctg cagcctgggc tggtcagtcc tgggctcgct ggcaacactc ctgggcaaga    92040
cagggcacag cccctgcagc ctcaggtaca agtgctgagc cctggaccag atgagtgcac    92100
ctctatctca atcagaaaaa aacacagcaa actccgcgtc cacgtggagc agacaacagc    92160
tcacatttgc cactttgcct ccaggctgtg ccagctctcc tgtccaggca tgagtgccca    92220
gagacctaga actggatgct gaccaggtag acaagctgg tggtcagtgt gttaagacac       92280
acacacccga gagcatgaga agccaggagg cacagcccaa ctctccgaaa tccttagggt    92340
gtctgagcag ggagtaccag acaacccat cccagtgcca gacaagcttg tgcacctgca      92400
cttcccacag aggagagaag cctgtgcacc tgcacttccc acagtggaaa ggaggaggcc    92460
caaggccagg cccccccacc cccaggaact tcccacagtg gagaggaggc caaggccag      92520 gcgccctcca gggttctgca ggtagcgagg ccccccacc cccaggaact tctctggcct      92580
acagacaggt cccacacaga ggccgccaac ccctcaaggg accctgcagt gtgccggctg    92640
tctgctgctg acacaaggga gcaggcggac cctaaggtgg agacctctgt ggcaggaggg    92700
gcggctctgt ggaggctgca gcaagcccag tgagagaatc tccacgtggc tcctgggct     92760 tctgagcagg gtggcagaag gttcatgtgc aaccgggtcc tggaccatgg gaccacgtgg    92820
ccagagccac ccatcacacc taccaggcac aaggtgcaca gcccagcagg gccgcagtgg    92880
acgggagcga cacctcaggg ctgagtgcgg gcaggaccca gagccccacg ccccagtgga    92940
ggcgtcacag cagtggtcat tgtggggtgc cccacaagga gggggaagag ggaggtgtcc    93000
cagcgtggct cctggctggc cagctgaccc cagtggagca gtcagaggga ctgtgggtct    93060
```

```
gagttttct  cccccagcagc  aatgggagct  ccccaactgc  aaagtgccag  ccagcctgag    93120
agactagtgt  tacagcaaag  aacccaggag  ctgaggtcct  ggcacatgcc  acacatgtgg    93180
acaccaaccc  agggtccagc  cccaggacga  ggccaattcg  caatgacgcc  cctttctgtg    93240
gtgctggctc  tgcacaagga  tgcaggatac  aggaaccagg  gtgggagcag  gggcctccct    93300
tccggtccct  cccagtgacc  taggggggtc  cctgcagctg  atcctcccag  ctctgagctc    93360
agcagggtca  ggggtcccgg  ccactagagc  agcacatact  cagcagacac  gctgaatgac    93420
gagccacagc  tgcctcatgg  gcatgacttg  cacctcatgt  ctaggagacc  ctggtgggca    93480
ggagatgggg  ctgccatccc  acagctgtcc  cacagctggg  gacccaggga  gccactggcc    93540
ccaccacggt  ggtgtctgga  gaagggctca  gactgccagg  aagtcgcacc  ccagcagaag    93600
tggtagtgaa  ttgggagggc  actcaaggaa  gggctgtgca  gccccaagac  cagcagcaag    93660
gatgggctac  agtggccccc  ttaagtctcc  ctcttccagt  ttcgccttaa  gagaggccct    93720
caggaccttg  gaggaacccc  tctccaacgt  ggaagtgtgg  gtccacatag  ggctgcagct    93780
gtggccagtg  caggcatctc  tggccccact  gtattcttgc  ttcatgttgg  agaacactgc    93840
accagcagat  ggtctcattt  tggtttctgt  gggacccact  ttggctgcaa  agagccacac    93900
tgccaggtca  cacctgccca  gggcagccca  cactggggac  ccaccaggcc  atggtgtgaa    93960
gtcccggcca  gcctggcccc  acatggcaca  gcatagccag  ttctcctcca  gggctccctg    94020
ctgggccaac  cacagctctg  cggatcctgc  tgcctgagtc  gacctctcct  ctcccgtcct    94080
ccctgccttc  ctggtgccga  ccccagtgt  gcatcctgta  cctcgacctg  tctcagcatc    94140
tgtgcctgag  acaccggcct  gtgacaagat  catcatcatc  tgtgtcactc  cccaagcatg    94200
ctgcgcactg  gacacacagg  ccctgactca  acttgtcctg  tctgacttca  gtggtcctac    94260
aggatctatc  agagatcact  tggccatggg  agaaatgtct  tcttggctag  aagtcacagc    94320
aggaggggac  actttggggg  cgcctaggaa  aggggaacta  ggatcaaaaa  agagatcagg    94380
acctgggcac  tcagctctag  agatggcatc  agggcagcca  aggcactggg  gacacccac    94440 acccactgtg  ccagcctagg  gcagggagcc  cgaggaagcc  acaggctctg  ccctgctcag    94500
tgctggactc  agtgcctggc  ccaggctgag  aaggagataa  actgcagcct  tgggggtgtg    94560
gggaaggggc  accacactgg  gatctcagaa  atgcccaaaa  cctgtgtcaa  aataggagac    94620
tgccgctgtg  agaccctgag  gagtcttctg  gtgatcatgg  aagaacaaat  gttaagctag    94680
aactgaagga  acctcatcag  gggagaggca  gccatcctgc  cgtccccaca  tctggtcttt    94740
gccatttctg  tgtcctgtgg  tggtcagcag  caaggtctct  gagccgaaag  gaggcactca    94800
ctttggagga  gtgcagggtc  ccaggtcccc  cacactttgt  cttgtcctga  ctgagaaaga    94860
aacagactgc  cctgacctct  ctgacttggc  cagcgaggtt  gcccttaggc  tcaaacccaa    94920
gccagggttt  gaacattccc  agacacttgt  aagatgttta  ggttgttaac  ataatgttca    94980
ggtttcaaaa  cattgaaaga  aactagcccc  agccctgaac  ccagatcccc  ccggcttca    95040 ggcatgacca  gtgaacacgc  ccttctctca  ctggtcacct  gaggatgccg  cactctgtca    95100
acaggttccc  ctaatacatg  ctctgatctg  atcgccttgg  catttagtga  ttctttccct    95160
ggaattctcc  actggcccca  tcgcagggaa  ctcccaagtg  ggaaactccc  ctaccaccac    95220 ttttgggca  acttcagcta  agggttcagc  tgggacaaaa  cagggagcca  ctcgggaacc    95280
tgggacagga  ccagagagaa  aacccgaggg  acagagtggg  taaggaaagc  tgctgaggaa    95340
gggcccaaag  ggcactctgg  aaagaagtgg  cactggaggg  ctgggtgggg  ggtggtcctg    95400
gccagggagt  cttaccttgt  cccacaaaga  ctgcagctct  tcctgccctc  ctaagtccca    95460
```

-continued

```
gaacatgagc cgagcctttc ccacatccac agtgccgact ggggagagga ggaaacaggc    95520
aaggctcatg accttggtcc tcgacacacc cagtcccagc tctcccaggg gatggggcaa    95580
accatgctgg tgccactcaa atgagacttg agaggggccc gacagggctg tggccacggg    95640
ccagctggac tgtgaatatc acggcatcct caaggcccca aacccacagc ctgctattga    95700
gacccttact gtttaggccc acgtggtgg tgattttgga tagactcatc cccttgtagt    95760
tcttgttaaa tcgggttttc gactgctcca ggaaggtctg aggagagagg cagaggcgaa    95820
acacatcaag gagggctat actggcttcc aaatatcctt actcaggtct gttctttaaa    95880
agacagaaac agaaacagag caacactctg ctcttcagga ggctggtggt gactatcctg    95940
ccgtctcagt tgaaatttgg cttccgtctg ggtagtgaac gtgcagctga cagcacaaaa    96000
ccgaaggggg cgccgccagg ccgtgggaaa ggtgcgcgca agggcgtggg cactcaccgt    96060
cttcccagca ttgtccaggc ccaggatcag gatgcagtac tcgtccttct gaaacatgta    96120
cttgtacaag cccgacagca gcgtgtacat cctgccctgg gcaccccaac ataggtcagt    96180
gtgcagccag aaagcacctc ccctcccccg ggcttctcca cggtggtcag tggcgcccca    96240
cgtccagccg accgctcagg acgagagcct gggggccatt cccgactcct cgtccctctc    96300
ccacccgtc cctctgtaac ttctcccagg tcagccgcca ctgtgtcctg ctcacagcaa    96360
tgactgcgac ctctccgcat acacatcggt tccggcccct cccctgctcg cgggactacc    96420
cagccgggtg ttcacagtga gctcagccgc gctcccgccc tccccgagg cttcgctccc    96480
acgcttcacg cgcgcggaac ggggaacaca ctcgctgcag ccccgcctgg gccacggcac    96540
cctcgagcgc cagccccgcg ccccacccgg gagcagcgag ccaccggcgc gctccccagg    96600
agccctgca ggcgccgggt agggacgccc catcacccca tttcttaaaa cggggacggc    96660
cctgggggga gcggactaca gggcgggtga gcagcggcgc ggctgctcct ggagtgcacc    96720
tggaggcggc gcgcggctgg cagggaacga ctgcgaagga agaacctggg tcgcggcccc    96780
cggctacgtc cgccccaagc cgccgccgcc aggtctgagg ctccccgaca agcagccaaa    96840
gctggctcct gtcacacccg cgtcccacct cgagtcctgg gccgcccctc gggcctcgcg    96900
cctcaccgca cagcctgcgg cctacctgcg tccgccgcgc cctcggagcc gctgctgctg    96960
accccgctg acctccgctg accccgcgct aaccccgcgc ggcgcctgac gggacgcggg    97020
ccggcctcag ggaatgagct gaaccgcgtc ccagcggcct ccgcgctccg cttcccggct    97080
gccccgcgc gccaagcact tccggaagcg cggcgctcg ggaggaagtg ccgatcggct    97140
gctggggcga aaaggggcg ccgggccgct ctagccggtg aggccggcgg gctctctgtg    97200
gctgcggctg ggaaaccgcg cggaggaggt gcccggccgg ggaccaggtg gccgcggttt    97260
gcggggacgc ggccctggcc agacagaaga gacgccgggc ggggggcgc ggccggcctg    97320
gaaggcggcg ggcgcggcgg gtgggctcgg cggagggtga ggcggcgggg cgcccgcgcg    97380
ggaagggggct ccggagtgac gcgggacccg gctagcggcg agcccacggc ggctcggaag    97440
ggaagcgcgg agcctgagcg ggggtacccg ggctgcgacc tctgcgctgg gagctgtgcc    97500
tctgagccgg tgtctccccg agggaaaggg gacgtgcccg tgcccgtgcc cgccctcagg    97560
ctgtggggtc ggtcccgaga cgcggggctc agctggcttc tcttcttgca gccctggtcc    97620
agcgcctccc tctctcagca tggacgagga gagcctggac tcggccttgc agacctaccg    97680
tgcgcagctg cagcaggtgg agctggcctt gggcgccggc ctggattcgt ctgagcaggc    97740
tgacctgcgc cagctgcagg gggacctgaa ggagctcatc gagctcaccg aggccagcct    97800
```

```
ggtgtctgtc aggaagagca ggttgttggc cgcgctggac gaagagcgcc cgggccgcca   97860
ggaagatgct gagtaccagg ctttccggga ggccatcact gaggcggtgg aggcaccagc   97920
agcggcccgt gggtccggat cagagaccgt tcctaaagca gaggcggggc cagaatctgc   97980
ggcaggtggg caggaggagg aagagggaga ggacgaggaa gagctgagtg ggacaaaggt   98040
gagcgcgccc tactacagct cctggggcac tctggagtat cacaacgcca tggtggtggg   98100 aacgaagag gcggaggatg gctcggcggg tgtccgtgtg ctttacctgt accccactca   98160
caagtctctg aagccgtgcc cgttcttcct ggagggaaag tgccgcttta aggagaactg   98220
caggtaaagc cctttgttgt cagatgccaa ccttaggggc gtaaggggca cgcacacagg   98280
gtcgggtcag gatcggccct ccctttgctt tgcagttttg tctcagcttc ctgggcagg    98340 cgtgctttga cagctgtgtc tgtgttcagg cgtctacgtc ttccttctgg ggtgaatcaa   98400
gaagcatgga aggaggccag gcgcggtggc tcacgcctgt aatcccagca ctttaggaag   98460
ccgaggcggg cagatcacct gaggtcagga gttcaagacc acgctggtca acatggtgaa   98520
accccatctc cttaaaaaca caaaaatgaa ccggtcgtgg tggcgcgcac ctgtggtcct   98580
ggctactcag gaggctgagg caggagaatt ggttgaaccc aggaggccga gtttgcagtg   98640
agtggagatg cagccactgt actgcagccc gagcagcagt gcaaggctta tgtggaagag   98700
agtaggtctc cagcctatcg tcagtttttt tttggtggtt gttttaattt tttttgagac   98760
agggtcttac tttgtcaacc aggctggagt gcagtggcat agtcctggct cactgcagcc   98820
tggacctcct gggctcaacc gatcctcctg cctcagcccc ctaggagct gggctacaga    98880 ctcacgctac tacacccagc taatttttat attactataa ttttttatct ttttttgag    98940 acggagtctt gttctgttgc ccaggctgga gtgcagtggc gtgatctcgg ctcactgcaa   99000
gctccgcctc ccgggttcac gccattctcc tgcctcagcc tcccgagtag ctgggactac   99060
aggcgcccgc caccatgtct ggctaatttt ctgtattttt agtagagacg gggtttcacc   99120
atgttagcca ggatggtctc aatctcctga cctcgtgatc cgcccacctt ggcctcccaa   99180
agtgctggga tgacaagcgt gagccaccgc gcctggcctt ttttttttgg agacagagtt   99240
tcactctcct cacccaggct ggagtgtagt ggcgcaatct cagcttaccg caacctctgt   99300
ctcccgggtt gaagtaattc tctacctcag cgtccagagt agctggcatt acaggcgccc   99360
gccaccacac tcggctaatt ttttgtattt ttagtagagt cggagattca ccatcttggc   99420
caggctggtc ttgaactcct gacctcgtga tccacccacc ttggcctccc aaagtgctgg   99480
gatcacaggc gtgagccact gcgcctggcc ctgttgttag ttttattctc tagagttcaa   99540
cttttaaatt ttactttcat ggagattttc aaacataccc caaattagag agtttagcat   99600
aatcaccgcc cacggtccat catccaatgt cgtcatttat taatattttc ccagtctcat   99660
tttgtctgtt ctccctgccc tattttttc tttcctgggc cattttaaag caaattccag    99720
aagttactgg ttttttccaa ttatgaatac ttcatagttg catctctaat ctaactgatt   99780
aggaaattac ttaaaaagta acttttttgga agtccaagtc cgatgtgagg acaaaaaaga  99840
gtaacttctg tgtcataata ggtaacacat ttaatggtaa tacctcttcc atattcaaat   99900
atgaacaatt attactgtaa tgtctctatt tccctaagcg catagcttta tttttcctcc   99960
tttttacttt tctcttagaa gaaatattta ccaagccttc tagtaggtaa ttttcttttt  100020
tagccaatag ttcaggctga ccgtgtaacc atccctagtt ctagttctag ttctttgaat  100080
gtcttccttt ttttttttt ttgaaacagc gtcttgctgc tctgtcaccc aggctggagt   100140
gcagtggcac aatctcggct cactgcaatc tccgcctccc tggcccaagc catcctccca  100200
```

```
cctcagcctc cctaatagct gatactacaa gtgtgcactg ccacgcccag ctaattttg  100260
tatttttgt  agagacggga tttcaccata ttacccaggt ctcgaattcc tgatccctt   100320
gatgagagat ctgacacatc cctgtggtgc tccctctgga ccaggcactg ctccaagggt 100380
ttcatatact ttcattcatc tgtgcaacag ccctgtaggt aggccctgca gtcacaccat 100440
ctgacagagg aggaaacagg agtagaagaa ctgagtggtc cagggcttca aggctcagag 100500
ggctccagtt gcccccagcc ctcgttccgt cccctgctcc acccagtgct gcttgccatg 100560
tcggcatcag gcctgatctg aaagcttccg gagcatctta cagacgtcca ccttgccacc 100620
attcaggact gataagttct cttggatttg cgttggacct tttttttttt tttaagatgg 100680
agtttcactg ttgttgccca ggctagagta caatggcacg acctccacct cctgggttca 100740
agggattctc ctgcctcagc ctcccaagta gctgggatta caggcgcctg tcaccacgtg 100800
gtgcccagct aatttttata tttttagtag aggcagggtt tcaccgtgtt ggccaggctg 100860
gtctcgaacc cttgacctca ggtgatcccg ccttggtttc ccaaagtgct gggattacag 100920
gcatgagcca ccacacccgg cccaggattt ctttatatat tctggatatc atcccttatg 100980
aagtatatag tttgcagata tttgctccca ttgtttgggt tgtcttttca cttgatatag 101040
tgtcctttga tgcacaaaca ttttaaattt tgatgcagtg caatttattg tttctttatt 101100
gcctatgttt ttgtcatcag gtttaagaaa ccacctcatc catagttatg aggattttca 101160
cctatgtttt cttctaagag ttctgtagtt ttagctgtta aatttaggtc tttgatccat 101220
tttgagttaa ttttttgtata tgttattagg tgagggtcca cttttattctt ttgcatgtgg 101280
atttccagtt ttcccagcac catttgttta aaagactgct ttttctccac tgaatggtct 101340
tggcactttt gtccaaaatc aattggcaat atatgtaagg gttatttct  gagctctctc 101400
tcctgttcca ttggtgtata tgtgccagta ccacactgtt ctgattatta tagctttgtg 101460
ataagtttta aactcaggaa gtggtagtta ttcaccattt gctcctcttt ttcaagtttg 101520
ttttgttct  ggatccttg  caatttcata tgaattttag gatcggcttg tccaattctg 101580
cataaaagac agtttgaatt ttgatatgga ttgcatagaa tgtgtagatc tgtttggggc 101640
acattgtcat ctttacaata ttaagccttc tggctgggtg tggtggctga cgcctgtaat 101700
cccagtactt gggaggctg  aggcgggcat atcacttgag gtcaggagtt caagaccagc 101760
ctggccaacg tggtgaaacc ccgtctctac taaaaataaa aaacaaatta gtcggaggtg 101820
gtgcacacct gtaatcccag ctacaggaga gggtgaggca ggagaatcgc ttgaacctgg 101880
gaggaggagg ttgcagtgag ctgagatcat gccactgcac tccagcctgg gtaacagagg 101940
gagactccat cttaaacaac aacaataaca gaagaaaaaa acagtattaa gtcttccaat 102000
tcatgaatga aggatctgtc catttattta cgtctttaat ttctttcaac agtattttgt 102060
actgttcaag tcttgcacat tcttggttaa ataagtatta tttttgatgc ttctctaagg 102120
aattgttttt ctttccttt  tttttttga  dacagagtct tgctctgtca cccaggctgg 102180
agtgcagtgg cacaatcttg gctcactgca acctctgcct cccggttca  agcaattctt 102240
ctgctcagcc tcccaagtag ctgggatcac aggtgcctgc caccacaccc agctaatttt 102300
ttttttgag  atggagtctt gctctgttgc ccaggctgga gtgaagtggc ccaatcttgg 102360
ctcactgcaa gctccacctc ccgggttcac accattcttc cgcctcagcc tctgagtcg  102420
ctgggaatac aggtgcctgc caccacgccc agctaatttt tgtatttttt agtagagatg 102480
gggtttcacc atgtagccag gatggtctcg aactcttgac ctcaggtgat ctgcctgcct 102540
```

-continued

```
cggcctccca aagtgctggg attacagatg tgagccactg tgcccggctc gagttgtttt    102600
ccttagttac attttcaggc tgtttgttgc tagtatatag aaatacaagc tgggcaccgt    102660
ggctcacgcc tgtaatccca gcactttggg aggccaaggc gggtggatca cctgtggtca    102720
ggagttcgag accagcctgg ccaacatggt gaaatccagc ctctattaaa aatacaaaaa    102780
ttagtctggc atggtggcag gtgcctgtaa tcccatctac tcaggaggct gaggcaagag    102840
aattgcttga acctgggagg cggaggttgc agtgagctga gatcgcgcca ttgcactcca    102900
gcttggggaa caagagtgag acttcatctc aaaaaaaaaa aaaagaaat acagtggatt     102960 tttttatgtt aatcctgtat tgattgctga attggtttat tagtgctaat aggatttttt    103020
atgcactatt taggatttc gatatataca atcatatata ttcaatatat acaattaata    103080
tatatgtgaa tagagataat tgtagtcttt gtttctagtt tgcatggcat ttatttcttt    103140
ttcttgctta actgccttag ctagaacttc aagtacgatg ttgaataaaa gtgactagag    103200
cgggccgggg gtggtggctc acacctgtgt tcccagcact tgggaggtg gaagtgggca     103260 gatcacttga gatcagcagt ttgagaccag cctggccaac acggcgaaac cccatctcta    103320
ctaaaaatac aaaaattagc tgggtgaggt gatgtgcacc tgtagtccca gctacttgag    103380
agggtgagac atgagaattg cttgaacctg gggggcggag gttgcagtga gccaagatca    103440
tgccactcca ctccagcctg gacgacagag caagaaccct gtctttaaaa aaaaaaaaa    103500 aaaagtggct agaacaaaca tctttatctt gttcctgatc ttaggtggaa acttttttg     103560 ttcctgatat taggtggaaa acttttagtc tttcactgtt gaatatgatg ttacttgtag    103620
gttttctgta gattcccttt atcgagttga ggaaattctc ttatattcat agtgtgttga    103680 gtgttttta tcatgaaagg gtgttgattt tttttttaaa gatagggtct tgttctgtca    103740
cccaggctgg agggcagtgg catgatcatg gctcactgca acctcgaatt cctgggctca    103800
ggggatcctc ctacttcatc ctcctgagta ggtgagacta caggcatgag ccaccatgcc    103860
cagctaattt tttaatttt ctgtagaggt agggtcctgc tttgctgccc aggctggtct    103920
taaactccag ggctcaagca atcctgcctc agcctcccaa agtgctgaga ttacagggg    103980 gagtcactgc actgcaccca gctgtgtggg attttcaaa tgcttttttc ctttagatga    104040
tcatgtgtgg ttttttcct ttcattttgt taatgtggta tattgatttt cgtatgttga    104100
accatccttg aattcctcag ataaagcacg catattcatg gcgtattatc tctttattat    104160
tatttttttt gtagagatga gatttcactc tgttgcccaa gctggtctca aactcctggg    104220
ctaaagtgat cctcctgcct cagcctccga aagcgctggg attataggca tgagccactt    104280
ggccctatct ttttctttt tctttttttt ttttttttga cacagagtct cactctgtcg    104340
ccgggctgga gtgagtggcg cgatctcggc tcactgcaac ctccatctcc cgggttcaag    104400
caattctcct gcctcagcct cctgagtagc tgggactaca ggtgcccgcc actatgccca    104460
gctaattttt tgtgttttta gttgagacgg tgttttgcca tgttggacag ctggtcttg    104520 cactcctgac ctcgtgattc acccaccttg gcctcccgaa gtgctgggat tacaggcatg    104580
agccaccgca gcgagcctta tctttttaac agttaaaagt ttaaggcctt atcatgtaat    104640
aacattgctg gatttgattt gctgctgttt tgttgagaat atttgcatct gtattgataa    104700
gggatattgg tctgtagttt tcttttcttg gcatgtcttt gtatagcttt gatgccagca    104760
taatattggc ctcatagaat gagttaggaa gtattcttta tattatggga agaggtaaaa    104820
agggattggt gttaattctt cttcaaatgt ttgatagaat tcaacagtga agtgatatat    104880
acaatcatat atatagagag agagagagag agagatggac ttttcttttg ttggaagttt    104940
```

-continued

```
attgactatt gattcaattt ccttattgaa attgacttt ctttttggaa gctaaaatgt 105000
ataactgtag tgaaagtttc tgaacttttc tttcattgga agtttttga ctactgattc 105060
tttatttgtt ataggtctat tcagatttc tgtttcttct tgagtcagtt tggtctcgct 105120
ctgtcgccca ggctggagtg cagtggtgcc atcttggctc actgcaactt ctacctcccg 105180
agttcaagtg attctcccac ctcagcctcc cagtatctc ggactacagg cgcacgccaa 105240
cataccctggc taatttttgt attttagta ggaacagcat ttcaccatgt tggccaggct 105300
ggtctcgaac tcctgacctc aggtgatcca cccgcctcgg cctcacaaag tgctgggact 105360
acagacataa gccaccgcgt ccagccttga gtcagtttag atagtttgca tgcatgtttc 105420
taggaatttg tccattttgt ttatgttatc taatctgtta ccatacaatt gttcatagta 105480
tccttttata gccctagtta tttctgtaag atcagtagta atagctccac tttctctctt 105540
ggttttagca atttgagtca tctctttct tcttcttttt ttttttttga gatggagtct 105600
cactgtgtca cccaggctgg agtgcagtgg catgatcttg gctcactgca acccctgcct 105660
cccaggttca gcaattctg ccttagcctc ctgagtagct gggattacag gtgtgagcca 105720
ccacacccag ctagttttgt tttgtttttt tgttttgag acggagtctg tttctgtctc 105780
ccaggctgga gtgcagtggt gcaatctcac tcattgcaac ctccgactcc cagattccag 105840
caattctcct gcctcagcct cccgagtagc tggaactata ggcgtgcacc accacgcctg 105900
gctgatttt atatttttag tagagatggg atttcaccat gttggccagg ctggtcttgg 105960
actccctacc tgaggtgatc cgcccacctt ggcctcccaa agtgctggga ttataggcat 106020
gagccaccat gcccagccag ttttgtatt tttagtagag atggggtttc tccctgtcgg 106080
ccaggctggt cttgaaatcc tgacctcagg ttatccacca gccttggcct cccaaagtgc 106140
taggattaca ggcatgagcc accacgcatg gcctgtcttt tcttcttggt cattttcgct 106200
aaaggtttgt caattttgtt gatcttttt gttgctgatc tctattgttt tcccattctg 106260
tttcatttat ttccatttta acctttgttt ccttttttct gctggttggg gtttaatttg 106320
ctctttttt cccctaattt ttcaaggtat acagttaagt tattgatttg agatctcttt 106380
tttctttct ttttttttt tttttttttt tttggttgct gttgagatgg agtctccctc 106440
tgtcacccag actggagtgc agtggcatga tctcagctca ctgcagcctc cgccgccag 106500
gcgattctcc tgcctcagcc tcctgagtag acgtttcccg gccaaggtgt tctttttga 106560
atgtaagcat ttacagctac agatttccct ctaaacactg cttcactgc attccataag 106620
attgttttt gttgtttttt gttgttgttt tgttgtttga gacacagtct cactctgttg 106680
ccgtttggag agcagcgatg cgatcatagc tctgtagcct tgagctcctg gactcaatca 106740
gtcctcctgc ctcagcctcc caagtagctg ggactacagg tgtacaccac tgcacctaac 106800
taatttcttt tataagtttt tgcagaggcc aggcacagtg gctcacacct gtaatcccag 106860
cactttggga ggccaaggtg ggtggatcac ctaaggtcag gagttcgaga ccagcctggc 106920
cgacagggag aaacccatc tctactaaaa atacaaaaat tagctgggcg tggtggcagg 106980
tgcctgtaat cccagctact caggaggctg aggcaggaga atcgcttgaa cctgggaggc 107040
agaggttgca gtgagccagg atcacaccat tgcactccag cctgggtaac aaaagcaaaa 107100
ctccatctca agaaagaaa aaaaaaagtt tttgcagaga cagggtatca ctttgttgcc 107160
caggctggtc tcaaactcct gacttgaagg agtcctactg cctcagcctc ccaaagtgct 107220
gagattatgg gcaagagcca ccgcaccctg ccacttggct gttttgttct gttgtatttc 107280
```

```
cattttcatt gatctcaaga catcctaatc tcccttttgt ttttttgttc gacttactgg  107340
ttattcaaga gtgtctttat ttctgcatat ttgtaaattt tccaaaaaag tttttcttc   107400
tttttttttt gagaaagggt cttgctctgt cgcccaggct ggagaatggt ggtgcacaat  107460
cttgcctcac tgcaacctct gcctcccggg ttcaagtgat cctcccacct cagccttccc  107520
agtagctggg attacaggca cacaccacca cacctggcta attttgtat tttagtctta   107580
acgtgctggt cagactggtc tcgaattcct gacctcaggt gatctgcccg ccttggcctc  107640
ccaaagcact gggattacag gcgtgaaaca ccatgcccag ccccaattt ttttttta    107700
atagagagaa ggtctcactc aagcccaggc tggtcttgaa ctcctgagct caagctgtca  107760
tccctcctcg gcctcccaag gtgctgagat tacaggtgtg agtcacagta cctggccttc  107820
tttcaagact ttaaaaatgc catcttggct gggcacggtg gctcacgcct gtaatcccag  107880
cactttggga ggccgaggtg ggcagatcac gaggtcagga gatcaagacc accctggcta  107940
acatggtgaa accctgtctc tactaaaaat acaaaaaatt aaccaggtgt ggtggcaggt  108000
gcctgtagtc ccagctactc gggaagctga agcaggagaa tggcgtgaac ccgggaggtg  108060
gagcttgcag tgagctgaga tcacaccact gtactccagc ctgggcaaca gtgcgagact  108120
ccgtctcaaa aaaaaaaaaa aaatgtcat ctcactgcct tctggtccaa tagtttctga   108180
tgagaaattg gctgttaatc ttattgagga acatttatat attgactagt cacttgtctc  108240
ttgctgtttt aggagattct ctatctttgg gtttcagcag tttgattata atgtatcagt  108300
gtggatccct caatttataa gctacttgga gttcattgga cttcttggat gtgtaaattc  108360
atgtctttca ttaaatttgc aaagtttcag ctactattct ttgcatcttg aaatactagt  108420
tttgtttctt tctgtctgtt tgccgcttat ggaactttat gcatacattg atgtgcttca  108480
tggtgtagca caggtcccttt gggctctagg catttttctt tgttctttt ttctttctgc   108540
tcctcatttt ggataaaattc agctgacctg tcctcaagtt cactgtttct ttcttcttcc  108600
ttctcaaatc tgctgttgaa acttctggtg aaattttcac tacagttact gtacttttta  108660
gctccaaagt ttctatttgg tttctttctg tagtaattat cactttacta gtattctcta  108720
tttggttaga catggttctt ttgttttcct ttagttcatt atccatggtt tcctttattt  108780
ttaaatttct ttttatttag ttattaattt ttttttttt tgaagcgggg tttcactctt   108840
gtcacccagg ctggcaggca acgtcacaat cttggctcac tacaacctcc gcctcctggg  108900
ttcaagtgat tctcctgcct cagcctccca agtagctggg attataggca tgtgccacca  108960
cacccaccta attttggta ttttagtag aaactgggtt tcaccacatt ggccagactg    109020
gtcttaaact actaacctca ggtgatctgt ccgcctcagc ctcccaaaat gctgggatta  109080
cagatgtgag ccactgtgcc cagcctcttt ttttagtgta tttaaggtaa ttgattgaaa  109140
gttttttgtct agtcattcaa atgtctaggc ttcctcagga acagtttcta ttaatttctt  109200
tattttaaa aattttttt taattttctt ttttttttag atggagtctc actctatagc    109260
ctaggctgga gtgcaatggc ttgatcttgg ctcactgcaa cctctgcctc ctgggttcaa  109320
gcgattctcc tgcttcagcc tcctgagtag ctgggactat aggtgcgtgc caccactcct  109380
ggctaatttt ttgtattttc agtagagaca tggttttgcc gtgttagcca ggatggtctc  109440
gatctcgtga cctcatgatc ctcctgcctc ggcctcccaa agtgctggaa ttacaggtgt  109500
gagccaccgc gcccagccta ttttttattt tttgagacaa agtctccctc tctcacccag  109560
gctgtagtgc agtggcacaa ccctggcaca ctgcagcctt aaccgtccag cttaagtga   109620
gtctcccacc ttagtctcct gagtagctag aactacaagc atgtgccacc atgcctggct  109680
```

```
ggttgtgttg ttactgtttt agacacaggg tcttgctaca tttctctgac tggtcttgaa 109740
ctcctgggct caagcagtca tcccaccttg gcctcccaag gtgttgagat tacaggtgtg 109800
agccaccgca cccggcctgt taatttcttt atttccggtg aatgggccac actttcttgt 109860
ttctttgcat gccttgtaat ttttgttga aacctgcaca atttgaagat gataatgtgg 109920
ttactttgaa aatcagatcc tccgccctct gcagggttca ttgttgctgt ttgttgtgga 109980
ttgtcgtttc tcgtttgttt agttactttc ctgaccttt taaataaaga ctatattctg 110040
tcaggggtgc ttgtttctgt tcttttaggt tagtggttag cttgtgcttt gaaagagatt 110100
tctttaaata tctagtggca aaaggataa agaggccggg cgcagtggct cacgcctgta 110160
atgctaggac tttgggaagt ggaggcgggt ggatcacttg aggtcaggag tttaagatca 110220
gcctggccag tatggtgaaa ccctgtctct actaaaaata caaaaattaa ccgggcatgg 110280
tggcacctgc ctgtagtccc agctactggg aagactgagg caggagaatc gcttcaatcc 110340 aggggggcgga ggttgcagtg agctgagatt gcgccattgc actccagcct gggcaacaga 110400
gcgagactct gtctcaaata aaaaaaaaaa aaaaggata aagagtgtct tccatccttt 110460
ccaggttgcc tctgtactgg ggcaagtcct tcagtgtccg ccaggctgtt cacggctttt 110520
cctcagcctt tacttctcgc tcccatggag cctaaggatg aaccagaggt gaaagttgag 110580
ggcctcctca ggtgtttctg agcccctgtc tagcccagc tgtgtgcatg gccttctgga 110640
tttccaagca tgaacaggag ctttccaaag cccttagacc ttcatgtagc tcttttccca 110700
gcctcttcct tcctaggctt ttctgtcagc tctttgccca tctgttgttg tccctccccc 110760
acaacttcag gtagtatcta cctgtaaatg ccttcaggcc aggcgcggtg gctcatacct 110820
gttatcccag cactttggga ggccgaggcg ggtgaattgc ttgaggtcag gagttcgaga 110880
ccagcctggc caacatggtg aagccccgtc tctagtaaaa atacaaaaat tagctgggcg 110940
tggtgggtgc ctgtaatctc agctactcgg gaggctgaag caggagaatt gcttgagcct 111000
gggaggcgga ggttgcagtg agctgagatc gtgccattgc actccagcct gggcgacaga 111060
gtgagactcc atctcgggga aaaaaaaaa aaaaaatgc catcaacagc acgaccctgg 111120
aggctgcccc agccctgaga gagttcgagg gggtgaaaca aaggcaagcc cttcagggag 111180
acactagaaa gatccaaatg cataagcagg attccttgag aaaaggtctg tatcatccct 111240
tctgacacca gcaagccaca tcagaaatac aggttgcctt ccccatggct acatgtgagc 111300
tggtagtagt ggctgagcag aaatagccca gctgtcctcc tgaaatttag cagggtctta 111360
cttcattgag cagtcatctg gttcgtagac accagagtta cagaaaagtt tattgggagg 111420
ttttgacagt ttaatagaaa aaagtttatt gtgacagttt tgcacagctga atagaaaaaa 111480 gtttactgtg acagttttga cagcagaata gttgctttgc tggagagacg gatctttgga 111540
gctgccaact ccatcatttt ggtgatatcc agctctgttg ctgaattttt agctatgctg 111600
ttttaagtta ttttcttagt ggttgctcta gagatgacaa tgtgcatctt taacttacca 111660
caatgtactt cagattatta ctaacttaac acttaaagta cagcatttt ttttttatgg 111720 agtttcactc tgtcacccag gctggagtgc aatggtgtga tctcggctca ctgcaacctc 111780
cgcctcccag gttcacgcca ttctcctgcc tcagcctcct gagtagctgg gactacaggc 111840
acccccacca cacccggcta attttgtatt tttagtagag atgaggtttc accatgttgg 111900
tcaggctggt ctcgaactgc tgacctcagg tgatccgccc atcttggcct cccaaagtgc 111960
tgggattaca ggtgtgagcg actgcactga gcctaagtat ggcaacgtgt ctataacata 112020
```

```
gatctacttc cgttgtacta tgacatagtt cccctccat tttcctatag cacagtccca    112080
acctcccttt tcctctgaca tagttccatc ctccctcctc ctatgacgtc ctcccttctc    112140
ctctggcata gctccatcct cccttctcct atgacacagc tccatcctcc cttctcctct    112200
gacacagctc catcctccct tctcctatga cacagctcca tcctcccttc tcctctgaca    112260
tagctccatc ctcccttctc ctatgtcata gctccatcct cccttctcct ctgacacagc    112320
tccatcctcc cttctcctct ggcatagctc catcctccct tctcctatga cacagctcca    112380
tcctcccttc tcctatgaca cagctccatc ctcccttctc ctatgacaca gctccatcct    112440
cccttctcct atgacacagc tccatcctcc cttctcctct ggcatagctc catcctccct    112500
tctcctctga catagctcca tcctcccttc tcctctgaca tagctccatc ctcccttctc    112560
ctctgacata gctccatcct cccttctcct ctgacatagc tccatcctcc cttctcctct    112620
gacatagctc catcctccct tctcctctga catagttcca tcctcccttg tcctctgaca    112680
tagctccatc ctcccttctc ctctgacata gctccatccc ctcttctcct tcatgtatta    112740
ttgccatata tacatttatg tatgttataa cttcagctct tcagcgttat aattattgct    112800
tcaaaagtat tttgaaagaa gttgcctgga ggcagtggct tatgcccttta actccagcac    112860
ttttggggc tgaggtgggc agatcgcctg agccagggag ttggagacca gcctgggcaa    112920
catgacgaaa cccatctcca ccaaaattac aaaaaattag tctggcatgg tggcacgcgc    112980
ctgtagtccc agctatttgg gggaggatcc cagctaaggt gggaggatca cttgagcctg    113040
ggaagtcaag gctgcagtga gctgagattg tgccactgca ctccagcctg ggtgcagatc    113100
ttatctcaga agtaaaggga ctaggaatgg tggcttttat ctctaatccc agcactttgg    113160
gaggctgagg tgagtggatc accggaggtc aggagtttaa gaccagcctg ccaacatgg    113220
tgaaacccg tctctactaa aaatacaaaa agtagccggg tgtggtggtg ggtgtctgta    113280
atcccagcta ctcgggaggc tgaggcaaga gaatcgcttg aacctgggaa gcggaggttg    113340
cagtgagcaa gatcgcacca ctgcattaca gcctagatga cagagcgaga ctctgcctaa    113400
aaaaaaaaaa aaaagaaaa gaaaagaaat taagatctag acactgtggt tcatgcctgt    113460
aatcccaaag ccttgggagg ccaaggcagg aggatcactt gaggccagga gttcaacacc    113520
agcctgggca acatagcgag actccatctc tatttaaaaa agaaagaaat tcaaagagaa    113580
aaaaagtata cttgtttttt tgtatcatcc atattttacc tttctttttt ttgccccttt    113640
ttctttcctg tgaatttgag ttactgtcta gtgtcatttc cttttagtct gaagaacttc    113700
attttagaatt tttttttt tttgagacaa agtctcactg tgttgcccag gctggagtgc    113760
aatggtgcag tctcagatca ctgcaacctc tgcctcctg gttagagtga ttttcctgcc    113820
tcagcctccc aagtagctga gactgcaggc acctgccacc accccagcc aattttttg    113880
gtatttttag tagagacagg gtttcactat gttggccagg ctggtctcga attcatgacc    113940
tcatgatctg cctgtcctgg cctcccaaaa tgctgggatt accatgagcc accacgccca    114000
gcccatttag aatttctttt tttttttt ttttgagatg gggtctcgct cttgtttccc    114060
aggctggagt gcagtggcac gatctcggct cactgcgagc tccgcctccc gggttcacgc    114120
cattctcctg cctcagcctc ccgagtagct gggattacag gcgcctgcca ccacgcccac    114180
ctaatttttt gtatttttag gagagatggg gtttcaccat gttagccagg atggtcttga    114240
tctcctgacc tcgtgatccg ccccgccttgg cctcccaaag tgctgggatt acaggcgtga    114300
gccaccgcgc ccggctagaa tttcttgtag gacaggcttg ctagcaacca attcagtgtt    114360
tatttgggaa tgtctttatt tcagcttcat tttttgaagg atagtttagc tggctataga    114420
```

```
attattaatt gatcattctt ttcagtgttt aaaagtgtca tcatgctacc ttctgggttc    114480
cattgtttct gatgagaagt catctgtcaa attgtccctt tgtacttgaa gaattatctt    114540
tttttctctt gatgttttca agattttctc tttgtctttg gcctttagta gtttgtgatg    114600
tatctaggtg tggatctctt ggtgtgcatc gtatttgggc ttcagtaagc ctcttagatt    114660
catagattaa tgttttgttt tgttttacca aatttggaga gtttttactc atcatttcaa    114720 caaattttt tcctgcccct ctctcatctc cttttgggag taccactgca tgtatgttgg     114780
tgtgcgttct cta                                                       114793

<210> SEQ ID NO 4
<211> LENGTH: 25
<212> TYPE: DNA
<213> ORGANISM: Artificial Sequence
<220> FEATURE:
<223> OTHER INFORMATION: oligonucleotide

<400> SEQUENCE: 4
cacaggttca gcatgtttgt gcgtc                                          25

<210> SEQ ID NO 5
<211> LENGTH: 25
<212> TYPE: DNA
<213> ORGANISM: Artificial Sequence
<220> FEATURE:
<223> OTHER INFORMATION: oligonucleotide

<400> SEQUENCE: 5
cacagtccct gctggcctct gtcta                                          25

<210> SEQ ID NO 6
<211> LENGTH: 25
<212> TYPE: DNA
<213> ORGANISM: Artificial Sequence
<220> FEATURE:
<223> OTHER INFORMATION: oligonucleotide

<400> SEQUENCE: 6
caggacatct ccatcaagag gctgc                                          25

<210> SEQ ID NO 7
<211> LENGTH: 25
<212> TYPE: DNA
<213> ORGANISM: Artificial Sequence
<220> FEATURE:
<223> OTHER INFORMATION: oligonucleotide

<400> SEQUENCE: 7
aataagaggg ggccaggatc agtgc                                          25

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
gtgaatggca tcctggagag                                                20

<210> SEQ ID NO 9
<211> LENGTH: 20
<212> TYPE: DNA
```

```
<213> ORGANISM: Artificial Sequence
<220> FEATURE:
<223> OTHER INFORMATION: oligonucleotide

<400> SEQUENCE: 9
gtctccaggc agctcaacag                                               20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
accctgtccc tcctgtctga                                               20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
agaccctaag atgttcggag                                               20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
gatgacctgt gtgagttgcg                                               20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
cgcaactcac acaggtcatc                                               20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
ggagtcaggt caaaggatgc                                               20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
gcatcctttg acctgactcc                                               20
```

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
ggtctgaaac gtgatctggg                          20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
cccagatcac gtttcagacc                          20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide

<400> SEQUENCE: 18
cgatgatgtg tgggttctcc                          20

<210> SEQ ID NO 19
<211> LENGTH: 20
<212> TYPE: DNA
<213> ORGANISM: Artificial Sequence
<220> FEATURE:
<223> OTHER INFORMATION: oligonucleotide

<400> SEQUENCE: 19
ggagaaccca cacatcatcg                          20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
cgtgtctgag aagtccagcc                          20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
ggctggactt ctcagacacg                          20

<210> SEQ ID NO 22
<211> LENGTH: 20
<212> TYPE: DNA
<213> ORGANISM: Artificial Sequence
<220> FEATURE:

<223> OTHER INFORMATION: oligonucleotide

<400> SEQUENCE: 22
acagcatctt ctccacgcac    20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
agtcctctgg ctttgcagtg    20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
tgtgcgtgga gaagatgctg    20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
ggctggaaag ggaagtctac    20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
tggttcaggt gctcttgggg    20

<210> SEQ ID NO 27
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
cgtgaagcag gagttgagcc    20

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
atcttgctct gggtcttccc    20

```
<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
cactgcaaag ccagaggact                                            20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide

<400> SEQUENCE: 30
ataagcaaga cgacgacctc                                            20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
ctattctgtt gggtgggttc                                            20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide

<400> SEQUENCE: 32
cgtgcctcct gtgcttaccc                                            20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
cagaccccaa ggtagctcag                                            20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide

<400> SEQUENCE: 34
ggaagaccca gagcaagatc                                            20

<210> SEQ ID NO 35
<211> LENGTH: 780
<212> TYPE: PRT
<213> ORGANISM: Dictyostelium discoideum

<400> SEQUENCE: 35
```

-continued

```
Met Lys Phe Tyr Ile Glu Asp Leu Leu Val Tyr Phe Pro Tyr Ser Tyr
1               5                   10                  15

Ile Tyr Pro Glu Gln Tyr Ser Tyr Met Val Ala Leu Lys Arg Ser Leu
            20                  25                  30

Asp Asn Gly Gly Pro Cys Ile Leu Glu Met Pro Ser Gly Thr Gly Lys
            35                  40                  45

Thr Val Ser Leu Leu Ser Leu Ile Ser Ser Tyr Gln Val Lys Asn Pro
50                      55                  60

Ser Ile Lys Leu Ile Tyr Cys Ser Arg Thr Val Pro Glu Ile Glu Gln
65                  70                  75                  80

Ala Thr Glu Glu Ala Arg Arg Val Leu Gln Tyr Arg Asn Ser Glu Met
                85                  90                  95

Gly Glu Glu Ser Pro Lys Thr Leu Cys Met Ser Met Ser Ser Arg Arg
            100                 105                 110

Asn Leu Cys Ile Gln Pro Arg Val Ser Glu Glu Arg Asp Gly Lys Val
            115                 120                 125

Val Asp Ala Leu Cys Arg Glu Leu Thr Ser Ser Trp Asn Arg Glu Ser
    130                 135                 140

Pro Thr Ser Glu Lys Cys Lys Phe Phe Glu Asn Phe Glu Ser Asn Gly
145                 150                 155                 160

Lys Glu Ile Leu Leu Glu Gly Val Tyr Ser Leu Glu Asp Leu Lys Glu
                165                 170                 175

Tyr Gly Leu Lys His Gln Met Cys Pro Tyr Phe Leu Ser Arg His Met
            180                 185                 190

Leu Asn Phe Ala Asn Ile Val Ile Phe Ser Tyr Gln Tyr Leu Leu Asp
            195                 200                 205

Pro Lys Ile Ala Ser Leu Ile Ser Ser Ser Phe Pro Ser Asn Ser Ile
    210                 215                 220

Val Val Phe Asp Glu Ala His Asn Ile Asp Asn Val Cys Ile Asn Ala
225                 230                 235                 240

Leu Ser Ile Asn Ile Asp Asn Lys Leu Leu Asp Thr Ser Ser Lys Asn
                245                 250                 255

Ile Ala Lys Ile Asn Lys Gln Ile Glu Asp Ile Lys Lys Val Asp Glu
            260                 265                 270

Lys Arg Leu Lys Asp Glu Tyr Gln Arg Leu Val Asn Gly Leu Ala Arg
    275                 280                 285

Ser Gly Ser Thr Arg Ala Asp Glu Thr Thr Ser Asp Pro Val Leu Pro
290                 295                 300

Asn Asp Val Ile Gln Glu Ala Val Pro Gly Asn Ile Arg Lys Pro Ser
305                 310                 315                 320

Ile Phe Ile Ser Leu Leu Arg Arg Val Val Asp Tyr Leu Arg Glu Pro
            325                 330                 335

Asp Lys Ser Arg Leu Lys Ser Gln Met Leu Leu Ser Glu Ser Pro Leu
            340                 345                 350

Ala Phe Leu Gln Gly Leu Tyr His Ala Thr Gln Ile Ser Ser Arg Thr
            355                 360                 365

Leu Arg Phe Cys Ser Ser Arg Leu Ser Ser Leu Leu Arg Thr Leu Arg
    370                 375                 380

Ile Asn Asp Val Asn Gln Phe Ser Gly Ile Ser Leu Ile Ala Asp Phe
385                 390                 395                 400

Ala Thr Leu Val Gly Thr Tyr Asn Asn Gly Phe Leu Ile Ile Ile Glu
                405                 410                 415

Pro Tyr Tyr Gln Arg Gln Asn Asn Thr Tyr Asp Gln Ile Phe Gln Phe
```

```
                      420                 425                 430
Cys Cys Leu Asp Ala Ser Ile Gly Met Lys Pro Ile Phe Asp Lys Tyr
        435                 440                 445

Arg Ser Val Val Ile Thr Ser Gly Thr Leu Ser Pro Leu Asp Ile Tyr
    450                 455                 460

Thr Lys Met Leu Asn Phe Arg Pro Thr Val Glu Arg Leu Thr Met
465                 470                 475                 480

Ser Leu Asn Arg Asn Cys Ile Cys Pro Cys Ile Leu Thr Arg Gly Ser
                485                 490                 495

Asp Gln Ile Ser Ile Ser Thr Lys Phe Asp Val Arg Ser Asp Thr Ala
            500                 505                 510

Val Val Arg Asn Tyr Gly Ala Leu Leu Val Glu Val Ser Ala Ile Val
            515                 520                 525

Pro Asp Gly Ile Ile Cys Phe Phe Thr Ser Tyr Ser Tyr Met Glu Gln
        530                 535                 540

Ile Val Ser Val Trp Asn Glu Met Gly Leu Leu Asn Asn Ile Leu Thr
545                 550                 555                 560

Asn Lys Leu Ile Phe Val Glu Thr Ser Asp Pro Ala Glu Ser Ala Leu
                565                 570                 575

Ala Leu Gln Asn Tyr Lys Lys Ala Cys Asp Ser Gly Arg Gly Ala Val
            580                 585                 590

Leu Leu Ser Val Ala Arg Gly Lys Val Ser Glu Gly Ile Asp Phe Asp
        595                 600                 605

Asn Gln Tyr Gly Arg Cys Val Ile Leu Tyr Gly Ile Pro Tyr Ile Asn
    610                 615                 620

Thr Glu Ser Lys Val Leu Arg Ala Arg Leu Glu Phe Leu Arg Asp Arg
625                 630                 635                 640

Tyr Gln Ile Arg Glu Asn Glu Phe Leu Thr Phe Asp Ala Met Arg Thr
                645                 650                 655

Ala Ser Gln Cys Val Gly Arg Val Ile Arg Gly Lys Ser Asp Tyr Gly
            660                 665                 670

Ile Met Ile Phe Ala Asp Lys Arg Tyr Asn Arg Leu Asp Lys Arg Asn
        675                 680                 685

Lys Leu Pro Gln Trp Ile Leu Gln Phe Cys Gln Pro Gln His Leu Asn
    690                 695                 700

Leu Ser Thr Asp Met Ala Ile Ser Leu Ser Lys Thr Phe Leu Arg Glu
705                 710                 715                 720

Met Gly Gln Pro Phe Ser Arg Glu Glu Gln Leu Gly Lys Ser Leu Trp
                725                 730                 735

Ser Leu Glu His Val Glu Lys Gln Ser Thr Ser Lys Pro Pro Gln Gln
            740                 745                 750

Gln Asn Ser Ala Ile Asn Ser Thr Ile Thr Ser Thr Thr Thr Thr
        755                 760                 765

Thr Thr Thr Ser Thr Ile Ser Glu Thr His Leu Thr
    770                 775                 780

<210> SEQ ID NO 36
<211> LENGTH: 778
<212> TYPE: PRT
<213> ORGANISM: S. cerevisiae

<400> SEQUENCE: 36

Met Lys Phe Tyr Ile Asp Asp Leu Pro Val Leu Phe Pro Tyr Pro Lys
1               5                   10                  15
```

-continued

```
Ile Tyr Pro Glu Gln Tyr Asn Tyr Met Cys Asp Ile Lys Lys Thr Leu
            20                  25                  30

Asp Val Gly Gly Asn Ser Ile Leu Glu Met Pro Ser Gly Thr Gly Lys
        35                  40                  45

Thr Val Ser Leu Leu Ser Leu Thr Ile Ala Tyr Gln Met His Tyr Pro
    50                  55                  60

Glu His Arg Lys Ile Ile Tyr Cys Ser Arg Thr Met Ser Glu Ile Glu
65                  70                  75                  80

Lys Ala Leu Val Glu Leu Glu Asn Leu Met Asp Tyr Arg Thr Lys Glu
                85                  90                  95

Leu Gly Tyr Gln Glu Asp Phe Arg Gly Leu Gly Leu Thr Ser Arg Lys
            100                 105                 110

Asn Leu Cys Leu His Pro Glu Val Ser Lys Glu Arg Lys Gly Thr Val
        115                 120                 125

Val Asp Glu Lys Cys Arg Arg Met Thr Asn Gly Gln Ala Lys Arg Lys
    130                 135                 140

Leu Glu Glu Asp Pro Glu Ala Asn Val Glu Leu Cys Glu Tyr His Glu
145                 150                 155                 160

Asn Leu Tyr Asn Ile Glu Val Glu Asp Tyr Leu Pro Lys Gly Val Phe
                165                 170                 175

Ser Phe Glu Lys Leu Leu Lys Tyr Cys Glu Glu Lys Thr Leu Cys Pro
            180                 185                 190

Tyr Phe Ile Val Arg Arg Met Ile Ser Leu Cys Asn Ile Ile Ile Tyr
        195                 200                 205

Ser Tyr His Tyr Leu Leu Asp Pro Lys Ile Ala Glu Arg Val Ser Asn
    210                 215                 220

Glu Val Ser Lys Asp Ser Ile Val Ile Phe Asp Glu Ala His Asn Ile
225                 230                 235                 240

Asp Asn Val Cys Ile Glu Ser Leu Ser Leu Asp Leu Thr Thr Asp Ala
                245                 250                 255

Leu Arg Arg Ala Thr Arg Gly Ala Asn Ala Leu Asp Glu Arg Ile Ser
            260                 265                 270

Glu Val Arg Lys Val Asp Ser Gln Lys Leu Gln Asp Glu Tyr Glu Lys
        275                 280                 285

Leu Val Gln Gly Leu His Ser Ala Asp Ile Leu Thr Asp Gln Glu Glu
    290                 295                 300

Pro Phe Val Glu Thr Pro Val Leu Pro Gln Asp Leu Leu Thr Glu Ala
305                 310                 315                 320

Ile Pro Gly Asn Ile Arg Arg Ala Glu His Phe Val Ser Phe Leu Lys
                325                 330                 335

Arg Leu Ile Glu Tyr Leu Lys Thr Arg Met Lys Val Leu His Val Ile
            340                 345                 350

Ser Glu Thr Pro Lys Ser Phe Leu Gln His Leu Lys Gln Leu Thr Phe
        355                 360                 365

Ile Glu Arg Lys Pro Leu Arg Phe Cys Ser Glu Arg Leu Ser Leu Leu
    370                 375                 380

Val Arg Thr Leu Glu Val Thr Glu Val Glu Asp Phe Thr Ala Leu Lys
385                 390                 395                 400

Asp Ile Ala Thr Phe Ala Thr Leu Ile Ser Thr Tyr Glu Glu Gly Phe
                405                 410                 415

Leu Leu Ile Ile Glu Pro Tyr Glu Ile Glu Asn Ala Ala Val Pro Asn
            420                 425                 430

Pro Ile Met Arg Phe Thr Cys Leu Asp Ala Ser Ile Ala Ile Lys Pro
```

```
                435                 440                 445
Val Phe Glu Arg Phe Ser Ser Val Ile Ile Thr Ser Gly Thr Ile Ser
450                 455                 460

Pro Leu Asp Met Tyr Pro Arg Met Leu Asn Phe Lys Thr Val Leu Gln
465                 470                 475                 480

Lys Ser Tyr Ala Met Thr Leu Ala Lys Lys Ser Phe Leu Pro Met Ile
                485                 490                 495

Ile Thr Lys Gly Ser Asp Gln Val Ala Ile Ser Ser Arg Phe Glu Ile
                500                 505                 510

Arg Asn Asp Pro Ser Ile Val Arg Asn Tyr Gly Ser Met Leu Val Glu
            515                 520                 525

Phe Ala Lys Ile Thr Pro Asp Gly Met Val Val Phe Phe Pro Ser Tyr
530                 535                 540

Leu Tyr Met Glu Ser Ile Val Ser Met Trp Gln Thr Met Gly Ile Leu
545                 550                 555                 560

Asp Glu Val Trp Lys His Lys Leu Ile Leu Val Glu Thr Pro Asp Ala
                565                 570                 575

Gln Glu Thr Ser Leu Ala Leu Glu Thr Tyr Arg Lys Ala Cys Ser Asn
                580                 585                 590

Gly Arg Gly Ala Ile Leu Leu Ser Val Ala Arg Gly Lys Val Ser Glu
            595                 600                 605

Gly Ile Asp Phe Asp His Gln Tyr Gly Arg Thr Val Leu Met Ile Gly
610                 615                 620

Ile Pro Phe Gln Tyr Thr Glu Ser Arg Ile Leu Lys Ala Arg Leu Glu
625                 630                 635                 640

Phe Met Arg Glu Asn Tyr Arg Ile Arg Glu Asn Asp Phe Leu Ser Phe
                645                 650                 655

Asp Ala Met Arg His Ala Ala Gln Cys Leu Gly Arg Val Leu Arg Gly
                660                 665                 670

Lys Asp Asp Tyr Gly Val Met Val Leu Ala Asp Arg Arg Phe Ser Arg
            675                 680                 685

Lys Arg Ser Gln Leu Pro Lys Trp Ile Ala Gln Gly Leu Ser Asp Ala
690                 695                 700

Asp Leu Asn Leu Ser Thr Asp Met Ala Ile Ser Asn Thr Lys Gln Phe
705                 710                 715                 720

Leu Arg Thr Met Ala Gln Pro Thr Asp Pro Lys Asp Gln Glu Gly Val
                725                 730                 735

Ser Val Trp Ser Tyr Glu Asp Leu Ile Lys His Gln Asn Ser Arg Lys
                740                 745                 750

Asp Gln Gly Gly Phe Ile Glu Asn Glu Asn Lys Glu Gly Glu Gln Asp
            755                 760                 765

Glu Asp Glu Asp Glu Asp Ile Glu Met Gln
    770                 775

<210> SEQ ID NO 37
<211> LENGTH: 772
<212> TYPE: PRT
<213> ORGANISM: S. pombe

<400> SEQUENCE: 37

Met Lys Phe Tyr Ile Asp Asp Leu Pro Ile Leu Phe Pro Tyr Pro Arg
  1               5                  10                  15

Ile Tyr Pro Glu Gln Tyr Gln Tyr Met Cys Asp Leu Lys His Ser Leu
                20                  25                  30
```

```
Asp Ala Gly Gly Ile Ala Leu Leu Glu Met Pro Ser Gly Thr Gly Lys
         35                  40                  45

Thr Ile Ser Leu Leu Ser Leu Ile Val Ser Tyr Gln Gln His Tyr Pro
     50                  55                  60

Glu His Arg Lys Leu Ile Tyr Cys Ser Arg Thr Met Ser Glu Ile Asp
 65                  70                  75                  80

Lys Ala Leu Ala Glu Leu Lys Arg Leu Met Ala Tyr Arg Thr Ser Gln
                 85                  90                  95

Leu Gly Tyr Glu Glu Pro Phe Leu Gly Leu Gly Leu Thr Ser Arg Lys
             100                 105                 110

Asn Leu Cys Leu His Pro Ser Val Arg Arg Glu Lys Asn Gly Asn Val
         115                 120                 125

Val Asp Ala Arg Cys Arg Ser Leu Thr Ala Gly Phe Val Arg Glu Gln
 130                 135                 140

Arg Leu Ala Gly Met Asp Val Pro Thr Cys Glu Phe His Asp Asn Leu
145                 150                 155                 160

Glu Asp Leu Glu Pro His Ser Leu Ile Ser Asn Gly Val Trp Thr Leu
                 165                 170                 175

Asp Asp Ile Thr Glu Tyr Gly Glu Lys Thr Thr Arg Cys Pro Tyr Phe
             180                 185                 190

Thr Val Arg Arg Met Leu Pro Phe Cys Asn Val Ile Ile Tyr Ser Tyr
         195                 200                 205

His Tyr Leu Leu Asp Pro Lys Ile Ala Glu Arg Val Ser Arg Glu Leu
 210                 215                 220

Ser Lys Asp Cys Ile Val Val Phe Asp Glu Ala His Asn Ile Asp Asn
225                 230                 235                 240

Val Cys Ile Glu Ser Leu Ser Ile Asp Leu Thr Glu Ser Ser Leu Arg
                 245                 250                 255

Lys Ala Ser Lys Ser Ile Leu Ser Leu Glu Gln Lys Val Asn Glu Val
             260                 265                 270

Lys Gln Ser Asp Ser Lys Lys Leu Gln Asp Glu Tyr Gln Lys Leu Val
         275                 280                 285

Arg Gly Leu Gln Asp Ala Asn Ala Ala Asn Asp Glu Asp Gln Phe Met
 290                 295                 300

Ala Asn Pro Val Leu Pro Glu Asp Val Leu Lys Glu Ala Val Pro Gly
305                 310                 315                 320

Asn Ile Arg Arg Ala Glu His Phe Ile Ala Phe Leu Lys Arg Phe Val
                 325                 330                 335

Glu Tyr Leu Lys Thr Arg Met Lys Val Leu His Val Ile Ala Glu Thr
             340                 345                 350

Pro Thr Ser Phe Leu Gln His Val Lys Asp Ile Thr Phe Ile Asp Lys
         355                 360                 365

Lys Pro Leu Arg Phe Cys Ala Glu Arg Leu Thr Ser Leu Val Arg Ala
 370                 375                 380

Leu Gln Ile Ser Leu Val Glu Asp Phe His Ser Leu Gln Gln Val Val
385                 390                 395                 400

Ala Phe Ala Thr Leu Val Ala Thr Tyr Glu Arg Gly Phe Ile Leu Ile
                 405                 410                 415

Leu Glu Pro Phe Glu Thr Glu Asn Ala Thr Val Pro Asn Pro Ile Leu
             420                 425                 430

Arg Phe Ser Cys Leu Asp Ala Ser Ile Ala Ile Lys Pro Val Phe Glu
         435                 440                 445

Arg Phe Arg Ser Val Ile Ile Thr Ser Gly Thr Leu Ser Pro Leu Asp
```

```
                450             455             460
Met Tyr Pro Lys Met Leu Gln Phe Asn Thr Val Met Gln Glu Ser Tyr
465                 470                 475                 480

Gly Met Ser Leu Ala Arg Asn Cys Phe Leu Pro Met Val Val Thr Arg
                485                 490                 495

Gly Ser Asp Gln Val Ala Ile Ser Ser Lys Phe Glu Ala Arg Asn Asp
                500                 505                 510

Pro Ser Val Val Arg Asn Tyr Gly Asn Ile Leu Val Glu Phe Ser Lys
                515                 520                 525

Ile Thr Pro Asp Gly Leu Val Ala Phe Phe Pro Ser Tyr Leu Tyr Leu
530                 535                 540

Glu Ser Ile Val Ser Ser Trp Gln Ser Met Gly Ile Leu Asp Glu Val
545                 550                 555                 560

Trp Lys Tyr Lys Leu Ile Leu Val Glu Thr Pro Asp Pro His Glu Thr
                565                 570                 575

Thr Leu Ala Leu Glu Thr Tyr Arg Ala Ala Cys Ser Asn Gly Arg Gly
                580                 585                 590

Ala Val Leu Leu Ser Val Ala Arg Gly Lys Val Ser Glu Gly Val Asp
                595                 600                 605

Phe Asp His His Tyr Gly Arg Ala Val Ile Met Phe Gly Ile Pro Tyr
610                 615                 620

Gln Tyr Thr Glu Ser Arg Val Leu Lys Ala Arg Leu Glu Phe Leu Arg
625                 630                 635                 640

Asp Thr Tyr Gln Ile Arg Glu Ala Asp Phe Leu Thr Phe Asp Ala Met
                645                 650                 655

Arg His Ala Ala Gln Cys Leu Gly Arg Val Leu Arg Gly Lys Asp Asp
                660                 665                 670

His Gly Ile Met Val Leu Ala Asp Lys Arg Tyr Gly Arg Ser Asp Lys
                675                 680                 685

Arg Thr Lys Leu Pro Lys Trp Ile Gln Gln Tyr Ile Thr Glu Gly Ala
                690                 695                 700

Thr Asn Leu Ser Thr Asp Met Ser Leu Ala Leu Ala Lys Lys Phe Leu
705                 710                 715                 720

Arg Thr Met Ala Gln Pro Phe Thr Ala Ser Asp Gln Glu Gly Ile Ser
                725                 730                 735

Trp Trp Ser Leu Asp Asp Leu Leu Ile His Gln Lys Lys Ala Leu Lys
                740                 745                 750

Ser Ala Ala Ile Glu Gln Ser Lys His Glu Asp Glu Met Asp Ile Asp
                755                 760                 765

Val Val Glu Thr
        770

<210> SEQ ID NO 38
<211> LENGTH: 760
<212> TYPE: PRT
<213> ORGANISM: Homo sapien

<400> SEQUENCE: 38

Met Lys Leu Asn Val Asp Gly Leu Leu Val Tyr Phe Pro Tyr Asp Tyr
1               5                   10                  15

Ile Tyr Pro Glu Gln Phe Ser Tyr Met Arg Glu Leu Lys Arg Thr Leu
                20                  25                  30

Asp Ala Lys Gly His Gly Val Leu Glu Met Pro Ser Gly Thr Gly Lys
                35                  40                  45
```

-continued

```
Thr Val Ser Leu Leu Ala Leu Ile Met Ala Tyr Gln Arg Ala Tyr Pro
 50                  55                  60
Leu Glu Val Thr Lys Leu Ile Tyr Cys Ser Arg Thr Val Pro Glu Ile
 65                  70                  75                  80
Glu Lys Val Ile Glu Glu Leu Arg Lys Leu Leu Asn Phe Tyr Glu Lys
                     85                  90                  95
Gln Glu Gly Glu Lys Leu Pro Phe Leu Gly Leu Ala Leu Ser Ser Arg
                100                 105                 110
Lys Asn Leu Cys Ile His Pro Glu Val Thr Pro Leu Arg Phe Gly Lys
                115                 120                 125
Asp Val Asp Gly Lys Cys His Ser Leu Thr Ala Ser Tyr Val Arg Ala
130                 135                 140
Gln Tyr Gln His Asp Thr Ser Leu Pro His Cys Arg Phe Tyr Glu Glu
145                 150                 155                 160
Phe Asp Ala His Gly Arg Glu Val Pro Leu Pro Ala Gly Ile Tyr Asn
                165                 170                 175
Leu Asp Asp Leu Lys Ala Leu Gly Arg Arg Gln Gly Trp Cys Pro Tyr
                180                 185                 190
Phe Leu Ala Arg Tyr Ser Ile Leu His Ala Asn Val Val Val Tyr Ser
                195                 200                 205
Tyr His Tyr Leu Leu Asp Pro Lys Ile Ala Asp Leu Val Ser Lys Glu
210                 215                 220
Leu Ala Arg Lys Ala Val Val Phe Asp Glu Ala His Asn Ile Asp
225                 230                 235                 240
Asn Val Cys Ile Asp Ser Met Ser Val Asn Leu Thr Arg Arg Thr Leu
                245                 250                 255
Asp Arg Cys Gln Gly Asn Leu Glu Thr Leu Gln Lys Thr Val Leu Arg
                260                 265                 270
Ile Lys Glu Thr Asp Glu Gln Arg Leu Arg Asp Glu Tyr Arg Arg Leu
                275                 280                 285
Val Glu Gly Leu Arg Glu Ala Ser Ala Arg Glu Thr Asp Ala His
290                 295                 300
Leu Ala Asn Pro Val Leu Pro Asp Glu Val Leu Gln Glu Ala Val Pro
305                 310                 315                 320
Gly Ser Ile Arg Thr Ala Glu His Phe Leu Gly Phe Leu Arg Arg Leu
                325                 330                 335
Leu Glu Tyr Val Lys Trp Arg Leu Arg Val Gln His Val Val Gln Glu
                340                 345                 350
Ser Pro Pro Ala Phe Leu Ser Gly Leu Ala Gln Arg Val Cys Ile Gln
                355                 360                 365
Arg Lys Pro Leu Arg Phe Cys Ala Glu Arg Leu Arg Ser Leu Leu His
370                 375                 380
Thr Leu Glu Ile Thr Asp Leu Ala Asp Phe Ser Pro Leu Thr Leu Leu
385                 390                 395                 400
Ala Asn Phe Ala Thr Leu Val Ser Thr Tyr Ala Lys Gly Phe Thr Ile
                405                 410                 415
Ile Ile Glu Pro Phe Asp Asp Arg Thr Pro Thr Ile Ala Asn Pro Ile
                420                 425                 430
Leu His Phe Ser Cys Met Asp Ala Ser Leu Ala Ile Lys Pro Val Phe
                435                 440                 445
Glu Arg Phe Gln Ser Val Ile Ile Thr Ser Gly Thr Leu Ser Pro Leu
450                 455                 460
Asp Ile Tyr Pro Lys Ile Leu Asp Phe His Pro Val Thr Met Ala Thr
```

-continued

```
465                 470                 475                 480
Phe Thr Met Thr Leu Ala Arg Val Cys Leu Cys Pro Met Ile Ile Gly
                485                 490                 495
Arg Gly Asn Asp Gln Val Ala Ile Ser Ser Lys Phe Glu Thr Arg Glu
                500                 505                 510
Asp Ile Ala Val Ile Arg Asn Tyr Gly Asn Leu Leu Leu Glu Met Ser
                515                 520                 525
Ala Val Val Pro Asp Gly Ile Val Ala Phe Phe Thr Ser Tyr Gln Tyr
                530                 535                 540
Met Glu Ser Thr Val Ala Ser Trp Tyr Glu Gln Gly Ile Leu Glu Asn
545                 550                 555                 560
Ile Gln Arg Asn Lys Leu Leu Phe Ile Glu Thr Gln Asp Gly Ala Glu
                565                 570                 575
Thr Ser Val Ala Leu Glu Lys Tyr Gln Glu Ala Cys Glu Asn Gly Arg
                580                 585                 590
Gly Ala Ile Leu Leu Ser Val Ala Arg Gly Lys Val Ser Glu Gly Ile
                595                 600                 605
Asp Phe Val His His Tyr Gly Arg Ala Val Ile Met Phe Gly Val Pro
                610                 615                 620
Tyr Val Tyr Thr Gln Ser Arg Ile Leu Lys Ala Arg Leu Glu Tyr Leu
625                 630                 635                 640
Arg Asp Gln Phe Gln Ile Arg Glu Asn Asp Phe Leu Thr Phe Asp Ala
                645                 650                 655
Met Arg His Ala Ala Gln Cys Val Gly Arg Ala Ile Arg Gly Lys Thr
                660                 665                 670
Asp Tyr Gly Leu Met Val Phe Ala Asp Lys Arg Phe Ala Arg Gly Asp
                675                 680                 685
Lys Arg Gly Lys Leu Pro Arg Trp Ile Gln Glu His Leu Thr Asp Ala
                690                 695                 700
Asn Leu Asn Leu Thr Val Asp Glu Gly Val Gln Val Ala Lys Tyr Phe
705                 710                 715                 720
Leu Arg Gln Met Ala Gln Pro Phe His Arg Glu Asp Gln Leu Gly Leu
                725                 730                 735
Ser Leu Leu Ser Leu Glu Gln Leu Glu Ser Glu Glu Thr Leu Lys Arg
                740                 745                 750
Ile Glu Gln Ile Ala Gln Gln Leu
                755                 760
```

DNA MOLECULES ENCODING HUMAN NHL A DNA HELICASE

CROSS-REFERENCE TO RELATED APPLICATIONS

This application claims the benefit, under 35 U.S.C. §119(e), of U.S. provisional application 60/169,970 filed Dec. 9, 1999.

STATEMENT REGARDING FEDERALLY-SPONSORED R&D

Not Applicable

REFERENCE TO MICROFICHE APPENDIX

Not Applicable

FIELD OF THE INVENTION

The present invention relates in part to isolated nucleic acid molecules (polynucleotides) which encode NHL, a putative DNA helicase. The present invention also relates to recombinant vectors and recombinant hosts which contain a DNA fragment encoding NHL, substantially purified forms of associated NHL, associated mutant proteins, and methods associated with identifying compounds which modulate NHL, which will be useful in the treatment of various neoplastic disorders, given that this gene is located at 20q13.3 and immediately adjacent to M68/DcR3, which is involved in tumor growth. Also included within the present invention is a human genomic fragment representing this portion of the human genome, along with three additional genes (M68/DcR3, SCLIP, and ARP).

BACKGROUND OF THE INVENTION

Naumovski et al. (1985, *Mol. Cell Biol.* 5:17–26; Reynolds et al. (1985 *Nucleic Acid Res* 13:2357–2372) and Weber et al. (1990 *EMBO J.* 9:1437–1447) disclose members of the RAD3/FRCC2 gene family of DNA helicases.

It is known that several chemotherapeutic agents inhibit helicases, including actinomycin C1, daunorubicin and nogalamycin (Tuteja, et al., 1997, *Biochem. Biophys. Res. Comm.* 236(3):636–640), and a prostate cancer drug, C1-958 (Lun, et al., 1998, *Cancer Chemother. Pharmacol.* 42(6):447–453). In addition, some topoisomerases have been shown to have anti-cancer activity.

Despite the identification of the aforementioned helicase-encoding genes and chemotherapeutic agents, it would be advantageous to identify additional genes which reside within chromosomal regions associated with a disease state such as cancer as well as a gene which encodes a type of protein which may be associated with that disease. The present invention addresses and meets this need by disclosing a DNA molecule encoding a DNA helicase with a chromosomal location suggestive of association with cancer.

SUMMARY OF THE INVENTION

The present invention relates to an isolated or purified nucleic acid molecule (polynucleotide) which encodes a novel mammalian DNA helicase.

The present invention also relates to an isolated nucleic acid molecule (polynucleotide) which encodes mRNA which expresses a novel human DNA helicase, NHL.

A preferred aspect of the present invention relates to an isolated or purified DNA molecule which encodes human NHL, the nucleotide sequence as set forth in FIGS. 1A–B and SEQ ID NO: 1.

The present invention also relates to biologically active fragments or mutants of SEQ ID NO: 1 which encode a mRNA molecule expressing a novel DNA helicase, NHL. Any such biologically active fragment and/or mutant will encode either a protein or protein fragment which at least substantially mimics the biological properties of the human NHL protein disclosed herein in FIG. 2 and as set forth as SEQ ID NO: 2. Any such polynucleotide includes but is not necessarily limited to nucleotide substitutions, deletions, additions, amino-terminal truncations and carboxy-terminal truncations such that these mutations encode mRNA which express a functional NHL protein in a host cell, so as to be useful for screening for agonists and/or antagonists of NHL activity.

The present invention also relates to recombinant vectors and recombinant hosts, both prokaryotic and eukaryotic, which contain the substantially purified nucleic acid molecules disclosed throughout this specification.

The present invention also relates to a substantially purified form of a human NHL protein which comprises the amino acid sequence disclosed in FIG. 2 and set forth as SEQ ID NO: 2.

A preferred aspect of this portion of the present invention is a NHL protein which consists of the amino acid sequence disclosed in FIG. 2 and set forth as SEQ ID NO: 2.

Another preferred aspect of the present invention relates to a substantially purified NHL protein, preferably a human NHL protein, obtained from a recombinant host cell containing a DNA expression vector comprises a nucleotide sequence as set forth in SEQ ID NO: 1 and expresses the respective NHL protein. It is especially preferred is that the recombinant host cell be a eukaryotic host cell, such as a mammalian cell line.

The present invention also relates to biologically active fragments and/or mutants of a NHL protein comprising the amino acid sequence as set forth in SEQ ID NO: 2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/or antagonists for human NHL pharmacology.

A preferred aspect of the present invention is disclosed in FIG. 2 and is set forth as SEQ ID NO: 2, a respective amino acid sequence which encodes human NHL. Characterization of one or more of these DNA helicase-like proteins allows for screening methods to identify novel NHL modulators that may be useful in the treatment of human neoplastic disorders. The modulators selected through such screening and selection protocols may be used alone or in conjunction with other cancer therapies. As noted above, heterologous expression of a NHL protein will allow the pharmacological analysis of compounds which modulate NHL activity and hence may be useful in various cancer therapies. To this end, heterologous cell lines expressing a NHL protein can be used to establish functional or binding assays to identify novel NHL modulators.

The present invention also relates to polyclonal and monoclonal antibodies raised in response to either the NHL or a biologically active fragment of NHL.

The present invention relates to transgenic mice comprising altered genotypes and phenotypes in relation to NHL and its in vivo activity.

The present invention also relates to NHL fusion constructs, including but not limited to fusion constructs which express a portion of the NHL protein linked to various markers, including but in no way limited to GFP (Green fluorescent protein), the MYC epitope, and GST. Any such fusion constructs may be expressed in the cell line of interest and used to screen for NHL modulators.

Therefore, the present invention relates to methods of expressing mammalian NHL, and preferably human NHL, biological equivalents disclosed herein, assays employing these gene products, recombinant host cells which comprise DNA constructs which express these proteins, and compounds identified through these assays which act as agonists or antagonists of NHL activity.

The present invention also relates to the isolated genomic sequence which comprises SEQ ID NO: 1, a 115 kb genomic fragment set forth herein as SEQ ID NO: 3. As especially preferred aspect of this portion of the invention is the region of the genomic fragment of SEQ ID NO: 3 which comprises the regulatory and coding regions of human NHL, as well as intervening sequences (introns). This 115 kb fragment contains at least the coding region of four genes, NHL, M68/DcR3, SCLIP and ARP. As discussed herein, it has been shown that this region of chromosome 20 is associated with tumor growth. Therefore, an aspect of this invention also comprises the use of one or more regions of this 115 kb genomic sequence to identify compounds which up or downregulate expression of one or more of the genes localized within this 115 kb region, wherein this up or down regulation results in an interference of tumor growth. For example, a transcription element of one of these four genes may be responsible for M68/DcR3 (and/or NHL) overexpression in tumors, and if M68 or NHL overexpression in tumors has a caustic role, blockage of M68/DcR3 or NHL overexpression in tumors by interfering with this transcription site will be useful.

It is an object of the present invention to provide an isolated nucleic acid molecule (e.g., SEQ ID NO: 1) which encodes novel form of human NHL, or fragments, mutants or derivatives of human NHL as set forth in FIG. 2 and SEQ ID NO: 2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for selective modulators of human NHL activity.

It is a further object of the present invention to provide the mammalian, and especially human, NHL proteins or protein fragments encoded by the nucleic acid molecules referred to in the preceding paragraph.

It is a further object of the present invention to provide recombinant vectors and recombinant host cells which comprise a nucleic acid sequence encoding mammalian, and especially human, NHL protein and biological equivalent thereof.

It is an object of the present invention to provide a substantially purified form of human NHL, as set forth in FIG. 2 and SEQ ID NO: 2.

Is another object of the present invention to provide a substantially purified recombinant form of a NHL protein which has been obtained from a recombinant host cell transformed or transfected with a DNA expression vector which comprises and appropriately expresses a complete open reading frame as set forth in SEQ ID NO: 1, resulting in a functional, processed form of NHL. It is especially preferred is that the recombinant host cell be a eukaryotic host cell, such as a mammalian cell line.

It is an object of the present invention to provide for biologically active fragments and/or mutants of mammalian, and especially human, NHL, such as set forth in SEQ ID NO: 2, including but not necessarily limited to amino acid substitutions, deletions, additions, amino terminal truncations and carboxy-terminal truncations such that these mutations provide for proteins or protein fragments of diagnostic, therapeutic and/or prophylactic use.

It is also an object of the present invention to use NHL proteins or biological equivalent to screen for modulators, preferably selective modulators, of human NHL activity. Any such compound may be useful in screening for and selecting compounds active against human neoplastic disorders.

As used herein, "substantially free from other nucleic acids" means at least 90%, preferably 95%, more preferably 99%, and even more preferably 99.9%, free of other nucleic acids. Thus, a human NHL DNA preparation that is substantially free from other nucleic acids will contain, as a percent of its total nucleic acid, no more than 10%, preferably no more than 5%, more preferably no more than 1%, and even more preferably no more than 0.1%, of non-NHL nucleic acids. Whether a given NHL DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a NHL protein preparation that is substantially free from other proteins will contain, as a percent of its total protein, no more than 10%, preferably no more than 5%, more preferably no more than 1%, and even more preferably no more than 0.1%, of non-NHL proteins. Whether a given NHL protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated NHL protein" or "purified NHL protein" also refer to NHL protein that has been isolated from a natural source. Use of the term "isolated" or "purified" indicates that NHL protein has been removed from its normal cellular environment. Thus, an isolated NHL protein may be in a cell-free solution or placed in a different cellular environment from that in which it occurs naturally. The term isolated does not imply that an isolated NHL protein is the only protein present, but instead means that an isolated NHL protein is substantially free of other proteins and non-amino acid material (e.g., nucleic acids, lipids, carbohydrates) naturally associated with the NHL protein in vivo. Thus, a NHL protein that is recombinantly expressed in a prokaryotic or eukaryotic cell and substantially purified from this host cell which does not naturally (i.e., without intervention) express this protein is of course "isolated NHL protein" under any circumstances referred to herein. As noted above, a NHL protein preparation that is an isolated or purified NHL protein will be substantially free from other proteins will contain, as a percent of its total protein, no more than 10%, preferably no more than 5%, more preferably no more than 1%, and even more preferably no more than 0.1%, of non-NHL proteins.

As used interchangeably herein, "functional equivalent" or "biologically active equivalent" means a protein which does not have exactly the same amino acid sequence as naturally occurring NHL, due to alternative splicing, deletions, mutations, substitutions, or additions, but retains substantially the same biological activity as NHL. Such functional equivalents will have significant amino acid sequence identity with naturally occurring NHL and genes and cDNA encoding such functional equivalents can be detected by reduced stringency hybridization with a DNA sequence encoding naturally occurring NHL. For example, a naturally occurring NHL disclosed herein comprises the amino acid sequence shown as SEQ ID NO: 2 and is encoded by SEQ ID NO: 1. A nucleic acid encoding a functional equivalent has at least about 50% identity at the nucleotide level to SEQ ID NO: 1.

As used herein, "a conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, the term "mammalian" will refer to any mammal, including a human being.

BRIEF DESCRIPTION OF THE DRAWINGS

FIGS. 1A–B shows the nucleotide sequence which comprises the open reading frame which encodes human NHL, the nucleotide sequence set forth as SEQ ID NO: 1. The initiating Met residue (ATG) and the stop codon (TAG) are underlined.

FIG. 2 shows the amino acid sequence of human NHL as set forth in SEQ ID NO: 2.

DETAILED DESCRIPTION OF THE INVENTION

Figure 3A:
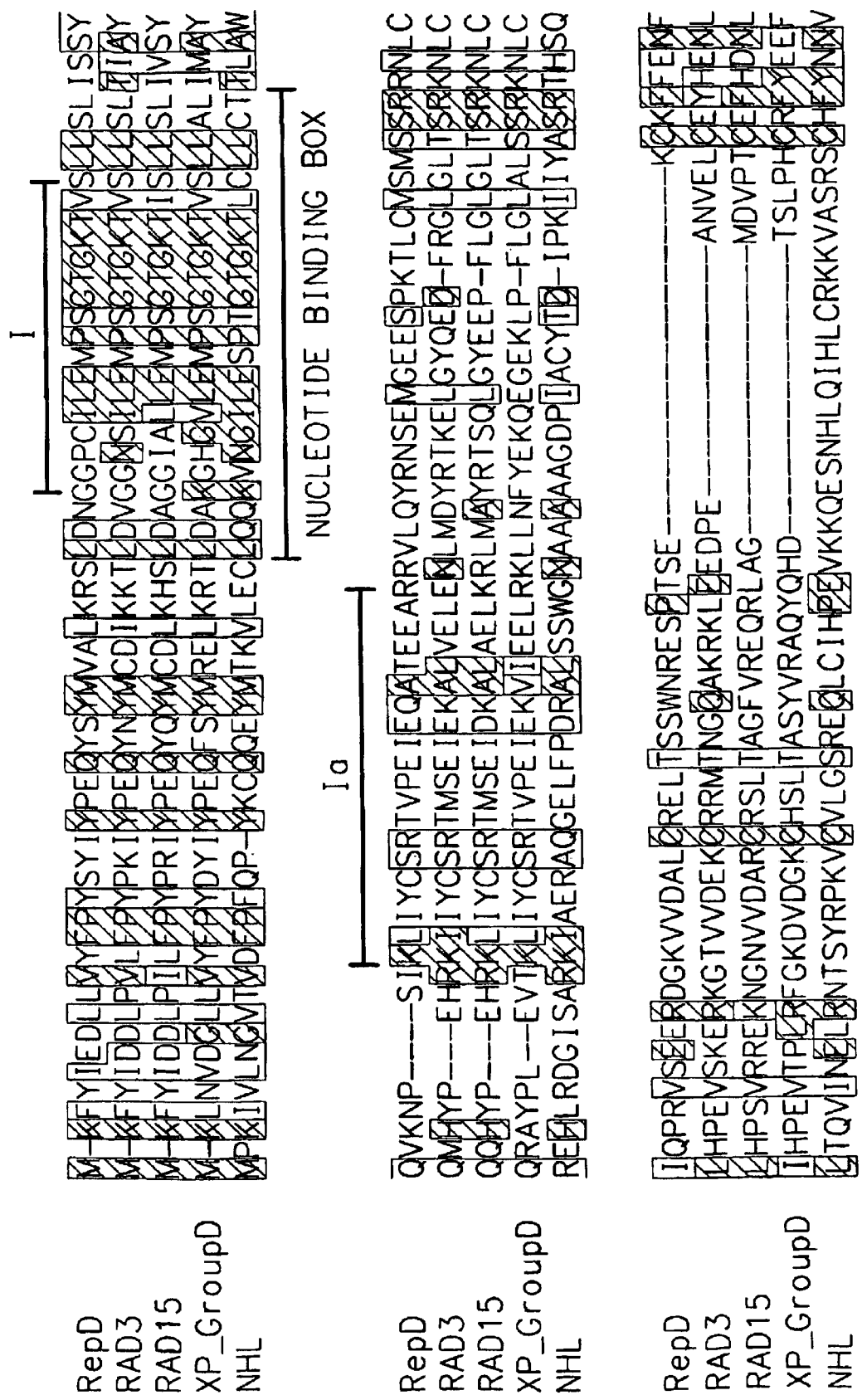
FIG. 3 shows the alignment of amino acid sequences of human NHL to ERCC2/RAD3 gene family members. Rep D (*Dictyosteliem discoideum*); RAD 3 (*S. cerevisiae*); RAD 15 (*S. pombe*) and XP_GroupD (*Homo sapien*).

The present invention relates to an isolated or purified nucleic acid molecule (polynucleotide) which encodes a novel mammalian DNA helicase. An especially preferred aspect of this invention relates to an isolated nucleic acid molecule (polynucleotide) which encodes mRNA which expresses a novel human DNA helicase, NHL.

The gene M68/DcR3 is a secreted TNFR member that is overexpressed in a number of human tumors. M68/DcR3 is located at 20q 13.3, a known site that is associated with frequent gene amplification in cancer. M68/DcR3 protein binds to FASL and inhibit FAS mediated apoptosis. Thus, genes tightly linked to M68/DcR3 may be coregulated (e.g. co overexpressed and/or amplified in tumors). During the course of cloning the genomic M68/DcR3 fragment and identifying genes that are linked to M68/DcR3 at 20q13.3, three genes, including a novel gene that is similar to the Rad3/ERCC2 helicase family, were identified (termed NHL) in the immediately adjacent (overlapping) region. Given NHL's chromosomal location and the frequent association of DNA helicases with human genetic disorders (mutations in DNA helicases have been found associated with multiple diseases, including xeroderma pigmentosum, Cockayne's syndrome, Bloom's syndrome, and Werner's syndrome), NHL is a candidate for contribution to certain human neoplastic disorders. To this end, the genomic clone for this gene is disclosed and the complete sequence is determined. The transcript was identified through exon prediction using GRAIL2 and sequence alignment to a contiguous 4.5 kilobase region of chromosome 4 (88% sequence identity). The complete exon structure of NHL was subsequently confirmed by RT-PCR analysis. Multiple sequence alignment of NHL to known helicases showed that NHL contains all the seven critical helicase domains. BLAST analysis of the predicted 1,219 amino acid sequence revealed an approximately 26% sequence identity and 48% sequence similarity to the RAD3/ERCC2 gene family of DNA helicases (Naumovski et al., 1985 *Mol. Cell Biol.* 5:17–26; Reynolds et al., 1985 *Nucleic Acid Res* 13:2357–72; Weber et al., 1990 *EMBO J.* 9:1437–1447). The mRNA expression pattern of NHL was also examined in multiple human tissues. Radiation hybrid chromosomal mapping reconfirms that it is linked to M68/DcR3 locus.

A preferred aspect of the present invention relates to an isolated or purified DNA molecule which encodes human NHL, the nucleotide sequence as set forth in FIGS. 1A–B and SEQ ID NO: 1, which is as follows:

```
AGTCAGCCCT GCTGCCAGCC AGTGCCGGGT GCTGGCCACT CAGGGAGGCC GCCCGGCACC    (SEQ ID NO:1)

ACTGCGGGAC AGTGAGCCCA GCAGAAGCTG GAACGCAGGA GAGGAAGGAG AGGCGCCGGT

CAGGGCTCTC AGGAGCCGGG TCCTGGGCAA GGCGCAGCCG TTTTCAAATT TTCAGGAAAG

CGGTCGGCTC ACACTCGAGC AGTAAAAAGA TGCCTCTGGC GAGGAGGCCC GTGCAGCTCT

CCGGCCAATG GTGGTCGCTC GGCCTAGAGA GGCGGTAGTC GAACGCAGAC CCTGCTGGGG

GAATCACATC AAGGGAGGAG ACGGGCGGGA CCCCAGATTT CTGCCTGTGG GCGATGGAAG

TGAGGTTCAC TGGCCAGCGG AGCCGGACAC AGAACGCGCA AAACGCCGTC TAGGCCTGCA

GGAGCCGAAG AGCAGGCGGA CCCCCTCCGC GGGGGAACAG TTTCCGCCGG GAGCACAAAG

CAACGGACCG GAAGTGGGGG GCGGAAGTGC AGTGGGCTCA GCGCCGACTG CGCGCCTCTG
```

```
CCCGCGAAAA CTCTGAGCTG GCTGACAGCT GGGGACGCCT GCGGCCCTC GACTGGAGTC
GGTTGAGTTC CTGAGGGACC CCGGTTCTGG AAGGTTCGCC GCGGAGACAA GTGAGCAGTC
TGTGCCATAG GGATTCTCGA AGAGAACAGC GTTGTCTCCC AGTGCACATG CTCGCATCGC
TTACCAGGAG TGCCCGAGAC CCTAAGATGT TCGGAGTGGT TTTTTCGCAC AGACCCGAAT
AGCCTGCCCC TCAGCCACGC TCTGTGCCCT TCTGAGAACA GGCTGATATG CCCAAGATAG
TCCTGAATGG TGTGACCGTA GACTTCCCTT TCCAGCCCTA CAAATGCCAA CAGGAGTACA
TGACCAAGGT CCTGGAATGT CTGCAGCAGA AGGTGAATGC CATCCTGGAG AGCCCTACGG
GTACAGGGAA GACGCTGTGC CTGCTGTGCA CCACGCTCGC CTGGCGAGAA CACCTCCGAG
ACGGCATCTC TGCCCGCAAG ATTGCCGAGA GGGCGCAAGG AGAGCTTTTC CCGGATCGGG
CCTTGTCATC CTGGGGCAAC GCTGCTGCTG CTGCTGGAGA CCCCATAGCT TGCTACACGG
ACATCCCAAA GATTATTTAC GCCTCCAGGA CCCACTCGCA ACTCACACAG GTCATCAACG
AGCTTCGGAA CACCTCCTAC CGGCCTAAGG TGTGTGTGCT GGGCTCCCGG GAGCAGCTGT
GCATCCATCC TGAGGTCAAG AAACAAGAGA GTAACCATCT ACAGATCCAC TTGTGCCGTA
AGAAGGTCCC AAGTCGCTCC TGTCATTTCT ACAACAACGT ACAAGAAAAA AGCCTGGAGC
AGGAGCTGGC CAGCCCCATC CTGGACATTG AGGACTTGGT CAAGAGCGGA ACCAAGCACA
GGGTGTGCCC TTACTACCTG TCCCGGAACC TGAAGCAGCA AGCCGACATC ATATTCATGC
CGTACAATTA CTTGTTGGAT GCCAAGAGCC GCAGAGCACA CAACATTGAC CTGAAGGGCA
CAGTCGTGAT CTTTGACGAA GCTCACAACG TGGAGAAGAT GTCTGAAGAA TCGCCATCCT
TTGACCTGAC TCCCCATGAC CTGGCTTCAG GACTGGACGT CATAGACCAG GTGCTGGAGG
AGCAGACCAA GGCAGCGCAG CACCGTGAGC CCCACCCGGA GTTCAGCGCG GACTCCCCCA
GCCCAGGGCT GAACATGGAG CTGGAAGACA TTGCAAAGCT GAAGATGATC CTGCTGCGCC
TGGACGGGGC CATCGATGCT GTTGACCTGC CTGGAGACGA CAGCGGTGTC ACCAAGCCAG
GGAGCTACAT CTTTCAGCTG TTTGCTGAAG CCCAGATCAC GTTTCAGACC AAGGGCTGCA
TCCTGGACTC GCTGGACCAG ATCATCCAGC ACCTGGCAGG ACGTCCTGGA GTGTTCACCA
ACACGGCCCG ACTGCAGAAG CTGGCGGACA TTATCCAGAT TGTCTTCAGT GTGGACCCCT
CCGAGGGCAC CCCTGGTTCC CCAGCAGGGC TGGGGGCCTT ACAGTCCTAT AAGGTGCACA
TCCATCCTGA TCCTGGTCAC CGGAGGACGG CTCAGCGGTC TGATGCCTGG AGCACCACTG
CAGCCAGAAA GCGAGGGAAG GTGCTGAGCT ACTGGTGCTT CAGTCCCGGC CACAGCATGC
ACGAGCTGGT CCGCCAGGGC GTCCGCTCCC TCATCCTTAC CAGCGGCACG CTGGCCCCOG
TGTCCTCCTT TGCTCTGGAG ATGCAGATCC CTTTCCCAGT CTGCCTGGAG AACCCACACA
TCATCGACAA GCACCAGATC TGGGTGGGGG TCGTCCCCAG AGCCCCCGAT GGAGCCCAGT
TGAGCTCCGC GTTTGACAGA CGGTTTTCCG AGGAGTCCTT ATCCTCCCTG GGCAAGGCTC
TGGGCAACAT CGCCCGCGTG GTCCCCTATG GCCTCCTGAT CTTCTTCCCT TCCTATCCTG
TCATGGACAA GAGCCTGCAC TTCTGGCGGG CCCCCGACTT GGCCAGGAAG ATCGACGCGC
TGAAGCCGCT GTTTGTCGAG CCCAGGAGCA AAGGCAGCTT CTCCGAGACC ATCAGTGCTT
ACTATGCAAG GOTTGCCGCC CCTGGGTCCA CCGGCCCCAC CTTCCTGCCG GTCTGCCGGG
GCAAGGCCAG CGAGGGCTG GACTTCTCAG ACACGAATGG CCGTGGTGTG ATTGTCACGG
GCCTCCCGTA CCCCCCACGC ATGGACCCCC GGGTTCTCCT CAAGATGCAG TTCCTGGATG
AGATGAAGGG CCAGGGTGGG CCTGGGGGCC ACTTCCTCTC TGGGCAGCAG TGGTACCGGC
AGCAGGCGTC CAGGGCTGTG AACCAGGCCA TCGGGCGAGT GATCCGGCAC CGCCAGGACT
```

-continued

```
ACGGAGCTGT CTTCCTCTGT GACCACAGGT TCGCCTTTGC CGACGCAAGA GCCCAACTGC

CCTCCTCGGT GCGTCCCCAC GTCAGGGTGT ATGACAACTT TGGCCATGTC ATCCGAGACG

TGGCCCACTT CTTCCGTGTT GCCGAGCGAA CTATGCCAGC GCCGGCCCCC CGGGCTACAG

CACCCAGTGT GCGTGGAGAA GATGCTGTCA GCGAGGCCAA GTCGCCTGGC CCCTTCTTCT

CCACCAGGAA AGCTAAGAGT CTGGACCTGC ATGTCCCCAG CCTGAAGCAG AGGTCCTCAG

GGTCACCAGC TGCCGGGGAC CCCGAGAGTA GCCTGTGTGT GGAGTATGAG CAGGAGCCAG

TTCCTGCCCC GCAGAGGCCC AGGGGGCTGC TGGCCGCCCT GGAGCACAGC GAACAGCGGG

CGGGGAGCCC TGGCGAGGAG CAGGCCCACA GCTGCTCCAC CCTGTCCCTC CTGTCTCAGA

AGAGGCCGGC AGAAGAACCG CGAGGAGGGA GGAAGAAGAT CCGGCTCGTC AGCCACCCGG

AGGAGCCCGT GGCTGGTGCA CAGACGGACA GGGCCAAGCT CTTCATGGTG GCCGTGAAGC

AGGAGTTGAG CCAAGCCAAC TTTGCCACCT TCACCCAGGC CCTGCAGGAC TACAAGGGTT

CCGATGACTT CGCCGCCCTG GCCGCCTGTC TCGGCCCCCT CTTTGCTGAG GACCCCAAGA

AGCACAACCT GCTCCAAGGC TTCTACCAGT TTGTGCGGCC CCACCATAAG CAGCAGTTTG

AGGAGGTCTG TATCCAGCTG ACAGGACGAG GCTGTGGCTA TCGGCCTGAG CACAGCATTC

CCCGAAGGCA GCGGGCACAG CCCGTCCTGG ACCCCACTGG AAGAACGGCG CCGGATCCCA

AGCTGACCGT GTCCACGGCT GCAGCCCAGC AGCTGGACCC CCAAGAGCAC CTGAACCAGG

GCAGGCCCCA CCTGTCGCCC AGGCCACCCC CAACAGGAGA CCCTGGCAGC CAACCACAGT

GGGGGTCTGG AGTGCCCAGA GCAGGGAAGC AGGGCCAGCA CGCCGTGAGC GCCTACCTGG

CTGATGCCCG CAGGGCCCTG GGGTCCGCGG GCTGTAGCCA ACTCTTGGCA GCGCTGACAG

CCTATAAGCA AGACGACGAC CTCGACAAGC TGCTGGCTGT GTTGGCCGCC CTGACCACTG

CAAAGCCACA GGACTTCCCC CTGCTGCACA GGTTCAGCAT GTTTGTGCGT CCACACCACA

AGCAGCGCTT CTCACAGACG TGCACAGACC TGACCGCCCG GCCCTACCCG GCCATGGACC

CACCGGGACC CCAGGAGGAG AGGCTTGCCG TGCCTCCTGT GCTTACCCAC AGGGCTCCCC

AACCAGGCCC cTCACGGTCC GAGAAGACCC GGAAGACCCA GAGCAAGATC TCGTCCTTCC

TTAGACACAG GCCAGCAGGG ACTGTGCGGG CGCGCCGTGA GGATGCAGGT CCCACCCACT

CCTCAGGACC TCCCCACGGG CCTGCAGCAT CTCAGTGGGG CCTCTAGGAT GTGCCCAGCC

TGCCACACCG CCTCCAGGAA GCAGAGCGTC ATGCAGGTCT TCTGGCCAGA GCCCCAGTGA

GTGCCCACGG AGGCCCCCAG CACACCCAAC GTGGCTTGAT CACCTGCCTG TCCAGCTCTG

GTGGGCCAAG AACCCACCCA ACAGAATAGG CCAGCCCATC CCAGCCGGCT TGGCCCCCTG

CAGGCCTCAC CCAGGCCGGG CCCATGGTTG GTCCCTCCGG TCGGACCGGA TCTGGGCCTG

CCTCTGAGAA GCCCTCACCT ACCTTGGGGT CTGCGGTGGG TTTCTGGGAA AGTGCTTCCC

CAGAACTTCC CTGCCTCCTG GCCTGTGAGT GGTGCCACAC GGGCACCCCA GCTGAGCCCC

TCACCGGGAA GGAGGAGACC CCCGTGGGCA CGTCTCCACT TTTAATCAGG GGACAGGGCT

CTCTAATAAA GCTGCTGGCA GTGCCC
```

The above-exemplified isolated DNA molecule shown in FIGS. 1A–B and SEQ ID NO: 1 comprise 4946 nucleotides, with an initiating Met at nucleotides 828-830 and a "TAG" termination codon at nucleotides 4485–4487. The initiating Met and TAG termination codon are underlined.

The present invention also relates to biologically active fragments or mutants of SEQ ID NO: 1 which encode a mRNA molecule expressing a novel DNA helicase, NHL. Any such biologically active fragment and/or mutant will encode either a protein or protein fragment which at least substantially mimics the biological properties of the human NHL protein disclosed herein in FIG. 2 and as set forth as SEQ ID NO: 2. Any such polynucleotide includes but is not necessarily limited to nucleotide substitutions, deletions, additions, amino-terminal truncations and carboxy-terminal truncations such that these mutations encode mRNA which express a functional NHL protein in a host cell, so as to be useful for screening for agonists and/or antagonists of NHL activity.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification.

The degeneracy of the genetic code is such that, for all but two amino acids, more than a single codon encodes a particular amino acid. This allows for the construction of synthetic DNA that encodes the NHL protein where the nucleotide sequence of the synthetic DNA differs significantly from the nucleotide sequence of SEQ ID NO: 1 but still encodes the same NHL protein as SEQ ID NO: 2. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the NHL protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ilc=Isoleucine: codons AUA, AUC, AUU
K=Lys=Lysinc: codons AAA, AAG
L=Leu=Leucinc: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGC, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

The present invention also relates to recombinant vectors and recombinant hosts, both prokaryotic and eukaryotic, which contain the substantially purified nucleic acid molecules disclosed throughout this specification. The nucleic acid molecules of the present invention encoding a NHL protein, in whole or in part, can be linked with other DNA molecules, i.e, DNA molecules to which the NHL coding sequence are not naturally linked, to form "recombinant DNA molecules" which encode a respective NHL protein. The novel DNA sequences of the present invention can be inserted into vectors which comprise nucleic acids encoding N or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a NHL protein. It is well within the purview of the skilled artisan to determine an appropriate vector for a particular gene transfer or other use.

Included in the present invention are DNA sequences that hybridize to SEQ ID NO: 1 under stringent conditions. By way of example, and not limitation, a procedure using conditions of high stringency is as follows: Prehybridization of filters containing DNA is carried out for 2 hours to overnight at 65° C. in buffer composed of 6×SSC, 5× Denhardt's solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5×Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook et al., 1989, *Molecular Cloning: A Laboratory Manual*; Cold Spring Harbor Laboratory, Cold Spring Harbor, N.Y. In addition to the foregoing, other conditions of high stringency which may be used are well known in the art.

The present invention also relates to a substantially purified form of a human NHL protein which comprises the amino acid sequence (1219 amino acid residues) disclosed in FIG. 2 and set forth as SEQ ID NO: 2. A preferred aspect of this portion of the present invention is a NHL protein which consists of the amino acid sequence disclosed in FIG. 2 and set forth as SEQ ID NO: 2, as follows:

```
MPKIVLNCVT VDFPFQPYKC QQEYMTKVLE CLQQKVNGTL ESPTGTGKTL CLLCTTLAWR  (SEQ ID NO:2)

EHLRDGISAR KIAERAQCEL FPDRALSSWG NAAAAAGDPI ACYTDLPKII YASRTHSQLT

QVINELRNTS YRPKVCVLGS REQLCIHPEV KKQESNHLQI HLCRKKVASR SCKFYNNVEE

KSLEQELASP ILDIEDLVKS GSKHRVCPYY LSRNLKQQAD IIFMPYNYLL DAKSRRAHNI

DLKGTVVIFD EAHNVEKMCE ESASFDLTPH DLASGLDVTD QVLEEQTKAA QQCEPHPEFS

ADSPSPGLNM ELEDIAKLKM ILLRLEGAID AVELPGDDSG VTKPGSYIFE LFAEAQITFQ

TKCCILDSLD QIIQHLAGRA GVFTNTACLQ KLADIIQIVF SVDPSEGSPG SPAGLGALQS

YKVHIHPDAG HRRTAQRSDA WSTTAARKRG KVLSYWCFSP GHSMHELVRO GVRSLILTSG

TLAPVSSFAL EMQIPFPVCL ENPHTIDKHQ IWVGVVPRGP DGAQLSSAFD RRFSEECLSS

LGKALGNIAR VVPYGLLIFF PSYPVMEKSL EFWRARDLAR KMEALKPLFV EPRSKGSFSE

TISAYYARVA APGSTGATPL AVCRGKASEG LDFSDTNGRG VIVTGLPYPP RMDPRVVLKN

QFLDEMKGQG GAGGQFLSGQ EWYRQQASRA VNQAIGRVIR HRQDYGAVFL CDHRFAFADA

RAQLPSWVRP HVRVYDNFGH VIRDVAQFFR VAERTMPAPA PRATAPSVRG EDAVSEAKSP

GPFFSTRKAK SLDLHVPSLK QRSSGSPAAG DPESSLCVEY EQEPVPARQR PRGLLAALEH

SEQRAGSPGE EQAHSCSTLS LLSEKRPAEE PRGGRKKIRL VSHPEEPVAG AQTDRAKLFM

VAVKQELSQA NFATFTQALQ DYKGSDDFAA LAACLCPLFA EDPKKHNLLQ GFYQFVRPHH

KQQFEEVCIQ LTGRGCGYRP EHSTPRRQRA QPVLDPTGRT APDPKLTVST AAAQQLDPQE

HLNQGRPHLS PRPPPTGDPG SQPQWGSGVP RAGKQGQHAV SAYLADARRA LGSAGCSQLL

AALTAYKQDD DLDKVLAVLA ALTTAKPEOF PLLHRPSMFV RPHHKQRFSQ TCTDLTCRPY

PGMEPPGPQE ERLAVPPVLT HRAPQPGPSR SEKTGKTQSK ISSFLRQRPA GTVGAGGEDA

GPSQSSGPPH GPAASEWCL*
```

The present invention also relates to biologically active fragments and/or mutants of the human NHL protein comprising the amino acid sequence as set forth in SEQ ID NO: 2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of NHL function.

Another preferred aspect of the present invention relates to a substantially purified, fully processed NHL protein obtained from a recombinant host cell containing a DNA expression vector which comprises a nucleotide sequence as set forth in SEQ ID NO: 1 and expresses the human NHL protein. It is especially preferred is that the recombinant host cell be a eukaryotic host cell, such as a mammalian cell line.

As with many proteins, it is possible to modify many of the amino acids of NHL protein and still retain substantially the same biological activity as the wild type protein. Thus this invention includes modified NHL polypeptides which have amino acid deletions, additions, or substitutions but that still retain substantially the same biological activity as a respective, corresponding NHL. It is generally accepted that single amino acid substitutions do not usually alter the biological activity of a protein (see, e.g., *Molecular Biology of the Genie*, Watson et al., 1987, Fourth Ed., The Benjamin/Cummings Publishing Co., Inc., page 226; and Cunningham & Wells, 1989, *Science* 244:1081–1085). Accordingly, the present invention includes a polypeptide where one amino acid substitution has been made in SEQ ID NO: 2 wherein the polypeptide still retains substantially the same biological activity as a corresponding NHL protein. The present invention also includes polypeptides where two or more amino acid substitutions have been made in SEQ ED NO: 2 wherein the polypeptide still retains substantially the same biological activity as a corresponding NHL protein. In particular, the present invention includes embodiments where the above-described substitutions are conservative substitutions.

One skilled in the art would also recognize that polypeptides that are functional equivalents of NHL and have changes from the NHL amino acid sequence that are small deletions or insertions of amino acids could also be produced by following the same guidelines, (i.e, minimizing the differences in amino acid sequence between NHL and related proteins. Small deletions or insertions are generally in the range of about 1 to 5 amino acids). The effect of such small deletions or insertions on the biological activity of the modified NHL polypeptide can easily be assayed by producing the polypeptide synthetically or by making the required changes in DNA encoding NHL and then expressing the DNA recombinantly and assaying the protein produced by such recombinant expression.

The present invention also includes truncated forms of NHL which contain the region comprising the active site of the enzyme. Such truncated proteins are useful in various assays described herein, for crystallization studies, and for structure-activity-relationship studies.

The present invention also relates to isolated nucleic acid molecules which are fusion constructions expressing fusion proteins useful in assays to identify compounds which modulate wild-type NHL activity, as well as generating antibodies against NHL. One aspect of this portion of the invention includes, but is not limited to, glutathione S-transferase (GST)-NHL fusion constructs. Recombinant GST-NHL fusion proteins may be expressed in various expression systems, including *Spodoptera frugiperda* (Sf21) insect cells (Invitrogen) using a baculovirus expression vector (pAcG2T, Pharmingen). Another aspect involves NHL fusion constructs linked to various markers, including but not limited to GFP (Green fluorescent protein), the MYC epitope, and GST. Again, any such fusion constructs may be expressed in the cell line of interest and used to screen for modulators of one or more of the NHL proteins disclosed herein.

Any of a variety of procedures may be used to clone NHL. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of NHL cDNA. These gene-specific primers are designed through identification of an expressed sequence tag (EST) nucleotide sequence which has been identified by searching any number of publicly available nucleic acid and protein databases; (2) direct functional expression of the NHL cDNA following the construction of a NHL-containing cDNA library in an appropriate expression vector system; (3) screening a NHL-containing cDNA library constructed in a bacteriophage or plasmid shuttle vector with a labeled degenerate oligonucleotide probe designed from the amino acid sequence of the NHL protein; (4) screening a NHL-containing cDNA library constructed in a bacteriophage or plasmid shuttle vector with a partial cDNA encoding the NHL protein. This partial cDNA is obtained by the specific PCR amplification of NHL DNA fragments through the design of degenerate oligonucleotide primers from the amino acid sequence known for other kinases which are related to the NHL protein; (5) screening a NHL-containing cDNA library constructed in a bacteriophage or plasmid shuttle vector with a partial cDNA or oligonucleotide with homology to a mammalian NHL protein. This strategy may also involve using gene-specific oligonucleotide primers for PCR amplification of NHL cDNA identified as an EST as described above; or (6) designing 5' and 3' gene specific oligonucleotides using SEQ ID NO: 1 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding NHL.

It is readily apparent to those skilled in the art that other types of libraries, as well as libraries constructed from other cell types or species types, may be useful for isolating a NHL-encoding DNA or a NHL homologue. Other types of libraries include, but are not limited to, cDNA libraries derived from other cells.

It is readily apparent to those skilled in the art that suitable cDNA libraries may be prepared from cells or cell lines which have NHL activity. The selection of cells or cell lines for use in preparing a cDNA library to isolate a cDNA encoding NHL may be done by first measuring cell-associated NHL activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding NHL may also be isolated from a suitable genomic DNA library. Construction of genomic DNA libraries can be performed by standard techniques well known in the art. Well known genomic DNA library construction techniques can be found in Sambrook, et al., supra. One may prepare genomic libraries, especially in P1 artificial chromosome vectors, from which genomic clones containing the NHL gene can be isolated, using probes based upon the NHL nucleotide sequences disclosed herein. Methods of preparing such libraries are known in the art (Ioannou et al., 1994, *Nature Genet.* 6:84–89).

In order to clone a NHL gene by one of the preferred methods, the amino acid sequence or DNA sequence of a NHL or a homologous protein may be necessary. To accomplish this, a respective NHL protein may be purified and the partial amino acid sequence determined by automated sequenators. It is not necessary to determine the entire amino acid sequence, but the linear sequence of two regions of 6 to 8 amino acids can be determined for the PCR amplification of a partial NHL DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the No sequence but others in the set will be capable of hybridizing to NHL DNA even in the presence of DNA oligonucleotides with mismatches. The mismatched DNA oligonucleotides may still sufficiently hybridize to the NHL DNA to permit identification and isolation of NHL encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1 either for the purpose of isolating overlapping 5' and 3' RACE products for generation of a full-length sequence coding for NHL, or to isolate a portion of the nucleotide sequence coding for NHL for use as a probe to screen one or more cDNA- or genomic-based libraries to isolate a full-length sequence encoding NHL or NHL-like proteins.

This invention also includes vectors containing a NHL gene, host cells containing the vectors, and methods of making substantially pure NHL protein comprising the steps of introducing the NHL gene into a host cell, and cultivating the host cell under appropriate conditions such that NHL is produced. The NHL so produced may be harvested from the host cells in conventional ways. Therefore, the present invention also relates to methods of expressing the NHL protein and biological equivalents disclosed herein, assays employing these gene products, recombinant host cells which comprise DNA constructs which express these proteins, and compounds identified through these assays which act as agonists or antagonists of NHL activity.

The cloned NHL cDNA obtained through the methods described above may be recombinantly expressed by molecular cloning into an expression vector (such as pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce recombinant NHL. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the NHL cDNA sequence(s) that yields optimal levels of NHL, cDNA molecules including but not limited to the following can be constructed: a cDNA fragment containing the full-length open reading frame for NHL as well as various constructs containing portions of the cDNA encoding only specific domains of the protein or rearranged domains of the protein. All constructs can be designed to contain none, all or portions of the 5' and/or 3' untranslated region of a NHL cDNA. The expression levels and activity of NHL can be determined following the introduction, both singly and in combination, of these constructs into appropriate host cells. Following determination of the NHL cDNA cassette yielding optimal expression in transient assays, this NHL cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al, supra, are well known and available to the artisan of ordinary skill in the art. Therefore, another aspect of the present invention includes host cells that have been engineered to contain and/or express DNA sequences encoding the NHL protein. An expression vector containing DNA encoding a NHL-like protein may be used for expression of NHL in a recombinant host cell. Such recombinant host cells can be cultured under suitable conditions to produce NHL or a biologically equivalent form. Expression vectors may include, but are not limited to, cloning vectors, modified cloning vectors, specifically designed plasmids or viruses. Commercially available mammalian expression vectors which may be suitable for recombinant NHL expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNA1, pcDNA1amp (Invitrogen), pcDNA3 (Invitrogen), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lZD35 (ATCC 37565). Also, a variety of bacterial expression vectors may be used to express recombinant NHL in bacterial cells. Commercially available bacterial expression vectors which may be suitable for recombinant NHL expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant NHL in fungal cells. Commercially available fungal cell expression vectors which may be suitable for recombinant NHL expression include but are not limited to pYES2 (Invitrogen) and Pichia expression vector (Invitrogen) Also, a variety of insect cell expression vectors may be used to express recombinant protein in insect cells. Commercially available insect cell expression vectors which may be suitable for recombinant expression of NHL include but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to Drosophiila and silkworm derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171) and CPAE (ATCC CCL 209).

Figure 5A:
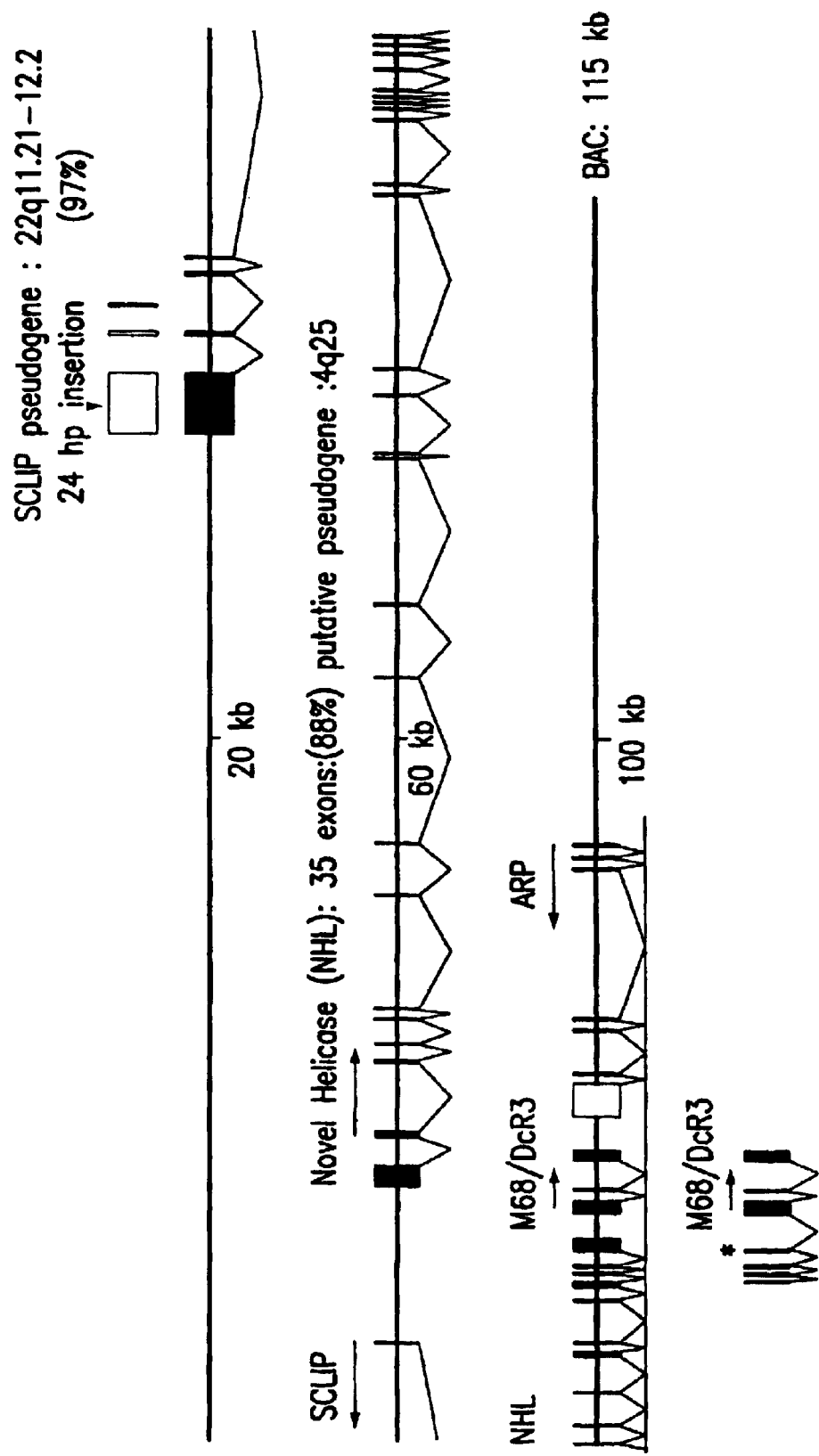
FIGS. 5A–B show the genomic structure of the NHL gene (FIG. 5A) and the entire 115 kb genomic region (FIG. 5B) containing the NHL, M68/DcR3, SCLIP and ARP genes.

As disclosed in Example section 1, a 115 kb BAC clone (from Genome Systems) was subcloned and subjected to restriction and sequence analysis. Four genes at chromosome location 20q13.3 were identified, including M68/DcR3, NHL, SCLIP and ARP (FIG. 5A). The nucleotide sequence of this BAC clone, hbm168, is presented as follows:

```
TGAAGAGCTT TCACCAAGAG GCTGTGACGA GGCCCTACGA GGACTCTGGC TCTCCTCCTG  60    (SEQ ID NO:3)

CTAAGCACAC CCAGGCACGT GTCCTGGCAG ATGAGGACCA CATGCACACC CTCGGCCAGC  120

CCACCAATGC CCGGATATGC AAGTGAGCCC AGCCTGGACC CCCCCCCGAC GCCCACCAGC  180

ACCAGCCCAG CCCCGAAAAC CTTAAGAAAT GACCAGTGTC TGCTGCTTTA AGCCACCAAG  240

CTCTGCGGTG GTTTGTTAGG CTCCAACCAT GGCTAATTCA GAAACTGCCA GAAACAAGCA  300

CTGCTGTCCC CACCCTCCGA CACACAGCAC CGCCTCTGCG TGGGGAGAGG GCACAGGCTA  360

AGGGCACAAA TGCCATCCCA GACCCGGCTC TTGTCTCTGG AAGGGGCCAC TGTCCCATGA  420
```

-continued

```
GGCAGAGCAA ACCTTGGCAG GACCTTATCC CACAGCAATT TAAAAGAGAA GAAACAGGCT    480

GGGCGTGGTC GCTCATGCCT ATAATCCCAO CACTTTGGGA GGCCAAGGTG GTGGATCACT    540

TCAGGTCAGG AGTTCAAGAC CAGCCTGGCC AATATCGTGA AACCCTGTCT CTACGAAAAA    600

TACAAAATTT AGGCAGGCGT GGTGGCGGGT GCCTGTAATC CCTGCTATTC AGGAGGCTGA    660

GGCAAGAGAT TTACTTGAAC CCAGGAGGTG GAGGCTGCTG CAGTGAGCTG AGATCATGCC    720

ACTGCACTCC ACCCTGTCTG ACGGAGTGAG ACTTGGTCTC AAAAAAAAAA AAGGAAACAC    780

ATCTGACTAG TGTGATCTCG CAAGGAACAT TCCAGACACA GTGGAGCTAG AAGGTTCTTC    840

TCCAAACAAG GAATCCCCAG GGCATCAAAT TCTTTTGCAT CGGCCAGACA TGCTGGCTCA    900

AGCCTGTAAC CCCACTGCTT CGGGAGCCTG AGGTGGGAGG ACTGCTTCAC TCCACGAGTT    960

CAACACTAGC TTGOGCAACA CAGTAGAGC CCATTAGCCA GGCGTGGTGG CACATGCCTG   1020

CAGTCCCAGC ACTGTACTAA AAATCTACAC GGCGCCCGCC ATGGTGGCAC ATGCCTGTAG   1080

AGTCCCACCT ACTCAGGAGG CTGAGGCACG ACGATTCCTT GAACCCAGGA GGTCACGGCT   1140

GCCATCAGCC GTGACTGTGC CACTGCACTC CAGTCTGTGC AACAGAACGA GACTCTGTTT   1200

CGAAAAACAA AAAATCATTT CATGTCTCCA GTTTCTCCAC TGGCAAAAGA CTCTGTCAAC   1260

GTAAAAAATC GTTCTGACCC ACAGAAATCT AAGAAAGGAA AAAATATAAA AAATAGAAAA   1320

TTTAAAAAAG AGATGGTCTC AGAATAAAGA CCAACCTGGG CTATGGTTGT CACTCTTCCC   1380

TCACACCTTA GAAAGCTTTC TGCCCGCATC TGGCCAAAGG GCCACCCTGC CCCATCTTGG   1440

ATCAGTGAGG TGCCTTCCAA CAAGCCACCT GCCCTGCAGC CCGTCCTGTC TTCTCTGCCA   1500

CCCCACGCTC AGTAGGGGAG GGGAAGTCGC TAGGTTTTAG TTCACCAGTC TCTGGATCAA   1560

GACGTGCCAT AACCAAGAAG CCCCAGCCAC ACCCAGACCC CATGTGGCCA CAAGCCGTGA   1620

GCTGGGAAGG CCCAGGAAAA GGCGGGAGCC GGACGAATCG AAATGTCATT CTGTGGCCAC   1680

AGAAATCATC TCAACCTTTT GTAACTTCCT ACCAAGACGC AGTCTTAGCT CTGCCCTTGA   1740

ACCAGCACTT GCTGATGTCG CTTGCGTCAA TCAAGGCAAC AGAAGTCAGC AGGAGGCCCA   1800

CTTTCCTCTG CAACTGTGCG CTTACGGGGC AAAGAAGTCC AGGCCTCCAG GTGGAGGATC   1860

ACACACCGGG CAAAGCAGAG GACAGCCACC CAGCCGAGCC TACCTGTGCC TCAGACTGCC   1920

TCCCTCCAGA GACCCCTGTG CCAAGGCCA CCCAGACCAC CAGGTCCTTG CCAAGCTGTC   1980

AGCTGACGAC AGCCGTTCCT GAGCCCGGCC CAGACCACCA GAACCACGAA CCAACCAACA   2040

GAATTAAAAA TAATAACAAC TATGTCTTGT CTTAAGCCAC TAAGTTTTGG ATGGTTTCTT   2100

TCTTTCTTTT TCTTTTTTTT TTTCGGAGAC GCAGTCTCAC TCTGTTGCCC AGGCTGGAGT   2160

GCAGTGGCGC AATCTTGGCT CACTGCAAGC TCTGCCCCCC GGATTCACGC CATTCCCCTG   2220

CCTCAGCCTC CTGAGTAACT GCGACTACAG GTGCCTGCCA TTGCGTGTTT TCTTAAACAG   2280

CAAAAGAAAA CTGACACAAT CATAAACAGA GCAAGCAAGA GAACTTGGCA ATTATTTCCT   2340

CTCTACTTCT CACTGTTCTT CAAAGAGTTA ACTCAAGCAT AAGATGTGAG CAAATTCTTT   2400

TAACATCCTA GAAAAAAAGC TCCTACTCAG TCTTCATAAA GCAAAGCTAA CCTACAGGAG   2460

CCACCTTCCA CAGTGACCAC AGGAAACCAA GACAGCAAGT GGGACACCAG CCTCCAGGGC   2520

ACTGCGCCAG CCGTGCGCCT GTGTCTGCCA CTGCCCTGGT CCGTCACTGC CACCAGCCGG   2580

CAAGACACCC ACAGAGGAGA GCTCTAAGCC ACAACTGTGT ACGAAGACAA CTGTGCACCA   2640

TTTTATTACT ACAACATTTT TGTTTTCTTT TTTTTTTTTT TTTGAGACTC AGTCTCGCTC   2700

TGTCACCCAG GCTGGAGTGC AGTGGCACAA TCTCGGCTCA CTGTAACCTC CATCTCCCTG   2760

GTTCAAGCAA TTCTCCTGCT GCAGCCTCCC AACTGGATTA CAGGCGCCCG CCACCACGCC   2820
```

```
TGGCTAATTT TTGTACTTT AGTAGAGATC CGGTTTCACC ATCTTGGCCA GACTGGTCTC    2880

AAATTCCTGA CAAGTCATCC ACCCACCCTG GCCTCCCAAA GTGCTGGGAT TACAGGTGTG    2940

AGCCACTCCG CCTGGCCCAT TTTTGTTTAT CAATAAAAAT CTACTTAATG TTGAACTCTC    3000

CACATTTCAA ATGGGTAACT CCAGTGTCCT TGATGCTCCT GCGACATGTT CGTGAGACTT    3060

CTCTTGGGTC TGAGAGTCTA GCATGTGGGT GGTCTGCACA CGACGGCCAG CCAAGACTGC    3120

ACAGCCGGCC AGGGTAAAGA GACCCCCTAG GATGTCAAGC CCGCCCTGCA TTTGTCAGAC    3180

TGGGCAACAC CCACTCCATC AGATGGACCC TGGTATGGGC CGCAAGCCAC CTAGGTGCCG    3240

AGGCAAGAGA CCGAGCGCAC GACCTGTTCC GGTGTAATAA AATGCATAAA ATAAGAATAG    3300

TTATACTAGA TATAGATCAT AAATATGATT ATATATGAAT ATCATTCATC ATTAGTTTGT    3360

ACCAATTACT CTTTATTCCA ATATTATAAT AATCCTTGCC TAAGCATAAC CTAGGAAAAA    3420

CTACGAAATC ATAACCTAGU AAAAACTAGG CCATACAGAG ATAGGAGCTG AGCGGACATA    3480

GTGACAACTC ACCACAAGAC AAGAGTGCGA GCCTTCTGTT ATGCCTCGAC ACGGCCACCA    3540

GAGGGCTCCT TGGTCTAGCG GTAACGCCAG CATCTGGGAA CACCCCGTT GCCAAGTGGA    3600

CCGTGGTCTA GCGGTAGCCT CAGTGTCAAG GAAAAACACC CCCTACTTAG CAAACCAGGA    3660

AAGAGAGTCT CCCTTTCCCC GGGGGAGTTT AGAGAAGACT CTACTCCTCC ACCTCTTGCG    3720

GAGGGCCTGA CATCAGTCAG GCCCGCCCGC AGTTATCCGG AGGCCTAACC GTCTCCCTGT    3780

GATCCTGTGC TTCAGTGGTC ACGCTCCTAG TCCGCCTTCA TGTTCCATCC TCTGCACCTC    3840

GCTCTGCCTT CTAGATAGCA GCAGCAAATT AGTGAAAGTA CTGAAAGTCT CTGATAAGCA    3900

GAAATAATGG CGTAAGCGGT CTCTCTCTCT CTCTCGTCTC TCTCTGCCTC AGCTGCCAGG    3960

AAGCGAAGCG CCCCCTGCCC AGTGGGCACG TGACCCACAT GACCTTACCT ATCACTGGAC    4020

ATGGTTCACA CTCCTTACCC TGCCCCTTTG TCTTGTATCC AATAAATAGC GCAACCTGGC    4080

ATTCGGGGCC GCTACCACTC TCCGCGTCTT GGTGGTAGTG GTCCCCCAGG CCCAGCTGTC    4140

TTTTTCTTTT ATCTTTCTCT TCTGTCTTTA TTTCTACACT CTCTCATCTC CGCATACGAG    4200

GAGAAAACCC ACCAACCCTG TCCGGCTGGT CCCTACACCC TGGCTTTCTA GACTGGAGCC    4260

TAGGCACGAC TCAGCTGCTG TAGTGAATTG CGATCCTCCA AACCCAGCAA GGCACCTGCA    4320

GGACATCTGG CCCAGTCTCC TCGTTGAGCC AGTTCACGAA AAAGAGACTT TTCTGAGTGA    4380

CATGCTAATG GGCAATATGA GGACTAAATG GGATGGTCTC CAACTTGGAC AAACCAACAG    4440

TAAAAGCCAC TTTGCGGCGA AAGAAACTTT TCCTTTTTTC TTTTTTTTGA GACAGGATCT    4500

CACCCTGTCA CCCAGGCTCC AGTGCAGTGG CATGACCTTG CCTCACTGCA GCCTCAACCT    4560

CTCTCAGGCT CAAGCAATCC TCCCGCCTCA ACCTCCCATC CAGCTGGGAC CATAGGTGCA    4620

TGCCACCACA CCCAAATAAT TTTTATATTT TTTGTAGAGA CGAGGTTTCA CTATGTTGCT    4680

CGGGCTGGTC TCAACTCCTG GGCTCAAGCA ACCCTCCCAC CTCAGCCTCC CAAACTGCTC    4740

AGATTACAGC CACCAGCCAC CAGGCCTGGC CAACATAGGA AGAAATTTAA ATTTGAATTG    4800

AATATTAGAA GAGATGAAAA TTCATCAACA TGGAAAGACA AAGATCATTA ACTAAAGCCA    4860

AACCAGAATG GAAGCTGTGT GTACACTGGG GTCTCATGCT GGGAACGCGA GGGGCACGTC    4920

CAGGGCTCCA CGGTGTGGCG ACGCCCCATG CTCCCTTTGT GGGGGTTCAT CCAGCGGAAC    4980

ATGAGGACCT GCGGTGCTTT TCAACATGTA CGTGAGTTTA ATAATAAAAA GGTTTAAGGA    5040

AAGAAAAATT CATATCTTTC TATATAAACA CAACATCTGG AAAGATCTAT TCTAAGGTCT    5100

TGACAGTAGG AATCTCTAGG TAGTAGTAAT ATGGCCTTTT TGAATTTTTG CTTATCACTA    5160

TTTTCTAATT TTCTTTTTCT TTCTAAATAA TTCTACCTAT GAAATAATTT TCTACCATAT    5220
```

```
                             -continued
ATATTTTGTA ATAAAAATGC TTATATTTAA TTTTTTAAAC CCTGTACAAA CTTCCTGATA 5280

AAATGGCAAA TTAGACACAC ACATGTGGGC CCCGTACAGT GGCTCGCGCC TGTAATTCCA 5340

GCACTTTGGG AGGCTCAGGC AGGCAGATCA CCTAAGGTCA GGAGTTTGAG ACCAGCCTGG 5400

CCAACATGGT GAAACCCCGT CTCTACTAAA TATACAAAAA TGAGCTGGAT GTGGTGCCAC 5460

ACACCTATAG TGCCAGCTAC TTGGGAAGCT GAGGCACGAA AATTGCTTCA ACCCGGGAGG 5520

CAGAGGTTGT AGTGAGCCGA GATCATGCCA CTGCACTCCA GCCTAGGCAA CAAGAGCGAC 5580

ACTCCAACTC AAAAAAAAAT AAAAATAACA CACACGTGAA TAGGCTCCTC ATGGAAGTCA 5640

TCACAACAAT CCAGAGGGAA GAGCTTCCAA AGTGTAAACC CAGAAGCGAG GAGCAGGAGG 5700

GTGCGCGCAG ACGCAGACAG CAGCAAGGTG CAGACTGAGA GGCGGAGGCT GGCCCTCGGG 5760

AGATGACTGA TGCTCAGTTT ATACCCCAAA TCCGTAAATC TAGAGGCCTG GCACATCAAC 5820

TACCTCTGCC AGCACGAATC AGGGAAAGCA CGGCAACCAA AAGATGTCCC ACCCTCACCC 5880

ATCCAGCTAC CTGCCATCCT CAGCCCCACT GGCAGAAGAC CCTGAGAGGT CGAGGCAGGC 5940

CCCTGCCTAC AGGACCCTCA GAGCTAGGGC AAGCCGTTTAT CCTGAACTGT CTCCCCCGTA 6000

AAATTCATAT GTTGAAGGCC TCATCCCCAC TGTGACTGTA TTTAAAGATG GCCTCTTCAG 6060

GAGATAATTT AAATGAGGTC ATATAAGTTG GCCCTCATCC AGTAAGACTT TGACCTTCTG 6120

GTGGTTTTTT TTTTTTTCGA GACTGGGTCT CACTCTNICA CTCAGGTTGG ACTACACTGG 6180

CACGATCACG GCTCACTGCT GTCTCCAACT CCTGGGCTCA GGTGATCCTC CTGCTTCAGC 6240

CTCCTCAGTA CCTGGGACTA CAGGTGCTTA CCACCGCACC CAGCTGCTGG TGCATTGTGT 6300

TTTTTGTAGA GATGGGGTTT TGCCATGTCG CCCAGGCTGG TCCTGAACTG GGCTCAAGTG 6360

ATCTGTCTCC CTCGCCCTCC TGCAGTCCTG GAATTACAGG TATGAGCCAC CGCGCCTGGC 6420

CGACCGTGAC CTTCTAAGAA OTGAAAGAGA AAGATCTTTC TCTCTCCCTC CCTCTCCATC 6480

ATGAGGACAC ACCAAGAAGT CCCCCATCTG CAAGCTAGAA AGCGAGTCCT CCCAACAGCT 6540

GAACCTCGCA GACCCTGATC TTGGACTTCA CCCTTCACAG CTGTAAGAAA ATAACTCTCT 6600

GCTGTTCACC CCACGCGGTC TACGGCAGCC CGAGCAGACT AAGACACACG CCATCTCGGG 6660

AGTCAGACCA GATCAGGAAG AAAGGCCTAG AGCTCAGGAT ACTGAAGGTC CCAACCCGGT 6720

GCTCGACCAG ACCACCCCGG CAGCCGCGGC CACGCAGTCA CGGCTCGGGT GAGGTGACCT 6780

GGACACCATC CCGGCAGCCC CGGCCACGGA GTCACGGCTC GGGTGAGGTG ACCTGGACAC 6840

CATCCCGGCA GCCCCGGCCA CGGTGTCACG GCTCGGATGA GATGACTCGG ACACCACCCC 6900

GGCAGCCCCC GCCACCGTCT CAGGGCTCAG GTCAGGAGAG TTGGATATGG CACTCGCCCT 6960

ACCCCGAGGC TGCTTCCACC CAGACGCCTC GGTGCGTGAC ACGAAAGCTC GGCTCAGTTG 7020

GGATCAGACC AGCCTCTCCC CAGGTCAGAA ATGACCCTGG GCTCCTCACA GTAGCCCTAG 7080

GGCACCATGA GAAAGCTACG TGGACTTCTC TGACCAAGGG TCACTGCTGC CACACTACTC 7140

ATTGCAGGCC ATGTCAGGGC TCAGCTGAGG AGACGTGGAC ACCACCCCAG CAGCCGCGCC 7200

CACGCCGTCC CAAGGGAGGG ACTTGGCCAC TGCCTCTCTG GGCAAGAGTG GGGAGGTGTG 7260

GGGTGGGACA TGTCTGGAAA CATCATGGAC ACATGCCGGG AAAACACGGA AGCTCTGCAC 7320

CAAGGTGCTG ACAAACGAAA AAGGAGAATG CACCTCTCAA CATCCAGCTA CCAGGTCCCA 7380

CTCAGAAACT CCTGCATTTC CAGACATGGC CACCAGCTCT GTGGATGAGA CAGGGGAGGA 7440

CAGGGTACCT CACACCAGGA ACCCACACAG GTCCATGTCT TGCTCTGTGA TCACACAACA 7500

GCCTCCACCA CCCTGACATG CAGGAGGGAG GTCAAAGCCT CGGGTCCAAC AACAGGCTCC 7560

ACAGCAAGGG AAGAAAGGCA GGAAGGAACT CAGGGCCAGG TCCTCCCAGG CAGCAGCTGC 7620
```

```
                                           -continued
CTGCACGCTG TCCACCAAGG GACCTCTGAC CTACACCGCA CAGGGGTTGG CAGTCTAGAG    7680

TCGTCCTCTG TCAAACGGTG AGAAAGTCAA AAGCTCATGC TCAGTGATAT GCTAGGTCAG    7740

CATCAAGATG CCACACATGA CACACAGCAA GGAPGAGACC AACGGGAAGA CTGCCCCAGA    7800

CCAGAGCCCC AGAGCCCTCT GGGGAGGAAG AATAAGGATG GCAGCCTGGG ACTGCCCGGG    7860

GCTGACTCTG CCTTTATTTC ACCCCAGCAG AGGCAGGAGT GACACCGCCT CACAGCAGGA    7920

GCAGCTCTGC CACCTCCTAC CAGTTCCACC TACGGGCAGC AAAACAAAGC TGGCAGTTTG    7980

GGCAAATGTT AGCGTTTTTG CCAACTAACA TTTGAATCGG ACATCTGGTA CAGAGATGAG    8040

GAAGAAAACA CTCACAGTTT CATGAAGACT GTCAAGAAAA TCACTGACTC TTCACTTCAT    8100

TTATGAAAGG CCAGCTCTCT GACATCCCTA CCACTCCCTC TCACATCAGA AATCACGGCC    8160

TTTCAGGACG TGGAGCCACG TGGCCATGCA GGTACGGGAG GCCTCCCCGC AGCTGCAGCT    8220

GGGTCTTCTG GTCCCCGTCC CATTTCTGCT TTTCTTCGCT CTCTACTTAC ACACACATTT    8280

GAGTCCAGTC TCAGAAGAAC TGCAACTAGA AAAATCCTGA CACTTGTCCC TTACTACGTT    8340

AATGCCAGCT GTGCCAAGGA CAGCCCAACC CAAGCCCCCA TCACCCCCAA TGGCACCGAG    8400

GCCCGAGCTT ACCCGTGAGG GGCCAAGTTG GTCGTCACCA ACACGGTCTT CACCCCCTCC    8460

ACACCACTGC CGTCCACTGC AGTGTCCGGA GTTGTCACAA CCACCACCTC CTCCATGTGC    8520

ACACTCACGT CGGGAGTCGC CATGGCTCAG CGGAAGGGGA CGCCCAGGCC AGCAGCGTCA    8580

GTCCTCCAGG GTCCCAAGTC CTGGAGGAAG CAAGGCAGGG CACAGGGATG GAGTCATCTC    8640

CACATCCACA CAACATAGCA CTCACAAAGG CATCTCTAAT CAGCTCCAAA GACCCACCCT    8700

TGACTCCCAG ACTGCTACCT CCTGACAAAA ACGAGCGGCA ACAGAAGGGC TACTCCAGGC    8760

TCTGGTTCCG AGGGCGGTGT AAGCGCACTC CACCCCTTTT TCCCACTGGA TAAGCCGAAA    8820

CCCTTGGCTA CPAAGCACAG AGCCACTCCC TCCACGTGGG CCTCACAGCA CGAGGACAGC    8880

AGGGGCCTGG AATTCCAAGC AACTTCCCTG GACGCACCCT CCCGGCTTGC CAGTTCTTCC    8940

GTCTCTCCTG GCCTGAACTC AAAGCCAGCC CCAATCCCTG AACTGAGTTT CAGGTGCAGA    9000

AACCACTCCA AGAAGTCCTC GCTGGTCTGT GGAACGGGAA GGGAAACCCA TTCAAGACAG    9060

AAAGAGAGGA GGGAAACGCC CTGGGTTTTT TTGGGTTTTT GGGTTTTTTT TGACACGGAG    9120

TCTCCCTCTG TCCCCCAGGC TGGAATGCAC TGGCACGACC TCCGCTCACT GCAAGCTCCA    9180

CCTCCTGGGT TCAAGTGATT CTCCTGCCTC AGCCTCTCCA ATTGCTGCGA TThCAGGTTT    9240

CACCATGTTG CCCAGCCTCG TCTCAAACTC CTGACCTCAC GTGATCCACT CACCTCCGCC    9300

TCCCAAAGTG CTGGGATTGC AGGTGTGAGG CACCATGCCT GGCCTGCCCC GGGTTTAAAA    9360

ATTATTATTA TTTTGTCTTT CCTGGCTTTG CCTTCAGCAA CTCCAACCCC TGCTAAAACC    9420

CGCTGATAAT GGCTGTCCTG GCCCAAAAAG CTTGGAGACA GGCGAATCTT CCTCCTGACT    9480

AAAGGAATGG TGGCCCAAGA GTGTGGGGGC TCCCTGTTGC CCTCTCACTC TCCATCCCCT    9540

ACCTAGCACA GGGAACACAA AACCCCCTGG TTTCCAGCCA GACGGCAACG AGCCTGGAGT    9600

CAGACTGTGG GCCAGGCCAC AAGACCAGAG GGGACAACAG AGGATGGCAC ACAGCTGTGT    9660

GTGAGCGCCT GGGTCCTCCC AACACAGTCT CTACGTGCTC CTGACCCTAA AGGGCAAAGG    9720

GAAGAAAACT CACCTACAGG ATAGGCCACT GCCCACGTCT CAGATGCGCC CCAGTGGCGC    9780

ATATGGGACA CATCCACAGT GCACTGGAAA GTCTCTAAAA TAAACTGGCC TAAGAACACA    9840

GACACAGGAA CGGGGTGCAA AATTTGCAGC CTGAACCTAA CCAGGTCGAT TTCTTGCTAT    9900

GAAAAAAAAA AGTCTACATT CTCTGTGAAA CTTAAAACAA GACCTAGAGT CCATAGCACA    9960

GTAGTCAAAG CATCCAGAAC ACGATCAAAC TTCCTGGCAA AGGGTAGTCT GGTTGATTCT   10020
```

```
                          -continued
CAAAGGAACA AATACACAAG AGAAGCTGGC TCTTGAACGC AGAATCCAGA GACTTTCAGG   10080

TGCTATCGGA CCAGCTCCAA GAGGAAAGCA AACATTCTCA ACCAAGTGGA AAGAAAATCT   10140

TGGTATACAA ACAGGAGTTA TAACCAAACA GAAATGTGAA AATTAAAAAC GACAACCAAA   10200

AGAAAATACA CAAAGCTGGG ATAGTCTCAG CTACTCGGAA GGCGGGGCTG GAGGATCGTT   10260

TGAGCCTAGG AGATTGAGGC TGCAATGAGC TGTGATCACA CCACCGCACT CCAGTCTCGG   10320

CAACACAGTG AGAACTCTCT CAAAAAACGA AAAAGAAAGA AACTAGAACA GAAGTGACCA   10380

GGGGCTGGGG GAGGGAGTAC AGGGAGTTGT TCTTTAATGA GTACAGAATT TCTGTTTGGG   10440

ATGATGAAAA GCTCTGGAAA TCGACGGCGG TGATGGCTGC ACAATCACTG TGGCTGTTCT   10500

GAATGGTGCT GAACCACACA TTTAAAAACA GTTAAAATGG GCTGGGCGTG GTGGCTCACG   10560

CCTGTAATCC CAGCACTTTG GGAGGCGGAT CGCCTGAGGT CAGGAGTTCG AGACCATCCT   10620

CCCCAACACA GTGAAATCCT GTCTTGACTA AAAATACTAA AAATTAGCCA GGCATGGTCG   10680

CAGGCACCTG TAGTCCCAGC TACTTGGGAG GCTGGGCAG GAGACCTGCT TGAACCCAGG   10740

AGGCAGAGGT TGCAGTGAGC CGAGATCGTG CCACTGCACT CCAGCCTGGC AACAAGAGC   10800

GAAACTCCAT CTCAAAAAAA AAAAAAAAAA AAAAAAAAAA AAGTTTAAAA TGGTTAAATT   10860

TTATGTTATG TATATTTTAC CCTAATAAAA ACACTGTAAT GCTACTATAA TAGAATCACT   10920

CATTAGGATT AGATATAGAC TAGAAAGTAC AGAATATAAA AACTTTTTAA ACAAAGAAAA   10980

ATTTTCATGG CCAGGCATGG TGTCACACCT GTAATCCCAG GACTTTGGGA CGCCAAGCCA   11040

AGAGGAATGC TTGAGCTCAG GGGTTTGAGA CCAGCCTGGG CAACACAGCA ACACCCCATC   11100

TCTGCTAAAT AAATAATAAA AAATAGCCAG GCATGGTGGT GTGCACGCCT GTAGTTGCAG   11160

CTACTCTGGA GGCTGACGCA GGAGGATCAC TTAAGCCCAG GAGGTCAAGG CTGCAGTGAG   11220

CCATGGTTGT GCCACTGCGC TCCAGCCTGG GCAACAGATC AAGACCTTGT CACAAAAAAA   11280

AGAAAGAAAG AAAAGAAAAA AGAAAGAAAA TAAAATCTTC CAGAACTTTT AAAATCATCA   11340

TTGTTAATAT AAAAATAACA TCACCTGCCC CTAGGACTGT AACAAACAAG TGTGTCTAAG   11400

GACAGGAGTG GGTCCACCCC AACCTGCCAC GCACTGGTCC CCTGCGGAGA GTCTGGCCCT   11460

GCACTCACTA AGAGGAGGCA CTCATAGCCC AGCCAGGCCT CTGCAATTAT GCCTTCAATG   11520

CCACAACTAA CTCACCCAAA CTGAACAATC GATCACAAAA TGTCCCTTCA GGTCTCAAGG   11580

TTCTTGCTAA ATCTTACTCA ACCGACATTT TCCAGCATGG GAACATTTTT CTGAATGTCT   11640

TAGGGAGAGG AAGTCCGCAA GAGAACAAAA GGTCCTCAGG CCACCCTAGC TTCTTTTCCT   11700

CCATTCCACA GGCTGTCTTT TGTCTGGGTA TCCACTGGAC CAGGGGCTC TACTTCTTCC   11760

TACCTGCGCA TGGGTCTCCA CACAACTCCA AGGTAAAGGG CCACAGGCAA GATAAAGGGG   11820

AGAAAAGAAA GCTACGATTT CCTGGGCCAC CAATCGCAAA TGGCAGCCAG TCTCTGAAGT   11880

AACCCTTGAC CAGAGATCCA AGGAACCAAG AAATGTAGGT GATCTGAACA CAGCGCATGG   11940

TGGTTAAACA CCATGAACGA AAGACCCATT CTCAAAGAAA AGGAAGCAAA AGAAACCGT   12000

GGGGAGCTGG GTACCACCCG CAGCAAAGAC CCCGCACGCG TTACTGACGC CAGCCTGGCC   12060

TGGGAGAGCA GTGAGTGTGG CGCACGGTGA GTGGCGGGA GGGCTGTGGT AGGTTTAGCG   12120

TAAGAAGGGG CAGCGCCCAG AGCCCAGAGA ACACCAGTGA GGGCTCCACA GGAACACTAC   12180

TCAAAGTATT CACGGAACAC ATCTAAACAC AAGCACTAAG GACTAAGTGC GAGGGACAAG   12240

AAAATATTCC CCGTTTCCTC TTTCAGGAGG GTATCGAAAA TGAGTGATGG AAGGAAAATG   12300

TATTGTTTAA ATCACGAAAA AAAATTTTTA CAAATTAAGA ACATCCTGGA ACATGATGAG   12360

CCGTTTACTG TCACTCAATT TAAATGGTGG CCATCTAGGA CAGAGCGCCT AAGGGGAAAG   12420
```

-continued

```
GGGGCTCACA GGTGAACCCC TCCAGCTGCT GGTGGGCAAT TTCCCATTAG GGCATCAGGG   12480

TCTCTGAAGA CTGTCTTCAG ATGCTTTTTA GCCAGGAAAG TTACAATGAT GAATTCGTTT   12540

ACACTGGCGG AATTACTTCG TATTTCTCAA ATATAATGTT TTCACTAGCA TAACTTTGTT   12600

GTTGTAGACT TAGGCTTCAA AATAAAGAAC TTTAAACAAA CATGAATAAA AACCCACTTT   12660

AGGCCGGGCG CGGTGGCTCA CACTTGTAAT CCCAGCACTT TGGGAGGCCG CGGCGGGTGG   12720

ATCATAAGGT CAGAAGTTCA AGACCAGCC TGATCAATAC GGTGAAACCC CGTCTCTACT   12780

AAAAATACAA AAATTAGCCG GGCGCGGTGG CAGGTGCCTG TAATCTCAGC TACTTGGGAG   12840

CCTGAGGCAG GAGAATCGCT TCAACCTGGG CAGCAGAGGT TGCAGTGAGC CAAGATCATG   12900

CCACTGCACT CAAGCCTGGG TGACACAGTG AGACTCTCTC TTAAAAAAAA AAAGCCACTT   12960

TAAAATTTTA CTCAGGCCAG GTGTGGTGGC TCACGCCCAT AATCCTAGCA CTTTGGGACC   13020

CCGAGGCCAG CAGATCACCT GAGGTCAGGA GTTAGACCAG CCTGGCCAAC ATGGTAAAAC   13080

CTTGTCTCTA CTCAAAACAC AAAAATTAGC TCGGCGTGGT GGTCTGCCCA TGTAATCCCA   13140

GCTACTCAGG AGGCTGAAGT CAGAGAACTG CTTGAACCCG CGAGGCACAG GCTGCACTGT   13200

GCCAAGACTG CACCACTACA CTTCAGCCTG GGCGACAGAG CAAGACCCTG TCTCAGAAAA   13260

AAAAAAAATT CAAAAATTTG GCCAGGCGTG GTGGCTCACC CCTGTAATCC CATCACTTTG   13320

GAAGGCCGAG GCGGGTGGAT CACCTGAGCT CAGGAATTCA AGACCAGCCT GGCCACCATG   13380

ATGAAACCCT CTCTCTACTA AAAATACAAA AAAAAAAAA CAAATTGGCC GGGCATGGTG   13440

GCGGGTGCCT GTAATCCCAC CTACTTGGGA CGCTGAGGCA GGAGAATCTC TCCAACTCCC   13500

GAGGCAGAGG TTGCAGCGAG CCAACATTGT GCCACTGCAC TCCAGCCTAG ACAACAGAGC   13560

CAGACTCTGT CTCAAAAAA AAAAAATTAA AATTAAAAAA TAAAAATTTC ATTTAAATA    13620

CTACTGATCT CCCGTCCTGA CTTCTCGCGG TTTAACTCTC ACTGAGGAGA CCCTGCTTTC   13680

ATAAGGGTAA GCTCAGCAGG GGCAACTAAA GTCATTTAAG CAGACACCTG CAAAGAGGCA   13740

ACAGCCTCAC TGCAGGCAGC OGTCCTCGTC ACAGCTTCAG GGCTTTGCAG AGGATTACCC   13800

AATGTACACG CACAAAACTG AATTCCAGCC TCTCCATTCG CAACTGCATA CATACATATA   13860

TTCTTTTTTT GAGACGGAGT CTCGCTCTGT AGCCCAGGTT GGACTGCAGT GGCCCGATCT   13920

CGGCTCAATG CAAGCTCTGC CTCCCGGGTT CAAGCGATTC TCTTCCCTCA CCCTCCTGAG   13980

TAGCTGGGAT TACAGGCGCC CACCACCACG CCCGGCTAAT TTTTGTATTT TTAGTACAGA   14040

CGGGGTTTCA CCATGTTGGC CAGGACACTC TCGATCTCCT GACCTCGTCA TCCGCCCGCC   14100

TCTGCCTCCC AAAGTGCTGG GATTACAGGC GTGAGCCACT GAGCCTGGCC TCCAATGGCA   14160

ACTATATTAA AGGTTCAAAG CAATATGCAC AAAAGTTACC TCACAGAAAA TAGTGCAAGT   14220

CCTTGATACA ATGCTCTTTA GACACAGAAG AAGCACTATA GAATAGAGCA CCTCCCCCTA   14280

TTGCCTTCCC AAGGGCGAGC ACCCCTCCT CTCTCCACAG CTCCTTCTTT CTTTTTTTGA   14340

GATGGGAGCT CGCTCTGTCA CCCAGGCTGG AGTGCAATGG CAAAATCTTC GCTCACTGCA   14400

ACCTCCGCCT CCCGGGTTGA AGTGATTCTC CTGCCTCAGC CTCCCGAGTA CCTGGCACTh   14460

CAGGCACCCA ACACGCCTAG CTAATTTTTG CATTTTTGGT AGAGACGCGG TTTCATCATG   14520

TTGGCCAGGC TGGTCTCGAA CTCCTCACCT CCAGTGATCC TCCCACCTTG ACCTCCCATA   14580

GTGCTGGGAT TATAGGTGTG ACCCACTACA CCTCGCCTCT CCACAGCCCC TTCTGTGTTG   14640

AAGCCAACAC CCACCCAGCT TGATCCCAA GGCTTGGGTT CCCCACTAGT GTGAAGTGAG   14700

TTTCCAAATT ATTAGGTAAA TCAGATATGA GAAAATATTT TATTTTACTT TTTTTTTTT   14760

GAGACGCAAT CTTGCTCCGT CACCCAGGCT GGAGTGCAAT GGCACCATCT CCACTCACTG   14820
```

-continued

```
CAACCTCTCC CTTCTGGGTT CAAGCAATTC TCCTGCCTCA GCCTCCCAAC TAGCTGGGAT   14880

TACAAGTGCA CACCACCACC CCCGGCTAAC TTTTGTATTT TTACTACAGA CAGCGTTTCA   14940

CCGTGTTAGC CAGGCTGCTC TCAAACTCCT GACCTCATGA TCCCCCCACG TCGGGCTCCC   15000

AAAGTGGTGG GATTACAGGT GTGAGCCATC ACACCTGGCC CAACAAAATA TTTTTAAACT   15060

AGTATTCTTG ACCCGCACGG TCAACACTGA TGTAATTGAA ACTGTTGTAT TTGAAGTGTT   15120

AGCAAAGAAA GAGAATTCTC GTTCAACAGA AAAGTCACTC ACGACTTTTC AGTCACGCAT   15180

GAATTACACA GTAACCAAAT AGATAACATG CCATCACTGA CGACGGGCCC ACAACAAATC   15240

AGCTCCGACC AACACGGTCC ACACCACCAT GGGTCTACAC AGATCCAGGT CCCGCCTGTG   15300

AGCCTACAGT GACGCGGGCC CCTGTGGGGT CGTCCCTCCA GGTCAGGTCC CTGACAGTGG   15360

GTCCCAGTGG GGTGATCCCT GCGGGTCGCG TCCCTGCCAG TTOGGTGCCT GCCGGGTGGC   15420

CCCTGCCCGT CGGGTGCCTG CGGGGTGGTC CCTATGGGTC GCGTCCCTGC GGGTCCCCTG   15480

CCTGCGGGGT GGCCCCTGOG AATCGCCTCC CTGCGGGTCG GGTGCCTGCC GGGTGCCCCC   15540

TGCCGATCGC GTCCCTGCGC CTCCGGTCCC TCCGCGGTCG CCCCTGGCGA TCGCGTCCCT   15600

CCGGCTCCGG TGCCTGCGGG GTGCTCCTTG TGGCTCGCGT CCCTGTGGGG TGGTCCCTGT   15660

GGGTCGCGTC CCTGTGGGGT GCCCCCTGCG GCTCCCGTGG TGGCCCCTGC GGOTCGGGTG   15720

CCTGCGGGGT GGTCCCTGTG GGTCGCCTCC CTGCGGGTCG GGTGCCTGCG GGGTGGTCCC   15780

TGCGGCTCGC ACCCCTGCGG CCTGGTCCCC CCGGCATCCC TCCACCGAGG AGGCCGCTGG   15840

AGGCCGAGCC CCCGCCCCCC CCCCGCGCCA ACATGGAGGC AGGAAGCGCC GCCGCCCGCG   15900

CCCGCCACCG CCCCCGCCGC CCGCCTGACG CCCCCGTTGC GCCTGACGCC GCCCCCCGCG   15960

CGGCCGCCCC TCCCCCGGCC CTCCCCTCCC CCCGCCGTAA CGTCCTGACG CTCCGCACCG   16020

ACCCCTGACT GGACCCCCGC GCGTGACCCC AGCGAGAGGC CTCGCCGCGG GGGGCCGCGC   16080

GGCTCGCCGG CGCCGCTTAC CTGGGGCCCC GCCGGGCCTG CTTAGGCACC CGGCCGGGGC   16140

GGCGGCGTCG GGAGCTGCGG CGGCGGCGGG CGGCGGCGGC GGCCGCGGGC TTCCCTCCTT   16200

GTTGCGGATT CCCCGGCGGC GGCGGCGCGC GCGCGCGCTT CCTAGTGACG CAGGCGCCGG   16260

GGCCGCGCAC GCACGGGGCT GGGAGGGCCG GACACTTATT TGGCGCTCGC GGACGAGGAA   16320

GGCGGCCCCC TGAAATAAGG CCCGACGGGC CCCGGGCGC GTGCGCGCAC CGACACTCTC   16380

AGCTCCTAAC GCCCCACGTT CCTCCTCGTC CCCCACGCCC CCGGTCGGGC GTTGCCTGCC   16440

CCGCGCCGCC GGCCGGGCCG AGGGACGATG GTCACTGGAC GGACGGCCCC AGGGAGCAGT   16500

GCCCACGCGC GCCACGGCGG TACCTTCAGG CCTCCAGGTA CGGGCGCTCC TCGCCCGGAC   16560

GCTGCTGTGT GrGAATGGGC CCGAGCGGAC TCCCCTGCGG GGCGGACGCC TGAACACGAG   16620

GCTGTCGAGG ACGACGCTGT AGGGTGCGCG GACTCACGCG GAACATGCCA CAGGCTCACC   16680

CAGCCACGCC GCTCCCAGCG TGGAGGGCGA GGGGCATCCG GGAGCGCCCC GCAGCGCTCC   16740

GTCACCCCTC AACCTCTCAC CCCAGTCCCA CAACCAGCAC CCCGATCCTA TCGCAGTCCC   16800

ACACCCGACA CCCCCATCCC ACCCCTGCCC AACAGCCCCC ACCCACCCCA ATCCCATAGC   16860

TAACACCCCC GTCCCACCGC TGTCCCACGC CCGGCACCCC GATCCCACCC CAGTCCCCCA   16920

GCTGCCACCC CGATCCCACC CCAGCCCAAC AGCTGGCACC CACCCCGATC CCACCGCTGT   16980

CCCACA[]CCG GCACCCCGAT CCCACCCCAC TCCCGCAGCC GGCACCCCGA TCCCA-      17040
CAGCC

GGCACTCACC CCGATCGCAT AGCATAGCTG ATACCCCGAT CCCACCCCAG TCCCATAGCC   17100

AGCACCCCGA TCCACCCCA GTCCCATAGC CAGCACCTCG ATCCCATAGA TGACACCCCG   17160

ATCACGCCCC AGTCCTATAG CCCGCACCCC GATCCCACCC CAGTCCCGCA GCCGGCACCC   17220
```

-continued

```
CATCCCACCC ATGTCCCACA GTCGGCACCC CGATCCCACT CGGATCCGGC AGCCAGCTTG    17280

GATCCTGTGG CCCTCCTCCA GCCCCCAGGG CTCATTTATA TGTTTTATTG GCAGAGGCTG    17340

GGGCTGGCTC TCTTGGCCTC TGTGCTGGGT TTCTTCCTCT GCACCGCAGO ACTGCCTCTC    17400

CTGACCTCTC CAGGTCTCAT CGAACACCCT TGTGCTTGCT GTCACCCGCT GCCTCTCTGC    17460

AGCATCCCGG ATTCCGTATC AGGGGACCGA AATTAGTCGC AAAATAGGAA GCAGGTGCTC    17520

CCTTCGATGG AACCCTCACC CTGTGCTCAC ACTTGTAGGA GGAGGGCTCT GCAGGCCGCC    17580

TCCCGGAACG GCACGTTCCC AAGCCACTGC ACTTCGGAGG GGCTGTAATT ACAGTTGCAC    17640

ATTCATTCAG TTCCCAGTAA AGTAGAACGT GCTCCAGCCA GTGAGGAAAA CGTCTTTTTA    17700

AAAATTAGAT TGGCCGAGTG CCGTCGCTCA TGCCTTTTAC CTCAACACTT TGGGAGACAA    17760

AGGTGCGAGG ATCACCTCTG GCCAGGAGTT CAAGACCAGC CTCGGCAACA GAGCCTGTCT    17620

CTGGGGAAGA ATAAAAAAAA AAATTCAGCC TTTGTCAGTG CTACTATTTT ATTATCTGGT    17860

AAATATGAGA CGGTTCACGC GGTCTATGTG TGTCATTTAT CTGAGTTTGC CTATCGTCAC    17940

GTTTTGGAAA TAAATGTCAA TAAACTCGAA GACGAGTGCT GAGGGGGCCC TGGGGATGGG    18000

AGGGTGGCTA CATCATGCCT CTGTGTTGCG CAACCCCACC GAGGTCGGCC TGGGGTCAGC    18060

CCTCCGGCCT GTTCTGCCTC CTTCACTCTG GCCCTCCAAG AGACAAACTG GCAACAAGA    18120

GAGAAACTCC ATCTAAAAAA AAAGAAAAAT CACCTCCAAC ATAACTTAGC TTTCTTCTGC    18180

TGGCATAACA AATTATCTCA AACTTAGTCG CTTAAAAATG CAAATTTAGG CTGAGTGCGC    18240

AGGCTCACGC CCATAATCCT AGCACTTTCC GAGGCCAAGG CAGGATTGCT TGAGGCCAGG    18300

AGTTCGAGAC CAACATGGCC ACAACTGTCT CTTTTTAAAA AATGCAAATG TGTCCGGCAC    18360

GGTGGCTCAC GCCTATAATC CCAGCACTTT CTGAGGCCAA CGCGGGCAGA TCACCAGGTC    18420

AGGAGATAGA GACCATCCTG GCTAACACTG TGAAACCCCC TCTCTACTAA AAATACAAAA    18480

AATTAGCCTG GCGTGGTGGC AGGCCCCTGT AGTCCCAGCT ACTCGGGAGC CTGAGGCAGG    18540

AGAATGGCGT GAACCCAGGA AGCGGAGCTT GCAGTGAGCC GAGATGGCGC CACTGCACTC    18600

CAGCCTAGGC AACAGAGCAA GACTCCGTCT CAAAAAATAA ATAAATAAAA CTGCAAATGT    18660

ATTCTCTAAC TGTTCTGTAG GTCGGAAGTC CAGCCCAGCC TCACTCCGCC AAAATCAGGG    18720

TGTCTGCAGG GCCGATTGCT TTTGGAGCTC CAGGGGAGAA GCTGTTCTGG CCTTTCCAGT    18780

TTCTGGAAGC ACTTGAGCCC CTTGTCTCGT GGCCTATCCC ACACCTGAAA GCCAGCCAAA    18840

GCCAGTTGAC TCCTCACCCT GTTGGCCCCG ACACTGATCT CCTGCCTCCC TCATCTGCTG    18900

TCAAGGCCCC TTGTGATGAC ATGGGGCCAC CAGCTGGCCC AGGGCACCTC CTGTCAGAGT    18960

CCGCCCACCA GTGACCTTCA TTCCATCTGT CGCTGTAATT CCCCTTTGCT TGGAACCAAC    19020

GTTCACAGAT CCCAGGGGTT AGGATGTGAA TATCTTGGGC AGGGCTGTGG GGGGCCTATT    19080

CTTCCTTCTA AAATATTTAT CATTTTTGTT TTGGGGATTT TTTTGGTTTG CTTTTTTTTC    19140

AGACAGAGTC TCGCTCTGTC GCCCAGGTTC GAGTGCAATG GTGCAATCTC AGCTCACTGC    19200

AACCTCTGCC TCCGGGCAGA CGTGAGCCAC TCCACCAGGC CTGTTTTTGT TTTTGTTTGT    19260

TTTGTTTTGT TTTTGAGATG GAGTCTCGGC CCGGCGCCGT GCCTCACGCC TGTAATCCCA    19320

GCACTTTCGG AGGCCCAGGC GCCCGGATCA GGAGCTCAGG AGATCGAGAC CATCCTGCCT    19380

AACACCGTGA AACCCCTCT CTACTAAAAA TACAAAAAAT TAGCCGGGCG TGGTAGCGGG    19440

CGCCTGTACT CCCAGCTACT CGGGAGGCTG AGGCAGCAGA ATGGCGTGAA CCCGGGAGCC    19500

GGAGCTTCCA CTGAGCCGAG ATCGCGCCAC TGCACTCCAG CCTCGCCGAC AGAGCGAGAC    19560

TCCGTCTCAA AAAAAAAAAA AAAAAAAAAA AAAAAAGAG ATGGACTCTC ACTTTGTCAC    19620
```

```
CCAGGCTGGA GTGTAGTCGC GGGATTATAG GTACGCGCCA TCATGCCCAG TTACTTTTG    19680

TATTTTTAGT AGAGACAGGG TTTTACCATG TTGGTCAGAC TGGTCTCAAA CTCCTGATCT  19740

CAGGTAATCC ACCCGCCTCA GCCTCCCAAA GTGCTGGGAT TACAGACGTC ACCCACCGTG  19800

TCTGGCCATA TTTATTAACT ACAAAGGGAA AGATGATAAT TTTTTTTTTT GAGATGGAGT  19860

CTCACTCTGT CACCCACGCT GGAGTACAAT AGCGTCATCT TGCCTCACTG AAACCTCTGC  19920

CTCCCAGGTT CAAGCGATTC TCCTGCCTCA GCCTCCCAAC TAGCTCGGAT TACACGCGCA  19980

CGCTACCAAG CCCAGCTAAT TTTTGTATTT TTAGTAGAAA CGGAGTTTCA CCATGTTGGT  20040

GAGGCTGGTC TCGAACTCCT GACCTTGTGA TCTCCCCACC TCGGCCTCCC AAAGTGCTGG  20100

GATTATAGGC ATGAGCCACT GCAACCGGCT GAAAGATGGT AATTTTAAAG TACACAAACT  20160

GGGTTGGCTG GGCATGGTGG CTTATGCCTG TAAGCTCAGC ACTTTGGAAG TCCAAGGCAA  20220

GAGGATCGCT TGAGTCCAGG AGTTTGAGAC CAGCCTGGAC AATATAGCAA GACCCCATCT  20280

CCGCAAAAGC TAAAAAGTTA GCCAGGTGTC GCGGCACATG CCTGTAGTCC CAGCTACTCA  20340

GGAGGCTGAC GTGGGAGCAT CACTTGAGAC CAGGAGGTCA AGGCTGAAGT GAGCTGTTAT  20400

TGTGCCACTG CACTCAGCCT GGGCAACAGA GCGAGAGTCT GTCTCCAAAG GTAAAAAAAG  20460

GTCCAGGCAC AGTGGCTCAC ACCTGTAATC TCAGCACTTT GGCAGCCCGA GGCGGGCAGA  20520

TTCGTTGAGG TCAGGAGTTC AAAACGAGCC TGGCTAAATG GTGAAACCCC GTCTCTACTA  20580

AAAATACAAA AAAATTAGCC AGGCATGGTG ACGGGCGCCT GTAATCTCAG CTACTTGCCA  20640

GACTGAGGCA GGAGAATCAT GTAAACCCAG GAGGCTGAGG TTGCAGCGAG CCAAGATCAT  20700

GCCACTGCAC TTCACCCTGG CCGACAGAGC AAGACTGTCT CAAAACAAAA CAAAACAATC  20760

TTGACTCCTG AGTTCCTCTA AGGGAAATTC CAGGCACCTC GCCACCCTTC ACAGGCAAAG  20820

GAACAATCTG ATGAGGAAGA AGATAGAAAC AGCTTAAACA ATAGTCTCCC GGCCGGGGC   20880

AGTGGCTCAC GCCTCTAATC TGAGCACTTT GGGAGGCCGA CGCGGGTGGA TCACAAGGTC  20940

AAGAGATCAA GACCATCCTG CCTAACATGG TGAAACCCCG TCTCTACTAA AAATACAAAA  21000

AATTAGCCGG GCGTGGTGGT GGGTGCCTGT AGTCCCAGCT ACTCGGGAGG CTGAGGCAGG  21060

AGAATGGCGT GAACCCACGA GGCGGAGCTT TCAGTGAGCT GAGATCGCGC CTCTGCACTC  21120

CAGCCTGGGC GACAGAGCCP CGAGACTCCA TCTCAAAAAA AAAAAAAAT TAGCTGGGTG    21180

TGGTGGCTCA CACCTGTAAT CCCAGCTACG TCCCAGGCTG AGGCAGGAGA ATCGCTTGAA  21240

CCTGGGACGC GGAGGTTGTA GGGAGCTGAG ATCCCACCAC TGCACTCCAG CCTGGGCAAC  21300

AGAGOGAGAC TCTGTCTCAA AAAAAAAAAA AAAAAACAAA AAAACAATAG TCTCCCAAGT  21360

AAGTCAGAGT CACAAGGTGT TTTGATTCCC TGTGCAAACT AAAATATAAC AGCTTAACAT  21420

ATGTTCTTGA GTTATTTTTC AGAAACTTGG ACATCCACCA GGTGGAAAAT GCTGAGCTAG  21480

GAACAGTGGC TATAATTTCA GCCTTTGAG AGGCCAAGGT GGAAGGATCA CTTGAGGCCA   21540

GGAGTTAGAG ACCAGCCTGG CCAACATGGT GAAACCCCGT CTCTAGTAAA AATACAAATA  21600

TTAGCTGGGC ATGGTGGTGC AACCTGAAAT CCCAGCTACT TCGGAGACCT AGCTGGGAGG  21660

ATCGCTTGAA CCTCGTAGGA GGAGTTTGCA GTGAGCTGAA ATTGTGCCAC TGCACTCTAG  21720

CCTGGGCAAC AGAGTGAGAC TCTGTCTCAA AAAATAAATA AATAAAAAGA GAAAAAGTG   21780

TTGCCTGCAG GCCGGGCACA GTGGCTCACG CCTGTAATCC AACACTTTG GGAGGCCGAG   21840

ATGGGCAGAT CACCTGAGGT CAGGAGTGCA AGAACAGCCT GGCCAACATG GTGAAACCCC  21900

ATCTCTACTA AAAATACAAA AGTTAGCTGG GTGTGTACAT GTAGTCTCAG CTACTTGGGA  21960

AGCTGAGGCA GGAGAATCTC TTCAACCGGG GAGGTGGAGG TTGCGATGAG CTGAGATCAC  22020
```

-continued

```
GCCACCACAC TCCATCCAGC CTGGGTGACA GAGTGAGACT CCATCTCAAA GCAAAAAAAG  22080

AAACATAGGT GGGACCCTTG GTGTGTCCTT AGGGCATGAT GGTTGACGTA TACTGCTGGT  22140

CCTGTCATGT AAAAGAAAAC GAGCCGACTC TGTGTCTACT CGAGAAAGCA CTGCATATAT  22200

CAGCCACAGT CAATACCTCG CTTCTGCAGG GACGGTGGCT GCCAGAGTGG GAGGCTTTGG  22260

TAGCACCCAT GTCGTGGAAT CACAATGTTG TCGATAGCTC TGGGGTCTTG TACAAAATGC  22320

CAGATCCTCC CATTTGGTTT CCTTATGGGA AGGATCGCAG TACTATAATA CATGGGCTTG  22380

TGCAAGGGAT CATTATACCC TTTTCTCTTT TTTTGCTTTT CTTTGAGACA GACTTTCACT  22440

CTCGTCACCC AGGCTGGAGT GCAATGGCGC GATCTTGGCT CACTGCAACC TCCACCTCCT  22500

GGGTTCAAGT GATTTTCCTG GCTCAGCCTT CTGACTAGCT GGGATTACAC ATGCCCGCCA  22560

CCAGGCCTGA CTTATTTTTG TATTTTTACT AGAGACAGGG TTTCACCAAG TTGGTCAGGC  22620

TGGTCTTGAA CTCCTGACCT CAGGTGATCC ACCCACCTCG GCCTCCCAAA GTGTTGGGAT  22680

TCAGGCATA AGCCACCAGG CCCAGCCTTT CTTTCTTTTT AAAATTAATC TTTGTTTAAA  22740

AATACTCTCA TTTTTTATTT AATTGTAGCA CTCCTAGATC CCGAAAGCAG ATACACTCTT  22800

GTTATGGGTC TGATTCTTTT CATTGCTTCA CGCCTTAGAG GATATTGTCC AATACTGGAT  22860

AAAAGTTTAC TCAGGTCTAC TTCCACTTTA ACGGGCATGG CTGAATATCT CTTCCACTTG  22920

GCTGTTTGTT TATAATGAAC TGACAAACAT ACAAATTTTC TTGAGTTCTG TGAGACATTC  22980

TAGTAAATCA TCTAACCTGA AGAGCAGGTT GTGAGAACCC CTGATTTAGA AAGCCCAGTG  23040

GTCATAAATA TAAGTGGCTC TGGACTGCCT CCCGGGTCT GAAGTGTGGG CAGTCGGTTA  23100

GGATTCAGCC CTTGTAATTT GTAGGATCTG ACACACACTC CAGGAAGGCA GTGTCAGAAT  23160

TTACCTCTAT TATATTGGAC ACCCAGTTAG CGTTTCGAGA ATTGGTTGCT CCTATAGAAA  23220

AATACCAAAT ATTTTATGTC AGGGGAGTGA AGAAAAAAC AAAAACCCGG CCCGGCGCGG  23280

TGGCTCACGC CTGTCATCCC AGCACTTTGG GAGGCCGAGA CGCGCGGATC ACGAGGTCAG  23340

GAGATCGAGA CCATCCTGGC TAACACCGTG AAACCCCATC TCTACTAAAA ATACAAAAAT  23400

TAGCCGCGCG TGGTGGCGCC CGCCTCTAGT CCCAGCTACT CGGCAGGCTG ACGCAGGAGA  23460

ATCGCGTCAA CCCGGGAGGC GGAGCTTCCA GTGAGCCCAG ATCGCGCCAC CCCACTCCAG  23520

CCTGGGCGAC AGAGCGAGAC TCCGTCTCAA AAAAAAAAA CAAAAAAAAA AAACAAAAAA  23580

AAAAAACCCA TACACTTTHA GGAAAGCAAC TGACAGCATT TGTTACCAGT GATAAAATTT  23640

GAGCTTTGAA GTAACAATAA CAATTTTCCC ATTGTGCCCG GCCCAACAAA AAAAAAAGAA  23700

TTTTGCCATT CTGAAAGGCT TCCCAGTACT TTCTGATGAC CTTGACGGTG ATATTAACAA  23760

ATAACTTTTT TTTTTTTTTT TTGAGATGG GTCTTCCTCT GTCACCCAGC CTGGACTGCA  23820

GTGGTTCAAT CTCAGCTCAC TGCAACCTCC GCCTCCCAGG TTCAAGCGAT TCTCCTGCCT  23880

CAACGTCCCA AGTCGCTGGA CTACAGGTGT GCGCCACCAC GTCCACATAA TTTTTCTATT  23940

TTTAGTAGAG ATGCGGTTTC ACCATGTTGC CCAGACTGGT CTCAAACTCG TGACCTCAGG  24000

CGACCCGCCC ACCTCGGCCT CCCAAAGCTC GGAGCCCTTG CTGGGATTAG AGGTATGAGC  24060

CGCTGCACCT GGCCTCTTCT CCTTCTGTTT TGCAGTCATG CAATGACCAT GTCTTACATT  24120

TCCAACCAGA AAAAAGGTT ACTCTAACAA TCTTTATCCT GTTTTTCCCA GAGTAGACAT  24180

TATGAAGATT AAAAAAATTT CAAAGTGTTT TGAATATAAT AAACTATGCT ATACACACAA  24240

CATTTTGGTG ACTAGAAATA CAACTTTATT GTTTGTTGTT TGTTGAGACA GGGCCCTGCT  24300

CTGTCTCCCA GGCTGGCTGG CACAATCATG GCTCACTACA GTCTTGAACT CCTGGGCTTA  24360

AGCGATCCTC CCACCTCAGC CTCCAGAGTA GCTCCCACTG CAAACGAGCA CCACCACGCC  24420
```

-continued

```
TGGCTAATAT TTGTATTTTT TGTAGAGATG GGGTTTCACC ATGTTGCCCA GACTGGTCTC    24480
AAACTCCTGG GCTCAAGCAA TGCTCCTGCC TCGCCCTCCC AAAGTGCTGG GATCACAACT    24540
ATGAGCCACT CCACCCCGCT CAGTTTCTCT TGTTTTAAGC CGCTTCATTT GTGGTACTTC    24600
TTACAGCAGT CCCAGGAAAC TCACCAACTG CAGAACATCA AAATTGTTTT TCTTCAGCAA    24660
AAGGAGAAGC AcTTGTGGTT CGCACCAGCT TTTCCTGTGC TCACTTCTGC ATGGCCGCAC    24720
CTTTGCCCGA CACGAGTGCA CAGCAGGCTO TGGGGGAGCA ACTGCTTGAG TCAGGCCTCC    24780
ACTTGTGCCC TATCCCCACC TGCTTTGCTG GACACCCCTG TTTGGGGGGC ACCCACTGCT    24840
GCCCCAGACA CCAAGCAAGC ACCAGCTGTC TCCAAAACTT ACAGTCACTG TCTTGGCCCG    24900
TTTTGTGCTG CTGTAACAGA ATGCCACACA CTGGGTAATT TAATACAGAA CAGAAATTTA    24960
TTTCCTCAAA GTTTTCGACG CTGGGAAGTC CAAGAGCAAG CGGCCATCAG GTCAGGGCCT    25020
GGTCTCTGCT TCCACGATGC CACCTTGACC ACCGTGTCCT CACGTGGTCA GAGAGAGCCC    25080
ACTCCCAGGA GCCCTTTTAA TAGAGCAOAA CACTCGCTCG CTGCGCTTAA GTTTCCAACA    25140
CGTGAACTTC GCAGCTGACA CATTCAGATC ATAGCACTCA CTCTAGGCAG ACTGTCTGAT    25200
GTGGTTTTAA AATACGTTCA CAGACTGGCC GGGCACTGTA GCTCACGTCT GTAATCCCAA    25260
CAGTTTGGGA GGCCAAGGTG GGTCGATCAC CTGAGGTCAG GAGTTCAAGA CCAGCCTCAC    25320
CAACATGGTG AAACCCCATC TCTACTAAAA ATACAAAATT AGCCAGGTGG TGCATGCCTG    25380
TAATCCCAGC TACTCGGCAG GCCGAGGCTG GAGAATCCCT TGAATCCAGG AGGTGGAGG     25440
TACAGTGACT CGAGATCATG CCATTGCACT CCAGCCTGGG CAACAAGAGC GAAACTCTGT    25500
CTCAAAAAAT AAAATAAAAT AAAATACATT CACAAGCCCG GCCACTGTGG CTCACGCCTC    25560
TAATCCCAGC TACTTGGGAG ACTGAGGCAG GAGAATCGCT TATAACCTGC GAGGTGGAGG    25620
TTGCAGTGAG CTGAGATCAC ACCGCTACAC TCTACCTTGG GCAACAACAG TGAAACTCCG    25680
TCTCAAAAAA GTAAAATAAG CCCCTGCAGG CATGGTGGCC CACACCTGTA ATCCCAGCAC    25740
TTTAGGAGGC CAAGGCGGTC GGATCACGAG GTCAGGAGTT CGAGACCAGC CTGGCCAACA    25800
TGATGAAACC CCGTCTCTAC TAGCCTAGCC AACATGGGA AACCCTGTCT CTACTAAAAA     25860
TACAAAAATT AGCCGGGCAT GGTGGTGCGT GCCTGTAATC CCAGCTACTC AGCAGCCTGA    25920
GGCAGGAGAA TCGCTTGAAC CCAGGAACCA GAGGGTGCAG TGAGCCAAGA TTGCGCCGCT    25980
CCTCTCTAGC CTGGGCGACA GAGCCAGACT CCATCTCTAA ATAAATAAAT AAAATAAGAA    26040
AATAPAATAT GTTCACAAAT CCTTTGACAT TCCTCACCTC AAAGCTGCA ACCCAACTCC     26100
CTCCTAAGCA TGAGTCTTCT CAGTGACTCA CTTCTAACAG CAGAACTTAC ATGGTTCCCC    26160
ACACCCAGAG GACATTGGGT TCCTCCCAAT ATCCCCCCAC CCACCGACCC CCACCCAGCT    26220
CGCTCCCTTT GGGTCCCCCA GACCCATGTT TCAAGGACAC TCAGGCAGCC CCTGGATGTC    26280
CATCTGGTAA GGAATGAAGG CCTCCTGCCT GCAGCCTCGG GAGGGAGCAT TCTCAGAAGA    26340
GGATGCCCCA CCTCCTGCCC ACCCTTCACA TGGCCAGGAC CTCGTCCAAC GTCCTGACTG    26400
CAACATCATG AGAGACTCCG AGCCAGAAAC CCCCAGGTTT TGTACTCCTG ACTTATCGGA    26460
ACTGACAGAT AATGTTCGTT GTTAATTAAC GGGTGACTTG TCACACACAA TAGGTCACTA    26520
AACAGCTCTG TCTGGCCTCC CAGGAGGAGC CTCCCTTTCC TTTTCTTCAT GGGAAAAGTG    26580
CGATCAGTTT GTGAAGGAAT GTCCGCCCCC ACTTGATGCC AGAGGCTCCA CATGGTGACT    26640
GTCATAAACT CCATCTGCCC TCAGTGCCTT CCCAGCACCC GGCCTGCGAT CAGCTTGCTC    26700
TTGCGGCAGC CCAAGGCCCA CGTGTGTTTG TGTCTGCTGT CTCTGTCTGC GTGCCCATGC    26760
ATGCCCAGGG TACAGGGATG CCATATACAA ATTCTTTCAA TGTTGTATGT GGCATGTGTG    26820
```

-continued

```
TGTCTGTATG CCCAGGATAC AGGGATGCTA TATACAAACT CTGTTTTTTC GTTTTTTTTT  26880
TTTTGAGACA CACTCTTGCT GTTTCGCCCA GGCCGGACTG CAGTGGCGCT ATCTCGGCTG  26940
ACTGCAAGCT CCACCTCCCC GGTTCACGCC ATCCTCCTGC CTCAGCCTCC TGAGTAGCTG  27000
GAACTACAGG CGCCCGCCAC CACACCCGGC TAATTTTTTG TATTTTTAGT AGAGACGGGG  27060
TTTCACCATG TTAGCCAGGA TGGTCTTGAT CTCCTGACCT CGTGATCCAC CCGCCTCACC  27120
CTCCCAAAGT GCTGGGATTA CACGCATGAG CCACCACGCC TGGCCTACAA ACTCTTTCTT  27180
TTTTTTTTTT TTTTTTTTCA GATGGAGTCT CACTGTCTTC CAGGCTCGAG TGCACTGATG  27240
CGATCTCAGC TCACTGCAAG CTCCACCTCC CGGGTTCATG CCATTCTCCT GCCTCAGCCT  27300
CCCAAGTAGC TGGGACTACA GGCACACACC ACCACGCCCA GCTAATTTTT TCTGTTTTTA  27360
GCAGAGATGG GCTTTCACCA TGTTAGCCAG GATGGTCTCG ATCTCCTCAC CTCGTCATCC  27420
GCCCCCCTCG CCCTCCCAAA GTGCTGGCAT TACAGCCGTG AGCCACTGCG CCCACCCTGC  27480
AAACTCTTTC AATGTCTTTC TTTTCTCTCT CCTGCCATCT TCTCCCTTGC ACATTTCTTT  27540
TGTCTCTACG TCTTCCCCAG CTGAGTCCGA GGTCCTGACT TGCCCACGCT CCCTGGACTG  27600
GAGGAGAGGT GATAGCAAGA GCTCCTTCAA CCCCAGGAAT GCCACCAGGG CTGCCCCGGG  27660
AGAGGAGGAA GCTGGGTCTC TCGGCGTTGT GGGGACCAGA CACCCTTCTA AGACATGGAC  27720
TCAGCACAGA AAGTCTACAC ATCCACTACA AACACATCTC CCTCCTAACA GGGGGCCCCT  27780
GGGCACCCCA AGTGGCTGTT TGGTGGGACA GGCATGTCCA TCAGTCAGAA TATCTTTATT  27840
TTTTATTTTT TATTTTVTAT TTTTGAGAGA GTTTCACTGG AGTGCAATGC CACGATCTCA  27900
GCTCCCTACA ACCTCCGCCT CCCAGGTTCA AGCGATTCTC CTCCCTCAGC CTGCCACGTA  27960
GCTGGGATTA CAGGTGTGAG CCACCACACC CAGCTAATTT TTTTTTTTTT TTTTTGAGAT  28020
GCAGTCTCGA GGCTCTGTCQ CCCAGGCTGG AGTGCAGAGG CGCGATCTCA GCTCACTGAA  28080
AGCTCCOCCT CCTGGGTTCA CGCCATTCTC CTGCCTCAGC CTCCCGAGTA GCTGGGATTA  28140
CAGGCATGAG CCACCGCGCC CGGCCAATTT TGTATTTTTA GTAGAGACAG GGTTTCACCA  28200
TGTTGGTCAG GCTGGTCTTG AACTCCTGAC CTCAGGTGAT CCACCTCCCT CGGCCTCCCA  28260
AACTGCTGGC ATTACAGCCC TGAGCCACCA CGCCCAGCCC AGAATGTCTT CTTACTTTTT  28320
ATTACTCTGT CCCCCATCCT GGGTCCGAC CTGTGACCGT GAACAACCGG CTGCCCAGCG  28380
GTGAATGGGG TGAGTGGGGT GAGTCCACAG AACAGTGGGG TGCACCCCCA GGGGTCTCGT  28440
AGCACCTGCC CCCAGGPCAG GAAGTCCCAC AGCCTAGAGG CTCCAGCCTC              28500
AGATG[ ]ATAC
ATATGTAGGC CCTGCCCTTT CCTCCTGACC GGCGGGCCAC AGACTCCTCA ACAACACCAA  28560
GCCCCTGAGG AGGCCTCCGC CCTCAGGGAC GGCAGGGGAG CCCCGCCAG CCCCACCCAC   28620
AGCAGCGGGC CCTGCCACCC CCCACCCTCA CACCTCACCC CTTGGATTCC AGAGAGCAAA  28680
GTGGGCTTGT GTGTAGTTTA CATGCTCATA TCTTAAAATC ACCGTTGTCA ATAGAACAAT  28740
TCATAATAAT GATGATAAAA TAAGATTTAT AACCAGCTTC AGTCTGGAGA TACACACAGA  28800
GCAGATCTTC ACTCCCAGAC AGGGAGCCCG CAGCTGCCCC CGACCCCACA GGTGCAGGAC  28860
ACACACAGAC AGTTCAACCA TGTCTTAAAC ACACAGGTGT TTATTTAATT GTTCATTTGA  28920
TTGAATTTTT AAGTTCACTT TACTACGTGG ATGAGATGGG TGCATATTAC AGTAGGCTTT  28980
CGCTATGAGC GCTGCCACCA TGAGGAATAT CCCAGCCCTC AGTTCTGCTT CCCTTTCTGA  29040
GTCCACAAAA AGCCAGATGT GGACAGCCTT GGGTTCCCAT CCCAGCTGGC TGCTCCTTCT  29100
GGGGCTGTCT TGGTGGGGAG AGGGAGATGG GGCAGTGGGT CCCTGCTGAC CCCTGAGCCC  29160
```

```
                              -continued
TGCAGGGGGT AGGATCCTCC CGTGGTCCCT GGGTGTGGCT CTGGAAGACA CTGGCAGTGC  29220

CCGGCCAAGG CCTCCCGCAG GATGGAAGTT GAGGGCCCTG GCTCTGGGTC CTAACAGAAC  29280

TCACCCGCCC CCTTCACACT TTACAGCAAG GGGCCAGGCA GCAGCTTTGG CATGGGCTT   29340

CCGTGGAGAA GTGGGCGATG CTGCAGTGGT ACAAAGACAG CCTCCCCCAC CGCCATCCTC  29400

CAGCTGACCG TCCTCCAAGC CCAGCACTGG GCGTCCAAGG GAAAGAAGCA ACTCACCCCA  29460

GAGGGTGTGG GCAGGAGAGG CCTGGACTCA GGCCTCCACC CACAGCCCCC TCTGCGTCCC  29520

AAGTGGGAAG GGTGTTGGGG CTGGCTTGGG AACCTTACCC GCTGCCCTTC CAACACCTGG  29580

ATCTGTGGGC AGCGGTCCCA CAAAATCCCC CTTGGGGCTC CCTGAGGAGG ACTTGTGGCT  29640

GCCGCTTCCA CCACGGCAGA GGGCACAGGA GGGGCCAGCA CTCCAAAGGG CTCTAGGGTG  29700

GCTCTTTCAA GGACATCTGC AAAGCCCTGG TOGOGAGGOG CCTGGGCCAG AGGCTCTTTG  29760

GAACTCTTGC ACTTCTGAGT GGGGGACTGT CCATGCTGCC CACAACCTCT AGACCATOCA  29820

GCCTGCTCAT GGGTCCCTGG CAGAGAATGC CCACTCCCCA CCACACTCAG GGCAGGCCCC  29880

CAACTGCAGG CTTCCAGGAA GGCCCAGGGT GTCCACCTCA CGCCAGGTGG TCTCAGAGGA  29940

CCCCTGTGCA ACCACATTAA GGAAAGCTGC AGCCCCCACC CACCCCCCTG CCAGTTCAAC  30000

AAGCACCGGC TGCACACGCA CGCTCCCAGG CACCATCACC CCCCTCCCCC GTCGCCCCTC  30060

CCTCACGGGG AGCCCCTTCC CCCTGGAAAG ACAGCAGGTA CTGTAGCCTC GCCTGCTGGC  30120

CAGGGGCGCC GGCTCAGAGG ACCTGCCCTG ACCTGCACGT CCTGACCAGA CAGCCCAGCG  30180

TAAGGACCCG CGATCCCACG CCACCGCCCT GGGTTTACCA CGGTCACCAC CACCTCTCTC  30240

ACAGGGCCCC CGGGGCACCC AGCCCCCCCC GGCCTGGTGT CTCCACCCAG GGACCGCGTC  30300

TCACGCCCGG CGGCTCCTGC AGGGGAACCC GTGCTCAGCG ACTCACCACG AGGACAGGGC  30360

AGGGCGGCTG AGTGCGGAAG AGAAGCATGA AGCTGGGGGC GGGGGTGGGG GAGGAGGAAC  30420

AAAAAGTTGCA TCTAGACAGA GGTGAACGAA ACAAAACCAA AACCCGAACG TGTTCCGTCG  30480

CAGGATCGGC GCCGCCCGTC CCCGGCCCTT AGCCCGACAT CTCTTCTCGC TGCTCCTTGT  30540

TCCTGCCCAC CTCGGCCGCG TGCAGCTCCT GCAGCACAGG GGGCGGGAGG GCCTGACGGC  30600

GGGGGTGGCT TCCGCCGACT CCGGGAACCC CCAGGCGCGC AGGCCGTGGC GCCCTGGCAC  30660

CCGCCCGGCC TCATCCGGGC TGGCCTTCGG CAGGACCCTG ACTGAGTTGA GGGCGCGGGA  30720

GCACCGGGGA GGCGCAGAGC AAGGCCAGGG ACCAAGGACG GGTTTCCTGG GAGCTGGCTG  30780

GGCCCCGCTT CTAGCTCGTA CCGCAGCCGA GCTTCCTTCA GGGCACTTTC AATATAATGA  30840

ATTTAGCCAT CTATTACTGC GGCTAGTTAC TGTCCCGCCA GGACCACACT CTGGACCTGC  30900

CTCGTGCGCT GCTGGGGACG CCCAGTAAAC ACGGGAGGAG CCCCCGACCC CCACCCCAGC  30960

TCAGCGCCTC GGAGTCCCCC GCCCCGCTCT GCGCCCCTCC GACCTCCGCC CTAGCCCCGC  31020

CCCCGCCCAG TGCCCCGCCC CCTGCCTGCT GCTAGCCCTG CCCCGCCCC GGCCCCTGCC   31080

CGCTCCGAGC TCCGCCCTCG CCCCGCCCCG GCCCTGCCC GCTCCGAGCT CCGCCCTCGC   31140

CCCGCCCCCC GCCCAGTGCC CCGCCCCCTG CCTGCTGCTA GCCCTGCCCC CGCCCCGGCC  31200

CCTGCCCGCT CCGAGCTCCG CCCCGGCCCC GCCCCGGCCC CTGCCCGCTC CGAGCTCCGC  31260

CCTGGCCCCG CCCCCGCCCA GTCCCCCGCC CCCTGACTGC TGCTAGCCCT GCCCCGCCCC  31320

CGGCCCCTGC CCGCTCCGAG CTCCCCCCCG GCCCGCCCC GGCCCCTGCC CCTCCGAGC    31380

TCCCCCCCGC CCCGCCCCG GCCCCTGCCC GCTCCGAGCT TCGCCCCGCC CCGCCCCGG    31440

CCCCTGCCCG CTCCCAGCTC CGCCCCGGCC CCCCCCCGC ACCTTCTCGC GCAGCCGCTC   31500

GCGCAGTGCG GCCAGGTGTG CCTCGCGGAT CTCCTTGCTG AGCTCCATCT TGTAGTTGAG  31560
```

-continued

```
CTTCTCCTCC CCCTGGCGGC TGAAGTTGTT ATTCTCCTCC AGCGCCTTGT GCAGCACCTC   31620

GCGCTCGTCC TCGCCCCCCT CCGCCACCTG CTTCACCACC TCCGCCTCCT CCCTCTGTCC   31680

GGGGCCGCCG GGCCCGCGTG AGCGGCAACC CCCCGCCCTG CCCCGCCGCA CTCCTCCCTG   31740

CTCTCCGCCT CCCCCCCACC GCCCGCTCGC CTCACCTGGC GCCTCCACCT GCCCAGGCCT   31800

CGGTGGGCCC CGGGACCCCC GGGCGCTCCC CTGGCAACCC TCGCCTGCCA TCCGCCCTGT   31860

GCTCGGGGCA CGGCCACGGG GTCGCGATCC GCCGCCCCCG CCCCCGTCCC TGCCTCGCGC   31920

GCGGGTCCCG CGCTCCTGGC TGCGCCCAGG GCCCCCGCCA TACCCTGCCC CCACTCCACA   31980

CCCTGCCCTG CGCGTCTGCC CCTCCAAGGA CCAGCAGCAA GAAACCCTAA ACTTCTGCCC   32040

GGTCTCTGAG CTTTGTCTCT TCCTCGGACA TCCCCCCACT GAGCAGAGTA CCTGCTTGTT   32100

ACACACCGGC TTCCCACCTC CCAATTAGGT GCCCAGGAGC GGAGGGTCCC CAGGGATGCT   32160

GGGGGAGGGG CCGGCTGGTG ACCCCTGGGA GGAGAGCGGG GCAGCAGGAC CCGCACCCAC   32220

ATGCCAGTCC CTACTAGTCA GCCCTGTGAA CCCTCGTCTC TGGCCTCACC GGGAACGGAA   32280

CGGAGCCGCT TCCCCTGCCC AATGCGTTGC CCTCCAGGGT CGCACCCCCA AAAGCACATT   32340

TTTATCTCTG TTTCAGTCTC AGAGGGCCTG GTGGGAGGGG AGGCTGCAGG GAGGGGACCT   32400

GCAGCCCACA CCCACCTCTC CCAGGGCCCC TCCGCCCTCC AGCAAGCCTC ACGCTCTTCA   32460

CACATGAGCC CCTTCCTCCA GCTTCCCTGT CTGGGAGAGG GATGCCCCAC CCGACGTCCC   32520

CAGGGCCCAT CTGGGGACCA CCCCCTAGCA TCCTGCTGGC CCTGACAAGG GTGCCTCCCA   32580

CCCTCACCAG AGGCTCCTCC TCCTTCCAGO TGGCCGCCTC GGAACCCTTC CTCCTCTCCA   32640

TCCCTTTCTT TTTTTGTTCT TGTTTGTTTT TTGAAATGGA GTCTCACCCT GTCGCCCGGG   32700

CTGAGGAGTG CAGTGGCGCA GTCTCGGCTC ACTGCATCCT CCACTTTCTTG CGTTCAAGCA   32760

ATTCCCCTGC CTCAGACTCC CTAGTAGGTG GGATTACAGG TGTGCACCAC CACACCTCCC   32820

TAATTTTGTA TTTTTAGTAC AGATGGGCTT TCACCATCTT GGCCAGGCTG ATCTTGAACT   32880

TCCAACCTCA AGTGATCTGC CTGCCTCACC TTCCCAAAGT TCTCGCATTA CACCCGTGAG   32940

CCACCACACC CGGCCTCTCC CCATCCCATT CTTATCTCTC AGAAAGAGGC CCAGGGACCC   33000

ACAGCCCCTC CTGCTCCAGG CCAAGGCACT GACCAACCCT GTCCGGGAGC ACCCTGCTTC   33060

TTGCAGGCCC TGTCCCCGTG GGCCGCCTCC GTTGAAACTC CTGGGGGGTG GGGGATGGAG   33120

GACTCCTTGC CTTCCTCCGC TCCTCGGCTG CCTCCAGCCG CTTTTGCAGC TCCTCCAGGG   33180

AGGTGTCCTT CTTCTTGGGT GGGGAGOAGA GCATAGGGCT CTCTGOGGAC ACGTCAGAAG   33240

GGGACTTGAG GATGACCTCG AAGCTCTGGC CTGAGGCCCG CTTGTCCAGC TGCTTCACCT   33300

CCATGTCTCC AGGGCAAGAC CAGACTAGAG CTTCAGAGGC CCGGCCAGGG CATGGCGTGG   33360

GCTGAGCGGG ATGCTCCCAG CACACATCCA ACCCCAGGGC TGGCGAGAG CCGGTGCCTG   33420

CTCCCGCAGG AATCCCAGGC TTCAGCCCCC AGGATGGGCC CCTTCCCCCT AGAACCTCCC   33480

TCTCCAGAGG CAGCCAGGAC GGGAGTTCAG AGAGACTGCC GCAGCCCGGG GGAAAAGGTG   33540

AGGTGGGCAG GCACCGCAGG GAAGGGCAGC CGGCAGCCAG GCACTCACCC CCGTACTGGT   33600

AGACGGTATT GGGGTGCGGC TGTGTGTAGA AGCAGGAGCA GATGAGCGAC AGCACCGACA   33660

GCTCCTTCAT CTTCTCCTTG TAGGCTGTGG GCACAAGGCT GGGCTGAGCA AGCACCACTG   33720

GGGCCTGCCC ACCIGGGCCC CCGTTTTCCC TCCCCATGGC TGCCTCTATC ATGTCTCTGT   33780

GAGACACGGA GCTGCCCAGC ACGCTCTCTT GTGTGTCTCC ACACCCCGG CCCCTTCGTC   33840

TCTCCAGCTC TCPCGCTTCC AGACGTCCGC ACTGTCTCCG TGGTGTGTCC CCTGCCTTCT   33900

GTCTCTCTCG CCCTCTGCCT CTCCCCGCTT TTCCTCTCTC TCGGCATTAA TGTCTGTCTC   33960
```

-continued

```
ATCTTCCACA CTGACTTGTT TCTCCATCCT TCTCCTGCCT GCTGTGGTCT GAATGTTTCC    34020

ATTACCCAAA ACTCATGTGT TGAAATCGTA ACCCCAAGGT GCCCCTGTGC GGAGGTGAGG    34080

CATTCGGAGG GAATTAGGCC ATGAGGATAG AGCCCTCCTA AGTGGCCCCA CAGTGGGGCT    34140

TCAGAGAACT CCCTCACCTT CCATCATGTG AGGACACAGC CACAAGACGC CACCCGTCTA    34200

TGTACCAGGA GGCGACACCT CTCCAGGCAC CGACTCTGCC GGCACCTTGA TCCTGGACTT    34260

TCTGGCCTCC AGAGCGATGG CAAATAAGTT CCTGTCGTCT ATAAACCACT CAGTCTCAGG    34320

TACCTGCCCA GACTGACAAA GTGGCTACCC CTGCCTGTCT CGGTCTCTGT TTACCTTCTG    34380

TGTGTCTGAC TCTGTCACTG TCATTGTATC TTTCTGTGTC TCTGGGCGTA GCCCCTGACT    34440

CTGTCTTTCT CCCTGAGTGC ATCTTTCTGT GATTCCTTGT CACTGTGTGT CTTTCTGACT    34500

CTTACCTCCC TCTGTCCCGC TACTTCTCTC TCCCCTCCTC CTCCTTCCCA CTCCTCGCCA    34560

GCTCAAGCAG GCAAGATTTA CTCATGACGG GACCAGCACA GATGCAAACC CTCTGTGGGC    34620

AGGACTTTCT TGGGCTGTAA ACCTGGATGA AGCCCTCACA CCCTCCTTTT TCCTTCCCAA    34680

TGATTGTGTG GTCACCTTGA GATGAAACCA GGCCCTCTCC AGGCACATGC TCTCTGTCTA    34740

TCTAGGGCTG GGCTTGGGCC ACTGATGCCA CCAAGGAGCA AGGGAGGGAA GCTGTCCCTT    34800

CAGCACCACA GCCAGCCCTC TTGCCCATTC AGGTCAATCA AGTGCCCACC AGCCAGTCTC    34860

CCTGCTGCCC AACCCAAACC AGAAGCAAGC CGGGCTCCTG TGGCCCTGTG CCCTGTCAGG    34920

GGAAGAGGAA GGCGCCTGCT CTCACAGTGA AAATAATTA GCTCTTTTGC TCTATTCAGG     34980

GCGAACCTCA TTCCTAAGCA GACACGCTGG CCCGGTTTCT CACTAGTGCT CGATAATCCT    35040

TTTGGCTGGG TGCAGTGGCT CATTTAACTG TAATCCCAGC ACTTTGGGAG GCCAAGGCAG    35100

GTGGAACACC TGAGCTCAGG AGTTTGAGAC CAGCCTGACC AACATGGTGA AACCCGATCT    35160

CTACTAAAAA TATAAAAATT AGCCAGGCGT GGTGGCAGGC ACCTGTAATC CTAGCTACTT    35220

GGGAGGCTGA GGCAGGAGAA TCGCTTGAAC CTGCGAGGCG GAGGTTGCAG TGAGCCGAGG    35280

TCGCGCCATC GCACTCCAGC CTGGGTGACA GTGTGAGACT CCGTCTCAAA ACAGAAAGAA    35340

AAAGAGAGAG AGGAAGAAAG GAAGGAGGGA GGGACGGAGG AAAAGAAGAA AGGAAAGGAA    35400

AGGAAGACAG ACAAGGCACA AGTAATCAAG CCTTTCATGG TGACCTGGGT CTTCTCGGTGA  35460

CAGTGCAGAG AATGGTCTGT CCTGACTTAA ATTTCCTCGT GACCTACACT TTTCBGGACA    35520

GAGCAGCACA GACCCCAAGA GcGTGTAACG AGCAGCAGAA AGCAATCCCA GGCTGGGCAG    35580

GCCCGTGCGA GAGCCTTTCG GGGAAGGAAT GAGACTTTGA GCCGGGAAGC CACGCAAACC    35640

TACCTGTCTT GGTCATTGTC TTCAGGCAGG GAGATGGAGG GGCACCAGGT GGCGGAGCCT    35700

CACAGOCOAC TTTGGTCTGA CTTGTCAAGT TTTCTTTTTT TCTTTTTGAG ATGGAGTCTT    35760

GCACTGTTGC CCAGGCTGCA GTGCAGTGGT GCGATCTCGG CTCACCGCAA GCTCCGCCTC    35820

CTGGGTTCAC ACCATTCTCC TGCCTCAGCC TCCCGAGTAG CTGGGACCAC AGGCACCGCC    35880

ACCACACCCA GCTAATTTTT TGTATTTTTA GTACAGACGG GGTTTCACTA TATTAGCAG    35940

GATAGTCTCG ATCTCCTGAC CTCGTGATCC GCCCGCCTCG ACCTCCCAAA GTGCTGGGAT    36000

TACAGGTGTG AGCCACTGTG CCTGGCCTAC TTTATTTTTT AGAAACAGGA CTGTGCTCTG    36060

TTGCCCATGC TGGAGTGTAG GGTGCAGCTG TGCGGTTCAC TGCAGCCTTG AACTTCTGGG    36120

CTTGACGGAT CCTGCCATCT TAGCAGCTGG GACTACAGOT GCATGCCACC ACACCAGTTT    36180

TCTTTTTTTT TTTATCTCTG CTCACTGCAA TTCCGCCTCC TGGGTTCTAG CGATTCTCCT    36240

GCCTCAGCCT CCCAAGTAGC AGGGATTACA CGCACATGCC ACCACACCCG GCTAATTTTT    36300

GTATTTTTAG TAGAGACAGG GTTTCACTAT GTTGGTCAGC CTGGTCTTGA GCCACCGCGC    36360
```

```
                                  -continued
CCGCCCGGCC TACACACCAG CTTAAAAAAA AGAAAAAAAT AGCTGGGCGT GGTGGCTCAT   36420

CCCTGTAATC CCAGCACTTT GGCAGGCTGA GGCAGGCAGA TCACCTGAGG TCAGGAGTTC   36480

AAGACCAACC TGGCCAACAT GGCGAAACCC TGTCTCTACT ACAAATATAA AAATCAGCCA   36540

GGCGTGGTGG CGGGCTCCTC TAATTCCAGC TACTTGGGAG GCTGAGGCAG GAGAATCACT   36600

TGAACCCGGG AGGTGGAGGT TGAAGTGAGC CAAGATCGAG CTACTGCACT CCAGCCTGGC   36660

AGCAAGACTC CCGTCTCAAA AAAAAAAAAA AAATTTGTAG TGGTATGGAG GCCGGGCATG   36720

GTGGCTCACG CCTGTAATCC CAGAACTTTG AGCGGCCAAG GCGGGCAGAT CATGAGGTCA   36780

GGAGTTCGAG ACCAGCCTGA CCAACATGAT CAAACCCTGT CTCTACTAAA AATAACAAAA   36840

ATTAGCCAGG CATGGTGGCG GCACGTGTA GTCCCAGCTA CTCGGGAGAC TGAGACGGGA   36900

GAATCGCTTG AACCCAGGAG GCAGAGGTTG CAGTGAGCTG AGATCACGCC ACTGCACTCC   36960

AGCCTGGGTG ACAGAGTGAG ACTCTGTCTC AAAAACAAAC ACAAACAAAC ATATATATAT   37020

ATACATGTAT ATATATAATA TATATATACC TATATATACA CGTGTATATA TATAATATAT   37080

ATACGTATAT ATACACGTGT ATATATAATA TATATACGTA TATATGTATA TATTAATATA   37140

TATACGTATA TATACACGTG TATATATTAA TATATATACG TATATATACA CGTGTGTATA   37200

TATTAATATA TATACGTATA TATGTGTGTG TGTGTATATA TATATGTATA TATATATATA   37260

TATATACATA TATATATACA GAGAGAGAGA GAGTAGTGAT AGGTCTTGCT GTCTTGTCCA   37320

CGCTGATCTT GAACTCCCGG CCTCAAGAGA CCCTCCCACC TCACCCTCCC AAAGCACTAC   37380

GATTATAGGT GTAAGCCACA CTACCTAGCC TATTATGAAT TAATCTTAAA CAACAGGATG   37440

TGATCAGGGA GTTAGAGGGT CTGCCAGCCA TGTGTTCCAC AGCACCAGGT CAGGAGACAT   37500

TGGGGACATT TAGAGGAGCT GAAGAGGTGG CCAACCCTGT GCTCAGGACG ACGGGGGACG   37560

GAGAGAGCAA GAGGGAGTTT GGGCTCGGGC AGAACGTACC TGGGTCCTGA GAGGATAAGA   37620

AGGTAGGCAC TTGGCCCCTC CAGGCCTGAC TCTGCCAGCA ACCAGCTCCC TATCAGCAGA   37680

CTCCAGGCCC CTACCCTTCA GCTCATCCTT CCTTATCACA CATCCAAAAC TCTGAATGTG   37740

GCCGGGCGCA GTGGCTCACG CCTGTAATCC CACAACTTTG GGAGGCTGAG CCAGCAGGAT   37800

CGCTTGAGAA CAAGAGTTTG AGACCAGCCT AGGCAACATG GTGAAACCCC ATCTCTACTA   37860

AAAATATAAA AATTAGCTGG GTGTGGTGGC ACATGCCTGT TGCCCCAGCT ACTCAGGAGG   37920

CTGAGGCAGG AGAATCACTT GAGCCTGGAA GGCGGAAGTT GTAGTGAGCA GAGATTGTGC   37980

CACTGCGTTC CAGCCTGGGC AACACAGCGA GACTCTGTCT CAAAAAACAA AAACTGGAAT   38040

GTGTTTACCA TAAAGGCCAG AAAATGTGAT TAACAGCTGC TCAAAGCCCC TGTCTGCCCT   38100

AAGCCTGAAA TTTTCACCGA AAAAAAGATC TGTAGCCTCA TACAGAGGAA GGACAAACAC   38160

CAGGGAGGCT CTCTTCCAGT TTGCTTCACC TCAGCAAGCA GACGGCTGGC AGCAATTTGG   38220

GGGCAGGTGT GAGCACCTCC ATCATCAGGA AGAAGGGGC ACGGTGGGGA CGCAGGTCAG   38280

ACCTCTCACA CGTCTTGGCT CTGCCCAGGA GACACGTGTC CAACTGAGAG GTGAGGAACT   38340

GGGTTCTGCA GCTGCAGACA CAGGTGCGGC TCAGCATCTG ATGGCCACGG AGACCCCCTG   38400

GCTTGGCTTC TCCCAGCTGG TGGCCCATGA GGAGCTTCTA TCCCAAGAGA CTGTCCCTCA   38460

AGGAGCAAGT GGGACCAGGT ACCCACAGGA CGGAGCCTGG GAGTGAGGCC TGCCCTGTGG   38520

TCTGGCTACA GGGAGGAAGG GCAGATTGGA GGGGCAGGA CAGCAGGTCA GGAATTGGCC   38580

AACTCTGGAG AGAGCAAGCA AGGGGAAGTC TGCGCACAGG GCAGGGCTGC TCAGGGGCGA   38640

GGCAGGGCAT TGGACCAGTA TTTTCAGAGC TGGTGAGGCT TAAAGAGCAT GTCTACTGCC   38700

TCTTATTACA GAGAGAGGAT GCCGAGGCCC AGACCCATCC AGCCCACCTC TCCACAGACA   38760
```

```
                                -continued
CAGCTCGTGC CAGGGAAGCC CCTCCCAGAG CCTCAAGGCA TTGCTCCCTC TCTCTCTCTC  38820

TTTTTGTTTT TTTGGAGACG GAGTCTCACT CTGTCTCCCA GGCTGGAGTG CAGTGGTACA  38880

ATCTCGGCTC ACGGCAAGCT CCGCCTCCCG GATTCACGCC ATTCTCCTGC CTCACCCTCC  38940

CGAATAGCTG GGACTACAGG CGCCCGCCAC CACGCCCACC TAATTTTTTG TATTTTTAGT  39000

AGAGACGGGG TTTCACTGTG TTAGCCAGGA TGGTCTCGAT CTCCTGACCT TGTGATCCGC  39060

CCGTCTCAGC CTCCCAAAGT GCTGGGATTA CAGGTGTGAG CCACCGCGCC TGGACTTTTT  39120

TTTTTTTTTA AGACGGGGTC TCACTCTGTC ACCCAGCCTG GAGTGCAGTG GCGCGATGTC  39180

GCCTCACTGC AACCTCTGCC TCCCAGTTC AAGTGATTCT CCTGCCTCAG CCTCCCAAGT   39240

AGCTAGAATT ACACGCACAT GCCACCATGC CCAGCTAATT TTCTGTATTT TTAGTAGAGA  39300

TGAGGTTTCA CCATGTTGGC CAGGCTGGTC TTGAACTCCT GACCTCCGGT GATCTGCCCA  39360

CCTCAGCCTC CCAAAGTGCT GGCATGACAG GCGTGAGCCC CCGCGCCTGG CCCCCCGCAG  39420

TCCTGGGATT ACAGGCGTGA GCCCCCCCGC CCGGCCCCTC CCTCTCTTTG ACTCCCTTCT  39480

TTCTCACCCC CCCCTCCCCA CCATCCTTCC CCTTCACTGA CTTCAGGGAG TTAAAAACAA  39540

TTCTCGCAGT GAGCTGGGCT TGTTTTGTCT CCCTGCTTCT CTTTGTACTA AACATTAGAT  39600

ACCGAGGAAA TGCGGATTGG CCTTTGGATG ATTCATCAGC ACCAGTCACA AAAAGGCACC  39660

AGGTTCGCCT CAACCAGCAG GCTATAGTAG TGCCCGCTCC CAGGGTCACA CCTCACGCCC  39720

ACCCCTCCCG CCCTCCAGGT GCATGGT(CC CACTCCCAGG GTCACACCTC ACGCCCACCC  39780

CTCCCCCCGT CCAGGTGGAT GGTGCCCACT CCCAGGGTCA CACCTCACGC CCACCCCTCC  39840

CCTCCCCCAG GTGGATGGTG CCCACTCCCA GGGTCACACC TCACGCCCGC CCCTCCCACC  39900

CACCCGCGTG GATGGTGCCC GCTCCCAGGG TCACACCTGA CGCCCACCCG GGTGCATGGT  39960

GCCCGCTCCC AGGGTCACAC CTCACGCCCA CCCCTCCCGC CCGCCCGGCT GGATGGTGCC  40020

CCCTCCCACG GTCACACCTC ACGCCCACCC CTCCCGCCGT CCAGGTGGAT GGTGCCCACT  40080

CCCAGGGTCA CACCTCACGC CCACCCCTCC CGCCGCCCAG GTGGATGGTC CCCACTCCCA  40140

GCCTCACACC TCACACCCAC CCTCCCGCC CACCCGGGTG GATGCCCTTA TCAGCTCTCC    40200

TTCTCCTTCT CTTTCGTCTT CTTCGTCTTC CTCCTCTTCT TTCTTCTTTT TTTTTTTTT   40260

TAGAAAGAGT TTCTACTCTT GCTGCCCACG CTGCAGTGCA ATCGCACAAT CTCAGCTCAC  40320

TGCAACCTCC CTCTCCCCGG GTCAACCAAT TATCCTGCCT CAGTCTCCCA GATTGCTGGG  40380

ATCACAGGAG TGTGTCACCA CACCTGGCTA ATTTTGTACT TTTAGCAGAG AGGGGGGATT  40440

TCACCATGTT CGCCAGCCTA CTCTCCAACT CTTGACCTCA CTTTATCCAC CGGCCTCAGC  40500

CTCTCAAAGT GCTCCGATTA CAGGCATGAG CCACCCTATC TGCCTCACTT CTACAGACGA  40560

GGAATGAAGC CTCAGAGAGG GCAAGCATTC CACCCAGCAT CACACAGAGT GCCGGGTGAG  40620

AGCCCAGTCA TGAGCCTGGG CCTCACTGCA GGCTCCTGTT GGGAGCTCGC CGAGGTGGGG  40680

GATCTGTCCA GAACTGAGAG GCCAGGGGAC CACAGTGGCC TCTGACCCCT GGACGGCCCT  40740

GGAGGCTCCT GCCCGCTCCC CCCGGGGGCA CATGGAGGTC ACTGTCACCC AGCCTGCTTC  40800

TCATGGTGCC AGGACCACAG CATGGCAGGA GCCACCAGCC GATTTGCCTT TCCCTGGGCA  40860

GGAAACTCAG AAATGTCCCT ACCACAGTCA GGCTGCTTGA CGTGCGCTGA GCACTCATCT  40920

CTTAGCAGGC AAGCGGCCAA GCACCTTTCC TGAAATATTG AGGCCTCAGA ACAAGCCCCA  40980

GGAGAGGTGC CAGCACCGTC ATCTCTACCC AGATAAGGAG ACCCACGTCC TGAGAGGTTA  41040

GCCAGCTCGG ACAACACCAC ACAGCTGGAG GAGGTCAGAC TCTGGGTTCC AGAAGGAGAA  41100

TGTGAGCAGA GGCCACAAAA GAGCGAGGAG CCAGTCCCCA GATGCCGAGA TGCCCTCGCC  41160
```

-continued

```
CTCCCAGCTC AGCCCCAGCA ACCGAGCCCA TGGGGACGGA CCGTCAGGGA AAGGCTGTCA    41220

GGAAGGGCAG GAGGCGGCCC TGGAGAGGAC GGCGCTGCCC TCACGGGCAG GAGGGGAGTC    41280

CCCTCCGCTG AGAGCCCCCC CACCCCCAGT ATCCCCGGGG GTGTCCAGGA GGAGGCGGAG    41340

GGAGGAAGCG CAGATGGACA GGACTCCCAG ATAGGGTGGG GAGGTGTGGC CGGTGACACA    41400

CACGGTCCCC TCCTGCCAGG TGCTGAACTC ACCTGGAGCC TCCAACCCCG TGCGGCCTGA    41460

CGGGCGGGGT CAGGTCGCCC ACGCGTGGGT GGGCCCAGTT CTGCGCCCCG GGCCAAGGCG    41520

CCCGAGTTCA ACCAGTCACC TCGCCAGAGG GACCGCCGCG ACCTCTCCCG GGGGCGTAAG    41580

AAAAGGTGCG AGGGACTGCG GCTCCTGAAC CGGGGCGGCG ATGGCAAGCA GGTGCGGCCC    41640

TTCGTCCTGT CCTCCCAAAC GTCGAGTGAA AAACCAAGCG GCTTCTGCGG CCTCGCGGCG    41700

CACCAGACCO TTTCGGGAAG GCGGGCCCA GCGTCCTCGC GCCCGAGGTC GCCCGGCAGC    41760

TCCCCTGCGT CCAGAATCCG CCCCCCGCCC GGGCCTGCGC CCGCCCCTCC GCCTGAGCTC    41820

CGCGCGGCAC GGGCCGGGAG GCCCGGGTGG GCGCTACCTT CGAAGCCGGT GGGTCCGCCC    41880

CGCGGGAGGT CCAGGGGCGG GAGGGGCGGA GCCCTCTGGT CTCCGCAGGG TTTGGCGATC    41940

GCAGTCGCCC CTCCCCCATC CAGACCCCGC GGCGCAAAGG GCAGTGCCTT TTCTGGCCAG    42000

AGCAGGTGGC GCGGGCGTCG CAAAGGGTGG TCCCCGAGGC CGCAGCGCTG TGCGGGGAGG    42060

GCGCGGTCCC CCTCACTCCG GGCTCCGCCG TGTCTGGCCC GCCCCCCTCC TTCAGCGCCC    42120

CCTCCAGCCC CTGTGCTGCA CTGGCGCGGG GAGCGCCGGG TTCCCGGCTG GGCTTTGGC    42180

AGAGGGTCCC ACCCTCTCCC CGCCTCCCCA CGAAGGCTCT GGCGGACCCA GATCTCGGGT    42240

CGCCGGACGC CCCAGGGACC CCGCCCGCAC ATCGCGAGCG CGCCCACCCG GTCGCGAGCC    42300

CACGCCCGGG TCTGGGACCC ACCCTGCGGC AGTCGCGCCC TCCGTCGCAC GCTGCTCCCC    42360

CAGGGGCGAG GCGCCCCCGC CCGACGTCCC GGTCCCGAGC GCTCCCCGCC GCGGCGCCTC    42420

GCAGCCCAGC GCCCCACCAG CCCCGCCGGC GCCGCAGACC CCAGCCTCGG GCGGGTCGGG    42480

CCCAGGCTTG CAACGCGCAG GGTAGGAGAA GGGAAATTGG CGTCCGCTGC CGGCCGCTGC    42540

CCCAGGCGAG GCCAGACGAG GCCTCTGCTC AGATCCCGCC GCCCCACAAA GCCCGTGGCC    42600

CCGGAGCCTA CCGGAAATGG TGCTCGCCAT GGTGCTGGCG GCGCTTGGGC CTGCGGAGGC    42660

TGGAGAGGCG CAAGTGGCGG CCGGAGCTGC AGACGGCTGG TGCTGCAGTG CCGGGGAGGG    42720

GAGGGGAGAG GAGTGGAGCG AGCGAGGGCG GGCGGGAGGC GGGCGCGGCG GGAGAGAGAG    42780

AGGGAGGGAG ACAGAGCGAG AGAGAGAGAG GGTTGGGGGA AGGAGCGGGG GCAGGAGCGA    42840

GGGAGGGTTG GGGGAAGGAG AGAGAGAGAG AGAGAGACTG CGGGGGCGGG GGAAGGAGGG    42900

AGGGAGGAAG GGAGGGAGGA AGAGAGAGAG GAGCAAGCGC CTGGCTGCGG AAGGGGCCGC    42960

GGCTCTCAGG GGGAGAGGGC GGAGGAGGGG GGCTACCCGA ACTGCAACAA GACCCCCCAC    43020

CCTCCAACCG CTCACAGCGG GACAGCTGCT TCTCCAACTT GGCTTTGTGA GGCCTGAGAG    43080

TGGGGTGGGG GTGGAGATGA GCCCCCATTC CCCAGGGCAG GCGGGCAGG GGCAATGCCG    43140

GAGGAGCAGG TCCCACCCAT GGGGTGGGGC CGCAGAGCTC TTCGCCGCCA AGGCCGCTGT    43200

AGGCTGGGCT GGCGCCAACA GGGTCCAGGT CTGTGCCTGC CATCGGAGAG GATGCCACAG    43260

CCACAGGGGT GGGCGCTGGC CTGGAGGCCT CCAAGGGGCA TCTCCTGTGA GCCCAGGGGA    43320

TGGGCAGCAT CTGAGCGGAG AAGAGTGAAA GTGGAGGAGT GAGGCAGAA CAAAGGCTTT    43380

GCCCTGAAAC AGGTGGTTTC CCGCCTGGGC TCAGACCTTC ACTCACTGTG TGGCCCAGGC    43440

CAAGGGCAAG CGTCTGACCT CGCTGGGCCT TTGTTTCTCA GGGTAAGAT GAAACAATGA    43500

TGCCCCCAGA CGATGGAGAG GAGGGGTGCC AGCGTTGTGC GCACTTAGTG AGTCGGCGGC    43560
```

```
                                  -continued
AACCTATCCT GCCTCCCCCT CTCCTCATAA CTCCCAAAGG GAAACCCTGG TAGCCAAACG  43620

GAGCGTCTTT GCCATTGCAG GCATGAAGCC ACCGAGGCAG GCACAAAACT CCTTTGCCCT  43680

ACAAGCAACT AAGTCATAGG GCCAGGACCA AAACCCTGAA AACCTCAGGA GACTTGCAGA  43740

GCCATGAGCC TGGCTCAGCA ACACAAAAGC CAGGGGCAAG CCTCAGCTCT AGCAGTGCGC  43800

TGGGAGCACC CAAGGCCAGT CACATCCTAG GGTCGCCTGG AGAGTCCTGA CCCCTGACGT  43860

GCAAGCCGGC ATCATCCCCG GGACTGTGAG TCTGCTGGGG CTGATGCCCA GGAATGTCAC  43920

ATTGTGTGGC CCAGAGGTAC CCTTAAGACT GGAGGATCAC CAGGCGGGCC CTCACCTCAT  43980

CACAGCAGCC CTTTAAAAGC AGTTTCCTTT GCCTGGTTGA AGAAATCGGA GGGATCAAAC  44040

CAAAGAAGGT TTTCTCTTGT TGAGATGAGG GGGCCACGTG GCAAGGATCT CAGAACTCCT  44100

CCCAGCCAAC AGCCAGCAAG ACAACAAGAC CTTAACTGCA AGGAAGTGAG TTCTGCCAAC  44160

AAGAAGAGAA TGGGCTTGGA GGCAGGTTTG ACCCCAGGGC CTCCACACAA GAACTGAGCC  44220

CAACTGCCCA CTTGGTTTCA GCCTTGGCTT ACTAAGAATT AGGAGGTAAT GAATGAGAGT  44280

TGTTTTAAGC TGTTGGTTTT CTGGTGATTT GCTATGAAGC CATATCAAAC TAATACTACAC 44340

ACACAGGTGT TGGCCCCTGC GCCATTCCTA G(AAGCCAGC TCTGCGAAGG AGGAAGAAG    44400

GCAGAGAGGC ACACAGAGCT GCCCACCACA GCAGCTGTGT CCTCCCTCTT GGCCACCACA  44460

CTAGCAGTTG GGCATGGTCA GCATCCTTCA CGCACACTCC AGCCCGGGT CCTGGACCTC   44520

AGGTGCTAGG GATCAAGACA AGTAGCCCTC TCTGGCACCT CCACAGTCTT CTCATGTGGG  44580

TGGGGTAGGA CCCACCCAGT CAGGCTCAGA GCACCGCAAT GCCTCACACT CATTGTGACT  44640

CTGGCCAGGC CCTCTCTGAG CCTCTGTGTC CTCATGTCGA GCACAGGGAC CAGGTGTGTG  44700

GAAGCCCGTG CCATAGTCCC AGGAACACAC TAGATGTCCA CAGTGTCCAC TAGCAGGAAC  44760

ACACAACAGG GCTACTGACT GTCAGCACCT AGGCAGGCAC ACGCAATGGG GTACTGACTG  44820

TCAGCCATAC TCACTCTCAG CGTGCTAGCA GCCATACACA ACAGCTCTAC TGACACCACA  44880

CTAGCACGCA CATOCCATAG GTGTACTGAC TCTCAGTGCA CTGGCAGGCA CACGCAATAG  44940

GAGTAATGAC AGCATGCTGG CAGGCACACA ATAGCTGTAC TGACTGTTTG CCCCAATATA  45000

GTGCCAGGTC TTGGAGCAGA TTTTGACTTC TCACCAAGAT CAAATGCAGA AAGTCCACGA  45060

GCATTTCAAA GATGTTTTTC ACATGCACAT TAGTGCTAGT TAAAAAAATG TTTTGACTGC  45120

GTGCAGTGGC TCACAACTGT AATCCCAACA CTTTGGGGGG CCGAGGTCGG CACATCACCT  45180

GAGGTCAGGA GTTTGAGACC AGCCTGGCCA ACATGGTGAA ACCCCATCTA CCCTAAAAAT  45240

ACAAAAATTA GCCAGGTGTC GTGGCAGGTG CCTGTAATCT CAGCTACTTT GGAGGCTGAA  45300

GCAGCAGAAT CACTTGAATC CAGGAGGCAG AGGTTGCAGT GAGCCGAGAT CCCACCACTG  45360

CACTCCAGCC TGGGCAACAA TATCAAGACT CCACCTCAAA AAAAAAAATG TTTTTCATAA  45420

AGTGTGACTT TTATCAGACC TCTGCATTCT TGAAATTAAC TCTGGCTTGG CTGGGCGTGC  45480

TGGCCCACAC CTGTAATCTT AACACTTTGG GAGCCTGAGG TGGGCAGATC ACGAGGTCAG  45540

GAGTTCAAGA CCAGCCTGAC CAACATGATG AAACCCCATC TCTACTAAAA ATACAAAAAT  45600

TAGCCGGGCG TGGTGGCATC CACCTGTAAT CCCAGCTACT CAGGAGGCTC AGOCAGGAGA  45660

ATCGCTTGAA CCCAGGAGGT CGAGGTTGCA GGGAGCCGAG ATCGCACCAC TCTATTCCAG  45720

CCTGGGCGAC AGAGCAACAC TCTCTCTCAA AAAAAAAAA GAAAGAAAGA AATTAACTCT   45780

GGCTCCTAGA AGCAGCCCTA TATCTCAGCA GGACACTCAG TCATTCAACA GACATCTGTC  45840

AAGCACCTGC TGTATGCTGG AGCTGTGGGT ACGTCAGCAA TTAGAGGAAG AGGCCAGGGG  45900

TACAGGAGTT CCTGACCACC CCAGGCCAGC ACGCTCCTAT AGCAGCTGGC AAGCAGCAGA  45960
```

```
                              -continued
TGACTCAGAC TTCAGCTCAG TCCACAGGAC ACCCTTTTCT GGCCACTGCT CTCACGAGAT    46020

GAGATGTGTG GCTGCAAAAG GTAAACTCCT GGCTCCTGAG CAGGCTCTGG CCAATCTGCT    46080

CAACGCTCTG TGCCTCACTT TCTCACCCAG AAAGTGTGGA CAATGAGAGG ACTTATCTGG    46140

CTGGGCGCGG TGGCTCACGC CTGTAATCCC AGCACTTTGG GAGGCCGAGG CGGGTGGATC    46200

ACCTGAGGTC AGGAGTTCAA GACCTGCCTG GCCAACACGG TCAAACTCCA TCTCTACTAA    46260

AAATATAAAA AATTAGCCGG GCTTAGTGGT CCACACCTGT AATCCCAGCT ACTTGAGAGG    46320

CTGAGGCAGG AGAATCACTT GAACCCAGGA GGTGGAGGTT GCAGTGAGCC AAGATTGTGC    46380

CACTGCACTC CAGCCTGGGC AAAAAGCCAA AACTCTGTCT CAAAGAAAAA AGAATCATGG    46440

CAGAAGGTGA AGTCTATGTT AGTCCCAGTT CCCAGGTCGT ACATGGCGGC AGGAGAAACA    46500

GAGAGAGAAG GGGAAACTGC CACTTTTAAA CCATCGGGTC TCCTGAGCAC TCACTGTCAG    46560

AACAGCCTGG AGGAAACTCA CCGCATGATC CAACCACCTC CCTCCAGGTC CCTCCCTCCA    46620

CACGTGGGGA TTACAATTCG AGGTGAGACT TGGGTGGAGA CACAGAGCCG AACCATATCA    46680

GCATGTATGG GGGGCACTCA AACTTGTGCT TGGTGCCCAT TCATTCAACG AGTCTGTCTG    46740

GCTGGTCTCC TCATCTTCAA CTCCCTGCCG AGTCTCAGAT AGGCACCCTG CAGTTCCTTC    46800

ACCACAACAG GCACATGGGG CTGGGTGCCA GTGAGTGCTG GGCTTCTCC  GAGCACTATC    46860

TCACACCCAG GAGCGTGGGC ACGCATGGCA TTCGCATGTG CCGTCAGTGG ACATTAAACA    46920

CAGCCATGAA GAAGCCACGA AGAAGTGCTG CCTGCCGGCC GTGCGCGGTC ACGCAGCGCC    46980

AACTCCCTCC TGCGGCCTTC TGGGGCCTTC TGGGGCATGG GAGCTGGGGC CGCCTGAGAC    47040

AAACATCCGT CACGCTGGGC TGACCCCACA GAACGGTGCG GGCCTCGCTC TTGCAGTCAG    47100

CCCTGCTGCC AGCCAGTGCC GGGTGCTGGG GACTCAGGGA GGCCCGCCGG GACCACTGCG    47160

GGACAGTGAG CCGAGCAGAA GCTGGAACGC AGCACAGGAA GGAGAGGGGG CGGTCAGGGC    47220

TCTCAGGAGC CGGGTCCTGG GCAAGGCGCA GCCGTTTTCA AATTTTCAGG AAAGCGGTCG    47280

GCTCACACTC GAGCAGTAAA AAGATGCCTC TGGGGAGGAG GCCCGTGCAG CTCTCCGGGC    47340

AATGGTGGTG GCTCGGCCTA GAGAGGCGGT AGTGGAACGC AGACCCTGGT GGGGGAATGA    47400

CATCAAGGGA GGAGACGGGC GGGACCCCAG ATTTCTGCCT GTGGGCGATG GAAGTGAGGT    47460

TCACTGGCCA GCGGAGCCGG ACACAGAACG CGCAAAACGC CGTGTAGGCC TGGAGGACCC    47520

GAACAGCAGG CGCACCCCCT CCGCGGGGCA ACAGTTTCCG CCGGGAGCAC AAAGCAACGG    47580

ACCGGAAGTG GGGGGCGGAA GTGCACTGGG CTCAGCGCCG ACTGCGCGCC TCTGCCCGCG    47640

AAAACTCTGA GCTGGCTGAC AGCTGGGGAC CGGTGGCGGC CCTCGACTGG AGTCGGTTCA    47700

GTTCCTCAGG GACCCCGGTT CTGGAAGGTT CCCCCCCGAG ACAAGTGAGC AGTGAGTCGC    47760

AGTGACCCTA CAACTGGTTC TTTTACCCCA GCCGCTCCTA GGCGCGTTGC GCTTTTTTCGA   47820

AACTACACCT CCCCGCAGGC CCCAAGCCCC CCTCGCGGCC GCCCGTCGGC GGATTGGCCG    47880

CGCTCCATTT TGGGACCTGT AGTTTCCTGC GCTCGTGGCG CTGGCGCCGC GGCGTTGGCT    47940

CAGCCCTTGA CCGGGGCTGG AGGGAAGGGC CGACATTCAG TGTGTCCGCG TCTGTTCTGT    48000

TAGTCCCAGT TCCCGGGCGG GATTGAOGCT TAGAGAAGTT GAGTGATTTG CTGACGGCTG    48060

CACGGGTTGG CATCCCGGCA TGCTCTTTCG CTACTTTGGC TGCATCTGGT TGCCCACCCG    48120

GGCGCATGGG CAATGGACTC CAGCCAGCCA GGAGGGCAGA GGGCTGGAGA CGCAGGCCCG    48180

GAGGTTCAGA CCCTCCGCTC TGACGTTGCG CCTGGTGAGG CCGGGAGGCC TGCCGCTTCC    48240

CTCTTCAGCC CTCACGCTCT TGTGGAAGTC GCGGAATTAC TGCAGGCGGA ACTTGCAGCA    48300

CTGTGGGCGT CTTTTCCAGA GAAGGACGGA GTTGTGGGCC GCGAGCATAA CGCAAGCCCC    48360
```

-continued

```
AGCCACTTCG CATCTTCGCC CCGCCAGCTC CTCCAGATCC GATATACCAG GGTTGCTCTC   48420

CAACCCTCTC COCAGGAGOG ACTGATGGAA ACGCCTGGGA AAGTAGCCCG GTACCCACAA   48480

AGGCTGTCTA CAAACAGAGT CTTACTGTCT TTCCCAGGTC TGTGCCATAG GGATTCTCGA   48540

AGAGAACAGC GTTGTGTCCC AGTGCACATG CTCGCATCCC TTACCAGGAG TGCCCGAGAC   48600

CCTAAGATGT TCGGAGTGGT TTTTTCGCAC AGACCCGAAT AGCCTGCCCC TCAGCCACGC   48660

TCTGTGCCCT TCTCACAACA GGCTCATATG CCCAAGATAG TCCTGAATGG TGTGACCGTA   48720

GACTTCCCTT TCCAGCCCTA CAAATGCCAA CAGGAGTACA TGACCAAGGT CCTGGAATGT   48780

CTGCACCAGG TAGAGCACAG GCCCCGAGGA AAGCACTGCG GGTGGGTGGA GCTTCAGCCA   48840

GGACGGGGTG TGCTTCCCTC TCCCGGCCCA TTCCAGCCAG GCCCCTCCGG GCCAGAGGCA   48900

GCGTCTGTCA TAAAAAGGGC TGCTGTTCCA GGTGGGGTCA GAGAGAGGAT TGACAAGTAA   48960

AAACGATCGT CCTTTGAAGG GGGCCGGCCC CTCCACACCT GTGGGTATTT CTCATCAGGC   49020

GGGACCACAG ACTGAGAAAA TGAATAAGAC ACAGAGACAA AGTATAGAGA GAAAAGTGGG   49080

CCCAGGGGAC CGGCGCTCAG CATACAGAGG ACCTGCACCG GCACCAGTCT CTGAGTTTCC   49140

TCAGTATTCA TTAATTACTA TTTTCACTAT CTCAGCAAGA GGAATGCGGC AGGACAGCAA   49200

GGTGATAGTG GGGAGAAGGT CAGCAAGAAA ACGTGAGCAA AGGAATCTGG GTCACAAATA   49260

AGTTCAAGGG AAGGTACTAT GCCTGGATGT GCACGTAGGC TAGTTTTATG CTTTTCTCCA   49320

CCCAAACATC TCGGTGGAGT AAAGAGTAAC AGACCACCAT TGCTGCCAAT ATGTCTCGCC   49380

TCCTGCCACA GGGCGGCTTT TCTCCTATCT CAGAATTGAA CAAATGTACA ATCGGGTTTT   49440

ATACCGAAAC ATTCAGTTCC CAGGGCAGG CAGGAGACAG TGGCCTTCCT CTATCTCGAC   49500

TGCAAGAGGC TTTCCTCTTT TACTAATCCT CACCACAGAC CCTTCACGGG TGTTGGGCTG   49560

GGGGACTGTC ACGTCTTTCC CATCCCACGA GGCCATATTT CACACTATCA CATGGAGAGA   49620

AACCTTGGGC AATACCCGGC TTTCAGGGC AGACGTCCCT GCGGCTTTCC GCAGTGCATC   49680

GTGCCCCTGC TTTATCGAGA CTGGAGAATG GCGATGACTT TTACCAAGCA TACTGCCTGT   49740

AAACATATTC TTAACAAGGC ATGTTCTGCA CAGCTCTAGA TCCCTTAAAC CTTGATTCCA   49800

TACAACACAT GTTTCTGTGA GCTCAAGGCT GCGGCAAAGT TACACATTAA CAGCATCTTA   49860

GGGCAAAGCA ATTGTTCAGG GTACAGGTCA AAATCGAGTG TGTTATGTCT TCCCTTTCTA   49920

CATAGACACA GTAACAGTCT CATCTCTCTT TTCCCTACAG TCCTTGAGGG TGACAGACTT   49980

AGGAGTGCCT TCGGGCCTC TCTGAGGAGC AGCTGATATT CACGGGTCAG GAGGAAGCAT   50040

TTCCATTAGA GGCGCAGCCG CTCGCCAGCC TCACTTGGAA GGTCTTTGAA CCTCGGGGGT   50100

GCAGCGAGGT GGCAGTGGTG CAGGTTGCCT TCTCCTGGGT TCCTTGAGCT GCCCTCTTGT   50160

ACCCGCCTCA CACCCTTCCC CTCCCCGAGT TTCCTGCTCA GGTTCCCGTC TGAGAGCTTG   50220

TATGTAGGAC GTCAGATACG ACAGCATAAA TGTTTGGATC CAGAAACGCA GAACAGTTTC   50280

CTATTTTGAG ACTTGACACC TAATTAGTCA TCTTACTATT TAAGCTGAAA ATAGTGTCG   50340

TGTTTTGGCT AACGTTCTGC AAATCGTTTG CTAATGGCGG CTGAGTTGCT TCACGCCCTT   50400

TAGGGCAACA GTGGGACTTG CCTGTGGACT TCTCCGCGGT CCCACAGGGC TCTCGCCACC   50460

TGGCAGTGGC CTCTGCATCT CCAAAGAGCT GCCCGCTGGC TGCCGAAGCT TGTCTCAGGG   50520

CAGCTTGTGT GGCCTCGCCT CTTCCTGGCT TCCCCGTAAC CCTTGCTCCG AACTCCGTTC   50580

AGAAGGTGAA TGGCATCCTG CAGAGCCCTA CGGGTACAGG GAAGACGCTG TGCCTGCTGT   50640

GCACCACGCT GGCCTGGCGA GAACACCTCC GAGACGGCAT CTCTCCCCGC AACATTGCCG   50700

AGAGGGCGCA AGGAGAGCTT TTCCCGGATC GGGCCTTGTC ATCCTGGGGC AACGCTGCTG   50760
```

```
CTGCTGCTGG AGACCCCATA GGTGACCCTA GTTCCCAGGC CTCTCCTGGC CTCCTGTGGG  50820
GATGCTTGGC AAGGGATGGC GCTGAGGGTG CGCTGGGCCC ATGGGGACTC CTGCCGTCTC  50880
TCAAGCAGAA CTCAAGGAGA ATTTTTTAGC TGCTGTATAA TTTCTCGCCA TCGTGGGTGT  50940
AAACCTAGGG TTGGGCTTTT TTGCTGAATT AGCGCACCGC AGATGCCCAC TTCACCCATT  51000
TTTGATAAAC CAGTATCTGG GGTCTCAGAT TCTTGGCTGT CTGCAGGGCC GAGTTAGCCG  52060
AATGCCACCT GCCTTTGATA CGTGAGAACG TTGTCTGAGA ACCGTGACTT CTGTGCTTGC  51120
TTGTGTCTGG TCAGCTTGCT ACACGACAT CCCAAAGATT ATTTACGCCT CCAGGACCCA  51180
CTCGCAACTC ACACAGGTCA TCAACGAGCT TCGGAACACC TCCTACCGGT GGGTCAGACG  51240
AGTTTACACC TGTCTCGGGG TCCTCAAGAG AACCACCTTG GCATGGTGCT GAGTCCACAG  51300
CCCCATGCTG TGCTGTGGTG GAGGGTGGTG GTCTTTCTAG ACGCTCCCCC CAAGTGTGCA  51360
GAGCGCTGGT GCCCAGGGGT GGGGTGCGGC CTGGGCTCCC TCCAATGCCC ATTACTTGTG  51420
AGGAAGCAGC TTTGCATCTG TGTCCTGACC TTGGGCGGGC GTCCTGAGCT CCTCGCAGGT  51480
GCTGTTGTAG CACCTGTGCA GTAGGTCAGG GCTGGCCCCC AGTGCAGCTT TGCACATCAA  51540
GTAGGAGGAG GCCCTGCTGC TTGTCAGAGC CCAGCAGAGT CTTGGTGTTC TGTCGGGTTC  51600
CTGTGGCCCG ACCAGTGGCA GGGTGCTGTG GAAGCTGTCG AATCTCCTCC CTCTGTCCAG  51660
TACCCCCGCT CGTCTTCTAG CTCCCTCCTA CGCCCGGGCC ACGTTTCAGT TATGCTCACT  51720
TCCTCTGACC GCCGAGGCTC CTGCGTGTCT CCAPACAGCT CACGCTGCAG GGCCACGCTC  51780
TGGGTGTTCC AGACAGCTCC TCCTCGACCC ACGGTGCTCT CTCCCACCAG GCCTAACGTG  51840
TCTGTGCTGG GCTCCCGGGA GCAGCTGTGC ATCCATCCTG ACGTCAAGAA ACAAGAGAGT  51900
AACCATCTAC AGGTAGGCTC CTGGGCTCCC GCTCCGGCTC AGTGTCCGAC AGGCGAGTFGC  51960
TGCTGGGTGT CCAGAGCCCC AGGCTCCGCT CCCGCTGGGC TAGGGTTTGA AGTTCACTCG  52020
GGGACTGCAC GGGAGGACCT GGTGGGGGTC GGCACTGGCT TCGGTCCTTT CTTCGCCCTO  52080
CTTCACCTGC GCACTCTGCC CTTCCTCCCA CAGATCCACT TGTGCCGTAA GAAGGTCGCA  52140
AGTCGCTCCT GTCATTTCTA CAACAACGTA GAAGCTACAA GCACCTGGGT CCGACCACCG  52200
TCCCCTTGGA CTCTGTCCAG CCTCTCAGGC TCGAGCTCAG TGGTGTCACA GCCTGGTTGT  52260
GCTTGCCCGG TGGGGCC3GCC AGTGCGGCCA TGTACCTGGG CCCTGTCTTC TGACTCGGGG  52320
CCACCCATGT TAGACTTCTG TGTGGAAGAG CTCACACACT GGTCTGACAC ACCCAGCCGG  52380
CAAGACTGCC TCTGGCTGGT GCCTGGGCCC TTGGATTTTG GAACGCTCC CTCCATTTCC  52440
TGATGAGACG GTCTCCCTGC ACCTAACCTG CTGGTGCAAA CAGTAGGGGT TTTGCTGAAC  52500
ACCGGCTTTC TCTTCGGGA CTTTGTTGCT TGCCCACCAG CAGGTGCTCC AGTGACCGGC  52560
CCTCATACCA TCTTGGGAGG GTGTCCTGGA AGCCGTCTCT GGCCTCCCGC GACCCTGCCC  52620
CGTGTGTCTT TTTCCTGTGC TGACCTTGCT GCGGAAAATT ATGGCCCTGA GTCTGACTCC  52680
ACGCTGAGTC CTGTCGGTCC AACACCGGAT GCCTTGGCGC CTCTTCTGGA GACGCGATGT  52740
GAGTGACAGG AGCCGCCCGG GGCAGCTTGC CCTCTGACTG CACGTGGCCA CAGCCTGTGA  52800
GCGCCGGGGG TCCTTCTCCA CCCACGTGGC TGCCCCTCGG GTATCTCAAG GCTTCTGGG  52860
GCTCATCACG GGGTCCTAGA GACAGTGGCA GGGTGCACCC CCGTTGGCTC CCCTTACACT  52920
TTCTGTGACC TCAGGCTGGC ATCTGTCCAG TCGGCGCGGT CTGTGCTTCT GTGGGATCAG  52980
GGTTCCCTCT GTTTCCTCCC TCAGTTGGGG CTCAAGCCTC AGCTGAGGTG GCCCCGGACC  53040
ACTCAGAACG CATCGGCGGT CCTGTGGGCT GCTTTCTGCA CTCACGTTTC CTGAGTGCTC  53100
AGTCTGCCAG GACTGAGGAC CCTGAAGCTG CTCTTGTATT TAGGGCGGCG CTCCCCTGCC  53160
```

-continued

```
AGAGACTGAG CCAGGTGGTC CCGCATGACC CACTACCAGC CGTTTCTGGG CCCTGGCCCT    53220

TGGAGGGACA GGGTGGGCGG AACATGGGCC TGCAGGGAGG CTCCCGCTTA CTGGAGGCAT    53280

GTGCTGTGTT GCTGGAGACA TCCTCTGTGT TGCTTCTTGT TCGCTGTCCT TTTTGGTCTG    53310

GTGGCACCAA GCACCCTCAG TCATCTTGAT GTGTGGTTGT CCAGGCCTTT TTGTTGGTCC    53400

TAAGAAGGGG CTCTCCCTTT GTGCCCCAG  CTTCCCTGAC AGGACCTGCC GGCTCGTCCC    534G0

GGTCATGCCT GCAGGACGTG ACTCTGGCAC GGGGGGTTGG GCAGATGTGC TGATGGAAAT    53520

TCTCAAGCAG GCGTCATTTC CGAGGTCCTC ACCTGGATTT CCAGGACACG AGTGCCTGCT    53580

GGGTGTCCCC AGTCCCATGC ACCGGGGCTC CTTGGGATAG CATGCAACGC TGAGCATGGG    53640

CCTGGCCGCC CGTGGTCCTG GACAAGGGCA GTGCCCCGGT GGCTGCTGGG CCTGGGACCT    53700

GGTGGGGACG CTGGCCCTGG TACCTGGTCG GGATGCTGGG CCTCGGACCT GGTGGGCAGG    53760

CCTCTCACTG CCTCCTGGTG CTGCTTCCGT CTGTGTTAGG CCTCTGGGTA TTGGCGCCCC    53820

CATCTGTCTC CTCCTCCACG CCTGTGGACT CAGACCAGGA AGACACAGCC CAGCCCCTGC    53880

CTGTCCCCCT TGGCTTCCCC TCTCACTGCC CGACCTGGCG GGAGGTTGCC TAGCCGTGAA    53940

CCTTCGCACC CTGTCTGCCA CCCGACACCC TGTCAGGGGG TGTCTGCAGC ACCTGCACCC    54000

GCCTGAGCAT CTTCAGAGTG GGCTGCAGCT CCTGGAGGGC TCTGAGAGGA AGGGAGGCAG    54060

GTATTTTGGG CGAATGAGGA GACACCTGGA GAGCTGGCAC CCTTCCTGGC CTGCGTCCTG    54120

TGAGCACTCT GGTTGGGGAC AGCAAGCTTG GGGTCAGCCT GGGGCACAGC CTCTGGCACC    54180

CCCCCGCCCC TCGTGCCCCT TCCCCTCCCA GCTCCTGTCC TCCCCCCGCC CTCAGCTCTC    54240

CGCCAGGCAA GGTTTGGCAA GTGCCGCTGT GCGGCAGTGC CTGCTGATTG GCTGGTCTCT    54300

TCCTATGGTC CTGCCCAGGG GTGTGCTTTT CCTCCCCTGC CTTCCCTGCT ATCCCTGGGA    54360

GTATCTGGGG TTGGGTCATC GCTGGTGTGT GTGAGTGTGT GTGTGTGTGT ATGTGCACGT    54420

GTCCATATGT GTGCCCTTCT GGCCTCTGCA CCTGAGTCCT GGCCCTCGGG GGCCCTCCCA    54480

CCTCCTGGGG ACAGGCACAA AGCACCCATG ATGGAGTCCG GAGCTGGCGG AGGCCCCATT    54540

GCCCCACGTG GCTGCCCTGT GACTCTGGGG TGCTTGTTAG AAGAGGTATC TGGTTCTGTC    54600

TGTGTTAAG  CAACTCCCTA AGGAATTCTT GTGGTTCCAG TTTGGGGGGC CTGTACTGTA    54660

GAGCCAAGGG AGGGGCAGGA CATCCCCCAG ACTCTGACTT CTGAAGCCTT TTCTGCCCGG    54720

GGCCTCTCCG CCAGTACAGG CAGTGTCCTT TCCCACGGCT GCCATGCTGC AGAGCGGAGT    54780

GGGCCACTGT TTAGCCCAGG AAAACCTGGC TCTCCCTTAG CTGGAAGTTC TGGGCCTGTT    54840

GTGGTTGGCA GGGAAGCTGA GTGACGGTGC TAATCACAGG GGCACCTGCA GGGGTTTGTG    54900

GGAGATGCCT CTGTGGGTTG GGGCGATAGG CTGAGGGGCT GTTCTTCCCT GCCCTGAGGA    54960

GGGCTGAGTG TAGCCGCCAC TCCTCTCCTG TCTTGGGCTG TCTCGGAGAG GATGCGTAGA    55020

ACCCTCGGCA TCCTGCTGGC CTCCCTCTGC TCCACCCTGA ACCTCAGGCC TTCTGGGGCC    55080

AGACCAGGAT TCCCTCAGGA TCACTCGGGT GGGGCCTCT  CTTGGGCACC TGAGACCCTC    55140

AGTGGGTGCT TTGTGGCGCG TTCACGGTTG GTGGGGACG  CCCAGCCCTG CCCGCCGTGT    55200

AGGAGCCGTT CTGTCCTGGG CATCCCCCTG TGGTCTGGGA CTTAGTGGAC CCTGAGGGTG    55260

TGTGTTTACC CCTGCCTCAC ACCTGCAGAA AAAAGCCTGG AGCAGGAGCT GGCCAGCCCC    55320

ATCCTGGACA TTGAGGACTT GGTCAAGAGC GGAACCAAGC ACAGGTGAGA CCCCTCAGTG    55380

AGGCCACGAC CACTGTCCTT CCATGGCCCA GCTCTCCTGT GACCTGTGGA GGCCCGGATA    55440

TATTTCTTCA CTTTTCTTTG TTCCTTTTTA AATTATGAAA CTAACCACCA TTCAGTACGA    55500

AAAAGTTTAA GCAGCTCTGA GGAAGATAGA GTAAAAAATT GTCTCCCTCT TCCCTGGCCC    55560
```

-continued

```
TCAGCCATCC CCGGTGGCCA CCGTGGAGTG TGGACGGAGC CCTGCAGGCC TGTGTCTGTG  55620

CGGAAGCACG CGCAGTTTTG TCTGCACAGA CTGTCCTGCA GTTGGCTGTT TTCACTCAGC  55680

GTTCTCGCTA TAGCTTCCCA TGCTGGTCCT GGCAGCTCGG CCTTGTTCTT TTGAGGACAC  55740

CAGATGTCTC CTATGTCTAC CTCTTACAGC TTCAGAGATT CAAGTTATAA TAAAGCTCTT  55800

CTTATATTGA GGGGGAAACC TCCCTCCCCC TTTTTTTTGA AACAGGGTCT CGCTCTGCTA  55860

CCCAGGCTGC AGTGCAGTGT CACAGTCTTG GCTCACTGCA GCCTCAGCCT CCCAGCCTCA  55920

AGCGATTTTC CCACCTCAGC CTCCCAAGTA GCCGGGACTG CAGGCACGCA CCACCATGCC  55980

TCCTTAATTT TTGTATTTTT TGTACAGACA GGGTCTCACT CTGTTGCTCA GGCCAGTCTC  56040

CTGAGCTCGA GAGTTCCACC TGCCTTCGCC TCCCAAAGTG CTGGGATTAC ACGCGTGAGA  56100

CCCCATGCCT GGCCAGCTCT TTTTTTTTTT TTTTTTTTTT TTGAGACGGA CTCTCGCTCT  56160

GTCGCCCAGG CTGGAGTGCA GTGGTGCCAT CTCGGCTCAC TGCAAGCTCC GCCTCCCGAG  56220

TTCACGCCAT TCTCCTGCCT CACCCTCCCC AGTAGCTGCG ACTACAGCTG CCCGCCACCA  56280

CCTCTGGCTA ATTTTCTGTA TTTTTAGTAG ACACCGGCTT TCACCCTCTT AGCCAGGATG  56340

GTCTCCATCT TCTGACCTTG TGATCCGCCC ACCTCGGCCT CCCAAAGTGC TGGGATTACA  56400

GGACTGAGCC ACCGCGCCCG GCCCAGCTCT GCTTTTTCTT AGTGGTTCTG CGTTGTGTTT  56460

GTTTCTATCC AGGAATAGGG TTGGTTTTAC TTTTCCATCG AGTTTTTAAA GAGACGACGA  56520

TTTACATGGT CCGAAACTCA CGAGGACTCC CCATCCCTTC GTCGCAAACT CACATGGACT  56580

CCCCATCCCT TGGTCAGAAA CTCACCTCGA CTCCCATCCA TCCCAGGCAG CAGCTTCCCA  56640

CCTGGGCCCT ACGTGCAGCA TGAGGCCTCC TTCCGGGTCA GAAGACATGG CGGCCTCGGG  56700

GCACCGTCCC CTGCATGGGG TGCTCACACG ATCTTCTCCT CTCTCCTTCC CAGGGTGTGC  56760

CCTTACTACC TGTCCCGGAA CCTCAAGCAG CAAGCCGACA TCATATTCAT GCCGTACAAT  56820

TACTTCTTGG ATGCCAAGGT GGGGGCTCAG TCCTGTAGCT GACGACTCCT GATGTCAGG   56880

GGTGTCCCTG GCTTGGGAA CAGCTGTCCG AGCCTTTGCT GCTTCAGGCC CTTAGATCAG   56940

CAGGCCTGGG TGGGAGGACT CACCTCTGTC ACTGGGCAGG GGCTCAACCT GGCCACACAC  57000

ACTTCTGAGC AGCCCCACGC CACAGCTCAG TTTTCTGAGC AGTCTGGGAG CGCGCAGGCT  57060

GGTGGGAGTG ACGAGAGACC TCCAGGCTGT GGTCCATAGG CCAGTCCCCG CTCTTGATCC  57120

TGACAGCTCA GGTTCTCTCC TTCACGTCAG GCCATGGOAG GCACCGAGAA CACAGGAACC  57180

CCACTGACTC CCCTCTTCCC AGCGCGTGCC CGGCCCCACA CTCACTCCCC CTCCCAGCAT  57240

GTGCCCGGCT TCACACTCAC TCCCCTCTTC CCAGTGCATG CCCGCCCCCA CACTCACTCC  57300

CCCCACAGCA TGTGCCCGGC CTGACACTCA CTCCCCTCCT CCCAGTGTGT GCCCAGCCCC  57360

ACTCCCTTCC GGCCCGTGTG CCCAGCCCCA CGCTCACTCC CCCCCCCAGC ATGTCCCCGG  57420

CCCCACACTC AACTCCCCTC CTCCCAGTGT GTGCCCGGCC CTGCTCCCCT CCTCCCCATG  57480

TGCCCTGCTT TTCTGCCCCA CACTTTTTAC TTAGTGCAGG TGGGATCACA CGCCACGGGT  57540

CAATGGTTTG TGTGTTCACG TGACCATGGC CTGCTGACGT TTCCAGATCC CGTCGTTGGT  57600

TCGCTCATTC TCGGGGTGTA TATTTATTGA GAGCTCATCA TGCTGGGTGC TATTCCAGGC  57660

ATAGCAAGAC TPGGCTTCACT CACATGGAGC TTTGATTCTA GTGGTGGGA CAGGTGGACA  57720

GCAAAAGAGT AAGCACCTGA GCTGACGATA CrGAAGGGAA ATAGAGGAGA GGGAGGAGGC  57780

OGAGACCOAG CCAAGCGGGC CCAAGTGCGA TGTCGGCGGG AGGTGGGGAA TGCTGGTGGG  57840

TCTGAGGGGA GCCTCAGCAG GTGCAGCAGA GCAAGGGAAG AGGTGAGTGG GGGCGGCTGG  57900

GGGGCCGACT CCTGGGAAGC TGTAGCAGAA CCCCACAGAG AGCTGGTGAG GTTTGCCGTG  57960
```

-continued

```
GTTGTGGGTG ACTCGGTGCT TTGAGCCCTG GCTGCCCCTG GGAACCATCT GGAGAGCTTC  58020

TAACCCAACC AGGCCCCTCC CTGGGACAGT TATATCACAG CTGGTAAGCC GAGTCTAACA  58080

CTTTCACGGA AACGCAGAAG ATCTAAAACA GCAAGATGAC CGTGAAGAAG AACAGAGCTG  58140

GAGGACTCAC CTCGCTGGTT TCAAGACTCC TCTAAAGCTG CAGGAGTGGA GGTGGAGATG  58200

GCCCAGCTCA GGCACAGGCC TGCAGGCCAT GGAGAAGGCA GCAAGCTCAA GCTGACCCAC  58260

ACGCATGTGG TCATTGTTTT TTTTTTCAGT TGGAATCTCA CTCTGTCACC CACGTTGGAG  58320

TGCAGTGGCA CCATCTCGGC TCACTGCAGC CCCCGCCCCT AGGTTCTAGC GATTCTCCCA  58380

CATCAGCCTC CCGAGTAGCT GOGATTACAG GCGTGCGCCA CCATGCCTGG CCCTTGGTGA  58440

TTGTTTTTTG ACAAACATGC CAATTTAATT GAGAGAGGAA ATGAAGGTTG ATTTCTGGTT  58500

TTCTGAAAAA ATGGTGCTAA GAACAGCTGG ATATCTGTTC GGAAAACAGT GAATCTTAAC  58560

TCTTGTTTTA CCCTGTATAA ACCTAAATGT AAAAGCTAAA CTAAAAGTTA TAGAAAGGAA  58620

CATGGGGGAG GTCTTTGCAA CTTTCGGGTA GGCAGAGATT TCTTAGTATG GATACACAAG  58680

GCACTAGCCA TGAAGAAAAA CATTAAAAATT TAGACTTCAC CAAAATTTAA AGCTTCAACT  58740

CTGTGGAAGA GTTGAGAAAA TGAAAAAGCA GTTAAAGAAA GGGAGAAAAT ACTTCTTTCA  58800

AAGGACTTAA AAAATTTTTT CAGCCCTCCT CTGATTTGAA AGGACCTTTG ACCAGAGTAT  58860

GTAAAATTCT CCCATAACTA AGCAAACAAC CCACTTAACC ACTGGGAAGG GATCTGGACA  58920

GACGTTTCAC CAAGATGGGT GGAATGGCCA GTTAACCACT GGGAGAGCAT CCGGACAGAC  58980

GTTTCGCCAA GATGGGTGGA ATGGCCAGTT AACCACTGGG AGAGCATPCCC GACAGACGTT  59040

TCGCCAAGAT GGGTGGAATG GCCAGTTAAC CACTGGCAGA GCATCCGGAC AGACGTTTCG  59100

CCAAGATGGG TGGAATGCC AGTTAACCAC TGGGAGAGCA TCCGGACAGA CGTTTCGCCA  59160

AGATGGGTGG AATGGCCAGT TAACCACTGG GAGAGCATCC OGACAGACOT TTCGCCAAGA  59220

TGGGTGGAAT GGCCAGTTAA CCACTGGGAG AGCArCCGGA CAGACGTTTC GCCAAGATGG  59280

GTGGAATGGC CAGTTAACCA CTGGGAGAGC ATCCGGACAC ACGTTTCGCC AAGATGGGTG  59340

GAATGGCCAG TTAACCACTG GGAGAGCATC CGGACAGACG TTTCGCCAAG ATGGGTGGAA  59400

TGGCCAGTTA ACCACTGGGA GAGCATCCGG ACAGACGTTT CGCCAAGATG GTGGAATGG  59460

CCAGTTAACC ACTOGGAGAG CATCCGGACA GACGTTTCGC CAAGATGGGT GGAATGGCCA  59520

GTTAACCACT GCGAGACCAT CCGGACAGAC GTTTCACCAA GGTGGATGGA ATGACCAGTT  59580

GAGCACATGG AAAGTCGCCC AGCATCTCCA GTCATAGGAG AAGGCAGATT AAAGCCACGG  59640

GGAGCCGACA CTGTGGTCCC ACTGGCATGG CTGAAATTCA GAAGCCCTGA GTGTGGCATG  59700

AGGATGTGGA ACAGCTGGAT CTCATCCATC GCTCTGAAGT TGTGTAGCCA CTCCACAAAC  59760

CTGTGGCAAA CAGCCCAGCC GCGAGAAGGG AAGACGTGTT CAAAGATTCA TATGTGGCCA  59820

GCCTCAGTGG CTCACGCCTG TAATCCCACA ACTTTAGGGG CCAAGGCTGG GGGATCCCTT  59880

AAGCCCAGCA GTTTGACACC AGCCTAGGCA ACATACCGAG ACCCCATCTC AAAAAAAAAA  59940

AAAAAGAAAA AAGAAAAGAC TTCAGTCTCC AGGTTTACCA CAGTTTTGTT TGCAGTTGCC  60000

AAAACTGGGA AGCAGCCCGC GTGAGCCCAT CCACACGTGA ATGGACAGAC CGTGGTACCC  60060

GAACACTAAC AGCAGCCACG GGCGTGGACT GTGGTCACAC AGCAGCAGGG AGCCGATGAG  60120

TCTCGGACAT GCTAACCCAG AGAGGCCCAT TGAGGAGGAC CTACTGTTTT                60180
TTGTGTTT[]I7T

GTTTTTTGTT TTGAAATGGA GTCTCGCTCT GTGGTCCAGG CTGCAGTCCA GTOCTGTGGT  60240

CTTGGCTCAC TGCAGCTTCC GCCTCTTGGG TTCAAACAGT TCTCCTGCCT CACCCTTCCG  60300

AGTAGCTGCG ACTACAGGCA CCCGCCACCA CACCCGGCTA ATTTTTGTAT TTTCAGTAGA  60360
```

```
                                        -continued
GACGGCACTT CGCCATGTTG GCCAGGCTGG TCCCAAACTC CTGACCTTGT CATCCACTCA   60420

CTTTGGCCTC CCAAAGTGCT GAGGTTGCAC GCATGAACCA CCCCACCCGG CTCGACCTAC   60480

TGTTTTATTC CATTTATGTG ACACTCTATT AATAGAAAAO GCAGGCGTGG GGCTGGTGGT   60540

TATATGGTGC ACATAACTGC CAGAACTCAC TACACTTAAA ATGAACATCT TAATGTGTGA   60600

AATTTTTTTT TTTGAGACGG GGTCTTGCTC TGTCACCCAG GCTAGAGTGC AGTCGTCCGA   60660

TCTCCACTCA CTGCAAGCTC TGCCTCCTGG GTTCACGCCA TTCTCCTGCC TCAGCCTCCC   60720

GACTAGCTGG GACTACAGGC GCCCGCCACC ACGCCTGGCT AATTTTTTTT TTTTTTTTGT   60780

ATTTTTAGTA CAGACGGGGT TTACAGTGT TCGCCAGGCT CGTCTCGATC TCCTGACCTC    60840

GTGATCCGCC TGCCTCGGCC TCCGAAAGTG CTGGGCTTGC AGGCGTGACC CACCATCCCC   60900

GGCCAATGTG TGAAAATTTA AAAGTACCAA AGCTGGACCC CACCCCAGAT TGCTCCCATG   60960

ACACTCTGTG GGTGGGACCT GGGAGTTGGG TTTTGTTTTG TTTTGTTTTG TTTTTGAGAT   61020

GAAGTCTCAC TCTGTCGCCT AGGCTCGAGT GCAGTGACAC AATCTCGGCT CACATTAACC   61080

TCTGCCTCCC AGATGAAAGC GATTCTCCTG CCTCAGCCTT CTGAGTAGCT GCGATTACAG   61140

GCACACACCA CCACCCCCTG CTAATTTTTG TATTTTAGT AGAGACGGGG TTTTACCATG     61200

TTGGCCAGGC TGGTCTTGAA CTCCTGACCT CGTGATCCGC CCGCCTCCGC CTCCCAAAGT   61260

GCTGGGATTA CAGGCGTGAG CCACCGCGCC TGGCTGGGAG TTGGGTTTGT AAATCTCCCT   61320

CAGTGGGGCT GGGGCAGGGA ACTCCTGCGT CTGCGTCTTC CTCCCTCCTC TCGTCTGTGG   61380

CTTCCTGACT GCGGTGGCCG GGGGCTCCCA GGGCATCGTG GCCGTCTGTC TTCCTCACCG   61440

TGGCACGTGC CTTTCCATGC TCTGCAGGAG CGTCTCCCGG TATGGCGAAC TGCTGGTTAG   61500

GGTGGGGCGG TGTTGCCAGG TCATCCAGCT CTGGCCTCTG CTCTCGACAT CGCCGGCGCT   61560

GTTGCTCATC TGCGCTTGTC ATCTTCGATG CCTGCTGCAC ATGTCTTGGC TTCCCTCTTT   61620

CCCGGCCTCT GTGAGCTCCA GCGCTGCGTC CCTTCTCTTC CTCCTGTAGA CCCGCAGAGC   61680

ACACAACATT GACCTGAAGG GGACAGTCGT GATCTTTGAC GAAGCTCACA ACGTGGTGAG   61740

TCTCCGCTGG CCTCCTAAAC ACCTCCTATT GCTTCTGGCC TTTTTGTCAA GAGCCACGCA   61800

AACCTTTCTC GAGGGGCTCT GGCCAAACTC CTGAAGCCCT AGGTCCCCAG GACTGGGGAC   61860

TGAGCACACC AGGAGCTTCT GCCACCCCCT CCCGCCCTGA TCCGATCCCT CTCCTCGGGC   61920

TOGAGACTOG CCAGCTGGGC CAGGGACCTG CCCGTCAGGC GCAGGGCCCC CACACGCCGC   61980

TCACCAGACC CTTTCCCTCC AGCCAGCTCG GGGTCAGCCT GGGCCAGGGC TGTCTCCTCT   62040

GCCCTCGGCA GCAGCACGCT TGTGGTCTTG CCTOCACTOT CTCTGCCCTT CCGGCCACAT   62100

GGCTTGAGAC TGAGGCAGGA GAATCGCTTG AACCTTGGAG GCAGAGGCTG CAGTGAGCCA   62160

GGATCACACC ACTGCATTCC ACCCTGGGTG ACAAAGCGGG ATTCTGTGTC AAAAAAAAAA   62220

ATGTTGACTG GGCGCGCTAG CTCATGCCTA TAATCCCAGC ACTTTGGGAG GCTGAGGTGG   62280

GCGGATCACG ACGTCAACAG ATCAAGACCA TCCTGGCCAA CATAGTGAAA CACCGTCTCT   62340

ACTAAAAATA CAAAAAAATT AGCTGGGCGT GGTGGCGTGT GCCTATAGTC CCAGCTACTC   62400

ACGAGGCTGA GGCAGGAGAA TCACTCGAAC CCAGGAGGTA GACGTTGCAA TGAGCCAAGA   62460

TCACACCACT GTACTCCAGC CTCGTGACAG AGCAAGACTC CGTCTCAAAA AAAATAAAAT   62520

CAAAAGAAT AATTGGCAAT TCCAGTGAAA TAATTGTTTG TTTGTTTGTT GAGACAGGGT    62580

CTCCTTCTGT CGTCCACGCT GGAGTTCAGT GGTATGATCT TGGCCCACTG CAACCTCCAC   62640

CTCCTGGGCT CAAGCCATCC TCCCACCTCA GCCTPCCCGAG TAGCCGGGAC TACAGOTCCA   62700

CACCACCACG CCCGGCTAAT TTTTGTATTT TTTCTAGAGG CGGGGTTTCC CAGCGITGCC   62760
```

```
CAGGCTGGTC TTGAACCCCT GAGCTCAAGT GATCTGCCCA CCTTGGCCTC CCAAAGTGCT    62820

GGGATTACAG GTGTGAGCCA CCGCGCCCGG CCTGAAACAA TCGTTTCTAA ATATTGGTGT    62880

GGGCCACACA GTCATGTTTG GACCTACTTG TGGCCTTTTA CAGACCCCAG GCCAACCCTT    62940

TGGGAACTTG GCTGTCAGCC TCCTGTGCCT TCTGCACCCC CACCCCATTT CTGCTTTCTG    63000

GAACCCCCGA TCCTGTCCTG TTCTGTGGTC ATTCGGGTGT GCTTGGGCTC TAGGAGAAGA    63060

TGTGTGAACA ATCGGCATCC TTTGACCTGA CTCCCCATGA CCTGGCTTCA GGACTGGACG    63120

TCATAGACCA CCTCCTGGAG GACCAGACCA AGGCAGCGCA GCAGGGTGAG CCCCACCCGG    63180

AGTTCAGCGC GCACTCCCCC AGCCCAGGTG CGTTCATAGC CACACTGCTT GGTCCTGAGG    63240

CCTGCGCTGC TGCAGGGTGA GCCCCACCCG GAGTTCAGCA CGGACTCCCC CAGCCCAGGT    63300

GCGTTCATAG CCAGGCTGCT TGGTCCTGAG GCCCGTGCTA CTGCAGTGGG CAGCCTGCCC    63360

TGTGGCTGTG TGTGGTCGGC CTGGGCACCA TCTATTCAGG CTGGCACTGC AGGGCATCCG    63420

CTTCTCTCAG AGGCTTCTTG GGTGTGAATT CTTCAGGGTC CTGTAGCCTG TGGAAGGCCT    63480

GGTATTGTTC AGTAGTTCTG GTATTTTCCA AAGACCTATG TCTTCTCCCA GCCAGTATCA    63540

ACTTCGCCTC TACTCTGTAA AACTGGAAAA CTCTACTTTG TGAAGCTGAG TTGGGAGCAT    63600

CGCTTGAGGC CAGGAGTTTG AGACCAGCCT GGGCAACATG GCGGAACCTC GCCCCTCCCA    63660

AAAAATTAGC CAGGTGTGGT GGTGTGCTCC TGTGGTCCAA GCTTTTCTGG AGGCCGAAGT    63720

GGGAGGCGTG CTTGAGCCTG GGAGGCAGAG CTTCCGGTGC CCCAGATGAC TCCACTGCAC    63780

TCCAGCCTGG GCGGCAGAGT GACGCCATCT CAAAAAAAAA AAAAAGGAAA ACTAAATATA    63840

TTCACTGTAA CGGCATTTTG CATCTTThAA TGACCCACAA ATCTGGCATG CATCAGCTGC    63900

TCTGCCTGTA CGTTCCTTCC CAGTGTTTGT CCAGAGGTGT ATTTCCACAC AGCGCTAGTC    63960

ACCGCATATG TGCAAAACGT GGAAACCCTT CATGGATGTT CTCACTTGGT CTATATTTTC    64020

TTTCTTTTTT TTTTTTTTGA GATGGACTTT CACTTTTGTT GCCCAGCCTG CAGTGCAATG    64080

GCGCGATCTT GGCTCACTCC AACCTCCGCC TCCTGGGTTC AAGCAATTCT CCTGCCTCAG    64140

CCTCCCAAGT AGCTCCGATC ACAGGCGTGC ACCACCACGC CCAGCTAATT TTGTATTTTT    64200

AGTAGAGATG CTTTCTCCGT GTTCGCCACG CTGGTCTCGA ACTCCTGACC TCACGTGATC    64260

CACCCGCTTC GGCCTCCCAA AGTGCTGGGA TTACAGGCGT GAGCCCCCAC GCCCCGCGTT    64320

TGTCCATATT TTCTACATGG CTTCTGTAAA CAGCTGACTA GGAGTCTGTG TGAATATCTT    64380

CATAGGTTCT GCTGTGACAC TACTTGCTCG TGACCATCTC CAGGTCTAAA CAGCATCACC    64440

TTCCCCCATT TTCCTTTAAA ATCGCACATG TGGACGCACA CCACGGGGAC CCTGGACCCT    64500

GGGGAGCCCC GTCCTCACCC TTCTCACCAG GATGGCTGCT TGGTAGAGAG TGAGTTTGCA    64560

AAGTTGGCAT TTCTTTAGTA CAGAAGTTAT CAGGTGTTCT GGCTTTAGAA TCCCTTTATA    64620

TATATATATA TATACATATA TTTAAGTGAC AGGGTCTCAC TCTGTTCCCC ACGCTGGAAT    64680

GTGGTGGTAC AATCAAAGTT CCCTGTAGCC TCGCCCTCCT GCGCTCATGG CATCTTCCCG    64740

TCTCAGCGTC TTAAACCCCC GGCACCACAG GTGTGCACCA CTCCCACCCG CTCTCAAGAT    64800

TGCCACGCAG GGACTTCCAG TGGGGGAAOG GGTTCCTGGG ACTTTGAACG CTCCACCTCC    64860

CTCCTCTCCA CAGTCCCCCA ACCCCACCTC TCTAACGGGG TGGACGCCCC CCTCTTTCCA    64920

TCCTTCGCTT GCCGCAGCCT GGGGAGAGTC ACAGGTCTCC TTCCCTCATC TCGGCAGCTC    64980

CCATTTCATC GCTTACATAA CGTGGGAGAA ACATCCACCC ACCCCCAGGC CTGTGTGAAC    65040

ATCACCACGC GGCCTTCTCC ACTCTTCAGT TTTGTTAGTT ACTTGATGTG CAGGGCTTTT    65100

TGTTCTAACT ACTOGGOQAC GTGTGGTGGG GTGGGCTTCT GCCATCTCAT TCAGGACCAG    65160
```

-continued

```
AACTTCAGTT TTCATCCCTA TCTGTTCCCC CACCCCTTTG GAGATGGGGT CTCACTCTGT    65220

CACCCACGCT GGAGAGCGGT GCTCCCATCA CGGCTCACTG CAGCCTCCAC CTCCTCCAGC    65280

CTCCACCTCT TGGGCTCAAG TGATCCTCCT GCCTCGCCCT CCCAAGCTCC TGGGACTACA    65340

GGCGTGTGCC ACTGTGCTTG GCAGGGTCCA TTCTTTTCCT CACACTTTAT TTATTGAAGA    65400

GCCCAGGCCG TTTACCCTGC AGAGTCGGAA TCTGTACAGG AGGGGCAGCC ACACGAGTTC    65460

CCCGGTTTAC TCTGAACTTA GGTGGCTTGA GGGCCCCAGT TAGACTGCGG CCACCGTTTG    65520

CCGGGCTCCA GATGGGACGT CCTTTCTATC AGAAGGCTCA CAGTATCTCC TTTCCCGTTT    65580

CTTCCCATGT GAACATTGTT GCTGCTGAAC ACCTGAATAT GTTAATCACT GGCGGCTTGC    65640

AAGATGGCAG TGTGCTAATT CCATCATCTA GTCAGTTACC AGGAATAACT TAGGACCACG    65700

CCCTGCACCA TATCAGCTAT GTGGTGATCC CATTCACACA GGAAAGGTGC GACAAATGCT    65760

GGGGGTGGGC CGGGTGTGCT GTCTCACACC TGTCATCCCA GCACTTTGGG AGGCCCAGGC    65820

AGGCGGATCA CGAGGTCAGA GATTGAGACC ATCCTGGCCA ACACGGTGAA ACCCCGTCTC    65880

TACTAAAAAT ACAAAAAAAT TAGCCAGGTG TGGTGGTGCA TCCTTCTAAT CCCAGOTACT    65940

TGGGAGGCTG AGOCAGGAGA ATCATTGAA CCCAGGACGC GGAGGTTGCA GTGAGCCGAG     66000

ATCGCACCAT TGCACTCCAG CCTCGCAACA GAGCGAGACT CCGTCTCAAA AATCAATCAG    66060

TCAATCAAGT GTCATCACTG AATGTTTGTG TGTGAACGTG GGGATTGGTC CTGCCCCATG    66120

CTCCCTCCTG AATCTCACTC CTGACCTCAG TTGCTGCACC TTGAGGTGTT TTCTGTGGGC    66180

TCTTGTGTCC TGACCCCGGC GGTTGTGGCC TCTGCTGTCT GGGAGTCAGG ATTTTTCACA    66240

CTCATGTCCT GCTCCAGACC TGGAATCAGC CAAGTCTCCA AGAAGCCCTG CTTCTTTTC    66300

CTGCAAGACG GTATTTCAAG ACCCGCCGTG CGGCACCGGG TTGGTCATGG TTACTGGGTT    66360

GGTCGTTGTG ACTGGGTGTT TCGTGGAGA TACAGCCATA CGCACAGGTG TGTTCACAAA    66420

TGTTAATTCT AAAGGTCAAA CACCCGGCCA GGCATAAGGG CTCAGCGGTA ATCCCAGCAC    66480

TTTGGGAGAC CAAGACTGGT GGATCACCTG AGGTCAGGAG TTTAAGACCA GCCTGAGCAA    66540

CAGGGTGAAA CCCCATCTCT ACTAAAAATG CGAAAATTAG CCGGGCATGG TGGCGCACAC    66600

CTATAGTCCC ACCTAGTCGG GAGACAGACA CGAGAATTGC TTGAACCTCG GACATGGAGG    66660

TTGCAGTGAG CAGAGATGGC GCTGCTGCAC CCCTGCCTGG GTGACAGAGT GACACCCTGT    66720

CTCAAAAATG AATAGATAAA TAAAGATAAA ACACCTGCTC CTCTTGGTGT CTCCAGTTTG    66780

GATTTGGCCT GTGTAGCCTC TTCCTTCCCC TGTTGGTGGA TTTGGCCTGC ACGGATTCTG    66840

TGTGGCCTCT TCCTTCCCCT GTTGGTGGAT TTGGCCTGCA CGGATTCTGT GTGGCCTCTT    66900

CCTTCCCCTG TTGGTGGATT TCGCCPGCAC GGATTCTGTG TGGCCTCTTC CTTCCCCTCT    66960

TGGTGGATTT GGCCTGCACG GATTCTGTGT GGCCTCTTCC TTCCCCTGTT GCTGGATTTG    67020

GCCTGCACGG ATTCTGTCTG CCCTCTTCCT TCCCCTGTTG GTGGATTTCG CCTGCACGGA    67080

TTCTGTGTGG CCTCTTCCTT CCCATGTTGG TGGATTTGGC CTGCATGGAT TCTGTGTGGC    67140

CTCTTCCTTT CCATGTTGGT GTCCTTTTTT CCATGCCAGG AATCCTGGTT CTCAAGGGCG    67200

GGGTTGTTGG CACGAGCGTG ATGCAGACTG CCTTTGCTGC CTTTCTCTTG CCCAGGGCTG    67260

AACATGGAGC TGGAAGACAT TGCAAAGCTG AAGAGTAAGT GTTGCCCTCC CCGCCTCCTT    67320

GCAGCTGGGT GGGGCCTCCT CCTTGCGAGG AGGTGGGTGA CACCTCCTCG ACCCACAGTG    67380

ATCCTGCTGC GCCTGGAGGG GGCCATCGAT GCTGTTGAGC TGCCTGGAGA CGACAGCGGT    67440

GTCACCAAGC CAGGGAGGTG AGAGGCGGGG AGCCAGCCCC TTCACTGCAG GCCCAGCCTA    67500

GAGCTAGAAA CGGGCCATGG TGCAGTCCTG GGCTGTCACA TCACGAGTGA GGCCTGTTTT    67560
```

-continued

```
CAGCCCTGTT TTCCCTTTTT GAGACCTGGG AGGAGCACCT GCTTTGCATG ATCTGGTTGC  67620
TGAGATGTTG AGAGGAGCAG CACACACTCC CACGGGACAG CACACAGCCC CCCACGGAAC  67680
GGCACACACA CCCATGGAAC AGCACACACA CTCCCACGAA CACCCACACAC ACTCCCACGA  67740
ACAGCACACA CACTCCCACG GAACACCACA CACACCCACG GAACGGCACA CACACCCACG  67800
GAACAGCACA CACACTCCCA CGGAACAGCA CACACACCCA CGGAACGGCA CACACTCCCA  67860
CGGAACAGCA CACTCTCCCA CGGAACAGCA CACTCTCCCA CGGAACAGCA CACACACTCC  67920
CACGGAACAG CACACACACC CACGCAACGG CACACACTCC CACGGAACAG CAGACTCTCC  67980
CACGGAACAG CACACACACT CCCACAGACA GCACACACAC ACCCACGGAA CAGCACACTC  68040
TCCCACGCGG GGCCGCTGGG TTTCCTCCAG TTTCTCCTCC TCCAGGCCTT TCCCTCCACC  68100
CTGGTCCAGT CCGTCATTTG AGCACAGCTG CCTGTTACAA CGAGACCTTC TTCTTAGCAC  68160
GATGAGTGTC CCAGCCACCA CCTCTTTTGG ACTCCGGGAG GCCTGGAACG TTCTGAACCC  68220
TCCGTGGGGC TCCAGTCTTC TCCGCAGCCA GGGCAGCAGG GTTTGCTCTC TGTCCTGCAG  68280
GCAGATGACG AGTCAGGGCT GGGGCCTGTG TGGGGGCTCT CCTGAGCGCG CAGCCGCCGA  68340
GGTGGAGCGT GTTCTGCCTC AGCGCCGACC TGGTCGGGGG AATCCCAGTT GCTTCCACCT  68400
GCACCCACTG TCCTCACCCT AATCCTCAAG GCTCTGGCCT GGCTCCTCCG CCACCCTGCA  68460
CCCTCAGGGT CCCCTCCTCT AGCTTCTGCT CCCCCATCAC TGTCACTCTC CAAAGCTTTG  68520
GGGACTCTGC CCAGAGCCAC CGCCTCCCAC AAGCCCCTGA CAACCTCTTG ACCACCCCT   68580
AGTGACCCCA TCCCTCCCCT CTGACGGCGG CCCCTGCTCT CAGGCGGCTT CTTTTCCTCG  68640
GTGCTCTTCT CGTCCTGGCC AGGCCTCCTC TCCCCACCTG GAGGCTCCTG AGGGCCGACG  68700
CCTCTCACCT CCAATGCTGG CGTCCCCTGG AGGGCTGAAT TTGTTTCCGA GGGAAGGAAA  68760
CTTCCACAGT TGTTGCCTTC AGTTCCAAAG CTGCAGCCTG ATTTCCCCCT CCAGGCTCGA  68820
GCCTGTTTTC TTCTCGGCAG CTACATCTTT GACCAGTGTC GTCCCCCCTC AGGCCCGAGC  68880
CTGCCTTCTT CTCCTCAGTT CCCAAAGCTG CAGTCTGGTC CCCCCGCCAG GCTCGAGCCT  68940
GCCTTCTTCT CCTCGGCAGC TACATCTTTG AGCTGTTTGC TGAAGCCCAG ATCACGTTTC  69000
AGACCAAGGG CTGCATCCTG GACTCGCTCG ACCAGATCAT CCAGCACCTG GCAGGACGTG  69060
AGTGCTGGCA CGGGGTCTTT GGTGCGGGCA AATGTGGCGT AGGGGGTGCA GCAGGCCTCC  69120
ATCTTGGCAG TCAGGGCTCC CCTGGCCGTC ACCTGGCCGT CAGCAGGAAC AGGCCCACAG  69180
AACCTCATCT TCTGATCGGG GCGTGCAGGC GTTAGTGCCA CTTGCCAGCT GCCGTAGAGC  69240
CTGTCCCAGT TCTGCACCTG GCGGCTTCCT CCTACAGCCT CATCCCATTA TTCTGCTTTT  69300
GAGAAAGAGC AGCCCAAGGC CCTAGCTCGC TTGTGGGGCC TCTGGCTTCT CCACACCACC  69360
CCGAGTTCTG CTTCTCAGAG TTGTGGGGTC CAGAGGCTTT GCCCAGAGGC CGTGTCCCCA  69420
TGGGCTGCTC TGGTTTGAGA CGCCGGGCCC AGCGGGGTCT CTCCTCTGCT GCGCTCCCGG  69480
GTGCTGGGGA GGGTGGCTTT TGCTGCTTCA ACCCTTAGGC GACCATAGAG CCTCTTTTCA  69540
AGTCCCACTG ACCCCCTTGG AGACTCTGTC CCTGCCTGCC TTCTCTCCTG GCTGCTGGGA  69600
AGAGCAGGCG AACTGCCCGC CCTGAATGGA TGCTGCGCTC CACCCTGGGC CCCCCATTGG  69660
GCAGGAGATG GAGCTTGGCA GTCGGGCTGA GCGGGCTCAT GCTGGAAGGG CCGGGGCTGG  69720
GGTCGGGGCC TCCCCTGCCT GCAGTGTGGG TGTCAGCGCC CTGCTGCCCT CCAGGTGCTG  69780
GAGTGTTCAC CAACACGGCC GGACTGCAGA AGCTGGCCGA CATTATCCAG GTGGGGCCTG  69840
CTCCTCTGTG GCATCTCCTT CCCTGATGGA AGCCGGGCGG CTGCCTTCTC CTGCTGTATT  69900
AGTTAACTGA TTCTAGACTT GGGGATGGGA GAAAGGCCCC TACACCACCT GTTTCTGATT  69960
```

-continued

```
CCCAAACTCT CGGCTCCTTT CCACTGCCCT AAACCCACAC TGGGCCTCCT GCAGGGATGG    70020

CCGAGGACGA GGTCTGGTGG CACATGCCCA CCGTOATGCT GGTGAGGGAG GACGCAAACC    70080

ACAGTGCGGG CCGGGGAGCC GCTCCTGCCC TGTCCGGGCC CTCAGGCCAG GGGGGACCCA    70140

CTGCTGGCAG CCCCAGCAGC CCCAGCTGCA CGCAGATGAA GAGCTCTGGA CACACGCGGC    70200

TTCCTGAACA GCTTCTCCAG GGACAGACAA ATGGGGACCC TCCAGCTTCC CGGCAGGGG     70260

GTCCCTGGGA GCCCATCATT GGGGGTGCGA CCCTCGCCCC CTTCTCATTG GCCCCGTCCT    70320

GTCCTGCAAT GCCCGTCCCA TGTGAGGTCT GCTTCTCCCT CCATGCCTAT GGCAGCACCT    70380

GCTTTCCCTC CCGTAGAGGT GCTTGTCCGG TTTGTGGAGG GCACGCCCCA TTTTGGGTGC    70440

TCTGGGCACC TTGCCTCTCC GGGGCCTCGC TGGCTTTTTT ACAAGCAGAC TCAGAAGTCC    70500

CTGACTGGGG AAGCCAAGGC ACAGGTGGCT GTGTGCAGCC CTGTGAGGCC TCCTCTCTGC    70560

TGCCCACGCT GTACCTGCTC GCCACACGAG ATCATGGCAG GGTTACCCAG GCCTGCCCAC    70620

CGCTATGACA GCTTCATGAG TGTCCATCTG GCCTGTGGGC TGCTTGAGCT CGCGGAGGCC    70680

GCAGAAGAAC CCTCGGATGC ATGGCTGGCC TGTGCATGCT GCTGGCCATG GACCTCCAGA    70740

TCCCGGAACA AGCAGCCACT GCCTTCTCCT TCACAGACGC ACCTCTCACC CGGCGCCAGA    70800

CCTGGGCAGG GACCAGOTOG GGTCGGCACA GGGTGGTGGG GCCCAGGCTC AGCCCTCCCT    70860

CCACTGTGCC CGTCTCTGTC GCCAGTGACG CCACAGCCTG TGTCTTCTCT CTGCGGTAGC    70920

TGCGGCTGGA AGGACAGUAC TGCCTTGTCC TCCCAACTCC TCCCCAAAGG CACGGTGGGC    70980

ATCCCAGGCC CAGACCCCTC TGTCTGTGGC TCCTGCCTGC CAAGGGCTGC TGTGCTGTCC    71040

CGCATGGAGT GTGGTTGGCT CTTCAAGCAG GAOGCCGTGC ACCTATCAGG CCGACCTGCT    71100

TCCATGTCCC TGATGGGTCA CTGCAAAGCA CCTCCAGCAC ATGGCCAGGC GAGGTAGCCC    71160

TGCAGCCCAG GGCCTGGAGG GCAGGTGTGA GCTGGCCCGG GCCTGTCCCT CCCTGGAATA    71220

CAGCTTCCCA GGCTCCCACT TATGGAGAAG TCTCCTCCAC ACTATGGAAC TGAATCCTAG    71280

AATGTGGCTT CTGAGGTTCC TACACTCGAA CTGAATCCTG GAATGCGGCT TCCAAGGCTT    71340

CCAGCTATGG AGAAGACTCC ACACTCTGGA ACCGAATCCT GGAACGCGGC CTCCCAGGCC    71400

CCCAGCTATG GAGAAGACTC CACACTCTGG AACCGAATCC GGGAACGCGG CCTCCCAGGC    71460

CCCCAGCTAT GGAGAAGACT CCACACTCTG GAACCGGATC CTGGAACGCG GCCTCCCAGC    71520

CTCCCACTTA GGAGAAGTC TCCACACTCT GGAACCGGAT CCTGGAACGT GGCCTCCCAG    71580

GCCCCCACTT AAGGAGAAGA CTCCACACTC TGGAACCGAA TCCTGCACAC TCCATCGGTT    71640

TGGAATTTCC TTTGGCTGCT GCTCTAAGTA GCCGCTGGTG GATGACTCAG CTTCTGCCAG    71700

CCCTCGGGTG CCTGGAGGAT GAGGGACTGC ACACAGTGCT CACCCGCGTT GGCTCCTGAG    71760

CCCCTGCAGG TGTGCGCGGT GCCCATAGGG CTGCTGCTGG GTTGGGCCTG CAGCCCTGAG    71820

TCACAGGTGA CCCTGGGGGC AGAGTGGGGC CAGTGGCCCC AGGAAGAGGA TGTGGGATGC    71880

ACAGCTCACC TGGAGGCGAA CTCCAGGCAG GGTCAGGCCG TGTGCTCGGA AGTCAGGGCT    71940

TAGCTGGAGG CAAACTCTGG GCAGTGCTGG CCCGTGTTGG GGAACCAGTT GCCCCTGGGC    72000

CCCCGTGAGA CTGCTCGGTC CTCATCCCTC TCTGCCTGAG GCCGGAGCTG CCCTGGCCTG    72060

AGGCACAGGG GGATTTGTGG TGGTCTTTTT TTCAGAAACG GTCTCGCTTT GTCACCCCGG    72120

CTGGACTGCA GGGCCTTGAT CACAGCTCAC TGCACCCTCA ACCTCCTGGG CCCAAGTGAT    72180

CCTCTTCCCT CAGCCACCCG AGGAGCTGTG AACACAGGTG TGCACCACCG CACTCAGCTA    72240

ATTTTTAAAA TTTTTTTGTA GAGATGAGGT CTTGCCATGT TTCCCAGGCT CGTCTCAAAC    72300

TCCTGGGCTC AGGCAGTCTG CCCGCCTTGG CCTCCCAAAG TGCTGGGATT ACAGGCAAGA    72360
```

-continued

```
GCTTCCATGC CTGCCCAGCA GAACGCTTTT CGAACGAAGC TGTTTCCTGA GGCAGACTCA    72420
GCCCTGCTCA TGGCAGCCAC CAGCGTGCGC GTCAACTTGT TCTGTTACTT CCATCCCCGT    72480
GGGCCAAATG CTTTTGGTAA ACACAAGGCC CTGTGTTTAG CTGTCTTGAC AGPQAAAATG    72540
GCTGGGAAGG AAGGAAGGAA CGGAAGCAAA TTTCTCTCTC CTTCTGTGCC TACCCAGGCA    72600
CGTGCACATG CATGCACAGT ACGCACACAC GCACGCACGC CTGCACAAAT CCACGCATCT    72660
TGCCAAGTCT CTGTGTTCCA GCCGTGGTGT CTGCCCCCCG GTGTTCTCTA GTTCGGCTTC    72720
TCCGCATTTC TGTGAATGAT TCCCGCTTCT TGGTGTTCCC AGCAGAACTC CCTCAAGTCT    72780
GCGGCCGGGC TCTGACCCCG GTGGCTTGCC TGACATGGCC ACATTGCTGA CCCTGTTGGG    72840
GGCTTTGCCT TCCTGTTCTC GCCCTTTTTG GCTCGTTTTC CAGGAACGGT CCTCACGCGC    72900
TCCTCTCCTA GTGCAGGCAT CATTCCTTTC CCATTGATTT GCAGGCTTCT CTGTAACTTC    72960
TGAGCATCCC ATATACATAT ACTCTCTGTA ACTTCTGAGG ATCCCATATA CATATTCTCT    73020
CTCTAAGTTC TCAGCATCCC ATATACATAT TCTCTCTCTA AGTTCTGAGC ATCCCATGCC    73080
GACATACATA TTCTTTCCTT CrCTCATGCT GGTCATTTTT TCCATTTTCA TCACAGGTTT    73140
GGTGAACACA TGTTTCCTTG TCAGATTTTT GTTCTGAGCT TGTCCCTCCC CACCAAGATG    73200
CTAAACCGGG TCTTGTGTAT TCTCCAAACT CCACTCTAGA GTCACGGAGC TTTGTGTCTG    73260
GGCCTCCATG CCTTCTGACG TCACCTGTGG GGTGTGAAA GGCACACTCT ACCTTGATTT    73320
TTCCCAGCAC CCCACACCGC TGGTTCTGTG CGCTGACCGA GCGGCTCGCC TTCCCCCAAC    73380
TCCACTGGGC ACCTGCCACA CTTTTCCTCA TGTTTTTGTT CACTGTGGTT TTGTCGTAAG    73440
TCCTGGTGTT CCCCTGAACC AATTTCTTTT TGTTTGTTTT TGAGACAGAG TTTTGCTCTT    73500
GTTGCCCAGG CTGGAGTGCA GTGCCGCGAT CTCGCTCAC TGCAACCTCC CCCTCCCCGG    73560
TTCACCCCAT TCTCCTGCCT CACCCTCCCA AATACCTGCG ATTATACGCA CCTGCCACCA    73620
CCCCTGCCTA ATTTTTTGTA TTTTTACTAG AGACGACGTT TCACCGTGTT AGCCAGGATG    73680
GTCTCCATCT CCTCACCTCG TGATCCCCCT CCCAAAGTCC TGGGATTACA GGCATGAGCC    73740
ACCGTGCCCA GCCTGATATT TTTAGTAGAA ATGGGGTTTT GCCATGTTGG CCAGGCTGCT    73800
CTCGAACTCC TGACCTCAGG TGATCCTCTC ACCTTGGCCT CCCAGAGTGC TGGGATTACG    73860
GGTGTGAGCC ACCACGCCCG GCCTCTTGTT CTTTTGAAAC CTGCCCTCAC GTTTTTTCCA    73920
TAGTGCATCT TGGAGTCAGC GTGTCTACTT CCTGTAAAAA TCTTACTGTG ATTTTGACTA    73980
GAATGTGTTG AATTCCTGTT TTTTTTTTGA GTCAGGGTCT CTCTGTTGCC CAGGCTGGAG    74040
TGCAGTGGCA CCATCACAGC TCACTGCAGC CTCAACCTCC TGGGCTCAGG GGATCCTCTC    74100
AGCTCAACCT CCCAAGTAGC TGGGACCACA GCCACATGCC ACCATGCCCG GCTAGGTTTT    74160
TTTTTTTTTT TTTTTCGTCA ACACCCTGCC GTTGCACCAT GTTGCCCAGG CTGGTCTCGA    74220
ACTCCTGGCT TCGGGCAGTT TGCTCCTCTC AGCCTCCCGC AGTCCTGGGA TTACAGGCCT    74280
GACCCACTGC ACTAGGCCAT GTTGAATTTC TAGATTAATT TGCCGCCCTC AGGGGCACAG    74340
ACAOGACGGC TGGGCCAGTT CGCGGGAGGA GAGGCCCCTC GGGCTGCCGC ATTTTCAGTG    74400
CATGGAGATG GCCTATGTTG GCGGAACACA GACCTCACCG GGGCTCCCTG CAGGGAGGAC    74460
AAAGGGTCAG GCAGGTGCCA GCTCCTGTCC ATTGCCCTGG GGCTCCATGA TGGCAGGGGC    74520
CGGTGAACCG ATGACCCCTG GCTCTCCTGT GACCTTCTGT GTATCCGCCT GATGCTGCAC    74580
AAAGTCGGGT GGCCTCAGGC TCCTGACGGG GCTGCACTTC CTCTGCCTTT CACATTGTGT    74640
TCAGTGTGGA CCCCTCCGAG GGCAGCCCTG GTTCCCAGC AGGCCTGGGG GCCTTACAGT    74700
CCTATAAGGT AGGGGCCACC TCCAGGAGGC AGGTGGAGGG CAGCCCTTGT TCCCCGGCAG    74760
```

-continued

```
GGCTGGGOGC CTTACAGTCC TATAAGGTGC GGGCCACCTC CAGGAGGCAG GTGCCGCTGG   74820

GGGTCTTCTG GTCCTAAAAC GTAAGGGGCT GCCCCCAGGA CATGGGCGGG GCCTCCACAC   74880

TCCTGGTCCT GTCCCCTCCA GGTGCACATC CATCCTGATC CTCCTCACCG GAGGACCGCT   74940

CACCGGTCTG ATGCCTGGAG CACCACTGCA GCCACAAAGC GACGTACAGA CCTGGGCCCA   75000

CACGCTCCCC GCCCGCCCCG GTGCAGTGCC CGGCACCACC ATGCCACAGG CTAGGCACAT   75060

GCCCAGCCGT GGATCTCCTG CCCCCATGGC CCTGGCCACC TTCTCCATAT CCAGGCCAAT   75120

CCAGAGCATT CTCCTCACTG TCCCTCTGAA GATTGGAGTT ACTCAGAGAC GVAGGAGATG   75180

GCCTGATGGC ACCGTGACCT GCCCAGAGTC ACCTGGTTGG TCCTGGCAGA GCCACAGCCC   75240

AGCCAGGCCT CCCTGCTCGC ACACGCTCGT TTATGCCGAG GCCGTCAGCA CAGAGCCTCC   75300

ACAGTGAGGC ACGGCTCTGC CTGCTGCCTC CACGCACCGC CTGGCCGGGC CAAGCCTCAC   75360

GGTCACATCT CAACGCGGCC CGCCTGGCCC TGTTGTCCGA AGCCCCTGCT GCGCTCAGCC   75420

CCGAGGCCCC ACGTGCCTTC TTGGCTTCCT GTGCTCCGTG GCGTcTTCGA GTCGCTGCTG   75480

CCGGGGACCC TGTGTGGATG GGTCTGTGA GTGTGCCCTC GGCTCCGTGT CCGGAGCCCT   75540

GTGGTTCTTG GCGTGTATCT GGCCCCACCC CCACTCCCTG GTGTCCAGCG TGCGGCTTCA   75600

CGGCTCCAGC TGCGGGACCT GCTGCCCCTC CCTTGTCCTC CACTGCGGCC TTCCCTCTGG   75660

GCTTGGTTCC TCCCTCTCTG GAACATTCTT TCTCAGCTGC TGTCCACCC ATGGTGGCAT   75720

CACGTCCCCC TGGCTGAACC AGCCCTTGTG CGGTTGCTGT GCTTGGGTCT GCCTCGCCGA   75780

GCCGGAAGCG AAGGGCTGGG AGGGCGTCAG GGTGGCGTGG CTTGACCCCC GCTCGGTGAT   75840

GGTCCTGCAG CAAGGCCTCT CCCAGCAGGA AGCGTCCATC CCGGGGGGAG GCCGGCGCCC   75900

CTCACGCAGT TGGGGTTGCG GGAGGCAGTG CGTGCCTGAG GCAGCCGGTG CACAGATTCC   75960

AAGGGCCTGG AATCTGTTTG TTCCATTGAC CTCTGATGTC ACTTCACTTC TCAGAAGCAC   76020

CCACTCCCTG CACTGGGCGT TTGTAGGAAA TGAGCTCCTG GAGGAGGGGG TGGGGAAGTT   76080

CCCCCATTGC AGGGCACACT CAGCCCCAGG AAGGAAACGT GCCTCGTCCC TGCTGACTCC   76140

GAATCGCAGT CAGAGTCGTT CTGCTTCTGC CGTGTTGAAT TCCCGGCATC CGCCATCCAG   76200

ACTCAGCCTC CTCCCCAGGC CACGGCCGCC GTGCCCAGTC GGTCAAGCCC TTCTACGAAC   76260

TTCCTTTGAG CTGGCCCCCT TGTTCACTGC TGACGCCACT CACAGCCTTG TGCACGTGTC   76320

CTGCTTCCAG GCAGAGCTGG GAACTCGCAC CCCGTCTTCT GCACGCGGCC GTGGAATGTC   76380

GGGATGCCGG CCCTTCCTTC CCGTGTGCTC TTGGCGGGGT GGGCTTCTTG CCCTGAGCCG   76440

CATGTCACAG TTTCTGCAGA AGTTTAGGGT TGGAGTGGCC TGACCTCTCT GCAGGTGTCC   76500

CCAGCCTCTC CCTGGGGTCT GCCTCCTACT CCCAGGACCC CCTGTCCCCC AGACGGGCCC   76560

CAAGCTGGCA CGCTCACACT CAGGCCAGCC TCCTTTGTTC TGACTTCTGC ACAGTGGGCC   76620

TGGGTGGCTG CCCGCGGCTC CCTTGCTTCA TGCCAGTGGC TGGAGAGGGT GATGGGCAGA   76680

GAGGCAGGTG GTCAGGCCCC CAGTCCCGTC CTCACACTCT GTGCCCTCTG CCGCCCCCCG   76740

CCCCACAGGG AAGCTCCTGA GCTACTGGTG CTTCAGTCCC GGCCACAGCA TGCACCAGCT   76800

GGTCCGCCAG GGCGTCCGCT CCCTCATCCT TACCAGCGGC ACGCTGGCCC CCGTGTCCTC   76860

CTTTGCTCTG GACATGCAGA TGTACCGCCC ACCCTGCCA GCCCTGAGC ACCCGTGACA   76920

CCTCTGACAT CAGCGCGGTG GAAGTGGTGG GGTCCCCAT GAGCCGCGTG CTCGGGGTCT   76980

CCGGCCTCGA GGGCTAAAGC GCTGCTGGTG CACTTCCCCA CTGTCTGCTC CCTCTGGCCA   77040

CGCTCAGCCC TTTCCCAGTC TGCCTGGAGA ACCCACACAT CATCGACAAG CACCAGATCT   77100

GGGTGGCGGT CGTCCCCAGA GGCCCCGATG GACCCCAGTT GAGCTCCGCC TTTGACAGAC   77160
```

```
GGTGACGGCC TGTCCCTGGG CCCTGCTGGG GTUGGAGGTG GCGCAGCACT CAGGCCTGAG   77220

GCCCTCACCA GTGGCCTCTC CGGCTCTAGG TTTTCCGAGG AGTGCTTATC CTCCCTGGCG   77280

AACGCTCTGG CTGACTGCCC TGAATGCCCC AGCTGTGCGC ATCCTCGATC CTGGACCCCT   77340

GCTCCCAAGA GCTGGTAGGC ACCCCTCCAC ACATCCTGCC CCTCCCTTGA CCCCGGCCCC   77400

TGCACTTCCA GGCAACATCG CCCCCGTGGT GCCCTATGCG CTCCTGATCT TCTTCCCTTC   77460

CTATCCTGTC ATGGAGAAGA GCCTGGAGTT CTGGCGGGTG CGTCTCCCCT GTGTTCTCGG   77520

CGGGGTGGGT UAGGGCAGGG CTGGAGCATG AAGCAGGCAG TGGTCACAGC TCCTGCTTGC   77580

CCTCATCGGA TCGGCGGCGT GACCAGGOCT ACCGTGTCCC TGCCTCTTCC TCCCACAGGC   77640

CCGCGACTTG GCCAGGAAGA TGGAGGCGCT GAAGCCGCTC TTTGTGGAGC CAGGAGCAA   77700

AGGCAGCTTC TCCCAGGTCG CCACTTGGCC GGGGCTCTGG CCCTGCTGCC CCTCGTGCC   77760

TCCCCTGCCT CTCACACCTT CCCCAAGGCT GACCACTGGC CCTGACCATG GGCTCCGGCG   77820

GCTCCCGCTG CCTCTTCAGG GCTCCTGCGT TTCCTTCCTG GCCCTGAGTG TTGCCTCTTA   77880

TCTTACAAAG CCCCCAGCAC CCGGTCGGTG TCCTAACAGT GGCCCTCCTG TCTGAGTAGC   77940

CCTAGTCGGC CACCCTGGCC CTGGGGTTCC CCGTGTTTTC TGGGAAGCAC TGAGCAGGCG   78000

TGGGGTCAGC CTGGGATCCG TGCCAGGAAG AAGCTTCCAG AACCCGATTG GCCTTCCTGG   78060

CTAGGACGAT CCTTCATCTT GGAGCATGAG ACCTGGGTCT CCCTCATGGG GGACCAACGC   78120

CCTGGGGGGG CGCTCCAGGC TCAGCCTCAC CAACTTTCCT TCCAGACCAT CACTGCTTAC   78180

TATGCAAGGG TTGCCGCCCC TGGGTCCACC GGCGCCACCT TCCTGGCGGT CTGCCCGGGC   78240

AAGGTGAGCT CTCCAGGGCC CTCTGCCCTG ACCTGGTTGC CTGTTCCCTG GTOGGTCCTT   78300

ATGGCTCCCC AGCAGACTCT GCGCCCTGGG GGCTGCCCGG TCCCCTCCTT GGGTCCCACG   78360

AGAGCGACTG CTGGCCCTGC TCGCAGCGTG TCCTGCTCTG GGCCTGGGCA GGCAGGATGG   78420

GAGTTTCCTG GCCACAAGAG TTGGAGGTCG CGTCTGGOAC CTGTGGACCC CAAGTGGGGT   78480

CCTCACCCAC AGATGGAGCT TCCTCCCACC CCTGGTTGGG GACGGAGCCT CCGCGAAGGT   78540

GGCTGGGCTG GGTGTGGGCA CCACGGAGAG GAGCCCCCAC GGCCCAGGC AGCTCCCTGG   78600

TGTCTCCCCT AGGCCAGCGA GGGGCTGGAC TTCTCAGACA CGAATGGCCG TGGTGTGATT   78660

GTCACGGGCC TCCCGTACCC CCCACCCATG CACCCCCCCG TTGTCCTCAA GATGCAGTTC   78720

CTGGATCAGA TGAAGGCCCA GCGTGGGCCT GGGCGCCAGG TGAGTTACAC CAGGGTGGGG   78780

CTGGGGTAAG GCGGTCTGGT GACTGAGCCC CCGCCCCGTG GCCAAGGGAC CCCCCGTGAC   78840

CGAGCCGCCT CGCCGCACAG TTCCTCTCTG GGCAGGAGTG GTACCGGCAG CAGGCGTCCA   78900

GGGCTGTGAA CCAGGCCATC CGCCGAGTGA TCCGGCACCG CCACGACTAC GGAGCTGTCT   78960

TCCTCTGTGA CCACAGGTGC GTCCAGTCCG GTGGCACGCG CGGCGCCACG GGACACGCCC   79020

ACACCCCACT GGGCCCCTGG ACTCTCCTTC CCCACATGAG GCCCCGTCTC CTCCAGAGCC   79080

TCTCCGGCTA CTCGGGGTCA GCGTGGCGCC CCTGCAGCAG ATGAGGGTCT TCACTTCGGT   79140

GAACTGAACC CTTGAAGCGG CTGTGGGCAG GOCACCAGOG CTATGCCAC CCCCCAGGTT   79200

CGCCTTTGCC GACGCAAGAG CCCAACTGCC CTCCTGGGTG CGTCCCCACG TCAGGGTGTA   79260

TGACAACTTT GGCCATGTCA TCCGAGACGT GGCCCAGTTC TTCCGTGTTG CCGAGCGAAC   79320

TGTGAGTTCC TCCCCAGGGA GCGGATGAGG GTGTTGTCCC CAGAGGAGCC AGAAATGGGT   79380

CCACCCACCC CCATGGTTCT GCAGATGCCA GCGCCGGCCC CCCGGGCTAC AGCACCCAGT   79440

GTGCGTGGAG AAGATGCTGT CAGCGAGGCC AACTCGCCTG GCCCCTTCTT CTCCACCAGG   79500

AAAGCTAACA CTCTGCACCT GCATGTCCCC AGCCTGAAGC AGAGGTCCTC AGGTGCGGAC   79560
```

-continued

```
GGGCAGCGCT GGGTGGGCGG TGTGGGGGTG GCGGAGCGGG CGGCGTGGGG CGGGCAGCAC  79620

CAGGCGCCCA GGGCGGAGGC GACTCACCTG GCTTTGTGCG CTTCCCCTCC CACCTCCAAA  79680

GGCTGCCTCT CCCTCCTAGG GCAGGGCCCC CACGGGCTGC AACCCTCCCC TACAGGCAGA  79740

GAACGCCCCA GGCAAGGATG CCCCCCGAGG CTGAGACTCC CCCCAATAGC AGGGAGGACA  79800

CCCACAGGCA GGACCCCAAG TGCTGGCACT CTCCCCCAAC AGGGGCTTTG CCACAGGCAG  79860

GGACCCCAGC TGGGGCCCCC CGTGGGCTTC ACTGCGCACT CGGGTGCCCC TGCAGGGTCA  79920

CCAGCTGCCG GGGACCCCGA GAGTAGCCTG TGTGTCGAGT ATGAGCAGGA GCCAGTTCCT  79980

GCCCGGCAGA GGCCCAGGGG GCTGCTGGCC GCCCTGGAGC ACAGCGAACA GCGGGCGGGG  80040

AGCCCTGGCG AGGAGCAGGT ACAGTTCCAG GGCCTTGGGA TGGACACAGA CCCTCTGTCT  80100

CCTGAGGCCA ACCCGACCCC GCCCATCTGG CCTCAGGCAC CTCCCCACAC ACCCCTGTAA  80160

ATCCCCTCCC GGCAGGCAG GCOGGCAAGC GGGCGGGCGA TCCCAGCTGC CTGCCTGTCT  80220

CTGGCTCCTC CACCCCACCT CACCCACAGG CTGCTGGCTC CAGGTG[ ]TG CATGC-      80280
CCTGG

CCCTCCGCGG GTGCCCCCCA CATCACTTTG GTTCTCTGGC GGGTCAGCTT GGCTCAGTGC  80340

ACTCAAGGTC GGCTCCCCCT GCCACTGGCT GCGCTTCAGG CTGGCCTTTC TCCAGGAATG  80400

TCCTGCGGGT CGAACCCAGG TTCCTTCTTC CTTGGGGCCT TTTGCCCCAG AAGCCCATAA  80460

TTCCTCAGGC CAACCCCAAA TTTTCTCCCT CCTTCCTCCT GGGAGCCATT CCCCTCTTCC  80520

TCCCCATCCC TCCCCTTCA[ ] GCCCCTCGAG TGACCTCCAG CTGCAGCCAC CACG-       80580
CACCTG

TGTCCCCTTC CTGCCAGCCC CTCGCTGTGG TCGGACTGTC TTCCCTGCAC CTCCTCTTAC  80640

AAGTCACCAC CTGCCAGCCT CATGAGCCGC TGGTGTCACT TOCACACCAC CAAGTTGTGG  80700

CACTGTCACC GGGGTGTGCT GTGCCCCCCT CCCCGACCT CCATCTTGGC TCAGGGCTCC   80760

TTGGGACCAT CTTCCCTCTG CGTCCACGTC CTTTGGGACC CCAGAGTGTG TGGTTGGCCT  80820

CTGTGTGTGG TTGTGAGCTC TGTCCTCCTC AGGCCCACAC CTGCTCCACC CTGTCCCTCC  80880

TCTCTGACAA GAGGCCGGCA GAAGAACCGC GAGCAGGGAG GAAGAAGATC CCGCTGGTCA  80940

CCCACCCGGT GCGTGAGCTG TCCCTGCACC TGTGCCGACC ACCATAGACA CGCATGGGAA  81000

CGCAGCCGTG GGTGCCCCCA GCCACGGCTG GTCCCGATGG GACCAGGGAA TCCACCCCCA  81060

GGAGCTGATG TCCAGGGCAG CTGTGATGCT GACGGCCAGG GGCTCAAGTC TGTCGTTTCT  81120

TCTGCACGGG CTCATGAGT CCCAGCTGGA ATCAGGCCCC ACCCTTGGGC AGGTTTGGCA   81180

TGGGGCCTGC AGCACTGGGC TTGGCCCTGG CATTTCCCTC AAGTGTGGAT GCACACCTGC  81240

CTCATGTGAG CGACACAGCC CATTCCTAGC CTTGGATCAA AGAACGGAGT TATAGCCGGA  81300

GCCAGGAAGC CCCCTGCCTG CTGGAAAACC CCAAGTGTGG CGGCCTTTGT CCATGTCCCT  81360

TGGCTTCTGG CIAACAACTGG GTCGTGCCCA GGCACGGCTG CTGCCATCAG GAAGTCGGTG  81420

CCTGCTGAGG GGCCTGGGCT GGCGAGGCCC TGGGTGGCGA GTGCCTGGGC CGCCCCTGCC  81480

TTGCTTTCCA CGTTTCCGTG TTGGTCTGGG GTGTGTAGAG AGATGGGCAC TGCTCATCCG  81540

GAAGCCCCTC CTTGTGCGCT GCCATCCTGG GAGCCTCAGC CGCATCCGCT GTGGGCCAGG  81600

CGGCTTCAGG GACCAGGAGA GAGACGCCCC ATGCACGACC CCTGGCTTGA GGCAGAGCCA  81660

ATCTACCCTT TGCCCATTCA CTCCTCTCAC TTCCCTCCCA GCCTCTCACT GTGTCACCTC  81720

AGACGGGCCC AGCCCCACAG CTTTCTTCCC GCAGCCCCTC CCTATGTCCA TCCACCCAGC  81780

CAGTTTCTCA GGCAGCAGCC CCACCTCGGC AGTCACTGTC CCAGGGAACG CTCAATGTTC  81840

CAAGGAAGGC TCTGCAGCCC CAGGGACCAG ATGATGAGCC TCGCCCTGAT GGAGCCTCGG  81900
```

-continued

```
GCCTGTGTCC TGCAGGAGGA GCCCGTGGCT GGTGCACACA CGGACAGGGC CAAGCTCTTC   81960

ATGGTGGCCG TGAAGCAGGA GTrGAGCCAA GCCAACTTTG CCACCTTCAC CCAGGCCCTG   82020

CAGGACTACA AGGGTTCCGA TGACTTCGCC GCCCTGGCCC CCTGTCTCGG CCCCCTCTTT   82080

GCTGAGGACC CCAAGAAGCA CAACCTGCTC CAAGCTGCCC TCGCTTGCAG AGGCCACCCA   82140

CCCTGAGGGC AGTGCTGCCG CCGCGTGTGG GGTGGGGGCC ATCTGGGTCC AAGGTGGTCT   82200

CTGTTCTCTPA GAGAAAAAGC CGCAGATGGG GACAGACGCC CCTTCCTCTA CAGGCTTCTA  82260

CCAGTTTGTC CGGCCCCACC ATAAGCAGCA GTTTGAGGAG GTCTGTATCC AGCTGACAGG   82320

ACCAGGCTGT GGCTATCGGC CTGAGCACAC CATTCCCCGA AGCCAGCGGG CACAGCCGGT   82380

CCTGCACCCC ACTGGTAAAT GGGGCCCCA5 GTCGGACCCT CAGACTCCTC CGTOGAAGGC   82440

AGTGTGGGCC AGAGTCCTGG GCTGCTTCGG CTCGGCATCC TCGGGCCCTC CTTGGCCCCG   82500

CCTCTCTCTT CCCCTATGGc[] AGTGATCGCC GCCTCCACCT CCACCACCAG CAC-       82560
CAGCAGC

ACCACCTCCA CCTTCACCAC CACCACCTCC ACCACCACCA CCTCCACCAC CTCCACCTCC   82620

ACCACCTCCA CCACCTCCAC CACCTCCACC ACCACCACCA CCTCCACCAC CACCACCACC   82680

ACCACCTCCA CCACCACCAC CACCACCACC ACCTCCACCT CCACCACCTC CACCACCACC   82740

TCCACCTCCA CCACCACCAC CACCTCCACC TCCACCACCT CCACCTCCAC CTCCACCACC   82800

ACCACCTCCA CCACCACCAC CACCACCTCC ACCTCCACCA GCAGCAGCAT CACTTGTTGG   82860

CGAGACCCTG TGCAACTCCA TCCACAGCCC TGTCCCTGCC ATACCCCGA CCCCTAAGCA    82920

CAGCCCTGTC CAACTGCCAC ACGTCCCCTG CCTCCCATGC ATGGTCCTCG GGGGTCAACT   82980

GCACACGCCA GGGTCCTAGG CTCCTAGACC CCT[]TCCTCC CTCTTTCTGC CTCT-       83040
GTTTGG

GGTGGAGTCC AAGTCTCCAG AGGCCGAAGC ATCTCTGTTC GTQTGTTM[]T GAACAC-     83100
CCCC

TACAGACTTC CCCTAGTTCA CCCAGGGGGG AACCTAGCCT GTTGGGACCA CCCCACATCC   83160

CTTCTGGGCT TGGTACTCAC TGGGATATCC TCATGCCTCC ACCCAGCCTA CGGCTCTGAG   83220

CTCCTGAGTG GCGCTTTGGC CTGCCCGCCA CTGTTCCAGC CCCCATCCAG CAGCCTGGTG   83280

TCTCCTCTGA TGCCCCCAGC ACCCACCCGT GTACCTGCCT GGGTTTTCCC CCCTGGTCT    83340

GACGTCGGTG AGGCCTCGCC TCCCTACCCA GCCCTGCCCC CCACCCCAG GGAACTTTCC    83400

ACATGCTCCC GACCAGCTTT GTGGCTCTAC ATCTCTTCAT CAGGAAGAAC GGCGCCGGAT   83460

CCCAAGCTGA CCGTGTCCAC GGCTGCACCC CAGCAGCTGG ACCCCAAGA GCACCTGAAC    83520

CAGCGCAGGC CCCACCTGTC GCCCAGGCCA CCCCCAACAG GTAGCTGACT CCTGAACCGT   83580

GTGCAGCCTA CGACTTGGTC CCTCCCTCAC TCGCTTCACC AGGCTAACTC TTGAGTGTGC   83640

CCGCGGCTGC CCCTGTGGGC AGCCATCTCA TCGTGGGCAC TGCTCCCGGT TCTGCACCCC   83700

GCAGTTGTCC TGAGCAGCTC TCCAGGAGTT CCTGGAGCAA GGGCGGGCAG GGCGGTGGGA   83760

CTCTCAGTCC TCCACCCCAG CGCCACTCTG AGCCATGCTA CTCCCACACC AGCAGACCCT   83820

GGCAGCCAAC CACAGTGGGG GTCTGGAGTG CCCAGAGCAG GGAAGCACGG CCAGCACGCC   83880

GTGAGCGCCT ACCTGGCTGA TGCCCGCACG GCCCTGGGGT CCGCGGGCTG TAGCCAACTC   83940

TTGGCAGCGC TGACAGCCTA TAAGCAAGAC GACGACCTCG ACAACGTGCT GGCTGTGTTG   84000

GCCGCCCTCA CCACTGCAAA CCCAGACGAC TTCCCCCTCC TGCACACCAA CTGGCCCTGG   84060

CCTGGGGAAC AGCCGGTGGG GTGGGGGGCA GGGGACAAPA TGGGGGCTGT GCCGGGTCTG   84120

ATTGAACCTC CCCGCAGGGT TCAGCATGTT TGTGCGTCCA CACCACAAGC AGCGCTTCTC   84180
```

-continued

```
ACAGACGTGC ACAGACCTGA CCGGCCGGCC CTACCCCGGC ATGGAGCCAC CGCGACCCCA    84240

GGAGGAGAGG CTIGCCGTCC CTCCTCTGCT TACCCACAGG GCTCCCCAAC CAGGTAGGGC    84300

ACCTGCCTGG CTGCTCCTGG CACCCCCCCA ACCGCACGCA GCCCTGGGAG TGAGCAGCXA    84360

AGCCCCAGGC CCCCCTCAGA CTCAACTCTC TGTCTCCAGG CCCCTCACCG TCCGACAAGA    84420

CCCGGAAGAC CCAGAGCAAG ATCTCCTCCT TCCTTAGACA GAGGCCAGCA GCGACTGTGG    84480

GCGCGCGCGG TGAGCATGCA GCTCCCAGCC ACTCCTCAGG ACCTCCCCAC GGGCCTGCAG    84540

CATCTCAGTG GGGTGAGCCT CATGGGAGAG ACATCGCTGG GCAGCAGGCC ACGCGAGCTC    84600

CGGCCGGGCC CCTCTCAGCA GGCTGTGTGT CCCAGGGCTG TGGGGCAGAG GACGTGGTGC    84660

CCTTCCAGTG CCCTGCCTGT GACTTCCAGC GCTGCCAAGC CTGCTGGCAA CGGCACCTTC    84720

AGGTTGGTGC CTGCCCACTA CAGTTCCTCC TGCGTGTAGC CCCAGCTGAT CGGCTGAGGG    84780

GGAAAGGGCA CCCCCTTGTC CTGGTGGCAA CGCCTCCCAG ACGTGTGCAG TGGGCCGGTT    84840

GTCTCACAGC CCTCTAGGAT GTGCCCAGCC TGCCACACCC CCTCCAGGAA GCAGACCCTC    84900

ATGCAGGTCT TCTGGCCACA GCCCCAGTCA GTGCCCACCG AGGCCCCCAG CACACCCAAC    84960

GTGCCTTGAT CACCTGCCTG TCCAGCTCTG GTGCGCCAAC AACCCACCCA ACAGAATAGG    85020

CCACCCCATG CCACCCGGCT TGGCCCGCTC CACCCCTCAG CCAGGCGCGG CCCATGGTTG    85080

GTCCCTGCGG TCGGACCGGA TCTGCGCCTG CCTCTCAGAA GCCCTCAGCT ACCTTGGGGT    85140

CTGGGGTGCG TTTCTGGGAA AGTGCTTCCC CAGAACTTCC CTGGCTCCTG GCCTGTGAGT    85200

GGTGCCACAG GGGCACCCCA GCTGAGCCCC TCACCGGGAA GGAGGAGACC CCCCTGGGCA    85260

CGTGTCCACT TTTAATCAGG GGACAGGGCT CTCTAATAAA GCTGCTGGCA GTGCCCAGCA    85320

CGGTGTCTTC GTGCCCTCGG CTTGGTGGTC CCAGTTGAGG GACAGGGAGT TGGCAGAGGC    85380

CCCTCCCAGC CTGCCATGTG ACACTGTACT TCCTCCACGG TGGGCTCAGC CCTCCCCTCA    85440

TCCTCACAGC CCCAGCCAAG CTGCAGTTGG TAGGGGATCC ACCGACACAC CAGGCTGCCT    85500

GGGCTGGTCT CTGGGTTGGG AGCTGCCCCA GGTGCTGAGG AGCCCAGCTC CCTGGCTGGT    85560

GACGCCCCTC CCAGAACCAC CCTTGGACTC ACCTCTGGGG AGGCATGGTA CCACGTGGGT    85620

GAGGGGGGCT CCCTGGGGAG CGAGGGGTTC CTATGGGGCG TGGCCAGGCT GGCCCAGCCC    85680

TCTCCCCGCC CATATATGTA GGGCAGCAGC AGGATGGGCT TCTGGACTTG GGCGGCCCCT    85740

CCGCAGGCGG ACCGGGCGCA AAGGAGGTGG CATGTCGGTC AGGCACAGCA GGGTCCTCTG    85800

TCCGCGCTGA GCCGCGCTCT CCCTGCTCCA GCAAGGACCA TGAGGGCGCT GGAGGGGCCA    85860

GGCCTGTCGC TGCTGTGCCT GGTGTTGGCG CTGCCTGCCC TGCTGCCGGT CCCCGCTGTA    85920

CGCGGAGTGC CAGAAACACC CACCTACCCC TGGCGGGACG CAGAGACAGC GGAGCGGCTG    85980

GTCTGTGCCA AGTGCCCCCC ACGCACCTTT GTCCAGCGCC CGTGCCGCCG AGACAGCCCC    86040

ACCACCTGTG GCCCGTGTCC ACCGCGCCAC TACACGCAGT TCTGGAACTA CCTGGAGCGC    86100

TGCCGCTACT CCAACGTCCT CTGCGCGCAG CGTGAGGAGG AGGCACGGGC TTGCCACGCC    86160

ACCCACAACC GCGCCTGCCG CTGCCGCACC GGCTTCTTCG CGCACGCTCG TTTCTGCTTG    86220

GACCACOCAT CGTGTCCACC TGGTGCCGGC GTGATTGCCC CGGGTGAGAG CTGGGCGAGG    86280

GCAGCGGCCC CCAGGAGTGG TGGCCGGAGG TGTGGCAGGG GTCAGGTTGC TGCTCCCAGC    86340

CTTCCACCCT GAGCTAGGAC ACCAGTTCCC CTGACCCTGT TCTTCCCTCC TGGCTGCAGG    86400

CACCCCCAGC CAGAACACGC AGTGCCAGCC GTGCCCCCCA GGCACCTTCT CACCCACCAG    86460

TTCCAGCTCA GAGCAGTGCC ACCCCCACCG CAACTGCACG GCCCTCGGCC TGGCCCTCAA    86520

TGTGCCAGGC TCTTCCTCCC.ATGACACCCT GTGCACCAGC TGCACTGGCT TCCCCCTCAG    86580
```

-continued

```
CACCAGGGTA CCAGCTGAGC CAcAGGCCTC AGCGGGCAGC ACACTGCAGG CCAGGCCCAC  86640

TTGTGCCCTC ACTCCTGCCC CTGCACGTGC ATCTAGCCTG AGGCATGCCA GCTGGCTCTG  86700

GGAAGGGGCC ACAGTGGATT TGAGGGGTCA GCGGTCCCTC CACTAGATCC CCACCAACTC  86760

TGCCCTCTCA GGGGTGGCTG AGAATTTGGA TCTGAGCCAG CCCACAGCCT CCCCTGGCGA  86820

GCTCTGGCAA AGTGGGCAGC AATCTCCTAA CTGCCCGAGG GGAAGGTGGC TCGCTCCTCT  86880

GACACGCAGA AACCGACGCC TGATCGTAAC TCTCCTAACT GCCTGAGAGG AAGGTGGCTG  86940

CCTCCTCTGA CATGGGAAAA CCGACGCCCA ATGTTAACCA CTGTTGAGAA GTCACAGGGG  87000

GAAGTGACCC CCTTAACATC AAGTCAGGTC CGTCCATCT GCAGGTCCCA ACTCCCCCCT   87060

TCCGATGCCC CAGGAGCCCC AAGCCCTTGC CTCGGCCCCC TTGCCTCTTG CAGCCAAGGT  87120

CCGACTGGCC ACTCCTGCCC CCTAGGCCTT TCCTCCAGCT CTCTGACCGA AGGCTCCTGC  87180

CCCTTCTCCA GTCCCCATCG TTGCACTGCC CTCTCCAGCA CGGCTCACTG CACAGGGATT  87240

TCTCTCTCCT GCAAACCCCC CGAGTCGGGC CCAGAAAGCA CGGTACCTGG CAGCCCCCGC  87300

CAGTGTGTGT GGGTGAAATG ATCGGACCGC TGCCTCCCCA CCCCACTGCA GGAGCTGACC  87360

AGTGTGAGCC TGCCGTCATC GACTTTGTCC CTTTCCACGA CATCTCCATC AAGAGCCTGC  87420

AGCGGCTCCT GCAGGCCCTC GAGGCCCCGG AGGGCTGGCG TCCGACACCA ACGCCGGGCC  87480

GCGCGGCCTT GCACCTGAAG CTGCGTCGGC CGCTCACGGA GCTCCTGGGG GCGCAGGACG  87540

GGGCCCTCCT GGTGCCGCTG CTGCAGGCGC TGCGCGTGCC CAGGATGCCC GGGCTCGAGC  87600

GGACCGTCCG TCAGCGCTTC CTCCCTGTGC ACTGATCCTG CCCCCCTCTT ATTTATTCTA  87660

CATCCTTGCC ACCCCACTTG CACTGAAAGA GCCTTTTTTT TAAATAGAAC AAATGAGCTT  87720

TCTTAAACCT TATTTTTATA AAGCTTTTTC ATAAAACTGG TTCTAGTTGC ACAGCTACTG  87780

CGAGGGCAGC CGGGGACACC TGAGCCGCCC GCTGTGCCCA GATCCCTCAG GCTGCCTGCC  87840

ATCAGAACTG CTGCCCCGGC CTTCCCCTAC CTCAGACACA CCCTCCCTGG GAGGATCAGT  87900

GGGGAGTGCC ACCTCTGCCC CCAGTGCCTC TGCCACCTCG CAGGGGCCCC TGAAGCTCAC  87960

CCAGGGTCAG GGCCTGGGAG CCTATCATTG CTGGAAGAAC AGGATCGGGC TCAGCCCAGC  88020

CCTAGTCGCG GGGGCCCACA CTAACCCCCC ACTTATGAAT TCCTCCCACT CCCAACTCAC  88080

AGGGGATTTC CCGACAGGGC ACCTGCCAAA GACCTCCTCC AGGCCTCCCA TGCTTCCCGG  88140

GAAGTGAAGC TTCTCCCCCT CTGGCGCACG CTCTGAAGCC TCCCGATGCA CCCAGAGCAA  88200

CCAGGGGGCT GCACCAGCCA CTCGCCTCCC CAGCACGGCC AGGTTCCCGG GGCTGGAGGT  88260

CCCCCCCAGG TCCTCGGAAC CAACCTGCAG AACACACACA GGGTCCCCTG GAGAGGACGC  88320

CGGGACTTCC AGGGCCCGAC TCCTGTGAGT CACACCCCCG CAGCTGCTGC GCCACCCCCA  88380

CCCTGACTCA TGCCCCTTCC CAGCAGCTCC TCCCAGGACC CCATGTCCTT CCCACATCCG  88440

CAGGAACGGA GTGCCTGGAC TCTCCAGGCC CACCTGGGGA CCCCCTCACC TGCCCACCAG  88500

CCCCTGACCA GCCCAGTAAC ACCATCACCC TGTCCAACAG CCAGGAGCCT CCACCCTCCA  88560

GGAGGCAAGG GATGGACAGA GCCACACTCG CCGTCTTTAT TTTGCACTCA CCCTGGGTGA  88620

CACTCGGCAG GCCGCTCCTC CCCACAGCCA GACTGAGGAA GAACACAGCA CTCGGCAGGC  88680

CCAGTGGGGT CCGTGCAGCG AGGACCCCAG GACCAGCCTT ACTCCCGAGC AGGCGACACA  88740

GGGCCCCACA GAGAACCCCT CCGGGACGTT CTCTCCTGGC TGCGGGAGGG CTCTCGACCC  88800

CCACAAACAC TCCCCAACTT GCGGGGCTGC GGCATAAAAA CAGCCACTCC CAGCACGCCC  88860

CCTCAGCTTT TTGCATCAGT CAGCTCCCTC CCGGGGGATT AGGGTGAGGT GAAGCCAGGC  88920

CCAGGCGTGG GGTATAGGTC TTCCCCCGCA GGCCTCAGCC CTGTCCCGAG GCTGCATCAC  88980
```

-continued

```
AATCCAGGGC CCCCGCTGGC CTTTGGGAAC ATGCCCTGGG TCTTCCTCAA GGCAAGATCA    89040

GCCCCAGACC ACTTCCGGGG TCACGGGGTC ACACOCCAGA AGCCAGATGG CAGCCATGGC    89100

TGACGGGCCT CCTCCTCGAT GGGGCGGAGA CAGCCACGGG GTCTCCCGAG GGTCCCACAG    89160

GGCTGTCCTC ATGCAGCCCA AGCCAGCCTG AGCACTGGAG CCCCAATTCC CAACCAGGTC    89220

TCCCTCAGAC CCCCCAGAAA GGGCCTCGAA AGGCCGCCGC TGCGCCCTGT GGAAAGGCTG    89280

CCGCTGCAGG GCCTGGGCCA GCCGGGCTGC CAGACTCCCC TCCAAAGCCT CCGGATCCCT    89340

ACGCTTTTCC AGACATAGAG GAAAGTTTGT CTTCGAGAAA ACAAAGTAAA TAGAAGAACC    89400

CCAAAGCAAA GCAAACCCAC CcCCCAGATC AGCAGCATGG GAGCCAACAG GAGGCCACTC    89460

CTCCAGCACC AGGOGACCAG CCGTCCCGAC GGCAGCCCGG CTGCGCCTAC GTGATGTCCC    89520

TCTGCCGCGG CGGCCGGTGC ACATTCCGCA CGACACACTT CACCATCCAC TCGATGCCCT    89580

CGCGCACCCC TTTGCTGTGA AGACACCOOG TGTGACGCGG GGGGTCTCGG TCCCCAAAGC    89640

CCCCGCAGGT GCAGCCCCCA CTCACCCTGT GAGGGCCGAG CAGGCCTGGG TCAGGCAATC    89700

GCGCCTGCCG ATCTTGCTGG TGCAGTCGCT GAAGGCCGTC TTGATGTCAG GGATTGAGAG    89760

GCACGTCTGG GGGAGGTAAG GCCGTGAGGA GCAGCCCCCA CGTCTGGCCC TGTCCTGCCT    89820

GTGGGCCCGG GACTCTCAGA AGGGCGTATG CCCTTCACCC CAGGGAAACA GCCAGAGCTC    89880

CACCAGGGTC CCAGTGTCTC CCACAGAGAC CACAGCAGTG AGGACCCTGT GCTCAGCCCG    89940

AGGCTGAACA TGGCTGGTAG TGCCTGAGAC AAACTAGACG TCCACACGGC TCCAAGGAGT    90000

CCACCCCCCA TCCCCTCCCT GGGGGACACC CTGAGCCCCG AGGTGGGGCG CTGAGGACTG    90060

AGGCCTCCTG GGCAGTGGCG GAGGCAGGTC CCAGGGGCCC ACACAGCCGG GGATGATGGA    90120

GAGGTGGGAG CCCTGCATCA GTGATGGGGG CAGTCTGCAG TCATGGTGGC TTCTGCTCAC    90180

AACCACCTGC CCAGTCTTCA AAAAGCAGCC CTCCCCTCCC CTTTTCCTCC GAGGGGAGAC    90240

CCCTGCCCCG TACCAGATGT CCCTCTTGTC GGCTGAGATT GTAGGGGAGG CCAGCCTTAC    90300

AGGCTGGGGG CAACAGAGCC ACCCCAGAGA AGGCACGAAG TGAAGATTCA CCCGGCCCTC    90360

TGGACGCCCG GCTGCTTCTC TGCAAAGCCA CTCCAAGAGA ACAGCTACAA CTCAGCCTGG    90420

CCAGTCCTCC CGGGGGCAGT CGCACCTCAG AGGGGTCTTG AGGGGCTGCC CTGGGGGTGG    90480

GGCTGGCACA CATGCCACCT CCAAGGCTAG CAGGAACAGG TAAGGCTCAG AGCTCACTCC    90540

CACCAGGGCC CCAGCATCAC TTCTTTCACC TCTGAGTTTC ACCTGGCTCT CCCCACAGCT    90600

TGGCCACACA CTCCTGAGAC ACGCCCGCCC TCCTGGGGAG AGGTCCCCTG CATACCAGGA    90660

AGAGGCCTCT GGGCGCCTGC CCTGAGGTGG GAGAACCTCC AGGGCTGGCA GCAGCAGGTC    90720

TGGAGAGGAA CCAAGCTTGG GAAGCTGCTG GGGGCAGGGC AGGCCTTGAG AATGGCTCTG    90780

TACCCCCTGG GCAGTCACTG GGCCTGGGGT GTCTGGGTGC ACACCTACTC CCCTTGCTGT    90840

GGGGGAGGCT GGGGACTCGG GAAGCTGCTG CGGGAGGCAG GGGTGCGGCT CACCTCCACA    90900

TCCTGCTTGT TGGCCAGCAC CAACACCGCG ACACCOCACA GCCCTCCCT GGTCACCACC     90960

TTCTCTGGGG AGCGCAGGAG AGGCAGCGCC TCACACCCAG CATCCTGCCT CTGACTGCCC    91020

ACGGGCCCAC AGGCGTGGAC ACTGTGACAG CCACTCCCTC TGCCCCCCCC CCGTCACCCA    91080

CTAGGCAGGA GCACTTCTGA CCAGACACTG AGCCTGCCCC AGGCACAGAG CTGCCCAAGC    91140

TGGACCTGCC CCCACTCACC ATCCATCCCT CCCAGACCAG CCAGGCCGCA CTCACCAAAC    91200

GCCTGCTTGG ACTCAGCCAG CCTCTCCTCG TCGGTGGAGT CAATGACGTA GATGACGCCG    91260

TCACACTCCG CATAATACTG GGAGGAAGCA CCACGAGTTG GGGCTCAGTC CCCACCCTGC    91320

CAACGGCCAG CAGAGCCAGG CCTGTGTCAT GGCCACAGTG AGGGGCTCAC ATGAGGAACG    91380
```

-continued

```
GGCAAGAGGG CAGCCCCCAA CTGCAAGACC CTTCTGGGAT GCATTCTGGG GTTGCGCGGA    91440

GATCTGGTGG AGGTGTCCCC AGACGCTCCT CCTGAGAACC TGCCGGCAAC CTTTCGCCTG    91500

ATGGTGGCCA AAGGTGAAAG ACAGGGATTG GGCCAGGCGT GGTGGCTCAC ACTTATTATC    91560

CCAACACTTT GGGAGGCAGA ACCAGGAGGA TCACCTGAGC CCACTTCACG GCCAACCTGG    91620

GCAACACAGT GAGACTCCOT CTGTACAAAA GCTThTGGTA ATGTGCGCCT GCAGTCCTAG    91680

CTACTCGGGA GGCTGAGGTG GGAGGATGGC TTGAGCCTGG GAGGTTGAGG CTGTAGTGAG    91740

CTCTGATCAC ACCACTGCAC TCCAGCCTGC GTGAGAATGA GAGACCCTGT CTCAAAAAAA    91800

AGATAGGGTT TGGGGGCTGG AGGAACCTAG ACCACAGCCT GGCCCGTTGA GGGAGTGCAC    91860

CTGTGGGGCT CTGTGCCAGC ACCTCGCACA GGGAGGGAGT GTGGCCATGC GGATAAGACT    91920

GACCAGCACC ATCTACGAAG CGAGCCTTCC CTGCCAGGAC AGGGCCAGAG TCACTGAGCT    91980

CAGACCTCTG CAGCCTGGGC TGGTCAGTCC TGGGCTCGCT CGCAACACTC CTGGGCAAGA    92040

CAGGGCACAG CCCCTGCAGC CTCAGGTACA AGTGCTGAGC CCTGGACCAG ATGAGTGCAC    92100

CTCTATCTCA ATCAGAAAAA AACACAGCAA ACTCCGCGTC CACGTGGAGC AGACAACAGC    92160

TCACATTTGC CACTTTGCCT CCAGGCTGTG CCAGCTCTCC TGTCCAGGCA TGAGTGCCCA    92220

GAGACCTAGA ACTGGATGCT GACCAGGTAG GACAAGCTGG TGGTCAGTGT GTTAAGACAC    92280

ACACACCCGA GAGCATGAGA AGCCAGGAGG CACAGCCCAA CTCTCCGAAA TCCTTAGGGT    92340

GTCTGAGCAG GGAGTACCAG ACAACCCCAT CCCAGTGCCA GACAAGCTTG TGCACCTGCA    92400

CTTCCCACAG AGGAGAGAAG CCTGTGCACC TGCACTTCCC ACAGTGGAAA GGAGGAGGCC    92460

CAAGCCCAGG CCCCCCCACC CCCAGGAACT TCCCACAGTG GAGAGGAGGC CCAAGGCCAG    92520

CCGCCCTCCA GGCTTCTGCA GGTAGCGAGG CCCCCCCACC CCCAGGAACT TCTCTGGCCT    92580

ACAGACAGGT CCCACACAGA GGCCGCCAAC CCCTCAAGGG ACCCTGCAGT GPGCCGGCTG    92640

TCTGCTGCTG ACACAAGGGA GCAGGCGGAC CCTAAGGTGG AGACCTCTGT GCCACGAGGG    92700

GCGGCTCTGT CGAGCCTGCA CCAACCCCAG TGAGACAATC TCCACCTGGC TCCTGGGGCT    92760

TCTGAGCAGG GTGGCAGAAG GTTCATGTCC AACCGCGTCC TCGACCATGG GACCACGTGG    92820

CCAGACCCAC CCATCACACC TACCAGGCAC AAGGTGCACA GCCCAGCAGG GCCGCAGTGG    92880

ACGGGAGCGA CACCTCAGGG CTCAGTGCCG CCAGGACCCA GAGCCCCACG CCCCAGTGGA    92940

GGCGTCACAG CAGTGGTCAT TGTGGGGTCC CCCACAAGCA GGGGGAAGAG CCAGGTGTCC    93000

CAGCGTGCCT CCTtGCTGCC CACCTGACCC CAGTGGAGCA GTCAGAGCCA CTGTGGGTCT    93060

CAGTTTTTCT CCCCAGCACC AATGGGAGCT CCCCAACTGC AAAGTGCCAG CCAGCCTGAG    93120

AGACTACTGT TACAGCAAAG AACCCAGGAG CTGAGGTCCT GGCACATCCC ACACATGTGG    93180

ACACCAACCC AGGGTCCAGC CCCAGGACGA GGCCAATTCG CAATGACCCC CCTTTCTGTG    93240

GTGCTGGCTC TGCACAAGGA TGCAGGATAC AGGAACCAGG GTGCCAGCAC GGGCCTCCCT    93300

TCCGGTCCCT CCCACTGACC TAGCCGGGTC CCTCCAGCTG ATCCTCCCAG CTCTGAGCTC    93360

AGCAGCGTCA GGGGTCCCGG CCACTAGAGC AGCACATACT CAGCAGACAC GCTGAATGAC    93420

GAGCCACAGC TGCCTCATCG GCATGACTTG CACCTCATGT CTAGGAGACC CTGGTGOGCA    93480

GGAGATGGGC CTGCCATCCC ACAGCTGTCC CACAGCTGGG ACCCAGGGA GCCACTCGCC    93540

CCACCACCGT CGTGTCTGGA GAAGGGCTCA GACTCCCACG AAGTCGCACC CCAGCAGAAG    93600

TGGTAGTGAA TTCGCAGCGC ACTCAAGGAA GGGCTCTGCA CCCCCAAGAC CAGCAGCAAC    93660

GATGGGCTAC AGTGGCCCCC TTAAGTCTCC CTCTTCCACT TTCCCCTTAA GAGAGGCCCT    93720

CAGGACCTTG GAGGAACCCC TCTCCAACGT GGAAGTGTGG GTCCACATAG GGCTGCAGCT    93780
```

-continued

```
GTGGCCAGTG CAGGCATCTC TGGCCCCACT CTATTCTTCC TTCATGTTGG ACAACACTGC   93840

ACCAGCAGAT GGTCTCATTT TGGTTTCTGT GGGACCCACT TTGGCTGCAA AGACCCACAC   93900

TGCCAGCTCA CACCTGCCCA GGGCAGCCCA CACTGGGGAC CCACCAGGCC ATGGTGTGAA   93960

GTCCCGGCCA GCCTCGCCCC ACATGGCACA CCATAGCCAG TTCTCCTCCA GGGCTCCCTG   94020

CTCGGCCAAC CACAGCTCTC CGGATCCTGC TGCCTGACTC GACCTCTCCT CTCCCGTCCT   94080

CCCTGCCTTC CTGGTGCCGA CCCCCAGTGT GCATCCTGTA CCTCGACCTG TCTCAGCATC   94140

TCTGCCTGAG ACACCGGCCT GTGACAAGAT CATCATCATC TGTGTCACTC CCCAAGCATG   94200

CTGCGCACTC GACACACAGG CCCTGACTCA ACTTGTCCTC TCTGACTTCA GTGGTCCTAC   94260

AGCATCTATC AGAGATCACT TGGCCATGGG AGAAATGTCT TCTTGGCTAG AAGTCACAGC   94320

AGGAGGGGAC ACTTTCCGCG CGCCTAGGAA AGGGGAACTA GGATCAAAAA AGAGATCAGG   94380

ACCTGGCCAC TCAGCTCTAG AGATGGCATC AGGGCAGCCA AGGCACTGGG GACACCCCAC   94440

ACCCACTGTG CCAGCCTAGG GCAGGGAGCC CGAGCAAGCC ACAGGCTCTG CCCTCCTCAG   94500

TGCTGGACTC AGTGCCTGGC CCAGGCTGAG AAGGACATAA ACTCCAGCCTTCGCGGTGTG    94560

GGGAAGGGGC ACCACACTGG GATCTCAGAA ATGCCCAAAA CCTCTGTCAA AATAGGACAC   94620

TGCCGCTGTG AGACCCTGAG GAGTCTTCTG GTGATCATGG AAGAACAAAT CTTAAGCTAG   94680

AACTGAAGGA ACCTCATCAG GGCACAGGCA GCCATCCTGC CCTCCCCACA TCTGGTCTTT   94740

GCCATTTCTG TGTCCTGTGG TGGTCAGCAG CAAGGTCTCT GAGCCGAAAG GAGGCACTCA   94800

CTTTCGAGGA GTGCAGGGTC CCCAGGTCCC CACACTTTGT CTTGTCCTGA CTGAGAAAGA   94860

AACAGACTGC CCTGACCTCT CTGACTTGCC CAGCGAGGTT GCCCTTAGGC TCAAACCCAA   94920

CCCAGGGTTT GAACATTCCC AGACACTTGT AAGATGTTTA GGTTGTTAAC ATAATCTTCA   94980

GGTTTCAAAA CATTCAAAGA AACTAGCCCC AGCCCTGAAC CCAGATCCCC CCCCGCTTCA   95040

CGCATGACCA GTGAACACGC CCTTCTCTCA CTGGTCACCT GAGCATGCCG CACTCTGTCA   95100

ACAGGTTCCC CTAATACATG CTCTCATCTG ATCGCCTTGG CATTTAGTGA TTCTTTCCCT   95160

GGAATTCTCC ACTGGCCCCA TCGCAGGGAA CTCCCAAGTG GGAAACTCCC CTACCACCAC   95220

TTTTGGGGCA ACTTCAGCTA AGGGTTCAGC TGGGACAAAA CAGGGAGCCA CTCGGGAACC   95280

TGGGACAGGA CCAGAGAGAA AACCCGAGGG ACAGAGTGGG TAAGGAAAGC TGCTGAGGAA   95340

GCGCCCAAAG GGCACTCTGG AAAGAAGTGG CACTGGAGGG CTGGGGTGGG GGTGGTCCTG   95400

GCCAGGGAGT CTTACCTTGT CCCACAAAGA CTGCAGCTCT TCCTGCCCTC CTAAGTCCCA   95460

GAACATGAGC CGAGCCTTTC CGACATCCAC AGTGCCGACT GGGGAGAGGA GGAAACAGGC   95520

AAGGCTCATG ACCTTGGTCC TCGACACACC CAGTCCCAGC TCTCCCAGGG GATGGGCAA    95580

ACCATGCTGG TGCCACTCAA ATGAGACTTG ACAGGGCCC GACAGGGCTG TGGCCACGGG    95640

CCAGCTGGAC TGTGAATATC ACGGCATCCT CAAGGCCCCA AACCCACAGC CTGCTATTGA   95700

GACCCTTACT GTTTAGGCCC ACGGTGGTGG TGATTTTGGA TAGACTCATC CCCTTGTAGT   95760

TCTTGTTAAA TCGGGTTTTC GACTGCTCCA GGAAGGTCTG ACGAGAGAGG CAGAGGCGAA   95820

ACACATCAAG GAGGGGCTAT ACTGGCTTCC AAATATCCTT ACTCAGGTCT GTTCTTTAAA   95880

AGACAGAAAC AGAAACAGAG CAACACTCTG CTCTTCAGGA GGCTGGTGGT GACTATCCTG   95940

CCGTCTCAGG TGAAATTTGG CTTCCGTCTG CGTAGTGAAC GTGCAGCTGA CAGCACAAAA   96000

CCGAAGGGGG CGCCGCCAGG CCGTGGGAAA GGTGCGCGCA AGGGCGTGGG CACTCACCGT   96060

CTTCCCAGCA TTGTCCAGGC CCAGGATCAG GATGCAGTAC TCGTCCTTCT GAAACATGTA   96120

CTTGTACAAG CCCGACAGCA GCGTGTACAT CCTGCCCTGG GCACCCCAAC ATAGGTCAGT   96180
```

-continued

```
GTGCAGCCAG AAAGCACCTC CCCTCCCCG GGCTTCTCCA CGGTGGTCAG TGGCGCCCCA    96240

CGTCCAGCCG ACCGCTCAGG ACGAGAGCCT GGGGGCCATT CCCGACTCCT CGTCCCTCTC    96300

CCACCCCGTC CCTCTGTAAC TTCTCCCAGG TCAGCCGCCA CTGTGTCCTG CTCACAGCAA    96360

TGACTGCGAC CTCTCCGCAT ACACATCGGT TCCGGCCCCT CCCCTGCTCG CGGGACTACC    96420

CAGCCGGGTG TTCACAGTGA GCTCAGCCGC GCTCCCGCCC TCCCCCGAGG CTTCGCTCCC    96480

ACGCTTCACG CGCGCGGAAC CGGCAACACA CTCGCTGCAG CCCCGCCTGC GCCACGGCAC    96540

CCTCGAGCGC CAGCCCCGCG CCCCACCCGG GAGCACCGAG CCACCGGCGC GCTCCCCAGC    96600

AGCCCCTGCA GGCGCCGCGT AGGGACGCCC CATCACCCCA TTTCTTAAAA CGGGGACGGC    96660

CCTGGGGGA CCGGACTACA GGGCGGGTGA GCAGCGCCCC GGCTGCTCCT GGAGTGCACC    96720

TGGAGGCGCC GCCCGGCTGG CAGGGAACGA CTGCGAACCA AGAACCTCGG TCGCGGCCCC    96780

CGGCTACGTC CGCCCCAAGC CGCCGCCGCC AGCTCTGAGC CTCCCCGACA AGCAGCCAAA    96840

GCTGGCTCCT CTCACACCCG CGTCCCACCT CGAGTCCTGG GCCGCCCCTC GGGCCTCGCG    96900

CCTCACCCCA CAGCCTGCGC CCTACCTGCG TCCGCCGCCC CCTCGGAGCC GCTGCTGCTG    96960

ACCCCCGCTG ACCTCCGCTG ACCCCGCGCT AACCCCGCGC GGCGCCTGAC GGGACGCCGG    97020

CCGGCCTCAG GGAATGAGCT GAACCGCGTC CCAGCGGCCT CCGCGCTCCG CTTCCCGGCT    97080

GCCCCCGCCC GCCAAGCACT TCCGGAAGCG GCGGCGCTCG GGAGGAAGTG CCGATCGGCT    97140

GCTGGGGCGA AAAGGGGGCG CCGGGCCGCT CTACCCGGTG AGGCCGGCGG GCTCTCTGTG    97200

GCTGCGGCTG GGAAACCGCG CGGAGGAGGT GCCCGGCCGG CGACCAGGTG GCCGCGGTTT    97260

GCCGGGACGC GCCCCTGGCC AGACAGAAGA GACGCCGGGC GGGGGGGCGC GGCCCGCCTG    97320

GAAGGGGCGG GGCGCGGCGG GTGGGCTCGG CGGAGGCTGA GCCGGCGGGG CGCCCCGCGG    97380

CGAACGGGCT CCGCACTGAC GCGGGACCCC GCTACCGGCG AGCCCACGCC GGCTCGGAAG    97440

GGAAGCGCGG ACCCTGAGCG GGGGTACCCG GGCTGCGACC TCTGCCCTCG GAGCTGTGCC    97500

TCTGAGCCCG TGTCTCCCCG AGGGAAAGGG GACGTGCCCG TGCCCGTGCC CGCCCTCAGC    97560

CTGTGGCGTC GGTCCCGAGA CGCGGOGCTC AGCTGGCTTC TCTTCTTGCA GCCCTGGTCC    97620

AGCCCCTCCC TCTCTCAGCA TGGACCAGGA GAGCCTGCAG TCGGCCTTGC AGACCTACCG    97680

TGCGCAGCTG CAGCAGGTGG AGCTGGCCTT GGGCGCCGGC CTGGATTCGT CTGAGCAGGC    97740

TGACCTGCGC CAGCTGCAGG GGGACCTGAA CGAGCTCATC GAGCTCACCG AGGCCAGCCT    97800

GGTGTCTGTC AGGAAGAGCA GGTTGTTGGC CGCGCTGGAC GAAGAGCGCC CGGGCCGCCA    97860

GGAAGATGCT GAGTACCAGG CTTTCCGGGA CGCCATCACT GAGGCGGTGG AGGCACCAGC    97920

AGCGGCCCGT GGGTCCCGAT CAGAGACCCT TCCTAAAGCA GAGGCGGGGC CAGAATCTGC    97980

GGCAGGTGGG CACGAGGAGG AAGAGGGAGA GGACGAGGAA GAGCTGAGTG GGACAAAGGT    98040

CAGCGCGCCC TACTACAGCT CCTGGGGCAC TCTGGAGTAT CACAACGCCA TGGTGGTGGG    98100

AACGGAAGAG GCGGAGGATG GCTCGGCGGG TGTCCGTGTG CTTTACCTGT ACCCCACTCA    98160

CAAGTCTCTG AAGCCGTGCC CGTTCTTCCT GGAGGGAAAG TGCCCCTTTA ACCAGAACTG    98220

CAGGTAAAGC CCTTTGTTGT CAGATGCCAA CCTTAGGGGC GTAAGGGCA CGCACACACG    98280

GTCGGGTCAG GATCGCCCCT CCCTTTGCTT TGCAGTTTTG TCTCAGCTTC CTGGGGCAGG    98340

CGTGCTTTCA CAGCTGTGTC TGTGTTCAGG CGTCTACGTC TTCCTTCTGG GGTGAATCAA    98400

GAAGCATGGA AGGACGCCAG GCGCGGTGGC TCACGCCTGT AATCCCAGCA CTTTAGGAAG    98460

CCGAGGCGGG CACATCACCT GAGGTCAGGA GTTCAAGACC ACGCTGGTCA ACATGGTGAA    98520

ACCCCATCTC CTTAAAAACA CAAAAATGAA CCGGTCGTGG TGGCGCGCAC CTGTGGTCCT    98580
```

-continued

```
GGCTACTCAG GAGGCTGAGG CACGACAATT GGTTGAACCC AGGAGGCCGA GTTTGCAGTG    98640

AGTGCACATG CAGCCACTGT ACTGCACCCC GGTGCAGCAGT GCAAGGCTTA TGTGGAAGAG   98700

AGTAGGTCTC CAGCCTATCG TCAGTTTTTT TTTGGTGGTT GTTTPAATTT TTTTTGAGAC    98760

AGGGTCTTAC TTTGTCAACC AGGCTGGAGT GCAGTGGCAT AGTCCTGGCT CACTGCAGCC    98820

TGGACCTCCT GGGCTCAACC GATCCTCCTG CCTcAGCCCC CCTACGAGCT CGGCTACAGA    98880

CTCACGCTAC TACACCCACC TAATTTTTAT ATTACTATAA TTTTTTATCT TTTTTTTGAG    98940

ACGGAGTCTT GTTCTGTTGC CCAGGCTCGA GTGCACTGGC GTGATCTCGG CTCACTGCAA    99000

CCTCCGCCTC CCGGGTTCAC GCCATTCTCC TGCCTCACCC TCCCGAGTAG CTGGGACTAC    99060

AGGCGCCCGC CACCATGTCT GGCTAATTTT CTGTATTTTT AGTACAGACG GGGTTTCACC    99120

ATGTTAGCCA GGATGGTCTC AATCTCCTGA CCTCCTCATC CGCCCACCTT GGCCTCCCAA    99180

AGTCCTGGCA TGACAAGCCT CACCCACCGC CCCTGGCCTT TTTTTTTTGG AGACACAGTT    99240

TCACTCTCCT CACCCAGGCT GGAOTGTAGT CGCGCAATCT CAGCTTACCG CAACCTCTGT    99300

CTCCCGCGTT GAAGTAATTC TCTACCTCAG CGTCCAGAGT AGCTGGCATT ACAGGCGCCC    99360

GCCACCACAC TCGGCTAATT TTTTCTATTT TTAGTAGAGT CGGAGATTCA CCATCTTGGC    99420

CAGGCTCGTC TTGAACTCCT GACCTCGTGA TCCACCCACC TTCGCCTCCC AAACTGCTGG    99480

GATCACAGCC GTGAGCCACT GCGCCTGCCC CTGTTGTTAG TTTTATTCTC TAGAGTTCAA    99540

CTTTTAAATT TTACTTTCAT GGAGATTTTC AAACATACCC CAAATTAGAG AGTTTAGCAT    99600

AATCACCGCC CACGGTCCAT CATCCAATGT CCTCATTTAT TAATATTTTC CCAGTCTCAT    99660

TTTGTCTGTT CTCCCTGCCC TATTTTTTTC TTTCCTGGGC CATTTTAAAC CAAATTCCAG    99720

AAGTTACTGC TTTTTTCCAA TTATGAATAC TTCATAGTTG CATCTCTAAT CTAACTGATT    99780

AGGAAATTAC TTAAAAACTA ACTTTTTGCA AGTCCAAGTC CGATGTGAGG ACAAAAAAGA    99840

GTAACTTCTG TGTCATAATA GGTAACACAT TTAATGGTAA TACCTCTTCC ATATTCAAAT    99900

ATGAACAATT ATTACTGTAA TGTCTCTATT TCCCTAAGCG CATAGCTTTA TTTTTCCTCC    99960

TTTTTACTTT TCTCTTAGAA GAAATATTTA CCAAGCCTTC TAGTAGGTAA TTTTCTTTTT   100020

TAGCCAATAC TTCAGGCTGA CCGTGTAACC ATCCCTAGTT CTAGTTCTAC TTCTTTGAAT   100080

GTCTTCCTTT TTTTTTTTTT TTGAAACAGC GTCTTCCTGC TCTGTCACCC ACGCTGGAG    100140

GCAGTGGCAC AATCTCGGCT CACTGCAATC TCCGCCTCCC TGGCCCAACC CArCCTCCCA   100200

CCTCAGCCTC CCTAATAGCT CATACTACAA GTCTGCACTG CCACGCCCAG CTAATTTTTC   100260

TATTTTTTGT AGAGACGGCA TTTCACCATA TTACCCAGCT CTCGAATTCC TGATCCCTTT   100320

GATOAGAGAT CTGACACATC CCTGTGGTGC TCCCTCTGGA CCAGGCACTG CTCCAAGGGT   100380

TTCATATACT TTCATTCATC TGTGCAACAG CCCTGTAGGT AGGCCCTGCA GTCACAGCAT   100440

CTGACAGAGG AGGAAACAGG AGTAGAAGAA GTGAGTGGTC CAGGGCTTCA AGGCTCAGAG   100500

GGCTCCAGTT GCCCCCAGCC CTCGTTCCGT CCCCTGCTCC ACCCAGTGCT GCTTGCCATG   100560

TCGGCATCAG GCCTGATCTG AAAGCTTCCC GAGCATCTTA CAGACGTCCA CCTTGCCACC   100620

ATTCAGGACT GATAAGTTCT CTTGGATTTG CGTTGGACCT TTTTTTTTTT TTAAGATGG    100680

AGTTTCACTG TTGTTGCCCA GGCTACAGTA CAATGGCACG ACCTCCACCT CCTGGGTTCA   100740

AGCGATTCTC CTGCCTCAGC CTCCCAAGTA GCTGGGATTA CAGGCGCCTG TCACCACGTG   100800

GTGCCCAGCT AATTTTTATA TTTTTAGTAG AGGCAGGGTT TCACCGTGTT GGCCAGGCTG   100860

GTCTCGAACC CTTGACCTCA GGTGATCCCG CCTTGGTTTC CCAAAGTGCT OGGATTACAG   100920

GCATGACCCA CCACACCCGG CCCAGGATTT CTTTATATAT TCTGGATATC ATCCCTTATG   100980
```

```
                      -continued
AAGTATATAG TTTGCAGATA TTTGCTCCCA TTGTTTGGGT TGTCTTTTCA CTTGATATAG   101040

TGTCCTTTGA TGCACAAACA TTTTAAATTT TGATGCAGTG CAATTTATTG TTTCTTTATT   101100

GCCTATGTTT TTGTCATCAG GTTAAGAAA CCACCTCATC CATAGTTATG AGGATTTTCA    101160

CCTATGTTTT CTTCTAAGAG TTCTGTAGTT TTAGCTGTTA AATTTAGGTC TTTGATCCAT   101220

TTTGAGTTAA TTTTTGTATA TGTTATTAGG TGAGGCTCCA CTTTATTCTT TTGCATGTGG   101280

ATTTCCAGTT TTCCCAGCAC CATTTGTTPA AAAGACTGCT TTTTCTCCAC TGAATGGTCT   101340

TGGCACTTTT GTCCAAAATC AATTGGCAAT ATATGTAAGG GTTTATTTCT GAGCTCTCTC   101400

TCCTGTTCCA TTGGTGTATA TGTGCCAGTA CCACACTGTT CTGATTATTA TAGCTTTGTG   101460

ATAAGTTTTA AACTCAGGAA GTGGTAGTTA TTCACCATTT GCTCCTCTTT TTCAAGTTTG   101520

TTTTGTTTCT GGATCCTTTG CAATTTCATA TGAATTTTAG GATCGGCTTG TCCAATTCTC   101580

CATAAAAGAC AGTTTGAATT TGATATGGA TTGCATAGAA TGTGTACATC TGTTTGGGGC    101640

ACATTGTCAT CTTTACAATA TTAAGCCTTC TGGCTGGGTC TGGTGGCTGA CGCCTGTAAT   101700

CCCAGTACTT TGGGAGGCTG ACGCGGGCAT ATCACTTGAG GTCAGGAGTT CAAGACCAGC   101760

CTGGCCAACG TGGTCAAACC CCGTCTCTAC TAAAAATAAA AAACAAATTA GTCGGAGGTG   101820

GTGCACACCT GTAATCCCAG CTACAGGAGA GGGTGAGGCA GGAGAATCGC TTCAACCTGG   101880

GAGGAGGAGG TTGCAGTGAG CTGAGATCAT GCCACTGCAC TCCAGCCTGG GTAACAGAGG   101940

GAGACTCCAT CTTAAACAAC AACAATAACA GAAGAAAAAA ACAGTATTAA GTCTTCCAAT   102000

TCATGAATGA AGGATCTGTC CATTTATTTA CGTCTTTAAT TTCTTTCAAC AGTATTTTGT   102060

ACTGTTCAAG TCTTGCACAT TCTTGGTTAA ATAAGTATTA TTTTTGATGC TTCTCTAAGG   102120

AATTGTTTTT CTTTTCCTTT TTTTTTTTGA GACAGAGTCT TGCTCTGTCA CCCAGGCTGG   102180

AGTGCAGTGG CACAATCTTG GCTCACTGCA ACCTCTGCCT CCCGGGTTCA AGCAATTCTT   102240

CTGCTCAGCC TCCCAAGTAG CTGGGATCAC AGGTGCCTGC CACCACACCC AGCTAATTTT   102300

TTTTTTTGAG ATGGAGTCTT GCTCTGTTGC CCAGGCTCGA GTGAACTGGC CAATCTTGG    102360

CTCACTGCAA GCTCCACCTC CCGGGTTCAC ACCATTCTTC CGCCTCAGCC TCCTGAGTCG   102420

CTGGGAATAC AGGTGCCTGC CACCACGCCC AGCTAATTTT TTGTATTTTT AGTAGAGATG   102480

GGGTTTCACC ATGTAGCCAG GATGGTCTCG AACTCTTGAC CTCAGGTGAT CTGCCTGCCT   102540

CGGCCTCCCA AAGTGCTGGG ATTACAGATG TGAGCCACTG TGCCCGGCTC GAGTTGTTTT   102600

CCTTAGTTAC ATTTTCACCC TGTTTGTTCC TACTATATAG AAATACAAGC TGGGCACCGT   102660

CGCTCACGCC TGTAATCCCA GCACTTTGGG AGGCCAACGC GGGTGGATCA CCTGTGGTCA   102720

GGAGTTCGAG ACCAGCCTCC CCAACATGCT CAAATCCACC CTCTATTAAA AATACAAAAA   102780

TTAGTCTGGC ATGGTGGCAC GTGCCTGTAA TCCCATCTAC TCAGCAGGCT GAGGCAAGAG   102840

AATTGCTTGA ACCTCCCAGC CGGAGGTTGC ACTCAGCTGA GATCGCGCCA TTGCACTCCA   102900

GCTTGGGAA CAAGAGTGAG ACTTCATCTC AAAAAAAAA AAAAGAAAT ACAGTGGATT      102960

TTTTTATCTT AATCCTGTAT TGATTGCTGA ATTGGTTTAT TACTCCTAAT AGGATTTTTT   103020

ATGCACTATT TAGGATTTTC GATATATACA ATCATATATA TTCAATATAT ACAATTAATA   103080

TATATGTGAA TAGAGATAAT TGTAGTCTTT GTTTCTAGTT TGCATCGCAT TTATTTCTTT   103140

TTCTTGCTTA ACTGCCTTAG CTAGAACTTC AAGTACGATG TTGAATAAAA GTGACTAGAG   103200

CGGGCCGCCG GTCGTGGCTC ACACCTGTGT TCCCAGCACT TTGGCAGGTG GAAGTGGGCA   103260

GATCACTTGA GATCAGCAGT TTGAGACCAG CCTGGCCAAC ACGGCGAAAC CCCATCTCTA   103320

CTAAAAATAC AAAAATTAGC TGGGTCAGGT GATGTCCACC TGTAGTCCCA GCTACTTGAG   103380
```

```
                              -continued
AGGGTGAGAC ATGAGAATTG CTTCAACCTG GGGGCCGGAG GTTGCAGTGA CCCAAGATCA    103440

TGCCACTCCA CTCCAGCCTG CACCACAGAG CAAGAACCCT GTCTTTAAAA AAAAAAAAAA    103500

AAAACTGGCT AGAACAAACA TCTTTATCTT GTTCCTGATC TTAGGTGGAA AACTTTTTTG    103560

TTCCTGATAT TAGGTGGAAA ACTTTTAGTC TTTCACTGTT GAATATGATG TTACTTGTAG    103620

GTTTTCTGTA GATTCCCTTT ATCGAGTTGA GGAAATTCTC TTATATTCAT AGTGTGTTGA    103680

GTGTTTTTTA TCATGAAAGG CTCTTGATTT TTTTTTTAAA GATAGGGTCT TGTTCTGTCA    103740

CCCAGGCTGG ACGGCAGTGG CATGATCATG GCTCACTGCA ACCTCGAATT CCTCGGCTCA    103800

GGGGATCCTC CTACTTCATC CTCCTGAGTA CCTCAGACTA CAGCCATGAG CCACCATGCC    103860

CAGCTAATTT TTTAATTTTT CTGTAGAGGT AGGGTCCTGC TTTCCTGCCC AGGCTGGTCT    103920

TAAACTCCAG GGCTCAAGCA ATCCTGCCTC AGCCTCCCAA AGTGCTGACA TTACACGCCT    103980

GAGTCACTGC ACTCCACCCA GCTGTGTGGG ATTTTTCAAA TGCTTTTTTC CTTTACATGA    104040

TCATGTGTCG TTTTTTTCCT TTCATTTTCT TAATCTGGTA TATTGATTTT CGTATGTTCA    104100

ACCATCCTTG AATTCCTCAG ATAAAGCACG CATATTCATG GCGTATTATC TCTTTATTAT    104160

TATTTTTTTT GTAGAGATGA GATTTCACTC TGTTGCCCAA GCTGGTCTCA AACTCCTGGG    104220

CTAAAGTGAT CCTCCTGCCT CAGCCTCCGA AAGCGCTGGG ATTATAGGCA TGAGCCACTT    104280

GGCCCTATCT TTTTTCTTTT TCTTTTTTTT TTTTTTTTCA GACAGACTCT CACTCTGTCG    104340

CCGGGCTGGA GTGAGTGGCG CGATCTCGGC TCACTGCAAC CTCCATCTCC CGGGTTCAAG    104400

CAATTCTCCT CCCTCAGCCT CCTGAGTAGC TGGGACTACA GGTGCCCGCC ACTATGCCCA    104460

GCTAATTTTT TGTGTTTTTA GTTGAGACGG TGTTTTGCCA TGTTGGACAG GCTGGTCTTG    104520

CACTCCTGAC CTCGTGATTC ACCCACCTTG GCCTCCCGAA GTGCTGGGAT TACAGGCATG    104580

AGCCACCGCA GCGAGCCTTA TCTTTTTAAC AGTTAAAAGT TTAAGGCCTT ATCATGTAAT    104640

AACATTGCTG GATTTCATTT GCTGCTGTTT TGTTGAGAAT ATTTCCATAA GTATTGATAA    104700

GGCATATTGG TCTGTAGTTT TCTTTTCTTC GCATGTCTTT GTATACCTTT CATGCCAGCA    104760

TAATATTGGC CTCATAGAAT GAGTTAGGAA GTATTCTTTA TATTATGGGA AGAGGTAAAA    104820

AGGGATTGGT GTTAATTCTT CTTCAAATCT TTGATAGAAT TCAACAGTGA AGTCATATA     104880

ACAATCATAT ATATAGAGAG AGAGAGAGAG AGAGATGGAC TTTTCTTTTC TTGGAAGTTT    104940

ATTGACTATT GATTCAATTT CCTTATTGAA ATTGACTTTT CTTTTTGGAA GCTAAAATGT    105000

ATAACTGTAG TGAAAGTTTC TGAACTTTTC TTTCATTGGA AGTTTTTTGA CTACTGATTC    105060

TTTATTTGTT ATAGGTCTAT TCAGATTTTC TGTTTCTTCT TGAGTCAGTT TGGTCTCGCT    105120

CTGTCCCCCA GGCTGGAGTG CAGTGGTGCC ATCTTGGCTC ACTGCAACTT CTACCTCCCG    105180

AGTTCAAGTG ATTCTCCCAC CTCAGCCTCC CCAGTATCTC GGACTACAGG CGCACGCCAG    105240

CATACCTGGC TAATTTTTGT ATTTTTAGTA GGAACACCAT TTCACCATGT TGGCCAGGCT    105300

GGTCTCGAAC TCCTGACCTC AGGTGATCCA CCCGCCTCGG CCTCACAAAG TGCTGGGACT    105360

ACAGACATAA GCCACCGCGT CCAGCCTTGA GTCAGTTTAG ATAGTTTGCA TGCATGTTTC    105420

TAGGAATTTG TCCATTTTGT TTATGTTATC TAATCTGTTA CCATACAATT GTTCATAGTA    105480

TCCTTTTATA GCCCTAGTTA TTTCTGTAAG ATCAGTAGTA ATAGCTCCAC TTTCTCTCTT    105540

GGTTTTAGCA ATTTGAGTCA TCTCTTTTCT TCTTCTTTTT TTTTTTTGA CATGGAGTCT     105600

CACTGTGTCA CCCAGGCTGG AGTGCAGTGG CATGATCTTG GCTCACTGCA ACCCTGCCT     105660

CCCACGTTCA AGCAATTCTG CCTTAGCCTC CTGAGTAGCT GGGATTACAG GTGTCAGCCA    105720

CCACACCCAG CTAGTTTTGT TTTGTFTTTT TGTTTTTGAG ACGGAGTCTG TTTCTGTCTC    105780
```

-continued

```
CCAGGCTGGA GTGCAGTGGT GCAATCTCAC TCATTGCAAC CTGCGACTCC CAGATTCCAG    105840

CAATTCTPCCT GCCTCAGCCT CCCGAGTAGC TGGAACTATA GGCGTGCACC ACCACGCCTG   105900

GCTGATTTTT ATATTTTTAG TAGAGATGGG ATTTCACCAT GTTGGCCAGG CTGGTCTTGG    105960

ACTCCCTACC TGAGGTGATC CGCCCACCTT GGCCTCCCAA AGTGCTGGGA TTATAGGCAT    106020

GAGCCACCAT GCCCAGCCAG TTTTTGTATT TTTAGTAGAG ATGCGGTTTC TCCCTGTCGG    106080

CCAGGCTGGT CTTGAAATCC TGACCTCAGG TTATCCACCA GCCTTGGCCT CCGAAAGTGC    106140

TAGGATTACA GGCATGAGCC ACCACGCATG GCCTGTCTTT TCTTCTTGGT CATTTTCGCT    106200

AAAGGTTTGT CAATTTTGTT GATCTTTTTT CTTGCTGATC TCTATTGTTT TCCCATTCTG    106260

TTTCATTTAT TTCCATTTTA ACCTTTGTTT CCTTTTTTCT GCTGGTTTGG GTTTAATTTG    106320

CTCTTTTTTT CCCCTAATTT TTCAAGGTAT ACAGTTAAGT TATTGATTTG AGATCTCTTT    106380

TTTCTTTTCT TTTTTTTTTT TTTTTTTTTT TTTGGTTGCT GTTGAGATGG AGTCTCCCTC    106440

TGTCACCCAG ACTGGAGTGC AGTGGCATGA TCTCAGCTCA CTGCAGCCTC CGCCGCCCAG    106500

GCGATTCTCC TGCCTCAGCC TCCTGAGTAG ACGTTTCCCG GCCAAGGTGT TTCTTTTTGA    106560

ATGTAAGCAT TTACAGCTAC AGATTTCCCT CTAAACACTG CTTTCACTGC ATTCCATAAG    106620

ATTGTTTTTT GTTGTTTTTT GTTGTTGTTT TGTTGTTTGA GACACAGTCT CACTCTGTTG    106680

CCGTTTGGAG AGCAGCGATG CGATCATAGC TCTGTAGCCT TGACCTCCTG GACTCAATCA    106740

GTCCTCCTGC CTCAGCCTCC CAAGTAGCTG GGACTACAGG TGTACACCAC TGCACCTAAC    106800

TAATTTCTTT TATAAGTTTT TGCAGAGCCC AGGCACAGTG GCTCACACCT GTAATCCCAC    106860

CACTTTGGCA GGCCAAGGTG GGTGGATCAC CTAAGGTCAG GAGTTCGAGA CCAGCCTGGC    106920

CGACAGGGAG AAACCCCATC TCTACTAAAA ATACAAAAAT TAGCTGGGCG TGGTGCCAGG    106980

TGCCTGTAAT CCCAGCTACT CAGGAGGCTG AGGCACCAGA ATCGCTTGAA CCTGGGACGC    107040

AGAGGTTGCA GTGAGCCAGC ATCACACCAT TGCACTCCAG CCTCGGTAAC AAAAGCAAAA    107100

CTCCATCTCA AGAAAAGAAA AAAAAAAGTT TTTGCAGAGA CAGCGTATCA CTTTGTTCCC    107160

CAGGCTCGTC TCAAACTCCT GACTTCAAGG AGTCCTACTC CCTCAGCCTC CCAAACTCCT    107220

GAGATTATGG GCAAGAGCCA CCGCACCCTG CCACTTGGCT GTTTTGTTCT GTTGTATTTC    107280

CATTTTCATT GATCTCAAGA CATCCTAATC TCCCTTTTGT TTTTTTGTTC CACTTACTGC    107340

TTATTCAAGA GTGTCTTTAT TTCTGCATAT TTGTAAATTT TCCAAAAAAC TTTTTCTTTC    107400

TTTTTTTTTT GAGAAAGGCT CTTGCTCTGT CGCCCAGGCT GGAGAATGGT GGTGCACAAT    107460

CTTGCCTCAC TGCAACCTCT GCCTCCCGGG TTCAAGTCAT CCTCCCACCT CAGCCTTCCC    107520

AGTAGCTGGG ATTACAGGCA CACACCACCA CACCTGCCTA ATTTTTGTAT TTTAGTCTTA    107580

ACGTGCTGGT CAGACTCGTC TCGAATTCCT GACCTCAGGT CATCTCCCCG CCTTGCCCTC    107640

CCAAAGCACT CGGATTACAG GCCTCAAACA CCATCCCCAC CCCCCAATTT TTTTTTTTTA    107700

ATAGACACAA GCTCTCACTC AAGCCCAGGC TGGTCTTGAA CTCCTGAGCT CAAGCTGTCA    107760

TCCCTCCTCC GCCTCCCAAG GTGCTGAGAT TACAGGTGTC AGTCACAGTA CCTGGCCTTC    107820

TTTCAACACT TTAAAAATGC CATCTTGGCT GGGCACGCTC GCTCACCCCT GTAATCCCAG    107880

CACTTTGGCA GGCCGAGGTG GGCAGATCAC GAGCTCAGGA GATCAAGACC ACCCTGGCTA    107940

ACATGGTCAA ACCCTGTCTC TACTAAAAAT ACAAAAAATT AACCAGGTCT GGTGGCACGT    108000

GCCTGTACTC CCACCTACTC CGGAACCTGA AGCAGGACAA TGGCGTGAAC CCGGGAGGTG    108060

GAGCTTGCAG TGAGCTCAGA TCACACCACT GTACTCCAGC CTGGGCAACA GTCCGAGACT    108120

CCGTCTCAAA AAAAAAAAA AAAATGTCAT CTCACTGCCT TCTGGTCCAA TACTTCTGA    108180
```

-continued

```
TGAGAAATTC GCTGTTAATC TTATTGACCA ACATTTATAT ATTCACTAGT CACTTGTCTC   108240

TTGCTCTTTT AGCACATTCT CTATCTTTGG GTTTCAGCAG TTTGATTATA ATGTATCAGT   108300

GTGGATCCCT CAATTTATAA GCTACTTGGA GTTCATTGGA CTTCTTGGAT CTGTAAATTC   108360

ATGTCTTTCA TTAAATTTGC AAAOTTTCAG CTACTATTCT TTGCATCTTG AAATACTAGT   108420

TTTGTTTCTT TCTGTCTGTT TGCCGCTTAT GGAACTTTAT GCATACATTG ATGTGCTTCA   108480

TGGTGTAGCA CAGGTCCCTT GGGCTCTAGG CATTTTTCTT TGTTCTTTTT TTCTTTCTGC   108540

TCCTCATTTT GCATAAAATTC AGCTGACCTG TCCTCAAGTT CACTGTTTCT TTCTTCTTCC   108600

TTCTCAAATC TGCTGTTGAA ACTTCTGGTG AAATTTTCAC TACAGTTACT GTACTTTTTA   108660

CCTCCAAAGT TTCTATTTGG TTTCTTTCTG TAGTAATTAT CACTTTACTA GTATTCTCTA   108720

TTTGGTTACA CATGGTTCTT TTGTTTTCCT TTAGTTCATT ATCCATGGTT TCCTTTATTT   108780

TTAAATTTCT TTTTATTTAG TTATTAATTT TTTTTTTTTT TGAAOCGGGG TTTCACTCTT   108840

GTCACCCACG CTCGCAGGCA ACGTCACAAT CTTCGCTCAC TACAACCTCC GCCTCCTGGG   108900

TTCAAGTGAT TCTCCTGCCT CAGCCTCCCA AGTAGCTGGG ATTATAGCCA TGTGCCACCA   108960

CACCCACCTA ATTTTTGGTA TTTTTAGTAG AAACTGGGTT TCACCACATT GGCCAGACTG   109020

GTCTTAAACT ACTAACCTCA GGTGATCTGT CCGCCTCAGC CTCCCAAAAT GCTGGGATTA   109080

CAGATCTGAG CCACTGTGCC CAGCCTCTPT TTTTAGTGTA TTTAAGGTAA TTGATTGAAA   109140

GTTTTTCTCT AGTCATTCAA ATGTCTAGGC TTCCTCAGGA ACAGTTTCTA TTAATTTCTT   109200

TATTTTTAAA AAATTTTTTT TAATTTTCTT TTTTTTTTAG ATGGAGTCTC ACTCTATAGC   109260

CTACCCTGGA GTGCAATGCC TTGATCTTGG CTCACTGCAA CCTCTCCCTC CTGGGTTCAA   109320

GCGATTCTCC TGCTTCAGCC TCCTGAGTAG CTGGGACTAT AGGTGCGTCAC CACCACCCCT  109380

GGCTAATTTT TTGTATTTTC AGTAGAGACA TGGTTTTGCC GTGTTAGCCA GGATGGTCTC   109440

GATCTCGTGA CCTCATCATC CTCCTCCCTC GGCCTCCCAA AGTGCTGGAA TTACAGGTGT   109500

GAGCCACCGC GCCCAGCCTA TTTTTTATTT TTTGAGACAA ACTCTCCCTC TCTCACCCAG   109560

GCTGTACTGC AGTGGCACAA CCCTGGCACA CTCCAGCCTT AACCGTCCAG GCTTAAGTGA   109620

GTCTCCCACC TTAGTCTCCT GAGTAGCTAG AACTACAAGC ATGTGCCACC ATGCCTGGCT   109680

GGTTGTGTTG TTACTGTTTT AGACACACOG TCTTGCTACA TTTCTCTGAC TGGTCTTGAA   109740

CTCCTGGGCT CAAGCAGTCA TCCCACCTTG GCCTCCCAAG GTGTTGAGAT TACAGGTGTG   109800

AGCCACCGCA CCCGGCCTGT TAATTTCTTT ATTTCCGGTG AATCGGCCAC ACTTTCTTGT   109860

TTCTTTGCAT GCCTTGTAAT TTTTTGTTGA AACCTGCACA ATTTGAAGAT GATAATGTGG   109920

TTACTTTGAA AATCAGATCC TCCGCCCTCT GCAGGGTTCA TTGTTGCTGT TGTTGTGGA   109980

TTGTCGTTTC TCGTTTGTTT AGTTACTTTC CTGACCTTTT TAAATAAAGA CTATATTCTG   110040

TCAGGGGTGC TTGTTTCTGT TCTTTTAGCT TAGTGGTTAG CTTGTGCTTT GAAAGAGAT    110100

TCTTTAAATA TCTAGTCGCA AAAAGGATAA AGAGGCCGGG CGCAGTGGCT CACGCCTGTA   110160

ATGCTAGGAC TTTGGGAAGT GGAGGCGGGT GGATCACTTG AGGTCAGGAG TTTAAGATCA   110220

GCCTGGCCAG TATGGTGAAA CCCTGTCTCT ACTAAAAAWA CAAAAATTAA CCGGGCATGG   110280

TGGCACCTGC CTGTAGTCCC AGCTACTGGG AAGACTGAGG CAGGAGAATC GCTTCAATCC   110340

AGGCGGCGCA GGTTGCAGTG AGCTGAGATT GCGCCATTGC ACTCCAGCCT GGGCAACAGA   110400

GCGAGACTCT GTCTCAAATA AAAAAAAAAA AAAAGGATA AAGAGTGTCT TCCATCCTTT    110460

CCAGGTTGCC TCTGTACTGG GGCAAGTCCT TCAGTGTCCG CCAGGCTGTT CACCCCTTTT   110520

CCTCAGCCTT TACTTCTCGC TCCCATGGAG CCTAAGGATG AACCAGACGT GAAAGTTGAG   110580
```

```
                     -continued
GGCCTCCTCA GGTGTTTCTG AGCCCCTGTC TAGCCCCAGC TGTGTGCATG GCCTTCTGGA  110640

TTTCCAACCA TGAACAGGAG CTTTCCAAAG CCCTTAGACC TTCATGTAGC TCTTTTCCCA  110700

GCCTCTTCCT TCCTAGGCTT TTCTGTCAGC TCTTTGCCCA TCTGTTGTTG TCCCTCCCCC  110760

ACAACTTCAG GTAGTATCTA CCTGTAAATG CCTTCAGGCC ACGCGCGGTG GCTCATACCT  110820

GTTATCCCAG CACTTTGGGA GCCCGAGGCG GGTGAATTCC TTCACGTCAG GAGTTCGAGA  110880

CCAGCCTGGC CAACATGGTG AAGCCCCGTC TCTAGTAPAA ATACAAAAAT TAGCTGGGCG  110940

TGGTGCGTCC CTGTAATCTC AGCTACTCGG GAGGCTGAAG CAGGAGAATT GCTTGAGCCT  111000

GCGAGGCGGA GGTTGCACTC ACCTGAGATC GTGCCATTGC ACTCCACCCT CGGCGACACA  111060

GTGAOACTCC ATCTCGGGCA AAAAAAAAAA AAAAAAATGC CATCAACACC ACGACCCTGG  111120

AGGCTGCCCC ACCCCTCAGA GAGTTCGAGG GCGTGAAACA AAGGCAAGCC CTTCACCGAC  111180

ACACTAGAAA CATCCAAATG CATAAGCAGG ATTCCTTGAG AAAAGCTCTG TATCATCCCT  111240

TCTGACACCA GCAAGCCACA TCAGAAATAC AGGTTGCCTT CCCCATGGCT ACATGTGAGC  111300

TGGTAGTAGT GGCTGAGCAG AAATAGCCCA GCTCTCCTCC TCAAATTTAG CAGGGTCTTA  111360

CTTCATTGAG CAGTCATCTG GTTCCTAGAC ACCAGAGTTA CAGAAAAGTT TATTGGGACG  111420

TTTTGACAGT TTAATAGAAA AAAGTTTATT GTGACAGTTT TGACACCTGA ATAGAAAAAA  111480

GTTTACTGTC ACAOTTTTGA CAGCAGAATA GTTGCTTTGC TGCACACACG GATCTTTGGA  111540

CCTGCCAACT CCATCATTTT GGTGATATCC AGCTCTGTTG CTCAATTTTT AGCTATGCTG  111600

TTTTAAGTTA TTTTCTTAGT CGTTGCTCTA GAGATGACAA TGTGCATCTT TAACTTACCA  111660

CAATGTACTT CACATTATTA CTAACTTAAC ACTTAAAGTA CAGCATTTTT TTTTTTATCG  111720

ACTTTCACTC TGTCACCCAG GCTGGAGTCC AATGGTGTGA TCTCGGCTCA CTCCAACCTC  111780

CGCCTCCCAG CTTCACGCCA TTCTCCTGCC TCAGCCTCCT GAGTAGCTGG GACPACAGGC  111840

ACCCCCACCA CACCCGGCTA ATTTTGTATT TTTAGTAGAG ATGACCTTTC ACCATQTTGG  111900

TCAGCCTGGT CTCGAACTCC TGACCTCACG TGATCCGCCC ATCTTGGCCT CCCAAAGTGC  111960

TCGGATTACA CGTGTGACCC ACTGCACTCA GCCTAACTAT CGCAACCTGT CTATAACATA  112020

GATCTACTTC COTTOTACTA TCACATAGTT CCCCCTCCAT TTTCCTATAG CACAGTCCCA  112080

ACCTCCCTTT TCCTCTGACA TAGTTCCATC CTCCCTCCTC CTATGACGTC CTCCCTTCTC  112140

CTCTGGCATA CCTCCATCCT CCCTTCTCCT ATGACACAGC TCCATCCTCC CTTCTCCTCT  112200

GACACAGCTC CATCCTCCCT TCTCCTATGA CACACCTCCA TCCTCCCTTC TCCTCTGACA  112260

TACCTCCATC CTCCCTTCTC CTATGTCATA GCTCCATCCT CCCTTCTCCT CTGACACAGC  112320

TCCATCCTCC CTTCTCCTCT GGCATAGCTC CATCCTCCCT TCTCCTATGA CACAGCTCCA  112380

TCCTCCCTTC TCCTATCACA CAGCTCCATC CTCCCTTCTC CTATGACACA GCTCCATCCT  112440

CCCTTCTCCT ATGACACAGC TCCATCCTCC CTTCTCCTCT GGCATAGCTC CATCCTCCCT  112500

TCTCCTCTCA CATAGCTCCA TCCTCCCTTC TCCTCTGACA TAGCTCCATC CTCCCTTCTC  112560

CTCTGACATA GCTCCATCCT CCCTTCTCCT CTGACATAGC TCCATCCTCC CTTCTCCTCT  112620

GACATAGCTC CATCCTCCCT TCTCCTCTGA CATAGTTCCA TCCTCCCTTG TCCTCTGACA  112680

TAGCTCCATC CTCCCTTCTC CTCTGACATA CCTCCATCCC CTCTTCTCCT TCATGTATTA  112740

TTGCCATATA TACATTTATG TATGTTATAA CTTCAGCTCT TCAGCGTTAT AATTATTGCT  112800

TCAAAAGTAT TTTCAAAGAA GTTGCCTGCA GGCAGTGGCT TATGCCTTTA ACTCCAGCAC  112860

TTTTCGGGCC TGACGTGGGC AGATCGCCTG AGCCAGGCAG TTGGAGACCA GCC2TGGGCAA 112920

CATGACGAAA CCCATCTCCA CCAAAATTAC AAAAAATTAG TCTGGCATGG TGCCACGCGC  112980
```

```
                                                 -continued
CTCTAGTCCC AGCTATTTGG GGGAGGATCC CAGCTAAGGT GGGAGGATCA CTTGAGCCTG   113040

GGAAGTCAAG GCTGCAGTCA GCTGACATTC TGCCACTGCA CTCCAGCCTG GGTGCAGATC   113100

TTATCTCAGA AGTAAAGGCA CTAGGAATGC TGGCTTTTAT CTCTAATCCC ACCACTTTGG   113160

CAGCCTGAGG TCAGTCGATC ACCCGAGCTC AGGAGTTTAA GACCACCCTG GCCAACATGC   113220

TCAAACCCCG TCTCTACTAA AAATACAAAA AGTAGCCGGG TCTGGTGGTG GGTGTCTGTA   113280

ATCCCAGCTA CTCGGGAGGC TGAGGCAACA GAATCGCTTG AACCTGGGAA GCGGAGGTTG   113340

CAGTGAGCAA GATCCCACCA CTGCATTACA GCCTAGATGA CAGAGCGAGA CTCTGCCTAA   113400

AAAAAAAAAA AAAAAGAAAA GAAAAGAAAT TAAGATCTAG ACACTGTCGT TCATGCCTCT   113460

AATCCCAAAG CCTTCGCAGG CCAAGGCAGG AGGATCACTT GACGCCAGGA GTTCAACACC   113520

AGCCTGCGCA ACATAGCGAG ACTCCATCTC TATTTAAAAA AGAAAGAAAT TCAAAGAGAA   113580

AAAAAGTATA CTTGTTTTTT TGTATCATCC ATATTTTACC TTTCTTTTTT TTGCCCCTTT   113640

TTCTTTCCTG TGAATTTGAG TTACTGTCTA GTGTCATTTC CTTTTAGTCT GAAGAACTTC   113700

ATTTAGAATT TTTTTTTTTT TTTCAGACAA AGTCTCACTG TGTTGCCCAG GCTCCACTGC   113760

AATGGTGCAG TCTCAGATCA CTGCAACCTC TGCCTCCCTG GTTAGAGTGA TTTTCCTGCC   113820

TCAGCCTCCC AACTACCTGA GACTGCAGGC ACCTGCCACC ACCCCCAGCC AATTTTTTTG   113880

GTATTTTTAG TAGAGACAGG GTTTCACTAT GTTGGCCAGG CTCGTCTCGA ATTCATGACC   113940

TCATGATCTG CCTGTCCTGG CCTCCCAAAA TCCPGGGATT ACCATGACCC ACCACGCCCA   114000

CCCCATTTAC AATTTCTTTT TTTTTPTTTT TTTTGAGATG GGGTCTCGCT CTTGTTTCCC   114060

ACGCTGCAGT GCAGTGGCAC GATCTCGGCT CACTGCGACC TCCGCCTCCC GGGTTCACGC   114120

CATTCTCCTG CCTCAGCCTC CCCAGTAGCT GOCATTACAG GCGCCTGCCA CCACGCCCAC   114180

CTAATTTTTT GTATTTTTAG GAGAGATGGG GTTTCACCAT GTTAGCCAGG ATGGTCTTGA   114240

TCTCCTCACC TCGTGATCCG CCCGCCTTGG CCTCCCAAAC TGCTGGGATT ACAGGCGTGA   114300

GCCACCGCGC CCGGCTAGAA TTTCTTGTAG GACAGGCTTG CTAGCAACCA ATTCAGTCTT   114360

TATTTGGGAA TGTCTTTATT TCAGCTTCAT TTTTTGAAGG ATAGTTTAGC TGGCTATACA   114420

ATTATTAATT GATCATTCTT TTCAGTGTTT AAAAGTGTCA TCATGCTACC TTCTGGGTTC   114480

CATTGTTTCT GATGAGAAGT CATCTGTCAA ATTGTCCCTT TGTACTTGAA GAATTATCTT   114540

TTTTTCTCTT GATGTTTTCA ACATTTTCTC TTTGTCTTTG GCCTTTAGTA GTTTGTGATG   114600

TATCTAGGTG TGGATCTCTT GGTGTGCATC GTATTTGGGC TTCAGTAACC CTCTTAGATT   114660

CATACATTAA TGTTTTGTTT TCTTTTACCA AATTTGGACA CTTTTTACTC ATCATTTCAA   114720

CAAATTTTTT TCCTGCCCCT CTCTCATCTC CTTTTGGGAG TACCACTGCA TCTATGTTCG   114780

TGTGCGTTCT CTA.                                                    114793
```

Figure 5B:
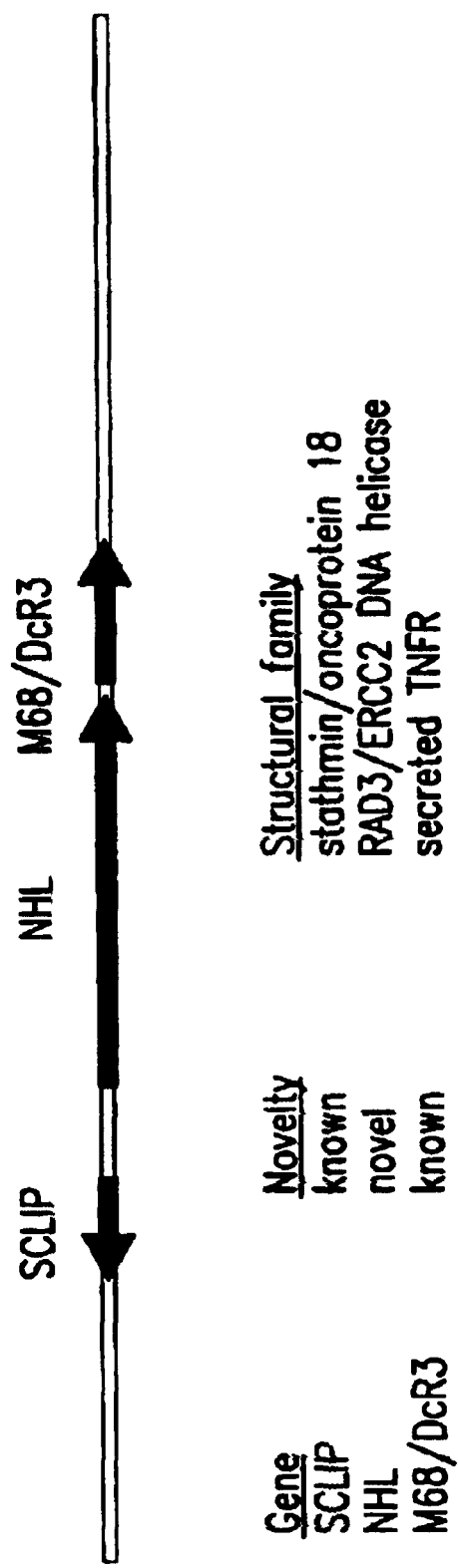

The present invention also relates to a portion of SEQ ID NO: 3 which comprises 5' regulatory regions, exons, introns and 3' non-translated regions which comprise the human NHL gene of the present invention. Such regulatory sequence may be found within the various regions of this 115 kb fragment. The 5' portion of SEQ ID NO: 1 begins at nucleotide 47095 of SEQ ID NO: 3, the initiating ATG of human NHL is from nucleotide 48687–48689 of SEQ ID NO: 3, the termination 'TAG' codon is from nucleotide 84855–84857, while the 3' terminus of SEQ ID NO: 1 as disclosed herein (GCAGTGCCC) corresponds to nucleotides 85308–85316. To this end, one preferred aspect of the invention is an isolated genomic fragment or fragments which comprise from about nucleotide 470000 to about nucleotide 85500 of SEQ ID NO: 3), which comprises the portion of the genomic clone encoding the mRNA transcript responsible for human NHL (see FIGS. 5A–B). The genomic sequence encoding NHL contains 35 exons (FIG. 5A). An especially preferred aspect of the invention is a human genomic fragment or fragments which comprise from about nucleotide 47095 to about nucleotide 85316 of SEQ ID NO: 3As noted in regard to SEQ ID NO: 1, the present invention also relates to DNA vectors and recombinant hosts which comprise at least a portion of SEQ ID NO: 3. Portions of the 115 kb genomic fragment may be housed in multiple vector/hosts so as to optimize handling of the DNA sequences within SEQ ID NO: 3. Therefore, the present invention relates to the isolated genomic sequence which set forth as SEQ ID NO: 3, a region of SEQ ID NO: 3 which contains the coding and non-coding region of human NHL, as well as cis-acting sequences within SEQ ID NO: 3 which effect regulation of transcription of one or more of the genes localized within this 115 kb human genomic fragment, including regulatory regions effecting levels of NHL, M68/DcR3, SCLIP and ARP. As noted above, this region of chromosome 20 (20q13.3) is associated with tumor growth. Therefore, an aspect of this invention also comprises, as one example, the use of one or more regulatory regions of this 115 kb genomic sequence as a target to antagonize the effect of a transcriptional factor(s) which normally upregulate expression of a gene which has a caustic role in tumor growth. Alternatively, compounds may be selected which interacts with a specific cis-acting sequence to upregulate a gene within this region, where upregulation results in a decrease in tumor growth.

The present invention is also directed to methods of screening for compounds which modulate the expression of DNA or RNA encoding a NHL protein Compounds which modulate these activities may be DNA, RNA, peptides, proteins, or non-proteinaceous organic molecules. Compounds may modulate by increasing or attenuating the expression of DNA or RNA encoding NHL, or the function of the NHL-based protein. Compounds that modulate the expression of DNA or RNA encoding NHL or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing NHL, antibodies to NHL, or modified NHL may be prepared by known methods for such uses.

The DNA molecules, RNA molecules, recombinant protein and antibodies of the present invention may be used to screen and measure levels of NHL. The recombinant proteins, DNA molecules, RNA molecules and antibodies lend themselves to the formulation of kits suitable for the detection and typing of NHL. Such a kit would comprise a compartmentalized carrier suitable to hold in close confinement at least one container. The carrier would further comprise reagents such as recombinant NHL or anti-NHL antibodies suitable for detecting NHL. The carrier may also contain a means for detection such as labeled antigen or enzyme substrates or the like.

The assays described above can be carried out with cells that have been transiently or stably transfected with NHL. The expression vector may be introduced into host cells via any one of a number of techniques including but not limited to transformation, transfection, protoplast fusion, and electroporation. Transfection is meant to include any method known in the art for introducing NHL into the test cells. For example, transfection includes calcium phosphate or calcium chloride mediated transfection, lipofection, infection with a retroviral construct containing NHL, and electroporation. The expression vector-containing cells are individually analyzed to determine whether they produce NHL protein. Identification of NHL expressing cells may be done by several means, including but not limited to immunological reactivity with anti-NHL antibodies, labeled ligand binding, the presence of host cell-associated NHL activity.

The specificity of binding of compounds showing affinity for NHL is shown by measuring the affinity of the compounds for recombinant cells expressing NHL. Expression of human NHL and screening for compounds that bind to NHL or that inhibit the binding of a known, radiolabeled ligand of NHL provides an effective method for the rapid selection of compounds with high affinity for NHL. Such ligands need not necessarily be radiolabeled but can also be nonisotopic compounds that can be used to displace bound radiolabeled compounds or that can be used as activators in functional assays. Compounds identified by the above method are likely to be agonists or antagonists of NHL and may be peptides, proteins, or non-proteinaceous organic molecules.

Accordingly, the present invention is directed to methods for screening for compounds which modulate the expression of DNA or RNA encoding a NHL protein as well as compounds which effect the function of the NHL protein. Methods for identifying agonists and antagonists of other receptors are well known in the art and, can be adapted to identify agonists and antagonists of NHL. For example, Cascieri et al. (1992, *Molec. Pharmacol.* 41:1096–1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to is measured, such binding can be measured by employing a labeled substance or agonist. The substance or agonist can be labeled in any convenient manner known to the art, e.g., radioactively, fluorescently, enzymatically.

Therefore, the present invention-includes assays by which modulators of NHL are identified. As noted above, methods for identifying agonists and antagonists are known in the art and can be adapted to identify compounds which effect in vivo levels of NHL. Accordingly, the present invention includes a method for determining whether a substance is a potential modulator of mammalian NHL levels that comprises:

(a) providing test cells by transfecting cells with an expression vector that directs the expression of NHL in the cells;

(b) exposing the test cells to the substance;

(c) measuring the amount of binding of the substance to NHL;

(d) comparing the amount of binding of the substance to NHL in the test cells with the amount of binding of the substance to control cells that have not been transfected with NHL or a portion thereof; wherein if the amount of binding of the substance is greater in the test cells as compared to the control cells, the substance is capable of binding to NHL.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C.

The assays described above can be carried out with cells that have been transiently or stably transfected with NHL. Transfection is meant to include any method known in the art for introducing NHL into the test cells. For example, transfection includes calcium phosphate or calcium chloride mediated transfection, lipofection, infection with a retroviral construct containing NHL, and electroporation.

Where binding of the substance or agonist to NHL is measured, such binding can be measured by employing a labeled substance or agonist. The substance or agonist can be labeled in any convenient manner known to the art, e.g., radioactively, fluorescently, enzymatically.

Therefore, the specificity of binding of compounds having affinity for NHL shown by measuring the affinity of the compounds for recombinant cells expressing the cloned receptor or for membranes from these cells. Expression of the cloned receptor and screening for compounds that bind to NHL or that inhibit the binding of a known, radiolabeled ligand of NHL to these cells provides an effective method for the rapid selection of compounds with high affinity for NHL. Such ligands need not necessarily be radiolabeled but can also be nonisotopic compounds that can be used to displace bound radiolabeled compounds or that can be used as activators in functional assays. It is also possible to construct assays wherein compounds are tested for an ability to modulate helicase activity in an in vitro- or in vivo-based assay. Compounds identified by the above method again are likely to be agonists or antagonists of NHL and may be peptides, proteins, or non-proteinaceous organic molecules. As noted elsewhere in this specification, compounds may modulate by increasing or attenuating the expression of DNA or RNA encoding NHL, or by acting as an agonist or antagonist of the NHL receptor protein. Again, these compounds that modulate the expression of DNA or RNA encoding NHL or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample.

Expression of NHL. DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of NHL in a host cell, NHL protein may be recovered to provide NHL protein in active form. Several NHL protein purification procedures are available and suitable for use. Recombinant NHL protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant NHL protein can be separated from other cellular proteins by use of an immunoaffinity column made with monoclonal or polyclonal antibodies specific for full-length NHL protein, or polypeptide fragments of NHL protein.

Polyclonal or monoclonal antibodies may be raised against NHL or a synthetic peptide (usually from about 9 to about 25 amino acids in length) from a portion of NHL disclosed in SEQ ID NO: 2. Monospecific antibodies to NHL are purified from mammalian antisera containing antibodies reactive against NHL or are prepared as monoclonal antibodies reactive with NHL using the technique of Kohler and Milstein (1975, *Nature* 256: 495–497). Monospecific antibody as used herein is defined as a single antibody species or multiple antibody species with homogenous binding characteristics for NHL. Homogenous binding as used herein refers to the ability of the antibody species to bind to a specific antigen or epitope, such as those associated with NHL, as described above. Human NHL-specific antibodies arc raised by immunizing animals such as mice, rats, guinea pigs, rabbits, goats, horses and the like, with an appropriate concentration of NHL protein or a synthetic peptide generated from a portion of NHL with or without an immune adjuvant.

Preimmune serum is collected prior to the first immunization. Each animal receives between about 0.1 mg and about 1000 mg of NHL protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of NHL protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of NHL in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with NHL are prepared by immunizing inbred mice, preferably Balb/c, with NHL protein. The mice are immunized by the IP or SC route with about 1 mg to about 100 mg, preferably about 10 mg, of NHL protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of NHL in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelotnas P3/NSI/Ag 4-1; MPC-11; S-1194 and Sp 2/0, with Sp 2/0 being preferred. The antibody producing cells and myeloma cells are fused in polyethylene glycol, about 1000 mol. wt., at concentrations from about 30% to about 50% Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using NHL as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti NHL mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of NHL in body fluids or tissue and cell extracts.

It is readily apparent to those skilled in the art that the above described methods for producing monospecific antibodies may be utilized to produce antibodies specific for NHL peptide fragments, or a respective full-length NHL.

NHL antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length NHL or NHL protein fragments are slowly passed through the column. The column is then washed with phosphate buffered saline until the optical density ($A_{280}$) falls to background, then the protein is eluted with 0.23 M glycine-HCl (pH 2.6). The purified NHL protein is then dialyzed against phosphate buffered saline.

Pharmaceutically useful compositions comprising modulators of NHL may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified NHL, or either NHL agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The present invention also relates to a non-human transgenic animal which is useful for studying the ability of a variety of compounds to act as modulators of NHL, or any alternative functional NHL in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art.

A type of target cell for transgene introduction is the embryonic stem cell (ES). ES cells can be obtained from pre-implantation embryos cultured in vitro and fused with embryos (Evans et al., 1981, *Nature* 292:154–156; Bradley et al., 1984, *Nature* 309:255–258; Gossler et al., 1986, *Proc. Natl. Acad. Sci* USA 83:9065–9069; and Robertson et al., 1986 *Nature* 322:445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468–1474). It will also be within the purview of the skilled artisan to produce transgenic or knock-out invertebrate animals (e.g., *C. elegans*) which express the NHL transgene in a wild type background as well in *C. elegatis* mutants knocked out for one or both of the NHL subunits. These organisms will be helpful in further determining the dominant negative effect of NHL as well as selecting from compounds which modulate this effect.

The present invention also relates to a non-human transgenic animal which is heterozygous for a functional NHL gene native to that animal. As used herein, functional is used to describe a gene or protein that, when present in a cell or in vitro system, performs normally as if in a native or unaltered condition or environment. The animal of this aspect of the invention is useful for the study of the retinal specific expression or activity of NHL in an animal having only one functional copy of the gene. The animal is also useful for studying the ability of a variety of compounds to act as modulators of NHL activity or expression in vivo or, by providing cells for culture, in vitro. It is reiterated that as used herein, a modulator is a compound that causes a change in the expression or activity of NHL, or causes a change in the effect of the interaction of NHL with its ligand(s), or other protein(s). In an embodiment of this aspect, the animal is used in a method for the preparation of a further animal which lacks a functional native NHL gene. In another embodiment, the animal of this aspect is used in a method to prepare an animal which expresses a non-native NHL gene in the absence of the expression of a native NHL gene. In particular embodiments the non-human animal is a mouse. In further embodiments the non-native NHL is a wild-type human NHL which is disclosed herein, or any other biologically equivalent form of human NHL gene as also disclosed herein.

In reference to the transgenic animals of this invention, reference is made to transgenes and genes. As used herein, a transgene is a genetic construct including a gene. The transgene is integrated into one or more chromosomes in the cells in an animal by methods known in the art Once integrated, the transgene is carried in at least one place in the chromosomes of a transgenic animal. Of course, a gene is a nucleotide sequence that encodes a protein, such as human or mouse NHL. The gene and/or transgene may also include genetic regulatory elements and/or structural elements known in the art.

Another aspect of the invention is a non-human animal embryo deficient for native NHL expression. This embryo is useful in studying the effects of the lack of NHL on the developing animal. In particular embodiments the animal is a mouse. The animal embryo is also useful as a source of cells lacking a functional native NHL gene. The cells are useful in in vitro culture studies in the absence of NHL.

An aspect of this invention is a method to obtain an animal in which the cells lack a functional gene NHL native to the animal. The method includes providing a gene for an altered form of the NHL gene native to the animal in the form of a transgene and targeting the transgene into a chromosome of the animal at the place of the native NHL gene. The transgene can be introduced into the embryonic stem cells by a variety of methods known in the art, including electroporation, microinjection, and lipofection. Cells carrying the transgene can then be injected into blastocysts which are then implanted into pseudopregnant animals. In alternate embodiments, the transgene-targeted embryonic stem cells can be coincubated with fertilized eggs or morulae followed by implantation into females. After gestation, the animals obtained are chimeric founder transgenic animals. The founder animals can be used in further embodiments to cross with wild-type animals to produce F1 animals heterozygous for the altered NHL gene. In further embodiments, these heterozygous animals can be interbred to obtain the non-viable transgenic embryos whose somatic and germ cells are homozygous for the altered NHL gene and thereby lack a functional NHL gene. In other embodiments, the heterozygous animals can be used to produce cells lines. In preferred embodiments, the animals are mice.

A further aspect of the present invention is a transgenic non-human animal which expresses a non-native NHL on a native NHL null background. In particular embodiments, the null background is generated by producing an animal with an altered native NHL gene that is non-functional, i.e. a knockout. The animal can be heterozygous (i.e., having a different allelic representation of a gene on each of a pair of chromosomes of a diploid genome) or homozygous (i.e., having the same representation of a gene on each of a pair of chromosomes of a diploid genome) for the altered NHL gene and can be hemizygous (i.e., having a gene represented on only one of a pair of chromosomes of a diploid genome) or homozygous for the non-native NHL gene. In preferred embodiments, the animal is a mouse In particular embodiments the non-native NHL gene can be a wild-type or mutant allele including those mutant alleles associated with a disease. In further embodiments, the non-native NHL is a human NHL. In a further embodiment the non-native NHL gene is operably linked to a promoter As used herein, operably linked is used to denote a functional connection between two elements whose orientation relevant to one another can vary. In this particular case, it is understood in the art that a promoter can be operably linked to the coding sequence of a gene to direct the expression of the coding sequence while placed at various distances from the coding sequence in a genetic construct.

An aspect of this invention is a method of producing transgenic animals having a transgene including a non-native NHL gene on a native NHL null background. The method includes providing transgenic animals of this invention whose cells are heterozygous for a native gene encoding a functional NHL protein and an altered native NHL gene. These animals are crossed with transgenic animals of this invention that are hemizygous for a transgene including a non-native NHL gene to obtain animals that are both heterozygous for an altered native NHL gene and hemizygous for a non-native NHL gene. The latter animals are interbred to obtain animals that are homozygous or hemizygous for the non-native NHL and are homozygous for the altered native NHL gene. In particular embodiments, cell lines are produced from any of the animals produced in the steps of the method.

The transgenic animals and cells of this invention are useful in the determination of the in vivo function of a non-native NHL in the central nervous system and in other tissues of an animal. The animals are also useful in studying the tissue and temporal specific expression patterns of a non-native NHL throughout the animals. The animals are also useful in determining the ability for various forms of wild-type and mutant alleles of a non-native NHL to rescue the native NHL null deficiency. The animals are also useful for identifying and studying the ability of a variety of compounds to act as modulators of the expression or activity of a non-native NHL in vivo, or by providing cells for culture, for in vitro studies.

As used herein, a "targeted gene" or "Knockout" (KO) is a DNA sequence introduced into the germline of a non-human animal by way of human intervention, including but not limited to, the methods described herein. The targeted genes of the invention include nucleic acid sequences which are designed to specifically alter cognate endogenous alleles. An altered NHL gene should not fully encode the same NHL as native to the host animal, and its expression product can be altered to a minor or great degree, or absent altogether. In cases where it is useful to express a non-native NHL gene in a transgenic animal in the absence of a native NHL gene we prefer that the altered NHL gene induce a null lethal knockout phenotype in the animal. However a more modestly modified NHL gene can also be useful and is within the scope of the present invention.

A type of target cell for transgene introduction is the embryonic stem cell (ES). ES cells can be obtained from pre-implantation embryos cultured in vitro and fused with embryos (Evans et al., 1981, Nature 292:154–156; Bradley et al., 1984, Nature 309:255–258; Gossler et al., 1986, Proc. Natl. Acad. Sci. USA 83:9065–9069; and Robertson et al., 1986 Nature 322:445–448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, Science 240: 1468–1474).

The methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

The following examples are provided to illustrate the present invention without, however, limiting the same hereto.

EXAMPLE 1

Characterization of DNA Molecules Encoding NHL

M68/DcR3 identification—The human osteoprotegerin (OPG) sequence (Acc. # U94332), which is a member of the TNFR-related family, was used to searched Genbank using the programs TBLASTN and TFASTX3 to identify novel gene family members. Two EST sequences (GenBank Acc. # AA155701 and AA025672) were identified that showed sequence similarities to the cysteine repeats of the OPG sequence. These EST sequences were then used to identify additional EST sequences, which formed a single EST cluster (GenBank Acc. #s aa577603, aa603704, aa613366, aa158406, w67560, aa325843, aa155646, aa025673, aa514270, m91489). Two clones were further characterized, which were derived from colon tumor and germ cell tumor libraries (Research Genetics, Inc). DNA sequence analysis revealed two alternatively spliced forms of the 5'-end UTR of M68/DcR3. The M68/DcR3 open reading frame was confirmed by sequence analysis of clones obtained by PCR cloning from a normal human cDNA library (Clontech).

M68/DcR3 BAC identification and sequencing—To further delineate the gene structure of M68/DcR3, genomic DNA was obtained using a human "Down to the Well"™ genomic bacterial artificial chromosome (BAC) library (Genome Systems, Inc.) according to the manufacturer's protocol. Two sets of PCR primers, C68.36F:
5'-CACAGGTTCAGCATGTTTGTGCGTC-3' (SEQ ID NO: 4) and C68.275R:
5'-CACAGTCCCTGCTGGCCTCTGTCTA-3' (SEQ ID NO: 5), and E68.715F:
5'-CAGGACATCTCCATCAAGAGGCTGC-3' (SEQ ID NO: 6) and E68.972R:
5'-AATAAGAGGGGGCCAGGATCAGTGC-3' (SEQ ID NO: 7), were used to carry out PCR reactions to identify positive wells that contained the full-length M68/DcR3 gene. The PCR conditions used were 94° C. for 9 min, 35 cycles of (94° C., 30 sec., 68° C. 3 min.) followed by 72° C. for 10 min. Two positive BAC clones were identified and characterized by restriction digestion and BAC-end sequence analyses, of which hbm168 was selected for shotgun sequencing.

A shot-gun library for BAC hbm168 was constructed using a conventional strategy. Briefly, two 150-ml bacterial cultures were combined and purified using a modified protocol of the plasmid-Maxi kit (QIAGEN) followed by CsCl gradient purification. After butanol extraction and isopropanol precipitation, BAC DNA was nebulizied at 10 psi for 60 seconds to generate randomly sheared fragments. Following ethanol precipitation, the fragments were end-repaired using T4 polymerase (Promega) and BstXI adaptors (Invitrogen) were ligated overnight. Removal of excess, unligated adaptors and size selection was performed using a cDNA sizing column (Life Technologies, Inc.) to generate genomic fragments in the size range of 1500 to 3000 bp. Adaptor ligated fragments were cloned into a modified pBlueScript SK+ vector (Stratagene) and transformed in XL2-Blue ultracompentent cells (Stratagene). Approximately 1000 clones were isolated, plasmids were purified using the Turbo miniprep kits (QIAGEN), and both plasmid ends were sequenced with the BigDye terminator kits (Perkin-Elmer). Sequence data were assembled using Phred/Phrap/Consed where single-stranded and gap regions were closed using a directed sequencing strategy.

NHL identification and sequencing—The genomic clone for the NHL, gene was obtained and sequenced. The transcript was identified through exon prediction using GRAIL2 and sequence alignment to a contiguous 4.5 kilobase region of chromosome 4 (88% sequence identity). The complete exon structure of NHL was subsequently confirmed by RT-PCR analysis. The exon structure was confirmed by RT-PCR using polyA RNA from a human colorectal adenocarcinoma cell line, SW480 (Clontech). Primers were designed based on the genomic sequence that were predicted to be exons. RT-PCR reaction were carried out with SW480 polyA RNA using standard conditions with TaqGold Enzyme at 94° C. for 12 min, 35 cycles of (94° C., 30 sec., 60 C., 30 sec., and 68° C. 2–6 min.) followed by 68° C. for 7 min. Most sequence confirmation was accomplished by RT-PCR, although first junction between exon 1 and 2 was confirmed by 5'RACE and junctions between exon 26–29 were by RCCA. The primers used were as follows:

| Junction of Exons | Confirmed by Primers |
|---|---|
| H01/H02 | hdkw (5'RACE) |
| H02/H03 | hdiy,hdiz |
| H03–H09 | hdid,hdie,hdja,hdjb |
| H09–H13 | hdja,hdie |
| H13–H18 | hdje,hdjf |
| H18–H23 | hdjg,hdjh |
| H23–H26 | hdji,hdjj |
| H26–H29 | hdkv,r543(RCCA) |
| H29–H31 | hdij,hdmu,hdnd,hdne |
| H31/H32 | hdij,hdmu |
| H32/H34 | hdip,hdil,hdmv,hdik,hdli |
| H34/H35 | hdng,hdnh |

HDID - 5'-GTGAATGGCATCCTGGAGAG-3'; (SEQ ID NO:8)

HDIE - 5'-GTCTCCAGGCAGCTCAACAG-3'; (SEQ ID NO:9)

HDIJ - 5'-ACCCTGTCCCTCCTGTCTGA-3'; (SEQ ID NO:10)

HDIY - 5'-AGACCCTAAGATGTTCGGAG-3'; (SEQ ID NO:11)

HDIZ - 5'-GATGACCTGTGTGAGTTGCG-3'; (SEQ ID NO:12)

HDJA - 5'-CGCAACTCACACAGGTCATC-3'; (SEQ ID NO:13)

HDJB - 5'-GGAGTCAGGTCAAAGGATGC-3'; (SEQ ID NO:14)

HDJC - 5'-GCATCCTTTGACCTGACTCC-3'; (SEQ ID NO:15)

HDJD - 5'-GGTCTGAAACGTGATCTGGG-3'; (SEQ ID NO:16)

HDJE - 5'-CCCAGATCACGTTTCAGACC-3'; (SEQ ID NO:17)

HDJF - 5'-CGATGATGTGTGGGTTCTCC-3'; (SEQ ID NO:18)

HDJG - 5'-GGAGAACCCACACATCATCG-3'; (SEQ ID NO:19)

HDJH - 5'-CGTGTCTGAGAAGTCCAGCC-3'; (SEQ ID NO:20)

HDJI - 5'-GGCTGGACTTCTCAGACACG-3'; (SEQ ID NO:21)

HDJJ - 5'-ACAGCATCTTCTCCACGCAC-3'; (SEQ ID NO:22)

HFMU - 5'-AGTCCTCTGGCTTTGCAGTG-3'; (SEQ ID NO:23)

HDKV - 5'-TGTGCGTGGAGAAGATGCTG-3'; (SEQ ID NO:24)

HDKW - 5'-GGCTGGAAAGGGAAGTCTAC-3'; (SEQ ID NO:25)

HDND - 5'-TGGTTCAGGTGCTCTTGGGG-3'; (SEQ ID NO:26)

HDNE - 5'-CGTGAAGCAGGAGTTGAGCC-3'; (SEQ ID NO:27)

HDIK - 5'-ATCTTGCTCTGGGTCTTCCC-3'; (SEQ ID NO:28)

HDIL - 5'-CACTGCAAAGCCAGAGGACT-3'; (SEQ ID NO:29)

HDIP - 5'-ATAAGCAAGACGACGACCTC-3'; (SEQ ID NO:30)

HDLI - 5'-CTATTCTGTTGGGTGGGTTC-3'; (SEQ ID NO:31)

HDMV - 5'-CGTGCCTCCTGTGCTTACCC-3'; (SEQ ID NO:32)

HDNG - 5'-CAGACCCCAAGGTAGCTCAG-3'; (SEQ ID NO:33)

HDNH - 5'-GGAAGACCCAGAGCAAGATC-3'. (SEQ ID NO:34)

Figure 3C:
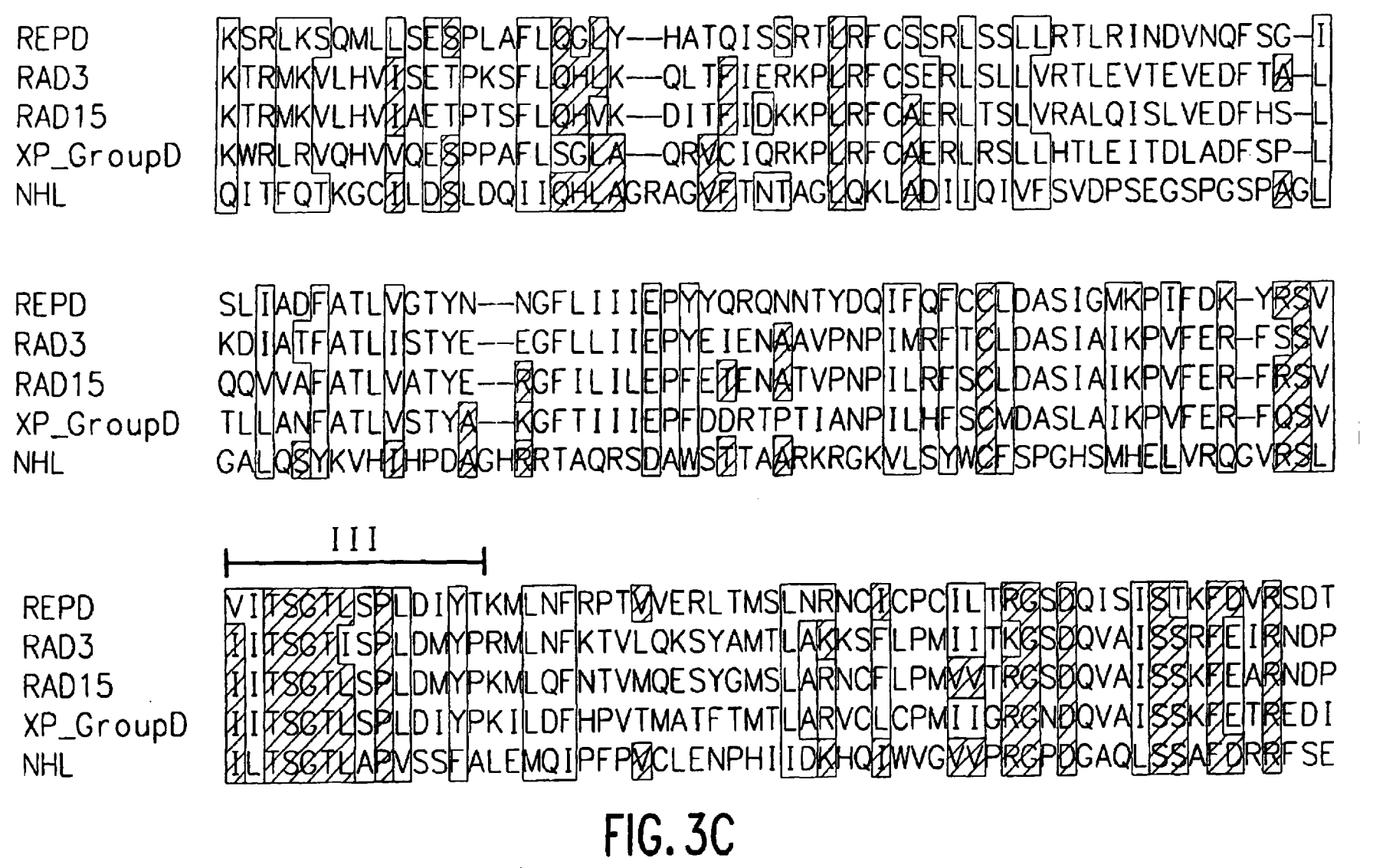
Figure 3D:
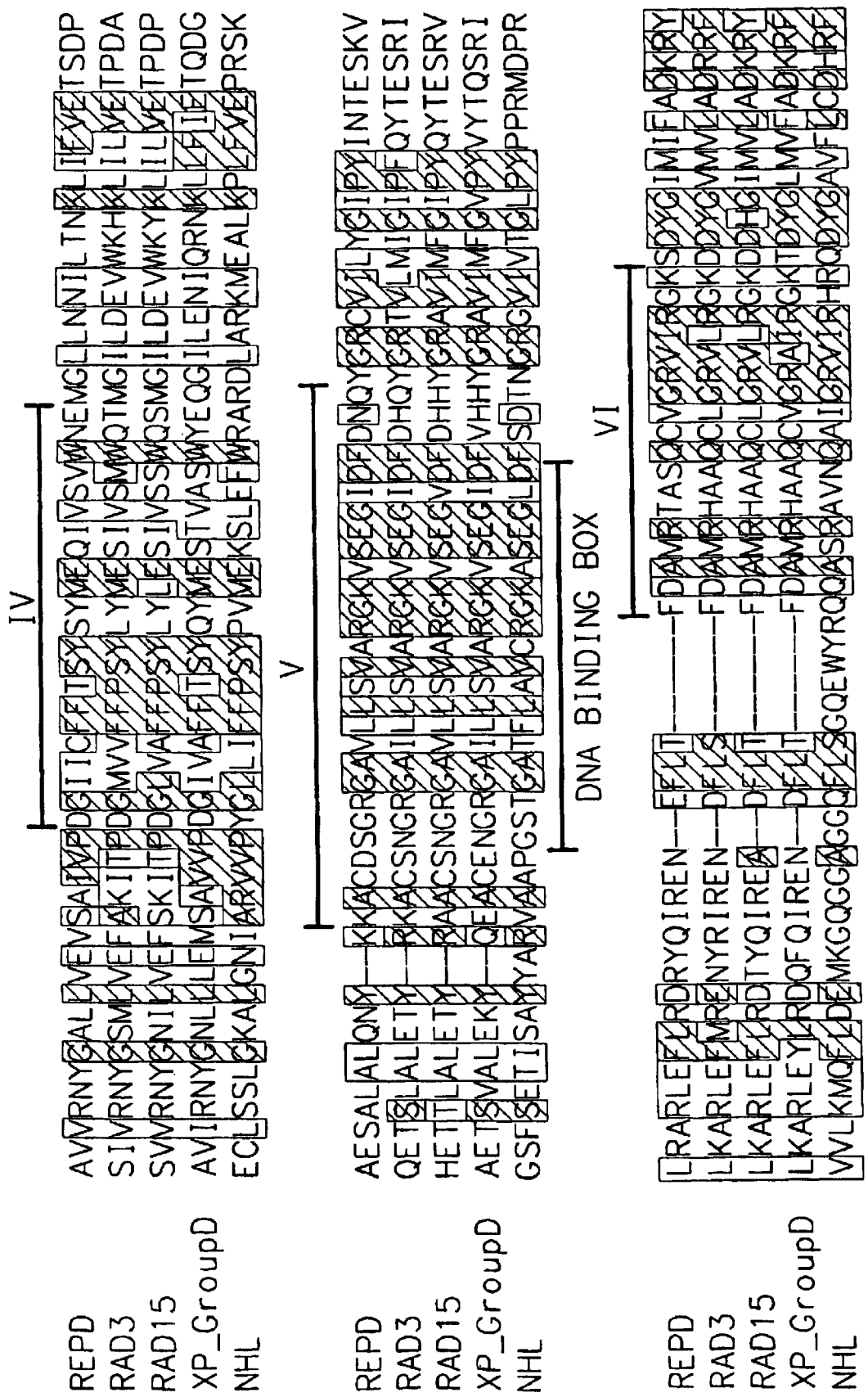

Amplified product were subject to direct sequencing after purification from an agarose gel or cloned into a TOPO PCR cloning vector (Invitrogen) for sequencing. Multiple sequence alignment of NHL to known helicases showed that NHL contains all the seven critical helicase domains. BLAST analysis of the predicted 1,219 amino acid sequence (see FIG. 2, SEQ ID NO: 2) reveal an approximately 26% sequence identity and 48% sequence similarity to the RAD3/ERCC2 gene family of DNA helicases (see FIG. 3). Review of this sequence data shows that two partial human cDNA clones (Acc. No. al080127 and ab029011) are deposited. No. al080127 covers exon 25–35 while ab029011 covers exons 9–35. Ab029011 starts at amino acid 240 of the full length human NHL protein disclosed herein, but also differs at exon 35 and appears to be a fusion transcript with M68. This cDNA was isolated from brain tissue, which has been known to express rare transcripts.

EXAMPLE 2

Northern Analysis of human NHL Expression

Figure 4:
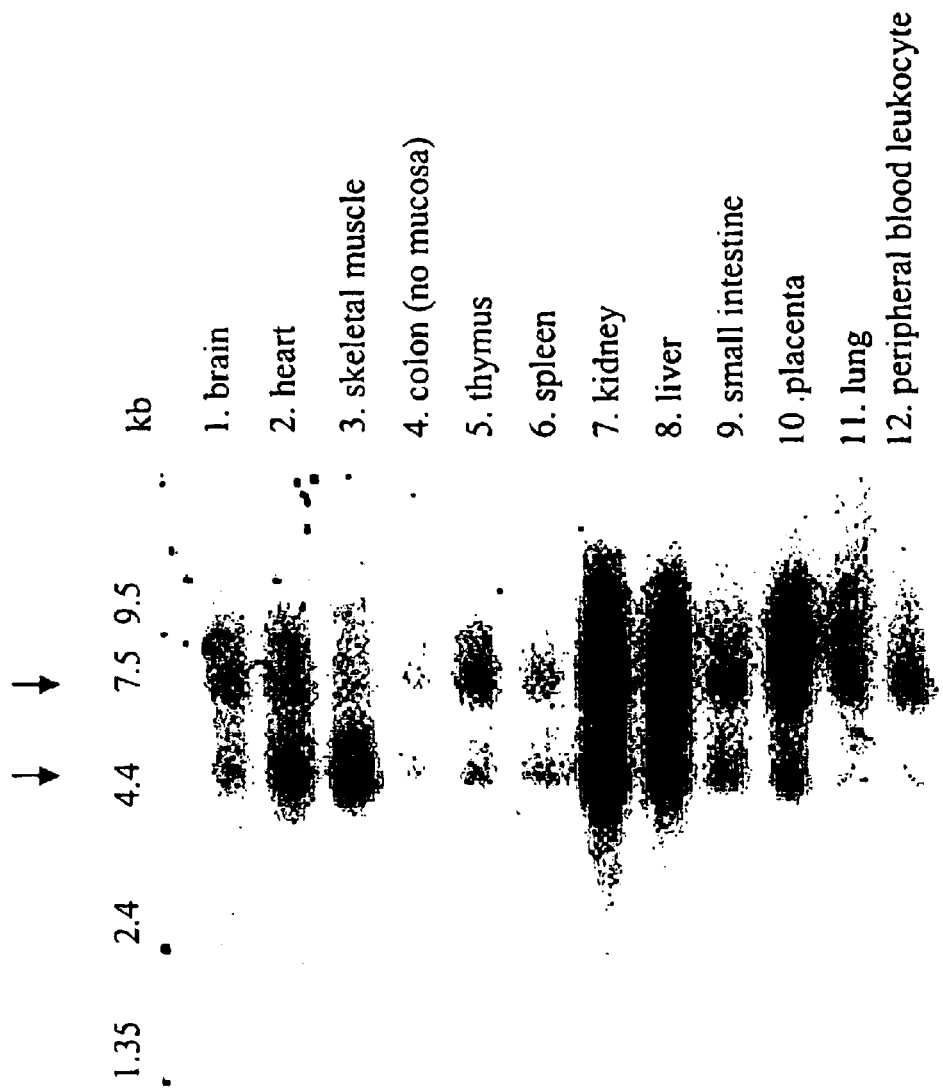
FIG. 4 shows Northern analysis of NHL expression in multi-human tissues.

Messenger RNA (mRNA) obtained from human brain, heart, skeletal muscle, colon, thymus, spleen, kidney, liver, small intestine, placenta, lung, and peripheral blood leukocytes. Two µg of polyA$^+$ RNA were run on each lane a denaturing formaldehyde 1% agarose gel, and transferred to a charged-modified nylon membrane. The probe was made using a 733 bp fragment derived from 1174–1907 nt of the NHL cDNA. This fragment was labeled via the $^{32}$P dCTP random priming method (Ambion). Hybridization was carried in ExpressHyb (Clontech) according to the manufacturer's protocol except for the final wash, which was at 55° C. Membranes were exposed to X-ray film with intensifying screen at −80° C. overnight. The Northern data is presented in FIG. 4. Note hybridization of the NHL probe to an approximately 4.4 kb transcript. The 7.5 kb transcript may suggest an alternative splicing of the NHL RNA.

EXAMPLE 3

Chromosomal Localization

To map the position of M68/NHL in the human genome, primers C68.36F and C68.275R, were used to carry out PCR reactions to 93 clones of the MIT GeneBridge 4 panel (Research Genetics) and results were submitted to MIT for analysis. M68/DcR3 was mapped to the extreme telomere of chromosome 20, at 20q13.3, 28cR from D20S173 with a lod score of 13. An analogous procedure was also carried out with the 83 clones of the Stanford G3 radiation hybrid panel, with PCR results submitted to the Stanford Genome Center for analysis. Analysis using another pair of PCR primers specific to NHL yielded the same result. For fluorescence in situ (FISH) analysis, the normal human male fibroblast cell line, L136 (Coriell Cell Repository, Camden, N.J.) was arrested in mitosis with colcemid (10 µg/ml). A human chromosome 20 α-satellite probe (Vysis, Downers Grove, Ill.) was directly labeled with Spectrum Orange dUTP and was used to identify chromosome 20. The M68 BAC clone was directly labeled with SpectrumGreen dUTP by nick translation (Vysis). Slides were counterstained with DAPI stain and viewed under an Olympus microscope with narrow blue and DAPI/TRITC filters. Fifty metaphase cells were scored to verify that the M68 probe was located on the same chromosome as the Human Chromosome 20 probe. Radiation hybrid chromosomal mapping reconfirms that it is linked to M68 locus, at 20q13.3.

What is claimed is:

1. A purified DNA molecule encoding a human helicase protein which comprises the amino acid sequence (SEQ ID NO:2)
```
MPKIVLNGVT VDFPFQPYKC QQEYMTKVLE CLQQKVNGIL
ESPTGTGKTL CLLCTTLAWR EHLRDGISAR KIAERAQGEL
FPDRALSSWG NAAAAAGDPI ACYTDIPKII YASRTHSQLT
QVINELRNTS YRPKVCVLGS REQLCIHPEV KKQESNHLQI
HLCRKKVASR SCHFYNNVEE KSLEQELASP ILDIEDLVKS
GSKHRVCPYY LSRNLKQQAD IIFMPYNYLL DAKSRRAHNI
DLKGTVVIFD EAHNVEKMCE ESASFDLTPH DLASGLDVID
QVLEEQTKAA QQGEPHPEFS ADSPSPGLNM ELEDIAKLKM
ILLRLEGAID AVELPGDDSG VTKPGSYIFE LFAEAQITFQ
TKGCILDSLD QIIQHLAGRA GVFTNTAGLQ KLADIIQIVF
SVDPSEGSPG SPAGLGALQS YKVHIHPDAG HRRTAQRSDA
WSTTAARKRG KVLSYWCFSP GHSMHELVRQ GVRSLILTSG
TLAPVSSFAL EMQIPFPVCL ENPHIIDKHQ IWVGVVPRGP
DGAQLSSAFD RRFSEECLSS LGKALGNIAR VVPYGLLIFF
PSYPVMEKSL EFWRARDLAR KMEALKPLFV EPRSKGSFSE
TISAYYARVA APGSTGATFL AVCRGKASEG LDFSDTNGRG
VIVTGLPYPP RMDPRVVLKM QFLDEMKGQG GAGGQFLSGQ
EWYRQQASRA VNQAIGRVIR HRQDYGAVFL CDHRFAFADA
RAQLPSWVRP HVRVYDNFGH VIROVAQFFR VAERTMPAPA
PRATAPSVRG EDAVSEAKSP GPFFSTRKAK SLDLHVPSLK
QRSSGSPAAG DPESSLCVEY EQEPVPARQR PRGLLAALEH
SEQRAGSPGE EQAHSCSTLS LLSEKRPAEE PRGGRKKIRL
VSHPEEPVAG AQTDRAKLFM VAVKQELSQA NFATFTQALQ
DYKGSDDFAA LAACLGPLFA EDPKKHNLLQ GFYQFVRPHH
KQQFEEVCIQ LTGRGCGYRP EHSIPRRQRA QPVLDPTGRT
APDPKLTVST AAAQQLDPQE HLNQGRPHLS PRPPPTGDPG
SQPQWGSGVP RAGKQGQHAV SAYLADARRA LGSAGCSQLL
AALTAYKQDD DLDKVLAVLA ALTTAKPEDF PLLHRFSMFV
RPHHKQRFSQ TCTDLTGRPY PGMEPPGPQE ERLAVPPVLT
HRAPQPGPSR SEKTGKTQSK ISSFLRQRPA GTVGAGGEDA
GPSQSSGPPH GPAASEWGL*.
```

2. An expression vector for expressing a helicase protein in a recombinant host cell wherein said expression vector comprises a DNA molecule of claim 1.

3. A host cell which expresses a recombinant helicase protein wherein said host cell contains the expression vector of claim 2.

4. A process for expressing a helicase protein in a recombinant host cell, comprising:
   (a) transfecting the expression vector of claim 2 into a suitable host cell; and,
   (b) culturing the host cells of step (a) under conditions which allow expression of said helicase protein from said expression vector.

5. A purified DNA molecule encoding a human helicase protein which consists of the amino acid sequence

```
                                            (SEQ ID NO:2)
MPKIVLNGVT VDFPFQPYKC QQEYMTKVLE CLQQKVNGIL
ESPTGTGKTL CLLCTTLAWR EHLRDGISAR KIAERAQGEL
FPDRALSSWG NAAAAAGDPI ACYTDIPKII YASRTHSQLT
QVINELRNTS YRPKVCVLGS REQLCIHPEV KKQESNHLQI
HLCRKKVASR SCHFYNNVEE KSLEQELASP ILDIEDLVKS
GSKHRVCPYY LSRNLKQQAD IIFMPYNYLL DAKSRRAHNI
DLKGTVVIFD EAHNVEKMCE ESASFDLTPH DLASGLDVID
QVLEEQTKAA QQGEPHPEFS ADSPSPGLNM ELEDIAKLKM
ILLRLEGAID AVELPGDDSG VTKPGSYIFE LFAEAQITFQ
TKGCILDSLD QIIQHLAGRA GVFTNTAGLQ KLADIIQIVF
SVDPSEGSPG SPAGLGALQS YKVHIHPDAG HRRTAQRSDA
WSTTAARKRG KVLSYWCFSP GHSMHELVRQ GVRSLILTSG
TLAPVSSFAL EMQIPFPVCL ENPHIIDKHQ IWVGVVPRGP
DGAQLSSAFD RRFSEECLSS LGKALGNIAR VVPYGLLIFF
PSYPVMEKSL EFWRARDLAR KMEALKPLFV EPRSKGSFSE
TISAYYARVA APGSTGATFL AVCRGKASEG LDFSDTNGRG
VIVTGLPYPP RMDPRVVLKM QFLDEMKGQG GAGGQFLSGQ
EWYRQQASRA VNQAIGRVIR HRQDYGAVFL CDHRFAFADA
RAQLPSWVRP HVRVYDNFGH VIROVAQFFR VAERTMPAPA
PRATAPSVRG EDAVSEAKSP GPFFSTRKAK SLDLHVPSLK
QRSSGSPAAG DPESSLCVEY EQEPVPARQR PRGLLAALEH
SEQRAGSPGE EQAHSCSTLS LLSEKRPAEE PRGGRKKIRL
VSHPEEPVAG AQTDRAKLFM VAVKQELSQA NFATFTQALQ
DYKGSDDFAA LAACLGPLFA EDPKKHNLLQ GFYQFVRPHH
KQQFEEVCIQ LTGRGCGYRP EHSIPRRQRA QPVLDPTGRT
APDPKLTVST AAAQQLDPQE HLNQGRPHLS PRPPPTGDPG
SQPQWGSGVP RAGKQGQHAV SAYLADARRA LGSAGCSQLL
AALTAYKQDD DLDKVLAVLA ALTTAKPEDF PLLHRFSMFV
RPHHKQRFSQ TCTDLTGRPY PGMEPPGPQE ERLAVPPVLT
HRAPQPGPSR SEKTGKTQSK ISSFLRQRPA GTVGAGGEDA
GPSQSSGPPH GPAASEWGL*.
```

6. An expression vector for expressing a helicase protein in a recombinant host cell wherein said expression vector comprises a DNA molecule of claim 5.

7. A host cell which expresses a recombinant helicase protein wherein said host cell contains the expression vector of claim 6.

8. A process for expressing a helicase protein in a recombinant host cell, comprising:
   (a) transfecting the expression vector of claim 6 into a suitable host cell; and,
   (b) culturing the host cell of step (a) under conditions which allow expression of said helicase protein from said expression vector.

9. A purified DNA molecule which comprises the nucleotide sequence as set forth in SEQ ID NO: 1.

10. An expression vector for expressing a helicase protein in a recombinant host cell wherein said expression vector comprises a DNA molecule of claim 9.

11. A host cell which expresses a recombinant helicase protein wherein said host cell contains the expression vector of claim 10.

12. A purified DNA molecule which consists of the nucleotide sequence as set forth in SEQ ID NO: 1.

13. An expression vector for expressing a helicase protein in a recombinant host cell wherein said expression vector comprises a DNA molecule of claim 12.

14. A host cell which expresses a recombinant helicase protein wherein said host cell contains the expression vector of claim 13.

15. A purified DNA molecule of which consists of the nucleotide sequence from about nucleotide 828 to about nucleotide 4487, as set forth in SEQ ID NO:1.

16. An expression vector for expressing a helicase protein in a recombinant host cell wherein said expression vector comprises a DNA molecule of claim 15.

17. A host cell which expresses a recombinant helicase protein wherein said host cell contains the expression vector of claim 16.

* * * * *